(12) United States Patent
Balog et al.

(10) Patent No.: US 10,689,331 B2
(45) Date of Patent: Jun. 23, 2020

(54) IDO INHIBITORS

(71) Applicant: Bristol-Myers Squibb Company, Princeton, NJ (US)

(72) Inventors: James Aaron Balog, Lambertville, NJ (US); Emily Charlotte Cherney, Newtown, PA (US); Jay A. Markwalder, Lahaska, PA (US); Weifang Shan, Princeton, NJ (US); David K. Williams, Delran, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/737,798

(22) PCT Filed: Jun. 27, 2016

(86) PCT No.: PCT/US2016/039564
§ 371 (c)(1),
(2) Date: Dec. 19, 2017

(87) PCT Pub. No.: WO2016/210414
PCT Pub. Date: Dec. 29, 2016

(65) Prior Publication Data
US 2019/0002402 A1 Jan. 3, 2019

Related U.S. Application Data

(60) Provisional application No. 62/184,984, filed on Jun. 26, 2015.

(51) Int. Cl.

| | |
|---|---|
| A61K 31/18 | (2006.01) |
| A61K 31/196 | (2006.01) |
| A61K 31/381 | (2006.01) |
| A61K 31/404 | (2006.01) |
| A61K 31/41 | (2006.01) |
| A61K 31/42 | (2006.01) |
| A61K 31/421 | (2006.01) |
| A61K 31/426 | (2006.01) |
| A61K 31/433 | (2006.01) |
| A61K 31/4406 | (2006.01) |
| A61K 31/505 | (2006.01) |
| A61K 31/513 | (2006.01) |
| C07C 275/42 | (2006.01) |
| C07D 239/42 | (2006.01) |
| C07D 261/14 | (2006.01) |
| C07D 285/12 | (2006.01) |
| C07C 311/51 | (2006.01) |
| C07C 311/49 | (2006.01) |
| C07C 275/40 | (2006.01) |
| C07C 233/44 | (2006.01) |
| A61K 45/06 | (2006.01) |
| C07C 311/46 | (2006.01) |
| C07D 209/08 | (2006.01) |
| C07D 213/72 | (2006.01) |
| C07D 239/47 | (2006.01) |
| C07D 257/04 | (2006.01) |
| C07D 263/32 | (2006.01) |
| C07D 277/38 | (2006.01) |
| C07D 285/135 | (2006.01) |
| C07D 333/34 | (2006.01) |

(52) U.S. Cl.
CPC ............ *C07C 275/42* (2013.01); *A61K 31/18* (2013.01); *A61K 31/196* (2013.01); *A61K 31/381* (2013.01); *A61K 31/404* (2013.01); *A61K 31/41* (2013.01); *A61K 31/42* (2013.01); *A61K 31/421* (2013.01); *A61K 31/426* (2013.01); *A61K 31/433* (2013.01); *A61K 31/4406* (2013.01); *A61K 31/505* (2013.01); *A61K 31/513* (2013.01); *A61K 45/06* (2013.01); *C07C 233/44* (2013.01); *C07C 275/40* (2013.01); *C07C 311/46* (2013.01); *C07C 311/49* (2013.01); *C07C 311/51* (2013.01); *C07D 209/08* (2013.01); *C07D 213/72* (2013.01); *C07D 239/42* (2013.01); *C07D 239/47* (2013.01); *C07D 257/04* (2013.01); *C07D 261/14* (2013.01); *C07D 263/32* (2013.01); *C07D 277/38* (2013.01); *C07D 285/12* (2013.01); *C07D 285/135* (2013.01); *C07D 333/34* (2013.01); *C07C 2601/02* (2017.05); *C07C 2601/14* (2017.05); *C07C 2601/16* (2017.05)

(58) Field of Classification Search
None
See application file for complete search history.

(56) References Cited

FOREIGN PATENT DOCUMENTS

| WO | WO-8605779 A1 * | 10/1986 | ............ C07C 45/71 |
| WO | WO-9900127 A1 * | 1/1999 | ............ A61K 31/00 |
| WO | WO2014/150646 A1 | 9/2014 | |

(Continued)

OTHER PUBLICATIONS

Allen, L.V. Jr. et al., *Remington: The Science and Practice of Pharmacy* (2 Volumes) 22nd Edition (2012) Pharmaceutical Press.

(Continued)

*Primary Examiner* — Samantha L Shterengarts
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

17 Claims, No Drawings

(56) References Cited

FOREIGN PATENT DOCUMENTS

| WO | WO2014/150677 A1 | 9/2014 |
| WO | WO2015/006520 A1 | 1/2015 |

OTHER PUBLICATIONS

Bundgaard, Hans, Editor, Design of Prodrugs, Elsevier (1985).
Bundgaard, Hans, "Means to Enhance Penetration, Prodrugs as a means to improve the delivery of peptide drugs", Advanced Drug Delivery Reviews, vol. 8, pp. 1-38 (1992).
Bundgaard, H. et al., J. Pharm. Sci., 77:285 (1988).
Bundgaard, Hans, Editor, Chapter 5, "Design and Application of Prodrugs", *A Textbook of Drug Design and Development*, pp. 113-191 (1991).
Goldstein, N. et al., "Biological Efficacy of a Chimeric Antibody to the Epidermal Growth Factor Receptor in a Human Tumor Xenograft Model", Clinical Cancer Research, vol. 1, pp. 1311-1318 (1995).
Greene, T.W. et al., *Protective Groups in Organic Synthesis*, Third Edition, Wiley-Interscience, NY (1999).
Greene, T.W., et al., *Protecting Groups in Organic Synthesis*, Fourth Edition, Wiley (2007).
Gross, E., *The Peptides: Analysis, Synthesis, Biology*, vol. 3, Academic Press, NY (1981).
Hamaguchi Wataru et al., "Design and synthesis of novel benzimidazole derivatives as phosphodiesterase 10A inhibitors with reduced CYP1A2 inhibition", Bioorganic Medicinal Chemistry, vol. 21, No. 24, pp. 7612-7623.
House, H.O., Modern Synthetic Reactions, Second Edition, W.A. Benjamin Inc., Menlo Park CA, (1972).
Ishiyama, T. et al., J. Org. Chem., 60:7508-7510 (1995).
Kakeya, N. et al., "Studies on Prodrugs of Cephalosporins. I. Synthesis and Biological Properties of Glycyloxbenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Phar. Bull., vol. 32(2), pp. 692-698 (1984).
King, Frank, Editor, Medicinal Chemistry: Principles and Practice (2006).
Kohl, Nancy E. et al., "Inhibition of farnesyltransferase induces regression of mammary and salivary carcinomas in ras transgenic mice", Nature Medicine, vol. 1(8), pp. 792-797 (1995).
Krosgaard-Larsen, P. et al., eds., Harwood Academic Publishers (1991).
Muci, A.R. et al., "Practical Palladium Catalysts for C-N and C-O Bond Formation", *Topics in Curr. Chem.*, 219:131-209 (2002).
Rautio, J. (Editor). *Prodrugs and Targeted Delivery (Methods and Principles in Medicinal Chemistry)*, vol. 47, Wiley-VCH, (2011).
Sausville, Edward A., "Cyclin-Dependent Kinase Modulators Studied at the NCI: Pre-Clinical and Clinical Studies", Current Med. Chemistry-Anti-Cancer Agents, vol. 3, pp. 47-56 (2003).
Scheller, B. et al., "Paclitaxel Balloon Coating, a Novel Method for Prevention and Therapy of Restenosis", Circulation, vol. 110, pp. 810-814 (2004).
Sekulić, A. et al., "A Direct Linkage between the Phosphoinositide 3-Kinase-AKT Signaling Pathway and the Mammalian Target of Rapamycin in Mitogen-stimulated and Transformed Cells", Cancer Research, vol. 60, pp. 3504-3513 (2000).
Smith, M.B. et al., "*March's Advanced Organic Chemistry Reactions, Mechanisms, and Structure*", Fifth Edition, Wiley-Interscience, NY (2001).
Testa, B. et al., *Hydrolysis in Drug and Prodrug Metabolism, Chemistry, Biochemistry and Enzymology*, VCHA and Wiley-VCH, Zurich, Switzerland (2003).
Vlahos, C. et al., "A Specific Inhibitor of Phosphatidylinositol 3-Kinase, 2-(4-Morpholinyl)-8-phenyl-4H-1-benzopyran-4-one (LY294002)", The J. of Biological Chemistry, vol. 269(7), pp. 5241-5248 (1994).
Wermuth, C.G. (Editor), *The Practice Medicinal Chemistry*, $3^{rd}$ Edition, Academic Press, San Diego, CA (2008).
Widder, K. et al., Editor, "*Methods in Enzymology*", vol. 112, pp. 309-396, Academic Press, (1985).
Wuts, P.G.M. and Greene, T. W. *Protecting Groups in Organic Synthesis*, $4^{th}$ Edition, Wiley (2007).

\* cited by examiner

IDO INHIBITORS

CROSS-REFERENCE TO RELATED APPLICATIONS

This application claims priority to U.S. Provisional Application Ser. No. 62/184,984, filed Jun. 26, 2015, the entire content of which is incorporated herein by reference.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. Indoleamine-2,3-dioxygenase is a heme-containing intracellular enzyme that catalyzes the first and rate-determining step in the degradation of the essential amino acid L-tryptophan to N-formyl-kynurenine. N-formyl-kynurenine is then metabolized by multiple steps to eventually produce nicotinamide adenine dinucleotide (NAD+). Tryptophan catabolites produced from N-formyl-kynurenine, such as kynurenine, are known to be preferentially cytotoxic to T-cells. Thus an overexpression of IDO can lead to increased tolerance in the tumor microenvironment. IDO overexpression has been shown to be an independent prognostic factor for decreased survival in patients with melanoma, pancreatic, colorectal and endometrial cancers among others. Moreover, IDO has been found to be implicated in neurologic and psychiatric disorders including mood disorders as well as other chronic diseases characterized by IDO activation and tryptophan depletion, such as viral infections, for example AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting the enzymatic function of IDO would be a most welcomed addition to the physician's armamentarium.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

According to one embodiment of the present invention, compounds of Formula I are provided,

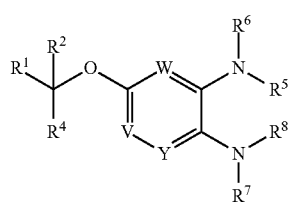

(I)

wherein:
W is $CR^x$ or —N—,
V is $CR^x$ or —N—,
Y is $CR^x$ or —N—;
Z is —O— or —NH—;
$R^x$ is hydrogen, halogen, CN, $CF_3$, $C_1$-$C_4$ alkyl or $C_1$-$C_4$ alkoxy;
$R^1$ is hydrogen, optionally substituted $C_1$-$C_6$ alkyl or $C_1$-$C_4$ alkoxy;
$R^2$ is hydrogen or methyl, or
$R^1$ and $R^2$ are taken together with the carbon to which they are attached to form a 3-6 membered cycloakyl ring;
$R^4$ is —$COZR^3$ or heterocyclyl; wherein
when Z is —O—, $R^3$ is H or $C_1$-$C_4$ alkyl; or
when Z is —NH—, $R^3$ is —$SO_2R^{11}$, $SO_2NR^{12}R^{13}$, halo ($C_1$-$C_4$ alkyl) or optionally substituted heteroaryl;
$R^5$ is hydrogen or $C_1$-$C_4$ alkyl;
$R^6$ is optionally substituted aryl, optionally substituted heteroaryl, —$COR^{10}$ or $CONR^5R^9$;
$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;
$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;
$R^y$ is hydrogen, halogen, CN, $CF_3$, $C_1$-$C_6$ alkyl, $C_1$-$C_6$ alkoxy or aryloxy;
$R^{10}$ is optionally substituted $C_1$-$C_6$ alkyl, optionally substituted $C_3$-$C_8$ cycloalkyl, optionally substituted aryl, optionally substituted benzyl, optionally substituted heteroaryl or optionally substituted heterocyclyl; wherein the optional substituents are 1-4 $R^z$;
$R^z$ is hydrogen, halogen, CN, $CF_3$, $C_1$-$C_6$ alkyl, $C_1$-$C_6$ alkoxy or aryloxy;
$R^{11}$ is optionally substituted $C_1$-$C_6$ alkyl, optionally substituted $C_3$-$C_8$ cycloalkyl, trifluoromethyl, phenyl or optionally substituted heterocyclyl;
$R^{12}$ is hydrogen or optionally substituted $C_1$-$C_6$ alkyl;
$R^{13}$ is hydrogen or optionally substituted $C_1$-$C_6$ alkyl;
including stereoisomers, a tautomers or a pharmaceutically acceptable salts thereof.

According to some embodiments of the present invention, $R^1$ and $R^2$ are independently H, $C_1$ to $C_4$ alkyl, $C_1$ to $C_4$ alkoxy, or join together to form cyclopropyl or cyclobutyl.

According to some embodiments of the present invention, Z is —NH— and $R^3$ is —$SO_2R^{11}$, halo ($C_1$-$C_4$ alkyl), thiazolyl or oxazolyl.

According to some embodiments of the present invention, $R^{11}$ is $C_1$ to $C_4$ alkyl, $C_3$ to $C_6$ cycloalkyl.

According to some embodiments of the present invention, Z is O and $R^3$ is H.

According to some embodiments of the present invention, $R^4$ is —$CO_2R^3$.

According to some embodiments of the present invention, $R^4$ is a 5 membered heterocycle containing from 1 to 4 heteroatoms selected from N, O, and S, such as tetrazolyl, isoxazolyl, triazolyl, or diazoylyl.

According to some embodiments of the present invention, $R^5$ is H and $R^6$ is —$COR^{10}$ or —$CONR^9R^{10}$; $R^9$ is H, and $R^{10}$ is phenyl, pyridyl, isoxazolyl, thiadiazolyl, indolinyl, or benzyl, wherein $R^{10}$ may optionally be substituted with from 1 to 3 substituents selected from the group consisting of halo, amino, phenoxy, benzoxy, isoxalyl, $C_1$ to $C_4$ alkoxy, $C_1$ to $C_4$ alkyl, halo-$C_1$ to $C_4$ alkyl, and CN.

According to some embodiments of the present invention, $R^7$ is $C_3$ to $C_7$ cycloalkyl optionally substituted with halo, —OH or $C_1$ to $C_4$ alkoxy; $C_1$ to $C_4$ alkyl optionally substituted with halo, —OH or phenyl, wherein said phenyl is optionally substituted with $C_1$ to $C_4$ haloalkyl, $C_1$ to $C_4$ alkoxy, halo or $C_1$ to $C_4$ alkyl; $C_1$ to $C_4$ alkenyl; $C_1$ to $C_4$ alkoxy; or benzyl optionally substituted with $C_1$ to $C_4$ alkyl, halo, $C_1$ to $C_4$ alkoxy, or haloalkyl.

According to some embodiments of the present invention, $R^7$ is a $C_3$ to $C_7$ heterocycloalkyl containing from 1 to 4 heteroatoms selected from O, N or S.

According to some embodiments of the present invention, $R^7$ is furanyl, oxetanyl, or piperidinyl optionally substituted with $C_1$ to $C_4$ alkenyl.

According to some embodiments of the present invention, $R^7$ is cyclohexyl optionally substituted with halo, —OH or $C_1$ to $C_4$ alkoxy or $C_1$ to $C_4$ alkenyl.

According to some embodiments of the present invention, $R^8$ is $C_1$ to $C_4$ alkyl or alkenyl wherein said alkyl is optionally substituted with halo, $C_1$ to $C_4$ alkoxy, $C_3$ to $C_6$ or cycloalkyl.

According to some embodiments of the present invention, W, V, and Y are —$CR^x$ wherein x is halo (preferably F) or CN.

According to some embodiments of the present invention, one of W, V, or Y is N.

According to some embodiments of the present invention, compounds having the following Formula I are presented:

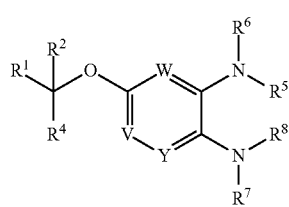

Formula I wherein
$R^1$ is H, $C_1$ to $C_4$ alkyl, or $C_3$ to $C_6$ cycloalkyl;
$R^2$ is H, $C_1$ to $C_4$ alkyl, or $C_1$ to $C_2$ alkoxy;
$R^3$ is H, $C_1$ to $C_4$ alkyl, halo-$C_1$ to $C_4$ alkyl;
$R^4$ is —$COZR^3$;
$R^5$ is H;
$R^6$ is —$COR^{10}$ or —$CONR^9R^{10}$;
$R^7$ is $C_1$ to $C_4$ alkyl; $C_1$ to $C_4$ alkenyl; cyclohexl; morpholinyl; oxetanyl; piperidinyl; furanyl; or benzyl; any of which may be optionally substituted with halo, —OH, alkyenyl, $C_1$ to $C_4$ alkyl, methoxy, ethoxy, haloalkyl;
$R^8$ is $C_1$ to $C_4$ alkyl, $C_1$ to $C_4$ alkoxy-$C_1$ to $C_4$ alkyl; —$C_1$ to $C_4$ alkyl-$C_3$ to $C_6$ cycloalkyl;
$R^9$ is H;
$R^{10}$ is phenyl, optionally substituted with halo, amino, $C_1$ to $C_4$ alkyl, haloalkyl, alkoxy, haloalkoxy, CN, isoxazolyl, benzoxy, phenoxy;
Z is O and $R^3$ is H or $C_1$ to $C_4$ alkyl; or Z is —NH— and $R^3$ is —$SO_2R^{11}$; and
$R^{11}$ is $C_1$ to $C_4$ alkyl or $C_3$ to $C_6$ cycloalkyl.

According to some embodiments of the present invention, methods for treating cancer are presented, wherein said cancer is susceptible to IDO inhibition in a patient in need thereof comprising administering to said patient a therapeutically acceptable amount of a compound according to Formula I, as defined herein, including pharmaceutically acceptable salts.

According to some embodiments of the present invention, said cancer is selected from the group consisting of bladder, pancreatic, prostate, lung, leukemia, breast, colorectal, melanoma, head and neck, ovarian, lymphoma and cervical.

According to some embodiments of the present invention, compounds of the present invention are administered together with additional anti-cancer agents, such as chemotherapeutic agents and immune-checkpoint inhibitors, such as ipilumumab and nivolumab.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

Compounds of the Invention

In a first aspect, the present invention provides compounds of Formula (I)

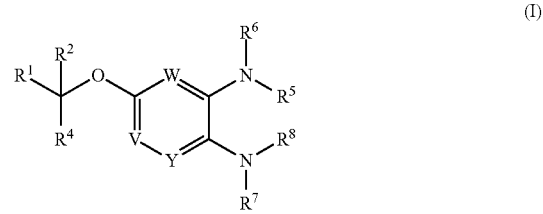

(I)

wherein:
W is $CR^x$ or —N—,
V is $CR^x$ or —N—,
Y is $CR^x$ or —N—;
Z is —O— or —NH—;
$R^x$ is hydrogen, halogen, CN, $CF_3$, $C_1$-$C_4$ alkyl or $C_1$-$C_4$ alkoxy;
$R^1$ is hydrogen, optionally substituted $C_1$-$C_6$ alkyl or $C_1$-$C_4$ alkoxy;
$R^2$ is hydrogen or methyl, or
$R^1$ and $R^2$ are taken together with the carbon to which they are attached to form a 3-6 membered cycloakyl ring;
$R^4$ is —$COZR^3$ or heterocyclyl; wherein
when Z is —O—, $R^3$ is H or $C_1$-$C_4$ alkyl; or
when Z is —NH—, $R^3$ is —$SO_2R^{11}$, $SO_2NR^{12}R^{13}$, halo ($C_1$-$C_4$ alkyl) or optionally substituted heteroaryl;
$R^5$ is hydrogen or $C_1$-$C_4$ alkyl;
$R^6$ is optionally substituted aryl, optionally substituted heteroaryl, —$COR^{10}$ or $CONR^5R^9$;
$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;
$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;
$R^y$ is hydrogen, halogen, CN, $CF_3$, $C_1$-$C_6$ alkyl, $C_1$-$C_6$ alkoxy or aryloxy;
$R^{10}$ is optionally substituted $C_1$-$C_6$ alkyl, optionally substituted $C_3$-$C_8$ cycloalkyl, optionally substituted aryl, optionally substituted benzyl, optionally substituted heteroaryl or optionally substituted heterocyclyl; wherein the optional substituents are 1-4 $R^z$;
$R^z$ is hydrogen, halogen, CN, $CF_3$, $C_1$-$C_6$ alkyl, $C_1$-$C_6$ alkoxy or aryloxy;
$R^{11}$ is optionally substituted $C_1$-$C_6$ alkyl, optionally substituted $C_3$-$C_8$ cycloalkyl, trifluoromethyl, phenyl or optionally substituted heterocyclyl;
$R^{12}$ is hydrogen or optionally substituted $C_1$-$C_6$ alkyl;
$R^{13}$ is hydrogen or optionally substituted $C_1$-$C_6$ alkyl;
and/or a stereoisomer, a tautomer or a pharmaceutically acceptable salt thereof.

In a second aspect, the invention provides a compound of Formula (II) within the scope of the first aspect of the structure

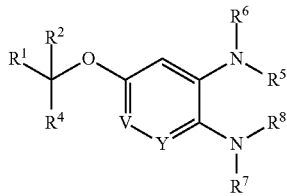

(II)

wherein:
V is $CR^x$ or —N—,
Y is $CR^x$ or —N—;
Z is —O— or —NH—;

$R^x$ is hydrogen, halogen, CN, $CF_3$, $C_1$-$C_4$ alkyl or $C_1$-$C_4$ alkoxy;
$R^1$ is hydrogen, optionally substituted $C_1$-$C_6$ alkyl or $C_1$-$C_4$ alkoxy;
$R^2$ is hydrogen or methyl, or
$R^1$ and $R^2$ are taken together with the carbon to which they are attached to form a 3-6 membered cycloakyl ring;
$R^4$ is —$COZR^3$ or heterocyclyl; wherein
when Z is —O—, $R^3$ is H or $C_1$-$C_4$ alkyl; or
when Z is —NH—, $R^3$ is —$SO_2R^{11}$, $SO_2NR^{12}R^{13}$, halo ($C_1$-$C_4$ alkyl) or optionally substituted heteroaryl;
$R^5$ is hydrogen or $C_1$-$C_4$ alkyl;
$R^6$ is optionally substituted aryl, optionally substituted heteroaryl, —$COR^1$ or $CONR^5R^9$;
$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;
$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;
$R^y$ is hydrogen, halogen, CN, $CF_3$, $C_1$-$C_6$ alkyl, $C_1$-$C_6$ alkoxy or aryloxy;
$R^{10}$ is optionally substituted $C_1$-$C_6$ alkyl, optionally substituted $C_3$-$C_8$ cycloalkyl, optionally substituted aryl, optionally substituted benzyl, optionally substituted heteroaryl or optionally substituted heterocyclyl; wherein the optional substituents are 1-4 $R^z$;
$R^z$ is hydrogen, halogen, CN, $CF_3$, $C_1$-$C_6$ alkyl, $C_1$-$C_6$ alkoxy or aryloxy;
$R^{11}$ is optionally substituted $C_1$-$C_6$ alkyl, optionally substituted $C_3$-$C_8$ cycloalkyl, trifluoromethyl, phenyl or optionally substituted heterocyclyl;
$R^{12}$ is hydrogen or optionally substituted $C_1$-$C_6$ alkyl;
$R^{13}$ is hydrogen or optionally substituted $C_1$-$C_6$ alkyl;
and/or a stereoisomer, a tautomer or a pharmaceutically acceptable salt thereof.

In a third aspect, the invention provides a compound of Formula (I) or (II) within the scope of the first or second aspect.
V is $CR^x$ or —N—,
Y is $CR^x$ or —N—;
Z is —O— or —NH—;
$R^x$ is hydrogen, halogen, CN, $CF_3$, $C_1$-$C_4$ alkyl or $C_1$-$C_4$ alkoxy;
$R^1$ is hydrogen, optionally substituted $C_1$-$C_6$ alkyl or $C_1$-$C_4$ alkoxy;
$R^2$ is hydrogen or optionally substituted $C_1$-$C_6$ alkyl;
$R^4$ is —$COZR^3$;
when Z is —O—, $R^3$ is H or $C_1$-$C_4$ alkyl; or
when Z is —NH—, $R^3$ is —$SO_2R^{11}$, $SO_2NR^{12}R^{13}$, halo ($C_1$-$C_4$ alkyl) or optionally substituted heteroaryl;
$R^5$ is hydrogen or $C_1$-$C_4$ alkyl;
$R^6$ is optionally substituted aryl, optionally substituted heteroaryl, —$COR^{10}$ or $CONR^5R^9$;
$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;

$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;

$R^y$ is hydrogen, halogen, CN, $CF_3$, $C_1$-$C_6$ alkyl, $C_1$-$C_6$ alkoxy or aryloxy;

$R^{10}$ is optionally substituted $C_1$-$C_6$ alkyl, optionally substituted $C_3$-$C_8$ cycloalkyl, optionally substituted aryl, optionally substituted benzyl, optionally substituted heteroaryl or optionally substituted heterocyclyl; wherein the optional substituents are 1-4 $R^z$;

$R^z$ is hydrogen, halogen, CN, $CF_3$, $C_1$-$C_6$ alkyl, $C_1$-$C_6$ alkoxy or aryloxy;

$R^{11}$ is optionally substituted $C_1$-$C_6$ alkyl, optionally substituted $C_3$-$C_8$ cycloalkyl, trifluoromethyl, phenyl or optionally substituted heterocyclyl;

$R^{12}$ is hydrogen or optionally substituted $C_1$-$C_6$ alkyl;

$R^{13}$ is hydrogen or optionally substituted $C_1$-$C_6$ alkyl;

and/or a stereoisomer, a tautomer or a pharmaceutically acceptable salt thereof.

In a fourth aspect, the invention provides a compound of Formula (I) or (II) within the scope of one or more of the previous aspects wherein.

Z is —O—.

In a fifth aspect, the invention provides a compound of Formula (I) or (II) within the scope of one or more of the previous aspects wherein Z is —NH—.

In a sixth aspect, the invention provides a compound of Formula (III) within the scope of one or more of the previous aspects wherein

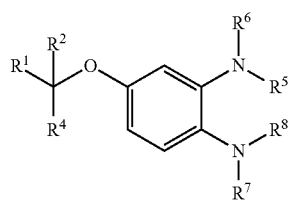

(III)

and/or a stereoisomer, a tautomer or a pharmaceutically acceptable salt thereof.

In another aspect, the invention provides a compound of Formula (III) within the scope of one or more of the previous aspects wherein Z is —O— or —NH—;

$R^x$ is hydrogen, halogen, CN, $CF_3$, $C_1$-$C_4$ alkyl or $C_1$-$C_4$ alkoxy;

$R^1$ is hydrogen, optionally substituted $C_1$-$C_6$ alkyl or $C_1$-$C_4$ alkoxy;

$R^2$ is hydrogen or methyl, or $R^1$ and $R^2$ are taken together with the carbon to which they are attached to form a 3-6 membered cycloakyl ring;

$R^4$ is —$COZR^3$ or heterocyclyl; wherein when Z is —O—, $R^3$ is H or $C_1$-$C_4$ alkyl; or when Z is —NH—, $R^3$ is —$SO_2R^{11}$, $SO_2NR^{12}R^{13}$, halo($C_1$-$C_4$ alkyl) or optionally substituted heteroaryl;

$R^5$ is hydrogen or $C_1$-$C_4$ alkyl;

$R^6$ is optionally substituted aryl, optionally substituted heteroaryl, —$COR^{10}$ or $CONR^5R^9$;

$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;

$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;

$R^y$ is hydrogen, halogen, CN, $CF_3$, $C_1$-$C_6$ alkyl, $C_1$-$C_6$ alkoxy or aryloxy;

$R^{10}$ is optionally substituted $C_1$-$C_6$ alkyl, optionally substituted $C_3$-$C_8$ cycloalkyl, optionally substituted aryl, optionally substituted benzyl, optionally substituted heteroaryl or optionally substituted heterocyclyl; wherein the optional substituents are 1-4 $R^z$;

$R^z$ is hydrogen, halogen, CN, $CF_3$, $C_1$-$C_6$ alkyl, $C_1$-$C_6$ alkoxy or aryloxy;

$R^{11}$ is optionally substituted $C_1$-$C_6$ alkyl, optionally substituted $C_3$-$C_8$ cycloalkyl, trifluoromethyl, phenyl or optionally substituted heterocyclyl;

$R^{12}$ is hydrogen or optionally substituted $C_1$-$C_6$ alkyl;

$R^{13}$ is hydrogen or optionally substituted $C_1$-$C_6$ alkyl;

and/or a stereoisomer, a tautomer or a pharmaceutically acceptable salt thereof.

In another aspect, the invention provides a compound of Formula (III) within the scope of one or more of the previous aspects wherein Z is —O— or —NH—;

$R^x$ is hydrogen, halogen, CN, $CF_3$, $C_1$-$C_4$ alkyl or $C_1$-$C_4$ alkoxy;

$R^1$ is hydrogen, $C_1$-$C_3$ alkyl or methoxymethyl;

$R^2$ is hydrogen or methyl;

$R^1$ and $R^2$ are taken together with the carbon to which they are attached to form a cyclopropyl ring;

$R^4$ is —$COZR^3$;

when Z is —O—, $R^3$ is H or $C_1$-$C_4$ alkyl; or when Z is —NH—, $R^3$ is —$SO_2R^{11}$, $SO_2NR^{12}R^{13}$, trifluoromethyl or optionally substituted heteroaryl;

$R^5$ is hydrogen or $C_1$-$C_4$ alkyl;

$R^6$ is optionally substituted aryl, optionally substituted heteroaryl, —$COR^1$ or $CONR^5R^9$;

$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl;

$R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;

$R^y$ is hydrogen, halogen, CN, $CF_3$, $C_1$-$C_6$ alkyl, $C_1$-$C_6$ alkoxy or aryloxy;

$R^{10}$ is optionally substituted $C_1$-$C_6$ alkyl, optionally substituted $C_3$-$C_8$ cycloalkyl, optionally substituted benzyl, optionally substituted benzyl, optionally substituted heteroaryl or optionally substituted heterocyclyl; wherein the optional substituents are 1-4 $R^z$;

$R^z$ is hydrogen, halogen, CN, $CF_3$, $C_1$-$C_6$ alkyl, $C_1$-$C_6$ alkoxy or aryloxy;

$R^{11}$ is optionally substituted $C_1$-$C_6$ alkyl, optionally substituted $C_3$-$C_8$ cycloalkyl, trifluoromethyl, phenyl or optionally substituted heterocyclyl;

$R^{12}$ is hydrogen or optionally substituted $C_1$-$C_6$ alkyl;

$R^{13}$ is hydrogen or optionally substituted $C_1$-$C_6$ alkyl;

and/or a stereoisomer, a tautomer or a pharmaceutically acceptable salt thereof.

In another aspect, the invention provides a compound selected from any of the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO $IC_{50}$ values ≥100 nM.

In another embodiment, the compounds of the invention have human IDO $IC_{50}$ values ≤100 nM.

In another embodiment, the compounds of the invention have human IDO $IC_{50}$ values ≤5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

IDO hads been show to play an important role in the process of immune evasion. The overexpression of IDO in tumor cells, as well as the dendritic cells that localize to the tumor draining lymph nodes, has been shown to be an independent prognostic variable for reduced overall survival in patients within a wide variety of tumors, especially ovarian, colorectal, pancreatic, melanoma, and hematological malignancies.

Many types of cancers may be treated with the compounds of this invention including brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-i, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethi ophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as farnesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-01 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J. Biol. Chem., 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., Circulation, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I or II, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22$^{nd}$ Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon containing one or more triple bonds and typically from 2 to 20 carbon atoms in length. For example, "C$_2$-C$_8$ alkynyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

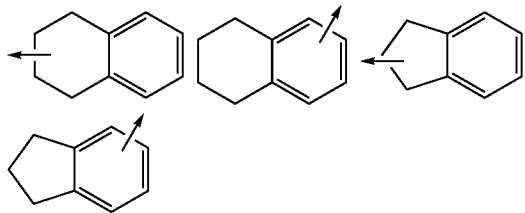

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N—O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4$^{th}$ Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane types such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., Design of Prodrugs, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). Prodrugs and Targeted Delivery (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism*. Chemistry, Biochemistry and Enzymology, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared from starting materials which are known in the chemical literature or are commercially available by methods such as those illustrated in the following Schemes utilizing chemical transformations known to those skilled in the art of organic chemistry. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "$T_r$" for retention time, "atm" for atmosphere, "psi" for pounds per square inch, "conc." For concentrate or concentrated, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Hex | hexanes |
| MeOH | methanol |
| EtOH | ethanol |
| i-PrOH or IPA | isopropanol |
| AcOH or HOAc | acetic acid |
| BOP | (Benzotriazol-1-yloxy)tris(dimethylamino)phosphonium hexafluorophosphate |
| $CDCl_3$ | deutero-chloroform |
| $CHCl_3$ | chloroform |
| cDNA | complimentary DNA |
| DMF | dimethyl formamide |
| DMSO | dimethyl sulfoxide |
| DIAD | Diisopropyl azodicarboxylate |
| EDTA | ethylenediaminetetraacetic acid |
| EtOAc | ethyl acetate |
| $Et_2O$ | diethyl ether |
| $AlCl_3$ | aluminum chloride |
| Boc | tert-butyloxycarbonyl |
| $CH_2Cl_2$ | dichloromethane |
| $CH_3CN$ or ACN | acetonitrile |
| $Cs_2CO_3$ | cesium carbonate |
| HCl | hydrochloric acid |
| $H_2SO_4$ | sulfuric acid |
| Hunig's base | diisopropylethylamine |
| $K_2CO_3$ | potassium carbonate |
| mCPBA or m-CPBA | meta-chloroperbenzoic acid |
| Pd/C | palladium on carbon |
| PS | polystyrene |
| $SiO_2$ | silica oxide |
| $SnCl_2$ | tin(II) chloride |
| TEA | triethylamine |
| TFA | trifluoroacetic acid |
| TFAA | trifluoroacetic anhydride |
| THF | tetrahydrofuran |
| $TMSCHN_2$ | trimethylsilyldiazomethane |
| KOAc | potassium acetate |
| LHMDS | Lithium hexamethyldisilazide |
| $MgSO_4$ | magnesium sulfate |
| NMP | N-Methylpyrrolidone |
| MsOH or MSA | methylsulfonic acid |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |

| | |
|---|---|
| NH₃ | ammonia |
| NH₄Cl | ammonium chloride |
| NH₄OH | ammonium hydroxide |
| LG | leaving group |
| RT | Room temperature |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

Referring to Scheme 1 set out below, treatment of compounds (i) where X is a halogen, such as Br or I, and Q is a halogen with amines $HNR^7R^8$ and a suitable base either neat or in a solvent such as THF, DMF, NMP, dioxane, EtOH or the like affords intermediates (ii). Generally heating is required. Suitable bases include, but are not limited to aliphatic tertiary amines, sodium or potassium carbonate, or an excess of the reacting amine $HNR^7R^8$. For ease of addition, sometimes a primary amine $R^7NH_2$ is used, and the $R^8$ group is appended by alkylation to afford intermediates (ii). This is generally accomplished by using an alkyl halide $R^8X$ and a base such as sodium hydride or potassium t-butoxide in a solvent such as DMF or THF. Alternatively, Q and/or X could be non-halogen activating groups such as triflates. Transformation of the group X in compounds (ii) to afford boronate esters (iii) is accomplished (Ishiyama, T. et al., *J. Org. Chem.*, 60:7508-7510 (1995)) by heating the aryl bromide and a boronate dimer such as bis(neopentylglycolato)diboron or bis(pinacolato)diboron with a weak base such as potassium acetate and a palladium catalyst (dppfPdCl₂ is widely used) in a solvent such as DMSO or dioxane to about 80° C. Boronates (iii) can be converted to phenols (iv) by the action of various oxidants including, but not limited to, sodium perborate, t-butyl hydroperoxide, hydrogen peroxide, and amine N-oxides, typically in mixed aqueous-organic solvent systems. In our hands, the reactions with sodium perborate at ambient temperature in THF-water were rapid and clean. Phenols (iv) can be alkylated under basic conditions with bromoacetates or α-bromo esters derivatives of higher carboxylic acids ($R^1$ is not H) to afford esters (v). Typically, a base such as potassium or cesium carbonate or sodium hydride is used in a solvent such as THF, DMF or NMP. Alternatively, the phenol can be alkylated by combining with an α-hydroxy ester (glycolate, lactate, etc.) and triphenylphosphine in a solvent such as THF and treating with a dialkyl azodicarboxylate such as DEAD or DiAD (Mitsunobu reaction). The use of dihalo esters enables preparation of products in which $R^1$ and $R^2$ are joined to form a ring. For example, alkylation of a phenol with a 2,4-dibromobutanoate ester followed by treatment with a base such as potassium t-butoxide affords a 1-(phenoxy)cyclopropyl carboxylic ester Nitro group reduction can be accomplished by catalytic hydrogenation or dissolving metal reductions both in their various forms. See House, H. O., Modern Synthetic Reactions, Second Edition, W. A. Benjamin, Inc., Menlo Park, Calif., publ. (1972). A preferred method for effecting this reduction involves stirring a solution of (v) in a wet alcoholic solvent with an acid such as ammonium chloride and finely divided zinc. Treatment of anilines (vi) with an isocyanate $R^9N=C=O$, affords urea compounds (vii). Typically, this reaction is performed in a solvent such as THF at a temperature between ambient and the boiling point of the solvent. Alternatively, anilines (vi) are treated with phenylcarbamate derivatives $R^9NHCO_2Ar$ and a base such as triethylamine in a solvent such as THF or DMF to afford ureas (vii). Alternatively, a phenylcarbamate or p-nitrophenylcarbamate derivative of (vi) can be generated in situ by treatment with PhOCOCl or p-NO₂PhOCOCl in a solvent such as THF. Addition of an aniline or amino-heterocycle $R^9NH_2$ and a base such as triethylamine afford ureas (vii). Heating at a temperature up to the boiling point of the solvent may be required. Carboxamide derivatives vii (E=CH₂) are prepared from anilines (vi) by any number of methods (peptide coupling reactions) known to those skilled in the art. A preferred method for this conversion involves treatment of a solution of aniline vi and a carboxylic acid $R^9CH_2CO_2H$ and a tertiary amine base such as triethylamine in a solvent such as THF or DMF with a coupling agent such as Bop. Esters (vii) may be saponified to compounds 1 of the invention, under various conditions familiar to those of ordinary skill in the art. Generally this is effected using an alkali metal hydroxide (MOH) in aqueous solution, preferably with one or more organic co-solvents such as methanol or THF. This transformation can be performed in the same reaction vessel that derivatives (vii) were prepared or as a separate step on isolated esters (vii).

Scheme 1

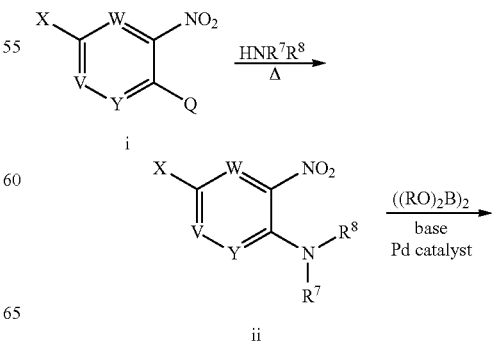

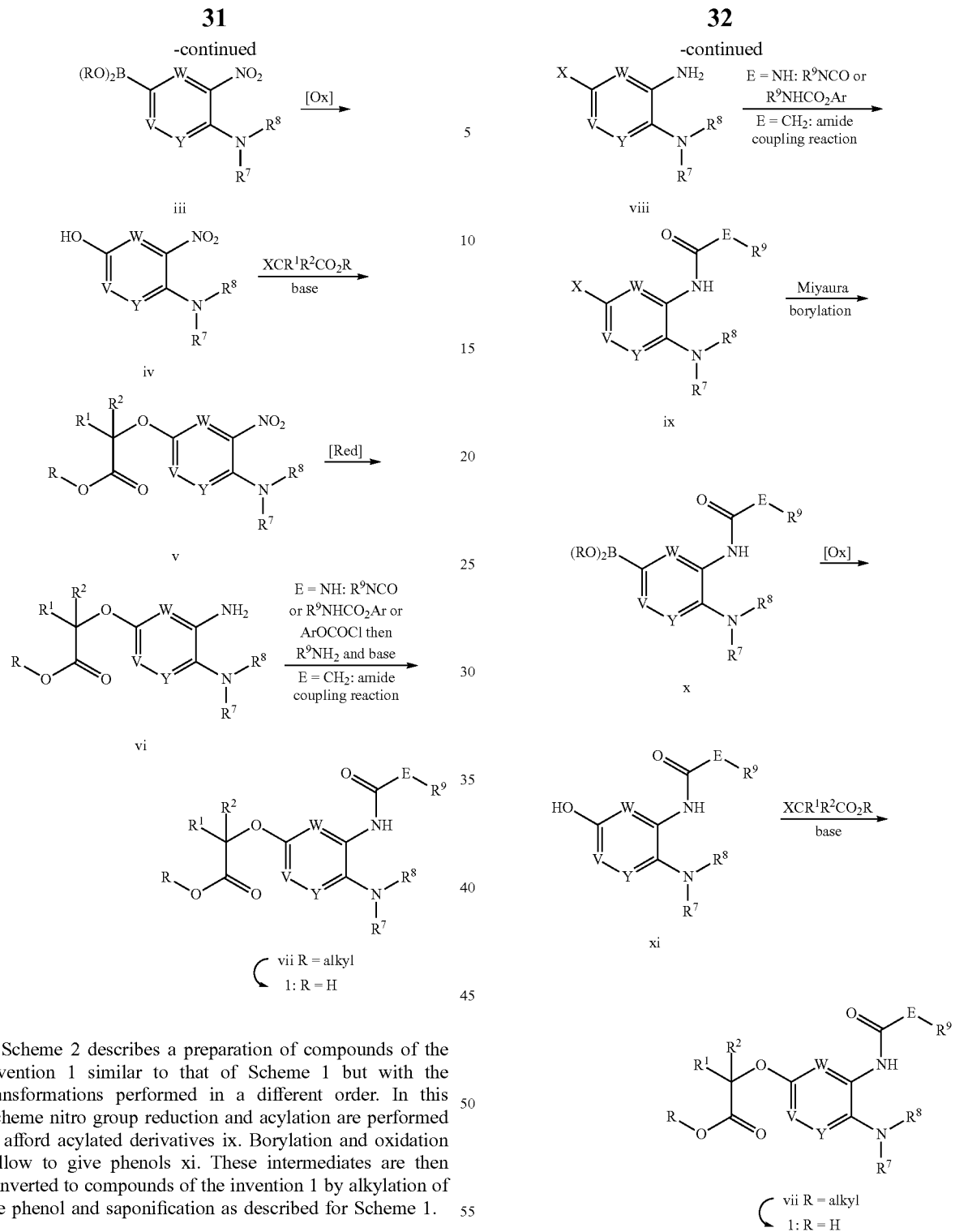

Scheme 2 describes a preparation of compounds of the invention 1 similar to that of Scheme 1 but with the transformations performed in a different order. In this Scheme nitro group reduction and acylation are performed to afford acylated derivatives ix. Borylation and oxidation follow to give phenols xi. These intermediates are then converted to compounds of the invention 1 by alkylation of the phenol and saponification as described for Scheme 1.

Scheme 2

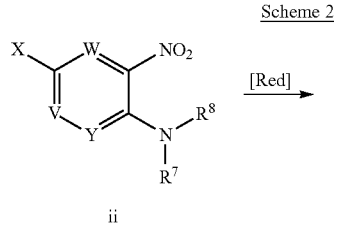

Scheme 3 illustrates a preparation of compounds of the invention starting from commercially-available phenols xiii. Alkylation of these materials under conditions described above affords phenoxyacetate esters xiv. These derivatives undergo $S_NAr$ reactions with amines $HNR^7R^8$ as above to afford intermediates v which may be converted into compounds of the invention as shown in Scheme 1. Alternatively, the order of the two steps shown in Scheme 3 may be reversed.

Scheme 3

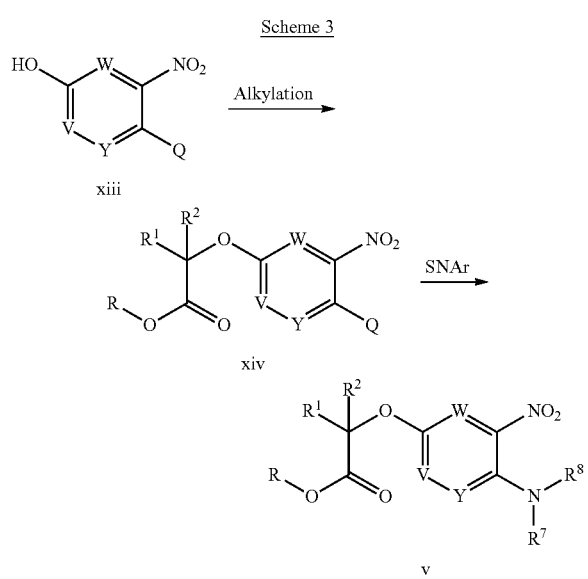

Carboxylic acids can be activated and treated with various amine-substituted nucleophiles $R^3NH_2$ in the presence of a base to afford carboxamide derivatives which are compounds of the invention 1 (Scheme 4). Reagents and conditions for effecting these amide bond couplings are well known to those or ordinary skill in the art and include but are not limited to the use of Bop (vide supra) and related (PyBop, HATU, TBTU, etc.) reagents. Activation by warming with CDI in a solvent such as THF gives acyl imidazolides which are reactive towards sulfonamides, sulfamides, aminoheterocycles, and related nucleophiles in the presence of bases such as DBU.

Scheme 4

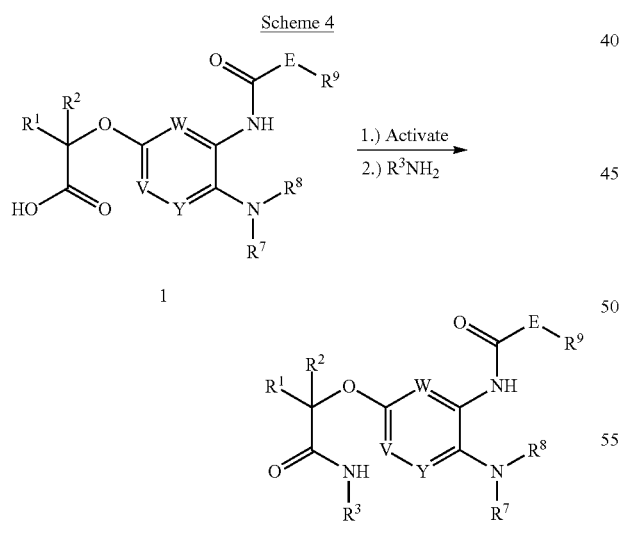

In addition to the carboxylic acid, acylsulfonamide, acylsulfamide, and acylaminoheterocycle derivatives shown above, the present invention describes phenoxymethyl tetrazoles shown below (Scheme 5). Alkylation of phenol or hydroxyheteroaryl xv with a chloro- or bromoacetonitrile affords nitrile derivatives xvi. These reactions are typically performed in a solvent such as DMF, NMP or THF using potassium and cesium carbonate as a base. Conversion to tetrazoles xvii is accomplished by heating with an azide, usually tributyltin azide in a solvent such as THF. Intermediates xvii can be converted to compounds of the formula 1 by methods described in the other schemes.

Scheme 5

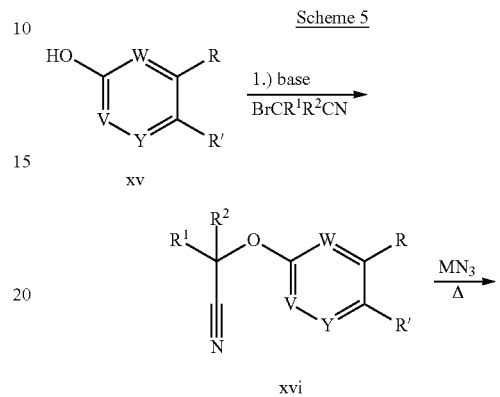

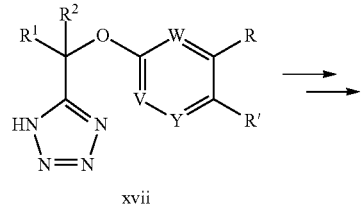

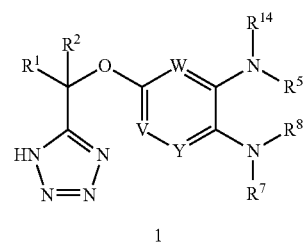

Numerous methods for N-methylation of anilines (including alkylation and reductive amination) have been described in the literature. Primary anilines xviii may be converted under these conditions to N-methyl derivatives xix. Further synthetic modifications using methods shown in the other schemes provide compounds of the formula 1.

Scheme 6

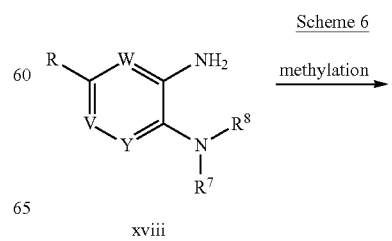

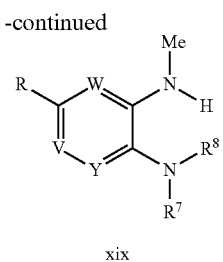

Derivatives in which $R^5$ is an aryl or heteroaryl group are compounds of the invention 1. Many methods for N-arylation of anilines and aminoheterocycles are familiar to those skilled in the art. These include but are not limited to thermal or base-mediated $S_NAr$ reactions and Buchwald-Hartwig amination (Muci, A. R. et al., "Practical Palladium Catalysts for C—N and C—O Bond Formation", *Topics in Curr. Chem.*, 219:131-209 (2002), doi:10.1007/3-540-45313-x_5). Accordingly, N-arylation of amine xii affords xx. Further synthetic modifications using methods shown in the other schemes provide compounds of the formula 1.

Scheme 7

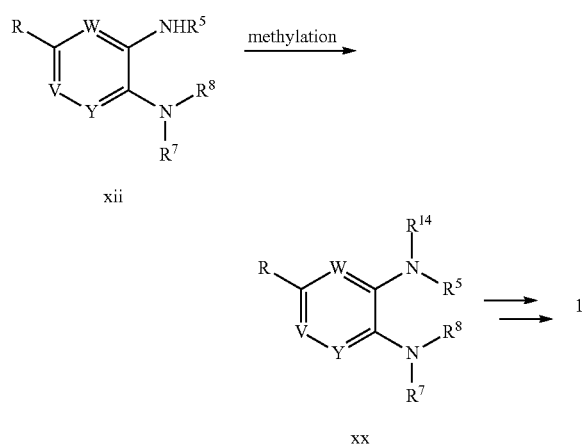

HPLC/Ms and Preparatory/Analytical HPLC Methods Employed in Characterization or Purification of Examples Analytical HPLC/MS was performed using the following methods:

Method A:
Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method B:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.00 mL/min; Detection: UV at 220 nm.

Method C:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Preparatory chiral SFC chromatography was performed using the following method:

Method D:
Aurora SFC MGII, Column: IC 25×3 cm ID, 5 μm, Flow rate: 85.0 mL/min, Mobile Phase: 75/25 $CO_2$/(50/50 MeOH/ACN w/0.2% FA and 0.2% DEA), Detector Wavelength: 220 nm Method E:
Berger SFC MGII, Column: IC 25×3 cm ID, 5 μm Flow rate: 85.0 mL/min, Mobile Phase: 85/15 $CO_2$/MeOH, Detector Wavelength: 220 nm Method F:
Berger SFC MGII, Column: IC 25×3 cm ID, 5 μm, Flow rate: 85.0 mL/min, Mobile Phase: 80/20 $CO_2$/MeOH w/0.1% DEA, Detector Wavelength: 220 nm Method G:
Berger SFC MGII, Column: OZ 25×3 cm ID, 5 μm, Flow rate: 85.0 mL/min, Mobile Phase: 80/20 $CO_2$/MeOH, Detector Wavelength: 220 nm Method H:
Berger SFC MGII, Column: IC 25×3 cm ID, 5 μm, Flow rate: 85.0 mL/min, Mobile Phase: 80/20 $CO_2$/MeOH w/0.1% DEA, Detector Wavelength: 220 nm Method I:
Aurora SFC MGII, Column: IC 25×3 cm ID, 5 m, Flow rate: 85.0 mL/min, Mobile Phase: 80/20 $CO_2$/(50/50 MeOH/ACN w/0.2% FA and 0.2% DEA), Detector Wavelength: 220 nm Method J:
Berger SFC MGII, Column: IC 25×3 cm ID, 5 m, Flow rate: 85.0 mL/min, Mobile Phase: 70/30 $CO_2$/(50/50 MeOH/ACN w/0.2% FA and 0.2% DEA), Detector Wavelength: 220 nm Analytical chiral SFC chromatography was performed on an Berger or Aurora Analytical SFC using the following method:

Method K:
Aurora analytical SFC, Column: Chiral IC 250×4.6 mm ID, 5 m, Flow rate: 2.0 mL/min, Mobile Phase: 75/25 $CO_2$/(50/50 MeOH/ACN w/0.2% FA and 0.2% DEA)

Method L:
Aurora analytical SFC, Column: Chiral IC 250×4.6 mm ID, 5 μm, Flow rate: 2.0 mL/min, Mobile Phase: 85/15 $CO_2$/MeOH Method M:
Aurora analytical SFC, Column: IC 250×4.6 mm ID, 5 μm, Flow rate: 2.0 mL/min, Mobile Phase: 80/20 $CO_2$/MeOH w/0.1% DEA Method N:
Berger analytical SFC, Column: OZ 250×4.6 mm ID, 5 μm, Flow rate: 2.0 mL/min, Mobile Phase: 80/20 $CO_2$/MeOH Method O:
Aurora analytical SFC, Column: IC 250×4.6 mm ID, 5 μm, Flow rate: 2.0 mL/min, Mobile Phase: 80/20 $CO_2$/MeOH Method P:
Aurora analytical SFC, Column: Chiral IC 250×4.6 mm ID, 5 m, Flow rate: 2.0 mL/min, Mobile Phase: 80/20 $CO_2$/(50/50 MeOH/ACN w/0.2% FA and 0.2% DEA)

Method Q:

Aurora analytical SFC, Column: Chiral IC 250×4.6 mm ID, 5 m, Flow rate: 2.0 mL/min, Mobile Phase: 70/30 $CO_2$/(50/50 MeOH/ACN w/0.2% FA and 0.2% DEA)

Method R:

Berger SFC MGII, Column: Whelkol Komosil 25×3 cm ID, 5 m, Flow rate: 85.0 mL/min, Mobile Phase: 87/13 $CO_2$/MeOH, Detector Wavelength: 256 nm Method S:

Aurora SFC, Column: Whelkol Komosil 250×4.6 mm ID, 5 m, Flow rate: 2.0 mL/min, Mobile Phase: 90/10 $CO_2$/MeOH NMR Employed in Characterization of Examples $^1$H NMR spectra (unless otherwise noted) were obtained with JEOL or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$). Abbreviations used in the description of NMR peaks: "a"=apparent, "br. s."=broad singlet Example 1

2-(3-(3-(4-chloro-2-fluorophenyl)ureido)-4-(cyclohexyl(isobutyl)amino)phenoxy)acetic acid

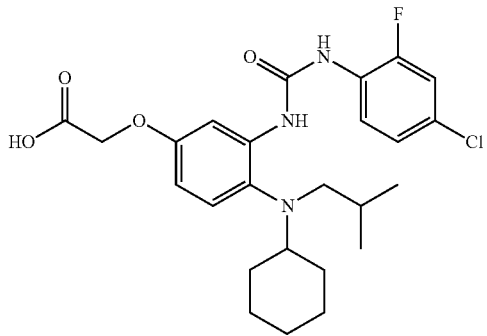 [SMILES: CC(C)CN(c1ccc(OCC(=O)O)cc1NC(=O)Nc1ccc(Cl)cc1F)C1CCCCC1]

1A. N-cyclohexylisobutyramide

Cyclohexanamine (1.262 mL, 11.01 mmol) and triethylamine (1.673 mL, 12.01 mmol) were dissolved in THF (10 mL) and cooled to 0° C. over an ice bath. Isobutyryl chloride (1.048 mL, 10.00 mmol) was added dropwise over 2 minutes (slurry forms immediately). The reaction was allowed to stir 30 minutes at 0° C. before warming to room temperature. After stirring another 30 minutes at room temperature, the reaction was then diluted with 1:1 hexanes-ether (200 mL) and washed with aq 1N HCl (50 mL) followed by sat'd aq. $NaHCO_3$ (50 mL). The organics were combined, dried with $MgSO_4$, filtered, and concentrated in vacuo to give Intermediate 1A (white solid, 1.55 g, 8.70 mmol, 87% yield). $^1$H NMR (400 MHz, chloroform-d) δ 5.24 (br. s., 1H), 3.70-3.81 (m, 1H), 2.28 (spt, J=6.9 Hz, 1H), 1.90 (dd, J=12.5, 3.6 Hz, 2H), 1.70 (dt, J=13.5, 3.6 Hz, 2H), 1.58-1.65 (m, 1H), 1.30-1.43 (m, 2H), 1.15-1.22 (m, 1H), 1.14 (d, J=6.8 Hz, 6H), 1.04-1.12 (m, 2H)

1B. N-isobutylcyclohexanamine

Intermediate 1A (18.71 g, 111 mmol) was dissolved in THF (221 ml) and cooled to 0° C. with an ice bath. Lithium Aluminum Hydride (5.45 g, 144 mmol) was added slowly to the solution at 0° C. After the addition was complete, the flask was equipped with a reflux condenser and heated to reflux (70° C.) for 24 hours. After 24 hours, the reaction was cooled to 0° C. and diluted with EtOAc (220 mL). The reaction was then quenched with the Feiser method (5.45 mL water then 10.9 mL 1N NaOH, then 16.5 mL water) (Caution: addition of water causes exotherm and bubbling) and after stirring for one hour the slurry was dried with sodium sulfate, filtered over packed celite, and concentrated in vacuo to afford Intermediate 1B (clear oil, 16.59 g, 101 mmol, 92% yield). $^1$H NMR (400 MHz, chloroform-d) δ 2.42 (d, J=6.7 Hz, 2H), 2.32-2.40 (m, 1H), 1.82-1.91 (m, 2H), 1.65-1.75 (m, 3H), 1.55-1.65 (m, 1H), 0.98-1.31 (m, 6H), 0.89 (d, J=6.6 Hz, 6H)

1C. Ethyl 2-(4-fluoro-3-nitrophenoxy)acetate

A solution of 4-fluoro-3-nitrophenol (6 g, 38.2 mmol) in DMF (38.2 mL, 1 molar) was treated with cesium carbonate (14.93 g, 45.8 mmol) followed by ethyl 2-bromoacetate (7.02 g, 42.0 mmol). This mixture was stirred 3 h at 60° C. Then it was cooled to room temperature. Water was added. The resulting precipitate was filtered, rinsed with water, and dried under vacuum to afford Intermediate 1C (tan solid, 9.00 g, 33.3 mmol, 87% yield). LC-MS Anal. Calc'd for $C_{10}H_{10}FNO_5$ 243.05, $T_r$=0.85 min (Method A) NOTE: product will not ionize on LC-MS (positive ion mode, acidic eluent). $^1$H NMR (400 MHz, DMSO-$d_6$) δ 7.68 (dd, J=5.9, 3.2 Hz, 1H), 7.55 (dd, J=10.8, 9.3 Hz, 1H), 7.49-7.33 (m, 1H), 4.94 (s, 2H), 4.19 (q, J=7.1 Hz, 2H), 1.30-1.16 (m, 3H)

1D. Ethyl 2-(4-(cyclohexyl(isobutyl)amino)-3-nitrophenoxy)acetate

Ester 1C (1.5 g, 6.17 mmol) was dissolved in Ethanol (6.17 ml). Amine 1B (2.87 g, 18.50 mmol) and Hunig's base (2.155 mL, 12.34 mmol) were added. The reaction was heated to 110° C. in a sealed tube. After 48 hours, the reaction was diluted with EtOAc (250 mL), washed with 1N HCl (100 mL), dried with sodium sulfate, filtered, and concentrated in vacuo. ISCO purification 80 g column, 60 mL/min, 0-40% EtOAc in Hexanes) gave Intermediate 1D (orange oil, 1.11 g, 2.93 mmol, 47.6% yield). LC-MS Anal. Calc'd for $C_{20}H_{30}N_2O_5$ 378.22, found [M+H] 379.5 $T_r$=1.20 min (Method A). $^1$H NMR (400 MHz, chloroform-d) δ: 7.20 (d, J=9.0 Hz, 1H), 7.16 (d, J=3.1 Hz, 1H), 7.04 (dd, J=9.0, 3.1 Hz, 1H), 4.60 (s, 2H), 4.28 (q, J=7.2 Hz, 2H), 2.79-2.84 (m, 1H), 2.78 (d, J=7.1 Hz, 2H), 1.78-1.86 (m, 2H), 1.74 (d, J=12.8 Hz, 2H), 1.56-1.62 (m, 2H), 1.47 (dt, J=13.4, 6.7 Hz, 1H), 1.34-1.39 (m, 2H), 1.31 (t, J=7.2 Hz, 3H), 1.18 (dt, J=13.0, 3.1 Hz, 1H), 1.05 (tt, J=12.7, 3.3 Hz, 1H), 0.82 (d, J=6.6 Hz, 6H)

1E. Ethyl 2-(3-amino-4-(cyclohexyl(isobutyl)amino)phenoxy)acetate

To a stirred solution of 1D (0.931 g, 2.460 mmol) in Ethanol (24.60 ml) was added 2.46 mL of water. The solution was then treated with zinc (0.965 g, 14.76 mmol) and ammonium chloride (0.790 g, 14.76 mmol). This mixture was stirred at room temperature. After 1 hour, the reaction was filtered, diluted with EtOAc, washed with sodium bicarbonate, dried with sodium sulfate, filtered, and concentrated to give Intermediate 1E (light tan oil, 0.836 g, 98%). LC-MS Anal. Calc'd for $C_{20}H_{32}N_2O_3$ 348.24, found [M+H] 349.3 $T_r$=0.80 min (Method A). $^1$H NMR (400 MHz, chloroform-d) δ: 6.93 (d, J=8.7 Hz, 1H), 6.32 (d, J=2.9 Hz, 1H), 6.22 (dd, J=8.7, 2.9 Hz, 1H), 4.53 (s, 2H), 4.22-4.30 (m, 2H), 2.54 (tt, J=11.4, 3.3 Hz, 1H), 1.82 (br. s., 2H), 1.68-1.77 (m, 2H), 1.57 (d, J=11.9 Hz, 1H), 1.36-1.48 (m, 3H), 1.26-1.31 (t, 3H), 1.10-1.26 (m, 5H), 1.00-1.09 (m, 2H), 0.81 (d, J=4.9 Hz, 6H)

Example 1

A suspension of 1E in THF (8.00 ml) was treated with 4-chloro-2-fluoro-1-isocyanatobenzene (0.426 ml, 3.36 mmol). After 1 hour, to this solution was added Water (8.00 mL) and MeOH (4.00 mL) to give a single phase followed by the addition of lithium hydroxide (0.253 g, 10.58 mmol). The reaction was stirred at 23° C. After stirring 1 hour, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was purified with flash chromatography to give Example 1 (white solid, 365 mg, 69.0% yield). LC-MS Anal. Calc'd for $C_{25}H_{31}ClFN_3O_4$ 491.20, found [M+H] 492.6 $T_r$=0.95 min (Method A). $^1$H NMR (400 MHz, chloroform-d) δ: 10.06 (br. s., 1H), 8.69 (br. s., 1H), 7.70 (t, J=8.4 Hz, 1H), 7.60 (br. s., 1H), 7.08-7.16 (m, 2H), 7.03 (d, J=9.0 Hz, 1H), 6.71 (dd, J=8.9, 2.9 Hz, 1H), 4.68 (s, 2H), 2.92 (br. s., 2H), 2.80 (br. s., 1H), 1.78 (d, J=12.4 Hz, 3H), 1.61 (d, J=12.7 Hz, 2H), 1.12-1.33 (m, 5H), 1.01-1.10 (m, J=12.5 Hz, 1H), 0.85 (d, J=6.4 Hz, 6H)

Example 2

2-(4-(cyclohexyl(isobutyl)amino)-3-(3-(pyrimidin-5-yl)ureido)phenoxy)acetic acid

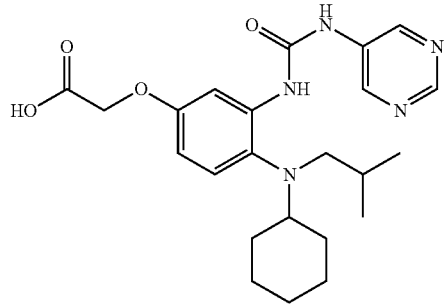 [SMILES: CC(C)CN(c1ccc(OCC(=O)O)cc1NC(=O)Nc1cncnc1)C1CCCCC1]

To a solution of 1E (0.025 g, 0.072 mmol) in THF (1.104 ml) was added 4-nitrophenyl carbonochloridate (0.015 g, 0.075 mmol). The reaction was stirred at rt for 30 min. To this reaction were added pyrimidin-5-amine (0.020 g, 0.215 mmol) and triethylamine (0.030 ml, 0.215 mmol). The reaction was heated at 50° C. overnight, then allowed to cool to room temperature. To this solution was added Water (1.104 mL) and MeOH (0.552 mL) followed by the addition of LiOH (0.017 g, 0.724 mmol). The reaction was stirred at room temperature. After stirring 1 h at room temperature, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude reaction mixture was dissolved in DMF and purified via preparative HPLC/MS to give Example 2 (12 mg, 0.027 mmol, 38%). LC-MS Anal. Calc'd for $C_{23}H_{31}N_5O_4$ 441.24, found [M+H] 442.5 $T_r$=0.76 min (Method C). $^1$H NMR (500 MHz, DMSO-$d_6$) δ: 10.04 (s, 1H), 8.89 (s, 2H), 8.77 (s, 1H), 8.43 (s, 1H), 7.70 (d, J=2.8 Hz, 1H), 7.09 (d, J=8.8 Hz, 1H), 6.45 (dd, J=8.7, 2.7 Hz, 1H), 4.45 (s, 2H), 1.87-1.95 (m, 2H), 1.60-1.69 (m, 2H), 1.47 (d, J=12.4 Hz, 1H), 1.21-1.33 (m, 1H), 1.09 (m, 6H), 0.88-0.98 (m, 2H), 0.70-0.85 (m, 6H)

Examples 3-41

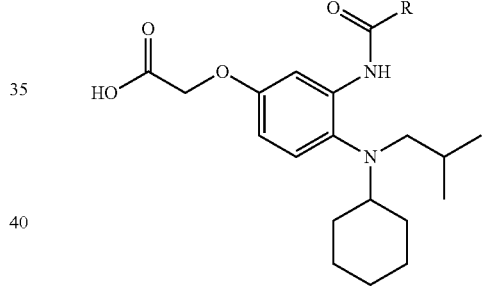

Examples 3-41 were prepared from intermediate 1E following the procedure for Example 2 using the corresponding anilines.

| Ex. No. | Name | R | Tr (min) Method B * *unless otherwise noted | [M + H]⁺ |
|---|---|---|---|---|
| 3 | 2-(4-(cyclohexyl(isobutyl)amino)-3-(3-(pyridin-3-yl)ureido)phenoxy)acetic acid | 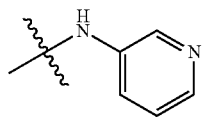 [SMILES: *Nc1cccnc1] | 1.614 | 441.25 |

-continued

| Ex. No. | Name | R | Tr (min) Method B * *unless otherwise noted | [M + H]+ |
|---|---|---|---|---|
| 4 | 2-(4-(cyclohexyl(isobutyl)amino)-3-(3-(3-methylisoxazol-5-yl)ureido)phenoxy)acetic acid | 3-methylisoxazol-5-yl-NH- | 1.669 | 445.24 |
| 5 | 2-(4-(cyclohexyl(isobutyl)amino)-3-(3-(pyridin-4-yl)ureido)phenoxy)acetic acid | pyridin-4-yl-NH- | 1.585 | 441.25 |
| 6 | 2-(3-(3-(1,3,4-thiadiazol-2-yl)ureido)-4-(cyclohexyl(isobutyl)amino)phenoxy)acetic acid | 1,3,4-thiadiazol-2-yl-NH- | 1.525 | 448.20 |
| 7 | 2-(4-(cyclohexyl(isobutyl)amino)-3-(3-(5-methylisoxazol-3-yl)ureido)phenoxy)acetic acid | 5-methylisoxazol-3-yl-NH- | 1.810 | 445.24 |
| 8 | 2-(4-(cyclohexyl(isobutyl)amino)-3-(3-(5-(trifluoromethyl)-1,3,4-thiadiazol-2-yl)ureido)phenoxy)acetic acid | 5-(trifluoromethyl)-1,3,4-thiadiazol-2-yl-NH- | 1.748 | 516.19 |
| 9 | 2-(4-(cyclohexyl(isobutyl)amino)-3-(3-(4-(dimethylamino)phenyl)ureido)phenoxy)acetic acid | 4-(dimethylamino)phenyl-NH- | 1.929 | 483.30 |
| 10 | 2-(4-(cyclohexyl(isobutyl)amino)-3-(3-(isoxazol-3-yl)ureido)phenoxy)acetic acid | isoxazol-3-yl-NH- | 1.727 | 431.23 |
| 11 | 2-(4-(cyclohexyl(isobutyl)amino)-3-(3-(5-methyl-1,3,4-thiadiazol-2-yl)ureido)phenoxy)acetic acid | 5-methyl-1,3,4-thiadiazol-2-yl-NH- | 1.548 | 462.22 |
| 12 | 2-(4-(cyclohexyl(isobutyl)amino)-3-(3-(thiazol-2-yl)ureido)phenoxy)acetic acid | thiazol-2-yl-NH- | 1.696 | 447.21 |
| 13 | 2-(4-(cyclohexyl(isobutyl)amino)-3-(3-(4-phenoxyphenyl)ureido)phenoxy)acetic acid | 4-phenoxyphenyl-NH- | 2.124 | 532.28 |

-continued

| Ex. No. | Name | R | Tr (min) Method B* *unless otherwise noted | [M + H]+ |
|---|---|---|---|---|
| 14 | 2-(4-(cyclohexyl(isobutyl)amino)-3-(3-(4-(oxazol-5-yl)phenyl)ureido)phenoxy)acetic acid | 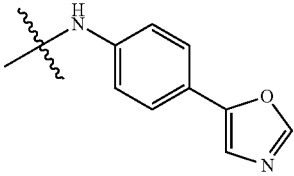 [SMILES: *Nc1ccc(-c2cnco2)cc1] | 1.756 | 506.26 |
| 15 | 2-(3-(3-(4-(benzyloxy)phenyl)ureido)-4-(cyclohexyl(isobutyl)amino)phenoxy)acetic acid | 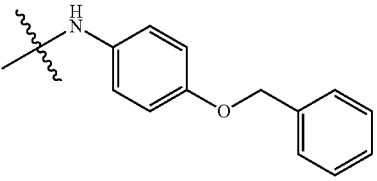 [SMILES: *Nc1ccc(OCc2ccccc2)cc1] | 2.122 | 546.30 |
| 16 | 2-(4-(cyclohexyl(isobutyl)amino)-3-(indoline-1-carboxamido)phenoxy)acetic acid | 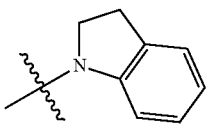 | 2.064 | 466.27 |
| 17 | 2-(4-(cyclohexyl(isobutyl)amino)-3-(3-(4-fluorophenyl)ureido)phenoxy)acetic acid | 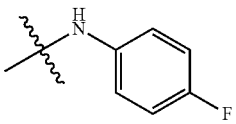 [SMILES: *Nc1ccc(F)cc1] | 2.036 | 458.24 |
| 18 | 2-(4-(cyclohexyl(isobutyl)amino)-3-(3-(2-fluorophenyl)ureido)phenoxy)acetic acid | 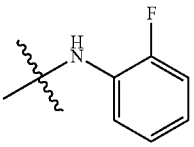 [SMILES: *Nc1ccccc1F] | 1.861 | 458.24 |
| 19 | 2-(4-(cyclohexyl(isobutyl)amino)-3-(3-(2,6-difluorophenyl)ureido)phenoxy)acetic acid | 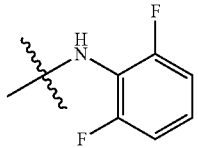 [SMILES: *Nc1c(F)cccc1F] | 1.882 | 476.24 |
| 20 | 2-(4-(cyclohexyl(isobutyl)amino)-3-(3-(2,5-difluorophenyl)ureido)phenoxy)acetic acid | 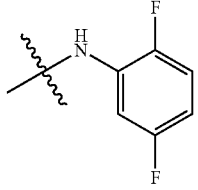 [SMILES: *Nc1cc(F)ccc1F] | 1.895 | 476.24 |
| 21 | 2-(4-(cyclohexyl(isobutyl)amino)-3-(3-(2,4-difluorophenyl)ureido)phenoxy)acetic acid | 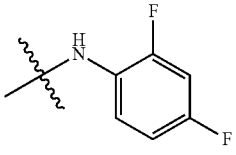 [SMILES: *Nc1ccc(F)cc1F] | 1.890 | 476.24 |

-continued

| Ex. No. | Name | R | Tr (min) Method B * *unless otherwise noted | [M + H]+ |
|---|---|---|---|---|
| 22 | 2-(3-(3-(5-chloro-2-fluorophenyl)ureido)-4-(cyclohexyl(isobutyl)amino)phenoxy)acetic acid | 2-F, 5-Cl phenyl-NH- | 1.990 | 492.21 |
| 23 | 2-(4-(cyclohexyl(isobutyl)amino)-3-(3-(2-fluoro-4-methylphenyl)ureido)phenoxy)acetic acid | 2-F, 4-Me phenyl-NH- | 2.135 | 472.26 |
| 24 | 2-(3-(3-(3-chloro-2,4-difluorophenyl)ureido)-4-(cyclohexyl(isobutyl)amino)phenoxy)acetic acid | 2-F, 3-Cl, 4-F phenyl-NH- | 1.810 | 510.20 |
| 25 | 2-(4-(cyclohexyl(isobutyl)amino)-3-(3-(2-fluoro-4-methoxyphenyl)ureido)phenoxy)acetic acid | 2-F, 4-OMe phenyl-NH- | 0.91 (Method A) | 488.3 |
| 26 | 2-(3-(3-(3-chloro-2-fluorophenyl)ureido)-4-(cyclohexyl(isobutyl)amino)phenoxy)acetic acid | 2-F, 3-Cl phenyl-NH- | 1.885 | 492.21 |
| 27 | 2-(4-(cylclohexyl(isobutyl)amino)-3-(3-(2-fluoro-3-(trifluoromethyl)phenyl)ureido)phenoxy)acetic acid | 2-F, 3-CF$_3$ phenyl-NH- | 1.956 | 526.23 |
| 28 | 2-(4-(cyclohexyl(isobutyl)amino)-3-(3-(3-fluoro-2-methylphenyl)ureido)phenoxy)acetic acid | 2-Me, 3-F phenyl-NH- | 1.836 | 472.26 |
| 29 | 2-(4-(cyclohexyl(isobutyl)amino)-3-(3-(2,5-difluoro-4-methoxyphenyl)ureido)phenoxy)acetic acid | 2-F, 5-F, 4-OMe phenyl-NH- | 1.725 | 506.25 |

-continued

| Ex. No. | Name | R | Tr (min) Method B * *unless otherwise noted | [M + H]+ |
|---|---|---|---|---|
| 30 | 2-(4-(cyclohexyl(isobutyl)amino)-3-(3-(5-fluoro-2-methylphenyl)ureido)phenoxy)acetic acid | 2-methyl-5-fluorophenyl-NH- | 0.93 (Method A) | 472.6 |
| 31 | 2-(4-(cyclohexyl(isobutyl)amino)-3-(3-(3,4-difluorophenyl)ureido)phenoxy)acetic acid | 3,4-difluorophenyl-NH- | 1.797 | 476.24 |
| 32 | 2-(4-(cyclohexyl(isobutyl)amino)-3-(3-(3,5-difluorophenyl)ureido)phenoxy)acetic acid | 3,5-difluorophenyl-NH- | 1.827 | 476.24 |
| 33 | 2-(4-(cyclohexyl(isobutyl)amino)-3-(3-(3-fluoro-4-methylphenyl)ureido)phenoxy)acetic acid | 3-fluoro-4-methylphenyl-NH- | 1.869 | 472.26 |
| 34 | 2-(4-(cyclohexyl(isobutyl)amino)-3-(3-(3-fluoro-4-methoxyphenyl)ureido)phenoxy)acetic acid | 3-fluoro-4-methoxyphenyl-NH- | 1.721 | 488.26 |
| 35 | 2-(4-(cyclohexyl(isobutyl)amino)-3-(3-(3-fluoro-4-(trifluoromethyl)phenyl)ureido)phenoxy)acetic acid | 3-fluoro-4-CF3-phenyl-NH- | 1.04 (Method A) | 526.5 |
| 36 | 2-(3-(3-(4-chloro-3-fluorophenyl)ureido)-4-(cyclohexyl(isobutyl)amino)phenoxy)acetic acid | 4-chloro-3-fluorophenyl-NH- | 1.01 (Method A) | 492.5 |
| 37 | 2-(3-(3-(3-chloro-5-fluorophenyl)ureido)-4-(cyclohexyl(isobutyl)amino)phenoxy)acetic acid | 3-chloro-5-fluorophenyl-NH- | 1.03 (Method A) | 492.5 |

| Ex. No. | Name | R | Tr (min) Method B * *unless otherwise noted | [M + H]⁺ |
|---|---|---|---|---|
| 38 | 2-(4-(cyclohexyl(isobutyl)amino)-3-(3-(4-fluoro-2-methylphenyl)ureido)phenoxy)acetic acid | | 0.94 (Method A) | 472.6 |
| 39 | 2-(3-(3-(4-cyanophenyl)ureido)-4-(cyclohexyl(isobutyl)amino)phenoxy)acetic acid | | 1.860 | 465.25 |
| 40 | 2-(4-(cyclohexyl(isobutyl)amino)-3-(3-methyl-3-(p-tolyl)ureido)phenoxy)acetic acid | | 1.10 (Method A) | 468.4 |
| 41 | 2-(4-(cyclohexyl(isobutyl)amino)-3-(3-(4-fluorophenyl)-3-methyl-ureido)phenoxy)acetic acid | | 1.06 (Method A) | 472.6 |

Example 42 ethyl 2-(3-(3-(4-chloro-2-fluorophenyl)ureido)-4-(cyclohexyl(isobutyl)amino)phenoxy)acetate

Example 43

2-(3-(3-(4-cyano-2-fluorophenyl)ureido)-4-(cyclohexyl(isobutyl)amino)phenoxy)acetic acid

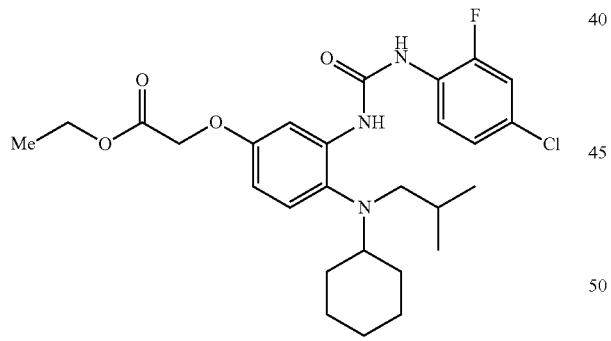

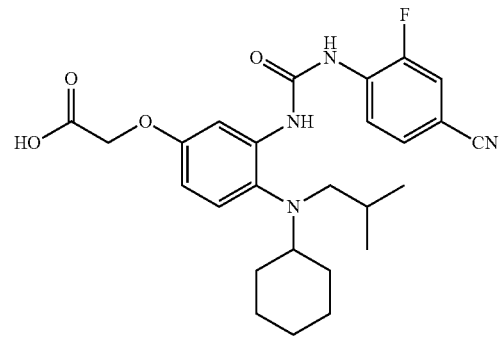 [SMILES: CC(C)CN(c1ccc(OCC(=O)O)cc1NC(=O)Nc1ccc(C#N)cc1F)C1CCCCC1]

A suspension of Intermediate 1E in THF (8.00 ml) was treated with 4-chloro-2-fluoro-1-isocyanatobenzene (0.426 ml, 3.36 mmol). After 1 hour, the reaction was concentrated in vacuo, taken up in DMF, filtered and purified directly via preparative HPLC to give Example 42 (off-white foam, 1.12 g, 90% yield). LC-MS Anal. Calc'd for $C_{27}H_{35}ClFN_3O_4$ 519.23, found [M+H] 520.2 $T_r$=2.640 min (Method C). $^1$H NMR (400 MHz, chloroform-d) δ: 8.37 (s, 1H), 7.98 (t, J=8.6 Hz, 1H), 7.84 (d, J=2.9 Hz, 1H), 7.11-7.18 (m, 2H), 7.07 (d, J=8.8 Hz, 1H), 6.59 (dd, J=8.7, 3.0 Hz, 1H), 4.62 (s, 2H), 4.28 (q, J=7.1 Hz, 2H), 2.72 (br. s., 2H), 2.51 (br. s., 1H), 1.73 (d, J=5.0 Hz, 5H), 1.34-1.44 (m, 1H), 1.28-1.33 (m, 3H), 1.15 (t, J=9.4 Hz, 4H), 0.93-1.05 (m, 1H), 0.81 (d, J=6.6 Hz, 6H)

Intermediate 1E (20 mg, 0.057 mmol) was taken up in THF and phenyl (4-cyano-2-fluorophenyl)carbamate (29.4 mg, 0.115 mmol) added along with triethylamine (24.00 µl, 0.172 mmol). The reaction was heated to 60° C. After 1 hour, the reaction was cooled to room temperature and stirred overnight. After overnight, Water (1 mL), MeOH (0.3 mL) and lithium hydroxide (13.74 mg, 0.574 mmol) were added. After 3 hours, the reaction concentrated in vacuo, acidified with 1N HCl, ext EtOAc, dried with sodium sulfate, filtered, and concentrated in vacuo. The crude residue was taken up in DMF, filtered, and purified via preparative HPLC to give Example 43 (17.3 mg, 0.034 mmol, 59.3%). LC-MS Anal. Calc'd for $C_{26}H_{31}FN_4O_4$ 482.23, found [M+H] 483.2 $T_r$=1.735 min (Method B). $^1$H NMR (500 MHz, DMSO-$d_6$)

δ: 10.04 (br. s., 1H), 8.73 (s, 1H), 8.36 (t, J=8.3 Hz, 1H), 7.86 (d, J=11.3 Hz, 1H), 7.61-7.67 (m, 2H), 7.12 (d, J=8.8 Hz, 1H), 6.53 (d, J=8.7 Hz, 1H), 4.52 (s, 2H), 1.87-1.97 (m, 2H), 1.67 (br. s., 2H), 1.51 (d, J=11.6 Hz, 1H), 1.32 (dt, J=13.0, 6.4 Hz, 1H), 1.03-1.18 (m, 6H), 0.91-1.03 (m, 2H), 0.72-0.87 (m, 6H)

Example 44

2-(3-(benzo[d]oxazol-2-ylamino)-4-(cyclohexyl (isobutyl)amino)phenoxy)acetic acid

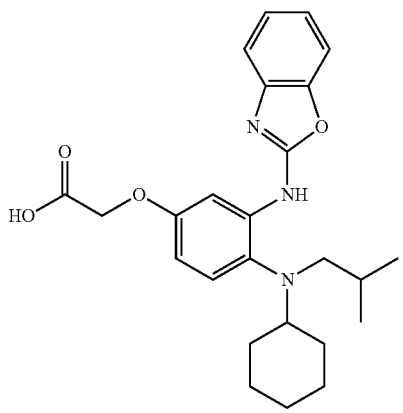 [SMILES: CC(C)CN(c1ccc(OCC(=O)O)cc1Nc1nc2ccccc2o1)C1CCCCC1]

Compound 1E (25 mg, 0.072 mmol), Hunig's Base (18.79 µl, 0.108 mmol) and 2-chlorobenzo[d]oxazole (12.29 µl, 0.108 mmol) were taken up in dry Xylenes (359 µl). Reaction was vacated and flushed with nitrogen gas several times. The reaction was sealed and heated to 150° C. After 8 hours, the crude reaction mixture was concentrated in vacuo and dissolved in THF (206 µl). This solution was treated with lithium hydroxide (6.17 mg, 0.258 mmol) in Water (206 µl). MeOH (~0.5 mL) was added to give a single phase, and the reaction was stirred at room temperature. After stirring 1 h at room temperature, the reaction was concentrated in vacuo to remove MeOH and THF, treated with 1N HCl until a precipitate forms and pH is acidic, and then extracted with EtOAc three times. Organic extracts were combined, dried with sodium sulfate, filtered and concentrated in vacuo. The crude residue was dissolved in 2 mL DMF, filtered, and purified via preparative HPLC to give Example 44 (1.4 mg, 0.003 mmol, 4.2%). LC-MS Anal. Calc'd for $C_{25}H_{31}N_3O_4$ 437.23, found [M+H] 438.3 $T_r$=1.99 min (Method C). $^1$H NMR (500 MHz, DMSO-$d_6$) δ: 8.91 (s, 1H), 7.98 (d, J=2.7 Hz, 1H), 7.53 (t, J=8.6 Hz, 2H), 7.22-7.29 (m, 2H), 7.17 (t, J=7.5 Hz, 1H), 6.58 (dd, J=8.7, 2.6 Hz, 1H), 4.67 (s, 2H), 1.85 (d, J=7.7 Hz, 2H), 1.68 (d, J=11.9 Hz, 2H), 1.50 (d, J=12.4 Hz, 1H), 1.32 (dt, J=13.2, 6.7 Hz, 1H), 1.07-1.27 (m, 6H), 1.00 (d, J=13.0 Hz, 2H), 0.82 (d, J=6.1 Hz, 6H)

Example 45 ethyl 2-(4-(cyclohexyl(isobutyl)amino)-3-(2,2,2-trifluoroacetamido) phenoxy)acetate

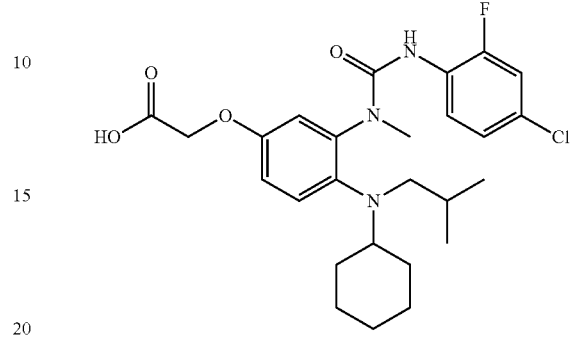

45A. ethyl 2-(4-(cyclohexyl(isobutyl)amino)-3-(2,2,2-trifluoroacetamido) phenoxy)acetate Compound 1E (155 mg, 0.445 mmol) was dissolved in trifluoroacetic anhydride (942 µl, 6.67 mmol) and the solution was allowed to stir at room temperature. After 1 hour, the reaction was diluted with water, basified with sat. NaHCO$_3$, and extracted with EtOAc (three times). The organic extracts were combined, dried with sodium sulfate, filtered, and concentrated in vacuo to give Intermediate 45A (pale yellow oil, 226 mg, 0.508 mmol, 114% yield) (some EtOAc and trifluoroacetic anhydride still present in sample). LC-MS Anal. Calc'd for $C_{22}H_{31}F_3N_2O_4$ 444.22, found [M+H] 445.2. $T_r$=1.29 min (Method A).

45B. ethyl 2-(4-(cyclohexyl(isobutyl)amino)-3-(2,2,2-trifluoro-N-methylacetamido)phenoxy)acetate Compound 45A (190 mg, 0.427 mmol) was dissolved in DMF (8549 µl) and cooled to 0° C. Sodium hydride (11.28 mg, 0.470 mmol) was added and, after 10 minutes, the reaction was allowed to warm to room temperature. After 15 minutes at room temperature, the reaction was re-cooled to 0° C. and methyl iodide (26.7 µl, 0.427 mmol) was added. Once addition was complete, the reaction was once again allowed to warm to room temperature. After 1 hour, the reaction was quenched with water, extracted with EtOAc, dried with sodium sulfate, filtered and concentrated. The crude residue was purified via silica gel column chromatography to give 45B (clear oil, 95 mg, 0.207 mmol, 48.5% yield) along with 45A (pale yellow oil, 44 mg, 0.099 mmol, 23.16% yield) (recovered SM). LC-MS Anal. Calc'd for $C_{23}H_{33}F_3N_2O_4$ 458.24, found [M+H]459.5. $T_r$=1.22 min (Method A).

45C. 2-(4-(cyclohexyl(isobutyl)amino)-3-(methylamino)phenoxy)acetic acid

Compound 45B (95 mg, 0.207 mmol) was dissolved in THF (1884 µl), MeOH (377 µl), and Water (1884 µl). Lithium hydroxide (49.6 mg, 2.072 mmol) was added and the reaction was stirred at room temperature. After 1 hour, the reaction was heated to 50° C. After 4 hours, the reaction was concentrated in vacuo, acidified with AcOH, and ext with EtOAc. Organics were washed with water (three times)

to remove AcOH, then dried with sodium sulfate, filtered, and concentrated in vacuo to give 45C (tan oil, 75 mg, 0.224 mmol, 108%). LC-MS Anal. Calc'd for $C_{19}H_{30}N_2O_3$ 334.23, found [M+H] 335.5. $T_r$=0.79 min (Method A).

Example 45

Compound 45C (25 mg, 0.075 mmol) was dissolved in THF (747 µl) and 4-chloro-2-fluoro-1-isocyanatobenzene (15.39 mg, 0.090 mmol) was added at room temp. Reaction stirred at room temp. After 1 hour, the reaction was concentrated, taken up in DMF, filtered, and purified via preparative HPLC to give example 45 (4.3 mg, 0.008 mmol, 11%). LC-MS Anal. Calc'd for $C_{26}H_{33}ClFN_3O_4$ 505.21, found [M+H] 506.4. $T_r$=1.904 min (Method B). $^1$H NMR (500 MHz, DMSO-$d_6$) δ: 7.78 (br. s., 1H), 7.33 (d, J=9.5 Hz, 1H), 7.17 (d, J=8.5 Hz, 1H), 7.02-7.11 (m, 1H), 6.73-6.87 (m, 3H), 4.42 (br. s., 2H), 3.14 (s, 3H), 1.49-1.78 (m, 6H), 0.85-1.48 (m, 8H), 0.57-0.84 (m, 6H)

Example 46

2-(3-(3-(4-chloro-2-fluorophenyl)ureido)-4-(cyclohexyl(isobutyl)amino)phenoxy)-N—(N,N-dimethylsulfamoyl)acetamide Example 1 (30 mg, 0.061 mmol) was dissolved in THF (305 µl) and N,N-carbonyldiimidazole (14.83 mg, 0.091 mmol) was added. The mixture was heated to reflux for 1 hour. After 1 hour, the resulting solution was added to a solution of N,N-dimethyl aminosulfonamide (11.36 mg, 0.091 mmol) in THF (305 µl) and then DBU (14.71 µl, 0.098 mmol) was added. The reaction was allowed to stir at room temperature. After 3 hours, the reaction was diluted with EtOAc. Organics were washed with 1N HCl, concentrated in vacuo, dissolved in DMF, filtered and purified directly via preparative HPLC to give example 46 (23.2 mg, 0.039 mmol, 63.6%). LC-MS Anal. Calc'd for $C_{27}H_{37}ClFN_5O_5S$ 597.22, found [M+H] 598.3. $T_r$=2.090 min (Method C). $^1$H NMR (500 MHz, DMSO-$d_6$) δ: 9.61 (s, 1H), 8.52 (s, 1H), 7.98 (t, J=8.8 Hz, 1H), 7.70 (d, J=2.9 Hz, 1H), 7.45 (dd, J=10.9, 2.1 Hz, 1H), 7.24 (d, J=9.1 Hz, 1H), 7.11 (d, J=8.8 Hz, 1H), 6.49 (dd, J=8.7, 2.8 Hz, 1H), 4.59 (s, 2H), 2.76 (s, 6H), 1.90 (d, J=4.8 Hz, 2H), 1.67 (d, J=3.9 Hz, 2H), 1.51 (d, J=11.6 Hz, 1H), 1.29 (dt, J=13.2, 6.5 Hz, 1H), 0.86-1.21 (m, 8H), 0.79 (br. s., 6H)

Example 47-49

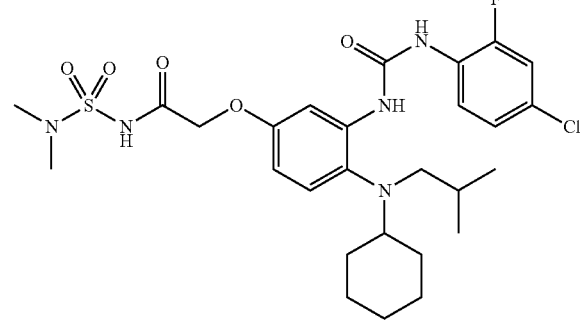

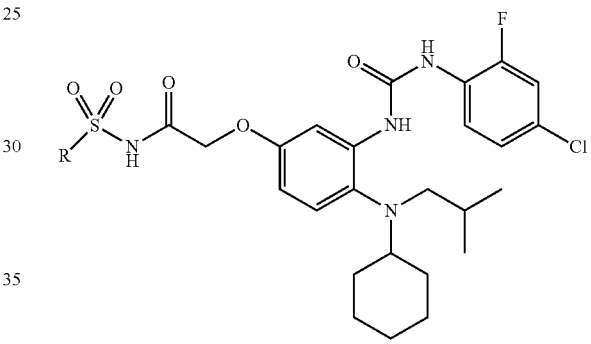

Examples 47-49 were prepared from Example 1 following the procedure for Example 46 using the corresponding sulfonamides.

| Ex. No. | Name | R | Tr (min) Method C | [M + H]+ |
|---|---|---|---|---|
| 47 | 2-(3-(3-(4-chloro-2-fluorophenyl)ureido)-4-(cyclohexyl (isobutyl)amino)phenoxy)-N-(cyclopropylsulfonyl)acetamide | cyclopropyl | 1.97 | 595.3 |
| 48 | N-(tert-butylsulfonyl)-2-(3-(3-(4-chloro-2-fluorophenyl)ureido)-4-(cyclohexyl(isobutyl)amino)phenoxy)acetamide | tert-butyl | 2.13 | 611.24 |
| 49 | 2-(3-(3-(4-chloro-2-fluorophenyl)ureido)-4-(cyclohexyl(isobutyl) | 2-thienyl | 1.95 | 637.16 |

Example 50

2-(4-(cyclohexyl(isobutyl)amino)-3-(3-(5-methyl-isoxazol-3-yl) ureido)phenoxy)-N-(cyclopropylsulfonyl)acetamide

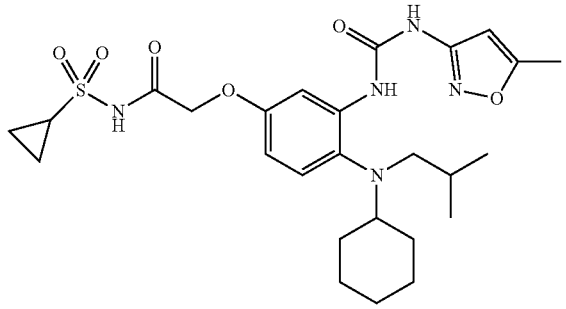 [SMILES: Cc1cc(NC(=O)Nc2cc(OCC(=O)NS(=O)(=O)C3CC3)ccc2N(CC(C)C)C2CCCCC2)no1]

Example 7 (14 mg, 0.031 mmol) was dissolved in THF (315 μl) and N, N-carbonyldiimidazole (7.66 mg, 0.047 mmol) was added. The mixture was heated to reflux for 1 hour. After 1 hour, the resulting solution was added to a solution of cyclopropanesulfonamide (5.72 mg, 0.047 mmol) in THF (315 μl) and then DBU (7.60 μl, 0.050 mmol) was added. The reaction was allowed to stir at room temperature for 3 hours. The reaction was then concentrated in vacuo, taken up in DMF, filtered, and purified directly via preparative HPLC to give example 50 (1.1 mg, 0.002 mmol, 6.4%). LC-MS Anal. Calc'd for $C_{26}H_{37}N_5O_6S$ 547.25, found [M+H] 548.25. $T_r$=1.68 min (Method C). $^1$H NMR (500 MHz, DMSO-$d_6$) δ: 10.44 (br. s., 1H), 8.86-9.02 (m, 1H), 7.75 (br. s., 1H), 7.11 (d, J=8.7 Hz, 1H), 6.48 (d, J=8.6 Hz, 1H), 6.41 (br. s., 1H), 4.42 (s, 2H), 2.35 (s, 3H), 1.90 (d, J=6.1 Hz, 2H), 1.66 (d, J=9.7 Hz, 2H), 1.51 (d, J=10.5 Hz, 1H), 1.28 (dt, J=12.5, 6.0 Hz, 1H), 0.95-1.21 (m, 6H), 0.90-0.94 (m, 2H), 0.82-0.89 (m, J=5.5 Hz, 4H), 0.64-0.81 (m, 6H)

Example 51

2-(4-(cyclohexyl(isobutyl)amino)-3-(3-(2-fluorophenyl) ureido)phenoxy)-N—(N,N-dimethylsulfamoyl)acetamide

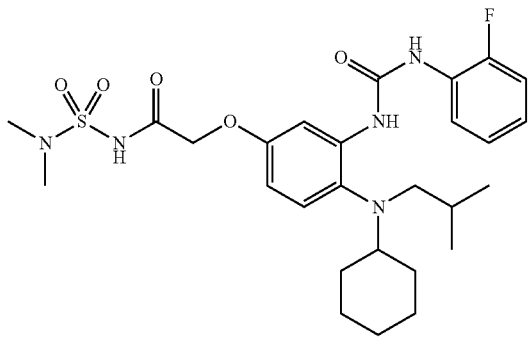 [SMILES: CC(C)CN(c1ccc(OCC(=O)NS(=O)(=O)N(C)C)cc1NC(=O)Nc1ccccc1F)C1CCCCC1]

Example 18 (16 mg, 0.035 mmol) was dissolved in THF (350 μl) and N, N-carbonyldiimidazole (8.51 mg, 0.052 mmol) was added. The mixture was heated to reflux for 1 hour. After 1 hour, the resulting solution was added to a solution of N,N-dimethyl aminosulfonamide (6.51 mg, 0.052 mmol) in THF (350 μl) and then DBU (8.43 μl, 0.056 mmol) was added. The reaction was allowed to stir at room temperature for 3 hours. The reaction was then concentrated in vacuo, taken up in DMF, filtered, and and purified directly via preparative HPLC to give example 51 (1.7 mg, 0.003 mmol, 8.6%). LC-MS Anal. Calc'd for $C_{27}H_{38}FN_5O_5S$ 563.26, found [M+H] 564.26. $T_r$=1.86 min (Method C). $^1$H NMR (500 MHz, DMSO-$d_6$) δ: 9.49 (br. s., 1H), 8.48 (s, 1H), 7.92 (t, J=8.2 Hz, 1H), 7.32 (d, J=8.0 Hz, 1H), 7.20-7.27 (m, 1H), 7.10-7.20 (m, 1H), 6.99-7.10 (m, 2H), 6.49 (d, J=8.6 Hz, 1H), 4.63 (s, 2H), 2.79 (s, 6H), 1.85-1.95 (m, J=3.5 Hz, 2H), 1.63-1.72 (m, J=3.7 Hz, 2H), 1.51 (d, J=12.5 Hz, 1H), 1.25-1.35 (m, J=5.7 Hz, 1H), 0.83-1.24 (m, 8H), 0.79 (br. s., 6H)

Example 52

2-(4-(cyclohexyl(isobutyl)amino)-3-(3-(p-tolyl) ureido) phenoxy)-N—(N,N-dimethylsulfamoyl)acetamide

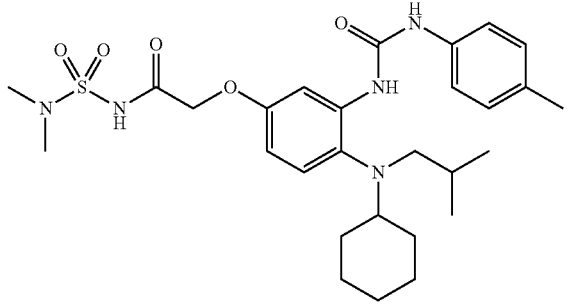

Example 109 (14 mg, 0.031 mmol) was dissolved in THF (309 μl) and N, N-carbonyldiimidazole (7.51 mg, 0.046 mmol) was added. The mixture was heated to reflux for 1 hour. After 1 hour, the resulting solution was added to a solution of N,N-dimethyl aminosulfonamide (5.75 mg, 0.046 mmol) in THF (309 μl) and then DBU (7.44 μl, 0.049 mmol) was added. The reaction was allowed to stir at room temperature for 3 hours. The reaction was then concentrated in vacuo, taken up in DMF, filtered, and purified via preparative HPLC to give Example 52 (4.1 mg, 0.007 mmol, 24%). LC-MS Anal. Calc'd for $C_{28}H_{41}N_5O_5S$ 559.28, found [M+H] 560.29. $T_r$=2.05 min (Method C). $^1$H NMR (500 MHz, DMSO-$d_6$) δ: 9.45 (s, 1H), 8.22 (s, 1H), 7.79 (d, J=2.6 Hz, 1H), 7.36 (d, J=8.2 Hz, 2H), 7.05-7.14 (m, 3H), 6.45 (dd, J=8.7, 2.5 Hz, 1H), 4.58 (s, 2H), 2.77 (s, 6H), 2.24 (s, 3H), 1.83-1.94 (m, 2H), 1.63-1.71 (m, 2H), 1.51 (d, J=12.4 Hz, 1H), 1.24-1.34 (m, 1H), 0.87-1.22 (m, 8H), 0.70-0.86 (m, 6H)

Example 53

2-(4-(cyclohexyl(isobutyl)amino)-3-(3-(p-tolyl)ureido)phenoxy)-N-(cyclopropylsulfonyl)acetamide

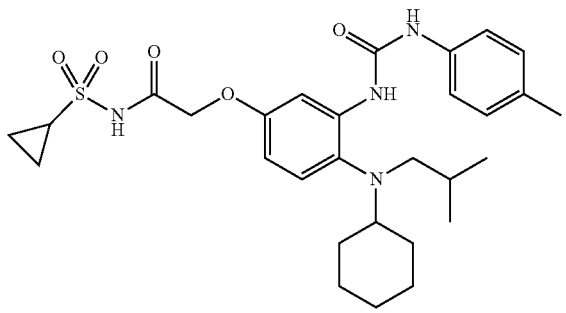 [SMILES: Cc1ccc(NC(=O)Nc2cc(OCC(=O)NS(=O)(=O)C3CC3)ccc2N(CC(C)C)C2CCCCC2)cc1]

Example 53 was obtained following the procedure of Example 52 using Example 109. LC-MS Anal. Calc'd for $C_{29}H_{40}N_4O_5S$ 556.27, found [M+H] 557.27. $T_r$=1.90 min (Method C). $^1$H NMR (500 MHz, DMSO-$d_6$) δ: 9.42 (s, 1H), 8.18 (s, 1H), 7.73 (d, J=2.4 Hz, 1H), 7.36 (d, J=8.1 Hz, 2H), 7.31 (d, J=8.2 Hz, 1H), 7.03-7.11 (m, J=8.3, 8.3 Hz, 3H), 6.43 (d, J=6.0 Hz, 1H), 4.39 (s, 2H), 2.24 (br. s., 3H), 1.83-1.93 (m, 2H), 1.63-1.72 (m, J=3.5 Hz, 2H), 1.51 (d, J=11.6 Hz, 1H), 1.25-1.35 (m, 1H), 0.93-1.24 (m, 8H), 0.90 (br. s., 4H), 0.69-0.85 (m, 6H)

Example 54

2-(3-(2-(4-chloro-3-fluorophenyl)acetamido)-4-(cyclohexyl(isobutyl)amino)phenoxy)acetic acid

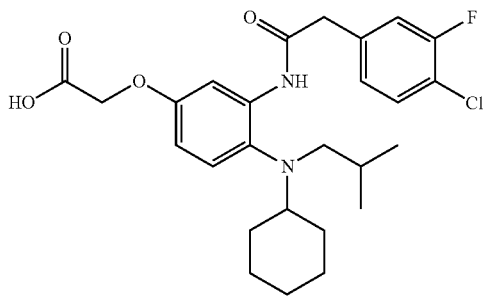 [SMILES: CC(C)CN(c1ccc(OCC(=O)O)cc1NC(=O)Cc1ccc(Cl)c(F)c1)C1CCCCC1]

To a solution of Intermediate 1E (21 mg, 0.060 mmol) in THF (603 µl) at RT was added 2-(4-chloro-3-fluorophenyl) acetic acid (34.1 mg, 0.181 mmol), EDC (34.7 mg, 0.181 mmol), and 1-hydroxybenzotriazole (24.43 mg, 0.181 mmol), followed by Hunig's Base (52.6 µl, 0.301 mmol). The reaction was stirred at room temperature for 16 h. The reaction was diluted with water (0.6 mL) and MeOH (0.3 mL) and LiOH (30 mg) were added. After 1 hour, the reaction was concentrated in vacuo, acidified with 1N HCl, ext EtOAc, dried with sodium sulfate, filtered and concentrated in vacuo. The crude residue was taken up in DMF, filtered, and purified via preparative HPLC to give Example 54 (18.1 mg, 0.036 mmol, 61%). LC-MS Anal. Calc'd for $C_{26}H_{32}ClFN_2O_4$ 490.20, found [M+H] 491.20. $T_r$=2.00 min (Method B). $^1$H NMR (500 MHz, DMSO-$d_6$) δ: 8.65 (s, 1H), 7.93 (br. s., 1H), 7.60 (t, J=8.0 Hz, 1H), 7.46 (d, J=9.8 Hz, 1H), 7.25 (d, J=7.8 Hz, 1H), 7.11 (d, J=8.8 Hz, 1H), 6.49-6.56 (m, 1H), 4.47 (s, 2H), 3.29-3.65 (m, J=17.5 Hz, 2H), 2.56-2.71 (m, 1H), 2.17-2.27 (m, 1H), 1.59 (d, J=10.3 Hz, 2H), 1.48 (d, J=10.4 Hz, 1H), 1.07-1.19 (m, 1H), 0.78-1.07 (m, 8H), 0.68 (d, J=6.5 Hz, 6H)

Examples 55-57

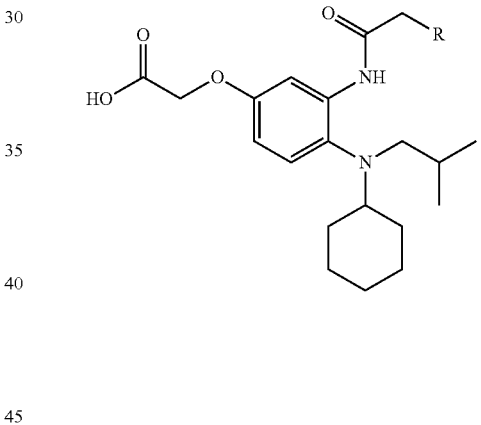

Examples 55-57 were prepared from intermediate 1E following the procedure for Example 54 using the corresponding phenylacetic acids.

| Ex. No. | Name | R | Tr (min) Method B | [M + H]+ |
|---|---|---|---|---|
| 55 | 2-(4-(cyclohexyl(isobutyl)amino)-3-(2-(2-fluoro-4-methylphenyl)acetamido)phenoxy)acetic acid | 2-fluoro-4-methylphenyl | 2.003 | 471.26 |
| 56 | 2-(4-(cyclohexyl(isobutyl)amino)-3-(2-(2,4-difluorophenyl)acetamido)phenoxy)acetic acid | 2,4-difluorophenyl | 1.914 | 475.23 |

| Ex. No. | Name | R | Tr (min) Method B | [M + H]+ |
|---|---|---|---|---|
| 57 | 2-(4-(cyclohexyl(isobutyl)amino)-3-(2-(4-fluorophenyl)acetamido)phenoxy)acetic acid | 4-fluorophenyl | 1.925 | 457.24 |

Example 58

Enantiomer 1 and Enantiomer 2

Enantiomer 1: 2-(4-(cyclohexyl(isobutyl)amino)-3-(3-(pyrimidin-5-yl)ureido)phenoxy)propanoic acid (Homochiral, Stereochemistry Unknown)

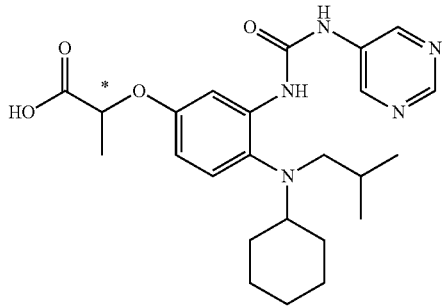 [SMILES: CC(C)CN(c1ccc(OC(C)C(=O)O)cc1NC(=O)Nc1cncnc1)C1CCCCC1]

Enantiomer 2: 2-(4-(cyclohexyl(isobutyl)amino)-3-(3-(pyrimidin-5-yl)ureido)phenoxy)propanoic acid (Homochiral, Stereochemistry Unknown)

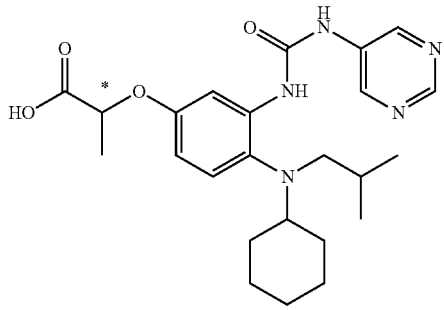 [SMILES: CC(C)CN(c1ccc(OC(C)C(=O)O)cc1NC(=O)Nc1cncnc1)C1CCCCC1]

58A. Racemic ethyl 2-(4-fluoro-3-nitrophenoxy)propanoate 4-fluoro-3-nitrophenol (500 mg, 3.18 mmol) was dissolved in DMF (6.365 mL) at room temperature. Cesium carbonate (1244 mg, 3.82 mmol) was added followed by racemic ethyl 2-bromopropanoate (634 mg, 3.50 mmol). The mixture was stirred at 60° C. After 2 hours, the reaction was then diluted with water and brine (1:1) and extracted with EtOAc. The organics were combined, dried with sodium sulfate, filtered, and concentrated in vacuo. The resulting tan oil was dried on high vac overnight to give 58A (tan oil, 759 mg, 2.95 mmol, 93% yield). LC-MS Anal. Calc'd for $C_{11}H_{12}FNO_5$ 257.70, $T_r$=0.91 min (Method A) (Note: product does not ionize well). $^1$H NMR (400 MHz, chloroform-d) δ: 7.51 (dd, J=5.8, 3.0 Hz, 1H), 7.11-7.23 (m, 2H), 4.75 (q, J=6.7 Hz, 1H), 4.24 (qd, J=7.1, 1.7 Hz, 2H), 1.65 (d, J=6.7 Hz, 3H), 1.28 (t, J=7.2 Hz, 3H)

58B. Racemic ethyl 2-(4-(cyclohexyl(isobutyl)amino)-3-nitrophenoxy)propanoate Compound 58A (0.75 g, 2.92 mmol) was dissolved in Ethanol (2.92 ml). Intermediate 1B (1.358 g, 8.75 mmol) was added and the reaction was heated to 100° C. in a sealed tube. After 48 hours, the reaction was diluted with EtOAc, washed with 1N HCl, dried with sodium sulfate, filtered, and concentrated in vacuo. Purification via silica gel column chromatography gave 58B (orange oil, 0.381 g, 0.971 mmol, 33.3% yield). LC-MS Anal. Calc'd for $C_{21}H_{32}N_2O_5$ 392.23, found [M+H] 393.2, $T_r$=1.24 min (Method A). $^1$H NMR (400 MHz, chloroform-d) δ: 7.18 (d, J=9.0 Hz, 1H), 7.12 (d, J=3.1 Hz, 1H), 6.99 (dd, J=8.9, 3.1 Hz, 1H), 4.68 (q, J=6.8 Hz, 1H), 4.24 (q, J=7.2 Hz, 2H), 2.73-2.84 (m, 3H), 1.81 (d, J=10.4 Hz, 2H), 1.74 (d, J=12.8 Hz, 2H), 1.61 (d, J=6.8 Hz, 3H), 1.46 (dt, J=13.4, 6.6 Hz, 1H), 1.29-1.38 (m, 3H), 1.27 (t, J=7.2 Hz, 3H), 1.11-1.24 (m, 2H), 1.05 (tt, J=12.7, 3.3 Hz, 1H), 0.81 (d, J=6.6 Hz, 6H)

58C. Racemic ethyl 2-(3-amino-4-(cyclohexyl(isobutyl)amino)phenoxy)propanoate To a stirred solution 58B (219 mg, 0.558 mmol) in Ethanol (5.580 mL) was added 0.56 mL of water. The solution was then treated with zinc (219 mg, 3.35 mmol) and ammonium chloride (179 mg, 3.35 mmol). This mixture was stirred at room temperature. After 3 hours the reaction was filtered, diluted with EtOAc, washed with NaHCO$_3$, dried with sodium sulfate, filtered, and concentrated in vacuo to give 58C (clear oil, 184 mg, 0.508 mmol, 91% yield). LC-MS Anal. Calc'd for $C_{21}H_{34}N_2O_3$ 362.26, found [M+H] 363.2, $T_r$=0.83 min (Method A). $^1$H NMR (400 MHz, chloroform-d) δ: 6.91 (d, J=8.6 Hz, 1H), 6.29 (d, J=2.8 Hz, 1H), 6.19 (dd, J=8.6, 2.9 Hz, 1H), 4.65 (q, J=6.8 Hz, 1H), 4.17-4.27 (m, 3H), 2.53 (t, J=11.3 Hz, 1H), 1.59-1.98 (m, 6H), 1.57 (d, J=6.8 Hz, 3H), 1.27-1.53 (m, 5H), 1.25 (t, J=7.1 Hz, 3H), 1.00-1.09 (m, 1H), 0.81 (d, J=5.6 Hz, 6H)

Racemic Example 58. (±)-2-(4-(cyclohexyl(isobutyl)amino)-3-(3-(pyrimidin-5-yl)ureido)phenoxy)propanoic acid To a solution of 58C (46 mg, 0.127 mmol) in THF (1269 μl) was added 4-nitrophenyl carbonochloridate (26.9 mg, 0.133 mmol). The reaction was stirred at room temperature for 30 min. To this reaction were added pyrimidin-5-amine (36.2 mg, 0.381 mmol) and triethylamine (53.1 μl, 0.381 mmol). The reaction was heated at 50° C. for 16 hours. Reaction was concentrated in vacuo and the crude residue was taken up in THF (1009 μl) and treated with lithium hydroxide (30.2 mg, 1.261 mmol) in water (1009 μl). MeOH (~0.5 mL) was added to give a single phase, and the reaction was stirred at room temperature. After stirring 1 h the reaction was concentrated in vacuo to remove MeOH and THF, treated with 1N HCl, and then extracted with EtOAc three times. Organic extracts were combined, dried with sodium sulfate, filtered and concentrated in vacuo. The crude residue was dissolved in 2 mL DMF, filtered, and purified via preparative HPLC to give racemic example 58 (12 mg, 0.026 mmol, 21% yield). LC-MS Anal. Calc'd for $C_{24}H_{33}N_5O_4$ 455.25, found [M+H] 456.25. $T_r$=1.35 min (Method C).

Example 58 Enantiomer 1 and Enantiomer 2: Chiral separation of the racemic sample (Method D) gave Enantiomer 1-$T_r$=7.55 min (Method K) and Enantiomer 2-$T_r$=8.61 min (Method K) Absolute stereochemistry was not determined.

Enantiomer 1: LC-MS Anal. Calc'd for $C_{24}H_{33}N_5O_4$ 455.25, found [M+H]456.25. $T_r$=1.35 min (Method C). $^1$H NMR (500 MHz, DMSO-$d_6$) δ: 10.04 (s, 1H), 8.91 (s, 2H), 8.81 (s, 1H), 8.45 (s, 1H), 7.72 (d, J=2.3 Hz, 1H), 7.12 (d, J=8.7 Hz, 1H), 6.46 (d, J=6.2 Hz, 1H), 4.67 (q, J=6.7 Hz, 1H), 1.86-1.97 (m, J=2.9 Hz, 2H), 1.68 (d, J=6.6 Hz, 2H), 1.51 (d, J=12.3 Hz, 1H), 1.47 (d, J=6.6 Hz, 3H), 1.28 (dt, J=13.1, 6.6 Hz, 1H), 0.89-1.23 (m, 8H), 0.80 (br. s., 6H)

Enantiomer 2: LC-MS Anal. Calc'd for $C_{24}H_{33}N_5O_4$ 455.25, found [M+H]456.25. $T_r$=1.35 min (Method C). $^1$H NMR (500 MHz, DMSO-$d_6$) δ: 10.05 (s, 1H), 8.91 (s, 2H), 8.81 (s, 1H), 8.44 (s, 1H), 7.71 (br. s., 1H), 7.11 (d, J=8.7 Hz, 1H), 6.45 (d, J=8.3 Hz, 1H), 4.58-4.65 (m, J=5.6 Hz, 1H), 1.88-1.97 (m, 2H), 1.67 (d, J=4.4 Hz, 2H), 1.51 (d, J=11.5 Hz, 1H), 1.46 (d, J=6.1 Hz, 3H), 0.89-1.37 (m, 9H), 0.80 (br. s., 6H)

Example 59

Enantiomer 1 and Enantiomer 2

Enantiomer 1: 2-(4-(cyclohexyl(isobutyl)amino)-3-(3-(2-fluoro-phenyl)ureido)phenoxy)propanoic acid (Homochiral, Stereochemistry Unknown)

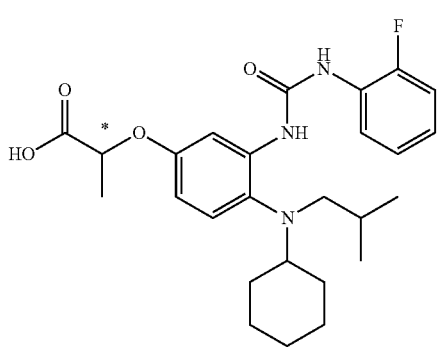 [SMILES: CC(C)CN(c1ccc(OC(C)C(=O)O)cc1NC(=O)Nc1ccccc1F)C1CCCCC1]

Enantiomer 2: 2-(4-(cyclohexyl(isobutyl)amino)-3-(3-(2-fluoro-phenyl)ureido)phenoxy)propanoic acid (Homochiral, Stereochemistry Unknown)

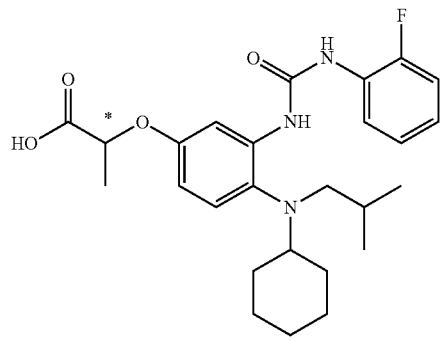 [SMILES: CC(C)CN(c1ccc(OC(C)C(=O)O)cc1NC(=O)Nc1ccccc1F)C1CCCCC1]

Racemic Example 59: (±)-2-(4-(cyclohexyl(isobutyl)amino)-3-(3-(2-fluoro-phenyl)ureido)phenoxy)propanoic acid Racemic Example 59 was obtained following the procedure for Racemic Example 58 using intermediate 58C and 2-fluoroaniline. LC-MS Anal. Calc'd for $C_{26}H_{34}FN_3O_4$ 471.25, found [M+H] 472.6. $T_r$=0.91 min (Method A).

Example 59 Enantiomer 1 and Enantiomer 2: Chiral separation of the racemic sample (Method E) gave Enantiomer 1-$T_r$=8.80 min (Method L) and Enantiomer 2-$T_r$=11.65 min (Method L) Absolute stereochemistry was not determined.

Enantiomer 1: LC-MS Anal. Calc'd for $C_{26}H_{34}FN_3O_4$ 471.25, found [M+H]472.25. $T_r$=1.70 min (Method C). $^1$H NMR (500 MHz, DMSO-$d_6$) δ: 9.45 (s, 1H), 8.43 (s, 1H), 7.92 (t, J=7.7 Hz, 1H), 7.66 (d, J=2.6 Hz, 1H), 7.19-7.26 (m, 1H), 7.12-7.17 (m, 1H), 7.08 (d, J=8.7 Hz, 2H), 6.44 (dd, J=8.7, 2.7 Hz, 1H), 4.66 (q, J=6.6 Hz, 1H), 1.83-1.92 (m, 2H), 1.63-1.70 (m, J=2.8 Hz, 2H), 1.51 (d, J=12.4 Hz, 1H), 1.47 (d, J=6.7 Hz, 3H), 1.29 (dt, J=13.2, 6.6 Hz, 1H), 1.10 (br. s., 8H), 0.79 (br. s., 6H)

Enantiomer 2: LC-MS Anal. Calc'd for $C_{26}H_{34}FN_3O_4$ 471.25, found [M+H]472.25. $T_r$=1.69 min (Method C). $^1$H NMR (500 MHz, DMSO-$d_6$) δ: 9.45 (s, 1H), 8.43 (s, 1H), 7.91 (t, J=7.9 Hz, 1H), 7.66 (d, J=2.7 Hz, 1H), 7.20-7.26 (m, 1H), 7.11-7.17 (m, 1H), 7.04-7.10 (m, J=8.8 Hz, 2H), 6.44 (dd, J=8.7, 2.8 Hz, 1H), 4.67 (q, J=6.6 Hz, 1H), 1.81-1.93 (m, 2H), 1.67 (d, J=3.7 Hz, 2H), 1.50 (d, J=12.6 Hz, 1H), 1.47 (d, J=6.7 Hz, 3H), 0.82-1.34 (m, 8H), 0.79 (br. s., 6H)

Example 60

Enantiomer 1 and Enantiomer 2

Enantiomer 1: 2-(4-(cyclohexyl(isobutyl)amino)-3-(3-(p-tolyl)ureido)phenoxy)propanoic acid (Homochiral, Stereochemistry Unknown)

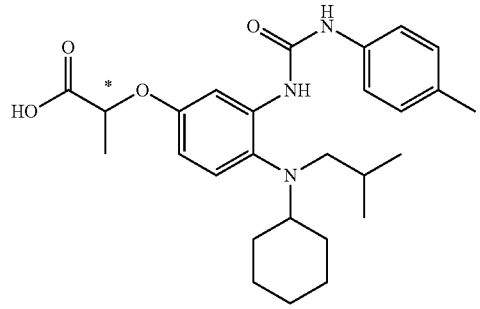 [SMILES: Cc1ccc(NC(=O)Nc2cc(OC(C)C(=O)O)ccc2N(CC(C)C)C2CCCCC2)cc1]

Enantiomer 2: 2-(4-(cyclohexyl(isobutyl)amino)-3-(3-(p-tolyl)ureido)phenoxy)propanoic acid (Homochiral, Stereochemistry Unknown)

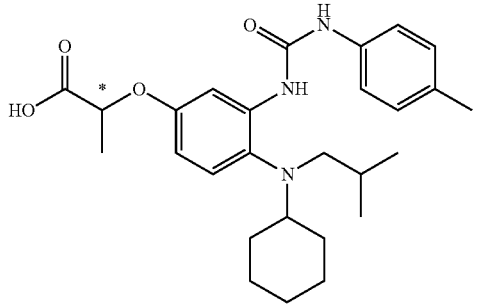

Racemic Example 60: (±)-2-(4-(cyclohexyl(isobutyl)amino)-3-(3-(p-tolyl)ureido)phenoxy)propanoic acid A suspension of racemic 58C (46 mg, 0.127 mmol) in THF (423 μl) was treated with 1-isocyanato-4-methylbenzene (22.40 μl, 0.178 mmol). After 1 hour, the reaction was concentrated in vacuo. This crude residue was dissolved in THF (1017 μl) and then treated with lithium hydroxide (30.4 mg, 1.271 mmol) in water (1017 μl). MeOH (~0.5 mL) was added to give a single phase, and the reaction was stirred at room temperature. After stirring 1 hour, the reaction was concentrated in vacuo to remove MeOH and THF, treated with 1N HCl until a precipitate forms and pH is acidic, and then extracted with EtOAc three times. Organic extracts were combined, dried with sodium sulfate, filtered and concentrated in vacuo. The crude residue was dissolved in 2 mL DMF, filtered, and purified via preparatory HPLC to give racemic example 60 (28 mg, 0.060 mmol, 47%). LC-MS Anal. Calc'd for $C_{27}H_{37}N_3O_4$ 467.28, found [M+H] 468.6. $T_r$=0.96 min (Method A).

Example 60 Enantiomer 1 and Enantiomer 2: Chiral separation of the racemic sample (Method F) gave Enantiomer 1 $T_r$=12.80 min (Method M) and Enantiomer 2—$T_r$=16.05 min (Method M) Absolute stereochemistry was not determined.

Enantiomer 1: LC-MS Anal. Calc'd for $C_{27}H_{37}N_3O_4$ 467.28, found [M+H]468.28. $T_r$=1.79 min (Method C). $^1$H NMR (500 MHz, DMSO-$d_6$) δ: 9.43 (s, 1H), 8.18 (s, 1H), 7.69 (br. s., 1H), 7.32 (d, J=8.2 Hz, 2H), 7.03-7.11 (m, 3H), 6.40 (dd, J=8.7, 2.8 Hz, 1H), 4.64 (d, J=6.7 Hz, 1H), 2.23 (s, 3H), 1.76-1.92 (m, 2H), 1.65 (d, J=3.8 Hz, 2H), 1.49 (d, J=12.7 Hz, 1H), 1.45 (d, J=6.6 Hz, 3H), 0.87-1.34 (m, 9H), 0.77 (br. s., 6H)

Enantiomer 2: LC-MS Anal. Calc'd for $C_{27}H_{37}N_3O_4$ 467.28, found [M+H]468.28. $T_r$=1.81 min (Method C). $^1$H NMR (500 MHz, DMSO-$d_6$) δ: 9.41 (s, 1H), 8.15 (s, 1H), 7.62 (br. s., 1H), 7.31 (d, J=8.2 Hz, 2H), 7.08 (d, J=8.2 Hz, 2H), 7.02 (d, J=8.8 Hz, 1H), 6.38 (dd, J=8.6, 2.6 Hz, 1H), 4.48 (q, J=6.3 Hz, 1H), 2.22 (s, 3H), 1.76-1.90 (m, 2H), 1.64 (d, J=5.5 Hz, 2H), 1.48 (d, J=11.1 Hz, 1H), 1.40 (d, J=6.6 Hz, 3H), 1.25 (dt, J=13.2, 6.6 Hz, 1H), 0.88-1.16 (m, 8H), 0.76 (br. s., 6H)

Example 61

Enantiomer 1 and Enantiomer 2

Enantiomer 1: 2-(3-(3-(4-chloro-2-fluorophenyl)ureido)-4-(cyclo-hexyl(isobutyl)amino)phenoxy)propanoic acid (Homochiral, Stereochemistry Unknown)

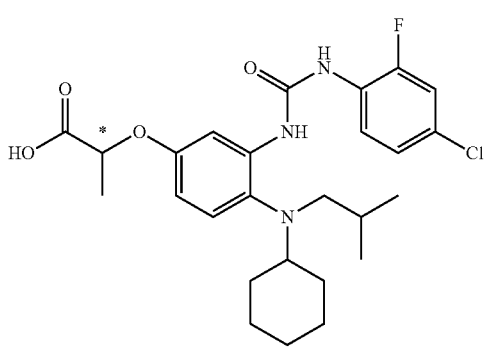 [SMILES: CC(C)CN(c1ccc(OC(C)C(=O)O)cc1NC(=O)Nc1ccc(Cl)cc1F)C1CCCCC1]

Enantiomer 2: 2-(3-(3-(4-chloro-2-fluorophenyl)ureido)-4-(cyclo-hexyl(isobutyl)amino)phenoxy)propanoic acid (Homochiral, Stereochemistry Unknown)

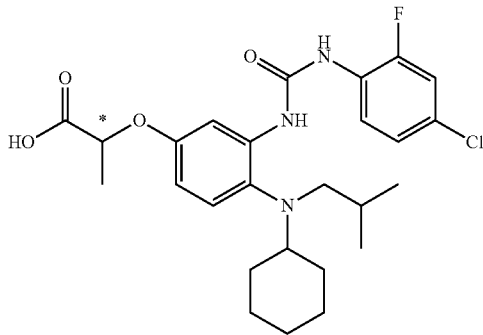 [SMILES: CC(C)CN(c1ccc(OC(C)C(=O)O)cc1NC(=O)Nc1ccc(Cl)cc1F)C1CCCCC1]

Racemic Example 61: (±)-2-(3-(3-(4-chloro-2-fluorophenyl)ureido)-4-(cyclo-hexyl(isobutyl)amino)phenoxy)propanoic acid Racemic Example 61 was obtained following the procedure for Racemic Example 60 using intermediate 58C and 4-chloro-2-fluoro-1-isocyanatobenzene. LC-MS Anal. Calc'd for $C_{26}H_{33}ClFN_3O_4$ 505.21, found [M+H] 506.6. $T_r$=0.98 min (Method A).

Example 61 Enantiomer 1 and Enantiomer 2: Chiral separation of the racemic sample (Method G) gave Enantiomer 1 $T_r$=4.70 min (Method N) and Enantiomer 2 $T_r$=6.15 min (Method N) Absolute stereochemistry was not determined.

Enantiomer 1: LC-MS Anal. Calc'd for $C_{26}H_{33}ClFN_3O_4$ 505.21, found [M+H]506.21. $T_r$=1.86 min (Method C). $^1$H NMR (500 MHz, DMSO-$d_6$) δ: 9.58 (s, 1H), 8.46 (s, 1H), 7.94 (t, J=8.8 Hz, 1H), 7.61 (d, J=2.4 Hz, 1H), 7.44 (dd, J=10.9, 2.0 Hz, 1H), 7.23 (d, J=8.7 Hz, 1H), 7.08 (d, J=8.8 Hz, 1H), 6.44 (dd, J=8.6, 2.6 Hz, 1H), 4.64 (q, J=6.4 Hz, 1H), 1.82-1.91 (m, 2H), 1.66 (d, J=5.0 Hz, 2H), 1.49 (d, J=12.2 Hz, 1H), 1.46 (d, J=6.7 Hz, 3H), 1.27 (dt, J=13.3, 6.8 Hz, 1H), 0.87-1.19 (m, 8H), 0.78 (br. s., 6H)

Enantiomer 2: LC-MS Anal. Calc'd for $C_{26}H_{33}ClFN_3O_4$ 505.21, found [M+H]506.21. $T_r$=1.86 min (Method C). $^1$H NMR (500 MHz, DMSO-d$_6$) δ: 9.58 (s, 1H), 8.46 (s, 1H), 7.94 (t, J=8.8 Hz, 1H), 7.61 (br. s., 1H), 7.44 (dd, J=10.9, 2.1 Hz, 1H), 7.23 (d, J=8.8 Hz, 1H), 7.08 (d, J=8.8 Hz, 1H), 6.44 (dd, J=8.6, 2.6 Hz, 1H), 4.64 (q, J=6.4 Hz, 1H), 1.83-1.90 (m, 2H), 1.66 (d, J=4.3 Hz, 2H), 1.49 (d, J=11.7 Hz, 1H), 1.46 (d, J=6.6 Hz, 3H), 1.27 (dt, J=13.1, 6.5 Hz, 1H), 0.86-1.19 (m, 8H), 0.78 (br. s., 6H)

Example 62

(±)-2-(3-(benzo[d]oxazol-2-ylamino)-4-(cyclohexyl(isobutyl)amino)phenoxy)propanoic acid

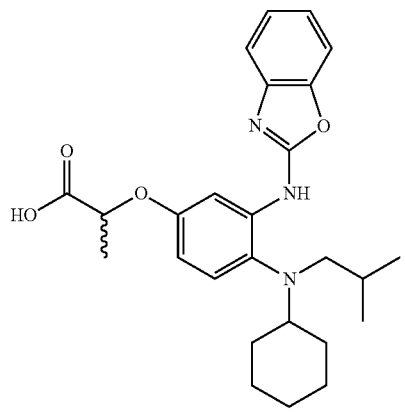 [SMILES: CC(C)CN(c1ccc(OC(C)C(=O)O)cc1Nc1nc2ccccc2o1)C1CCCCC1]

Racemic Example 62 was obtained following the procedure for Example 44 using intermediate 58C and 2-chlorobenzo[d]oxazole. LC-MS Anal. Calc'd for $C_{26}H_{33}N_3O_4$ 451.25, found [M+H] 452.25. $T_r$=2.08 min (Method C). $^1$H NMR (500 MHz, DMSO-d$_6$) δ: 7.92 (br. s., 1H), 7.52 (t, J=8.6 Hz, 2H), 7.22-7.28 (m, 1H), 7.20 (d, J=8.7 Hz, 1H), 7.13-7.18 (m, 1H), 6.49 (d, J=6.6 Hz, 1H), 4.67 (d, J=6.2 Hz, 1H), 2.72-2.81 (m, J=8.5 Hz, 1H), 1.84 (d, J=7.2 Hz, 2H), 1.67 (d, J=11.6 Hz, 2H), 1.49-1.54 (m, 1H), 1.47 (d, J=6.5 Hz, 3H), 1.32 (dt, J=13.1, 6.7 Hz, 1H), 0.88-1.26 (m, 7H), 0.82 (d, J=5.9 Hz, 6H)

Example 63

(±)-2-(4-(cyclohexyl(isobutyl)amino)-3-((5-methoxypyrimidin-2-yl)amino)phenoxy)propanoic acid

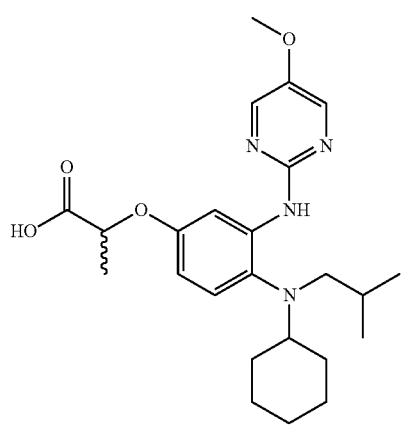 [SMILES: COc1cnc(Nc2cc(OC(C)C(=O)O)ccc2N(CC(C)C)C2CCCCC2)nc1]

Intermediate 58C (45 mg, 0.124 mmol) was dissolved in Dioxane (621 μl) and 2-chloro-5-methoxypyrimidine (26.9 mg, 0.186 mmol), dicyclohexyl(2',4',6'-triisopropyl-3,6-dimethoxy-[1,1'-biphenyl]-2-yl)phosphine (6.66 mg, 0.012 mmol), sodium tert-butoxide (17.89 mg, 0.186 mmol), and palladium(II) acetate (2.79 mg, 0.012 mmol) were added. Reaction was degassed with nitrogen bubbling/sonication for 5 minutes, then it was sealed at heated to 85° C. for 14 hours. The reaction was diluted with water, acidified with 1 N HCl, and extracted with EtOAc. The combined organics were dried with sodium sulfate, filtered and concentrated. The crude residue was dissolved in DMF, filtered, and purified via preparative HPLC to give Racemic Example 63 (2.5 mg, 0.006 mmol, 4.6%). LC-MS Anal. Calc'd for $C_{24}H_{34}N_4O_4$ 442.26, found [M+H] 443.3. $T_r$=1.869 min (Method B). $^1$H NMR (500 MHz, DMSO-d$_6$) δ: 8.62 (s, 1H), 8.34 (s, 2H), 8.12 (d, J=2.7 Hz, 1H), 7.14 (d, J=8.7 Hz, 1H), 6.35 (dd, J=8.5, 2.7 Hz, 1H), 4.72 (q, J=6.5 Hz, 1H), 3.83 (s, 3H), 1.76-1.91 (m, 2H), 1.67 (d, J=10.9 Hz, 2H), 1.51-1.54 (m, 1H), 1.49 (d, J=6.6 Hz, 3H), 1.15 (t, J=7.2 Hz, 9H), 0.81 (br. s., 6H)

Example 64

(±)-2-(4-(cyclohexyl(isobutyl)amino)-3-(3-(2-fluoro-4-methoxyphenyl)ureido)phenoxy)propanoic acid

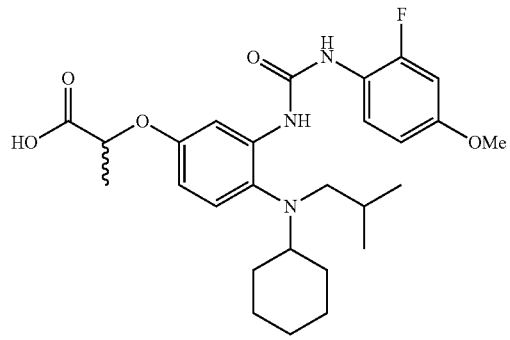 [SMILES: COc1ccc(NC(=O)Nc2cc(OC(C)C(=O)O)ccc2N(CC(C)C)C2CCCCC2)c(F)c1]

Enantiomer 1 2-(4-(cyclohexyl(isobutyl)amino)-3-(3-(2-fluoro-4-methoxyphenyl)ureido)phenoxy)propanoic acid (Homochiral, Stereochemistry Unknown)

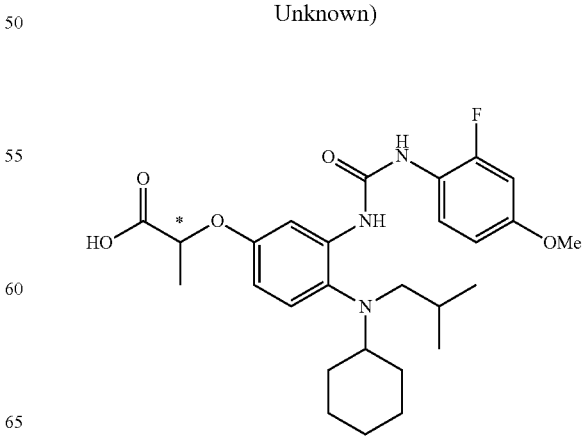

Enantiomer 2 2-(4-(cyclohexyl(isobutyl)amino)-3-(3-(2-fluoro-4-methoxyphenyl)ureido)phenoxy)propanoic acid (Homochiral, Stereochemistry Unknown)

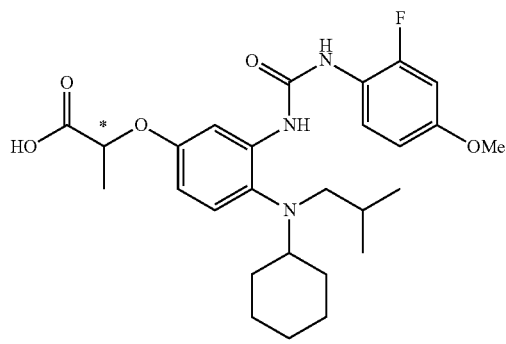 [SMILES: COc1ccc(NC(=O)Nc2cc(OC(C)C(=O)O)ccc2N(CC(C)C)C2CCCCC2)c(F)c1]

Racemic Example 64 was obtained following the procedure for Racemic Example 58 using intermediate 58C and 2-fluoro-4-methoxyaniline. LC-MS Anal. Calc'd for $C_{27}H_{36}FN_3O_5$ 501.26, found [M+H] 502.2. $T_r$=1.738 min (Method B). $^1$H NMR (500 MHz, DMSO-$d_6$) δ: 9.02 (br. s., 1H), 8.17 (br. s., 1H), 7.62 (br. s., 1H), 7.55 (t, J=9.1 Hz, 1H), 7.00 (d, J=8.8 Hz, 1H), 6.86 (dd, J=12.5, 2.4 Hz, 1H), 6.72 (d, J=7.0 Hz, 1H), 6.35 (dd, J=8.6, 2.5 Hz, 1H), 4.53 (d, J=6.6 Hz, 1H), 3.71 (s, 3H), 1.67-1.84 (m, 2H), 1.56-1.67 (m, 2H), 1.47 (d, J=12.0 Hz, 1H), 1.39 (d, J=6.6 Hz, 3H), 1.17-1.26 (m, J=13.1, 6.6 Hz, 1H), 0.85-1.14 (m, 8H), 0.73 (br. s., 6H)

Example 64 Enantiomer 1 and Enantiomer 2: Chiral separation of the racemic sample (Method E) gave Enantiomer 1 $T_r$=9.35 min (Method L) and Enantiomer 2 $T_r$=13.30 min (Method L) Absolute stereochemistry was not determined.

Enantiomer 1: LC-MS Anal. Calc'd for $C_{27}H_{36}FN_3O_5$ 501.26, found [M+H]502.2. $T_r$=1.733 min (Method B). $^1$H NMR (500 MHz, DMSO-$d_6$) δ: 9.06 (br. s., 1H), 8.22 (br. s., 1H), 7.68 (br. s., 1H), 7.57 (t, J=9.0 Hz, 1H), 7.06 (d, J=8.8 Hz, 1H), 6.90 (d, J=12.5 Hz, 1H), 6.76 (d, J=8.9 Hz, 1H), 6.40 (dd, J=8.5, 2.1 Hz, 1H), 4.63 (q, J=6.6 Hz, 1H), 3.75 (s, 3H), 2.39-2.47 (m, 1H), 1.71-1.92 (m, 2H), 1.61-1.70 (m, 2H), 1.51 (d, J=11.3 Hz, 1H), 1.45 (d, J=6.6 Hz, 3H), 1.25 (dt, J=13.0, 6.6 Hz, 1H), 0.91-1.17 (m, 6H), 0.85 (d, J=6.6 Hz, 1H), 0.77 (br. s., 6H)

Enantiomer 2: LC-MS Anal. Calc'd for $C_{27}H_{36}FN_3O_5$ 501.26, found [M+H]502.2. $T_r$=1.733 min (Method B). $^1$H NMR (500 MHz, DMSO-$d_6$) δ: 9.06 (br. s., 1H), 8.22 (br. s., 1H), 7.68 (br. s., 1H), 7.58 (t, J=9.0 Hz, 1H), 7.05 (d, J=8.6 Hz, 1H), 6.90 (d, J=12.5 Hz, 1H), 6.76 (d, J=9.0 Hz, 1H), 6.40 (d, J=6.5 Hz, 1H), 4.62 (q, J=6.4 Hz, 1H), 3.75 (s, 3H), 2.39-2.47 (m, 1H), 1.71-1.90 (m, 2H), 1.62-1.70 (m, 2H), 1.51 (d, J=11.5 Hz, 1H), 1.45 (d, J=6.6 Hz, 3H), 1.26 (dt, J=13.1, 6.6 Hz, 1H), 0.92-1.18 (m, 7H), 0.77 (br. s., 6H)

Example 65

(±)-2-(4-(cyclohexyl(isobutyl)amino)-3-(3-(2-fluoro-4-methylphenyl)ureido)phenoxy)propanoic acid

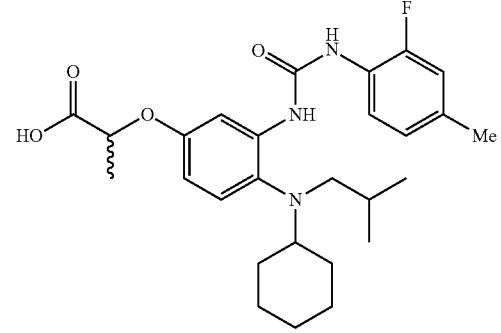 [SMILES: Cc1ccc(NC(=O)Nc2cc(OC(C)C(=O)O)ccc2N(CC(C)C)C2CCCCC2)c(F)c1]

Enantiomer 1: 2-(4-(cyclohexyl(isobutyl)amino)-3-(3-(2-fluoro-4-methylphenyl)ureido)phenoxy)propanoic acid (Homochiral, Absolute Stereochemistry Unknown)

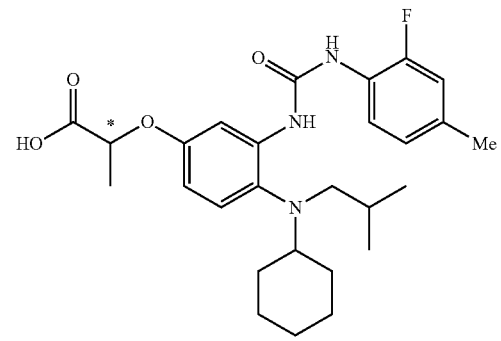 [SMILES: Cc1ccc(NC(=O)Nc2cc(OC(C)C(=O)O)ccc2N(CC(C)C)C2CCCCC2)c(F)c1]

Enantiomer 2 2-(4-(cyclohexyl(isobutyl)amino)-3-(3-(2-fluoro-4-methylphenyl)ureido)phenoxy)propanoic acid (Homochiral, Absolute Stereochemistry Unknown)

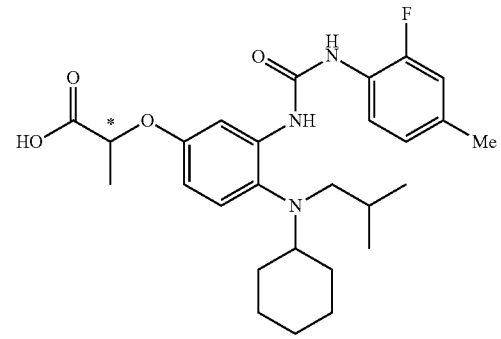 [SMILES: Cc1ccc(NC(=O)Nc2cc(OC(C)C(=O)O)ccc2N(CC(C)C)C2CCCCC2)c(F)c1]

Racemic Example 65 was obtained following the procedure for Racemic Example 58 using intermediate 58C and 2-fluoro-4-methylaniline. LC-MS Anal. Calc'd for $C_{27}H_{36}FN_3O_4$ 485.27, found [M+H] 486.2. $T_r$=1.868 min (Method B). $^1$H NMR (500 MHz, DMSO-$d_6$) δ: 9.26 (br. s., 1H), 8.31 (s, 1H), 7.68 (t, J=8.4 Hz, 1H), 7.64 (d, J=2.3 Hz, 1H), 6.88-7.20 (m, 3H), 6.39 (d, J=6.2 Hz, 1H), 4.58-4.68 (m, 1H), 2.24 (s, 3H), 1.74-1.88 (m, 2H), 1.63 (br. s., 2H), 1.46-1.52 (m, 1H), 1.44 (br. s., 3H), 1.24 (dt, J=13.0, 6.6 Hz, 1H), 0.86-1.15 (m, 7H), 0.81 (d, J=6.6 Hz, 1H), 0.75 (br. s., 6H)

Example 65 Enantiomer 1 and Enantiomer 2: Chiral separation of the racemic sample (Method H) gave Enantiomer 1 $T_r$=5.30 min (Method O) and Enantiomer 2 $T_r$=6.75 min (Method O) Absolute stereochemistry was not determined.

Enantiomer 1: LC-MS Anal. Calc'd for $C_{27}H_{36}FN_3O_4$ 485.27, found [M+H]468.27. $T_r$=1.863 min (Method B). $^1$H NMR (500 MHz, DMSO-$d_6$) δ: 9.29 (br. s., 1H), 8.34 (br. s., 1H), 7.63-7.73 (m, 2H), 7.03-7.10 (m, 2H), 6.96 (d, J=8.1 Hz, 1H), 6.42 (d, J=8.4 Hz, 1H), 4.67 (q, J=6.5 Hz, 1H), 2.27 (s, 3H), 1.78-1.91 (m, 2H), 1.60-1.71 (m, 2H), 1.50 (d, J=13.1 Hz, 1H), 1.47 (d, J=6.6 Hz, 3H), 1.27 (dt, J=12.8, 6.2 Hz, 1H), 0.83-1.20 (m, 8H), 0.78 (br. s., 6H)

Enantiomer 2: LC-MS Anal. Calc'd for $C_{27}H_{36}FN_3O_4$ 485.27 found [M+H]468.27. $T_r$=1.874 min (Method B). $^1$H NMR (500 MHz, DMSO-$d_6$) δ: 9.29 (br. s., 1H), 8.34 (br. s., 1H), 7.64-7.73 (m, 2H), 7.02-7.10 (m, 2H), 6.96 (d, J=8.2 Hz, 1H), 6.42 (d, J=6.1 Hz, 1H), 4.67 (q, J=6.5 Hz, 1H), 2.27 (s, 3H), 1.78-1.92 (m, 2H), 1.60-1.72 (m, 2H), 1.49-1.54 (m, 1H), 1.47 (d, J=6.6 Hz, 3H), 1.28 (dt, J=12.9, 6.2 Hz, 1H), 0.83-1.21 (m, 8H), 0.78 (br. s., 6H)

Example 66

(±)-2-(3-(3-(4-cyanophenyl)ureido)-4-(cyclohexyl (isobutyl)amino)phenoxy)propanoic acid

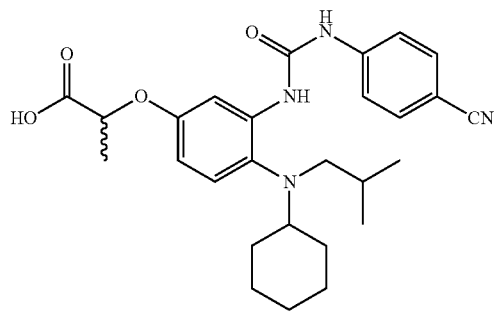 [SMILES: CC(C)CN(c1ccc(OC(C)C(=O)O)cc1NC(=O)Nc1ccc(C#N)cc1)C1CCCCC1]

Enantiomer 1 2-(3-(3-(4-cyanophenyl)ureido)-4-(cyclohexyl(isobutyl)amino)phenoxy)propanoic acid (Homochiral, Absolute Stereochemistry Unknown)

Enantiomer 2 2-(3-(3-(4-cyanophenyl)ureido)-4-(cyclohexyl(isobutyl)amino)phenoxy)propanoic acid (Homochiral, Absolute Stereochemistry Unknown)

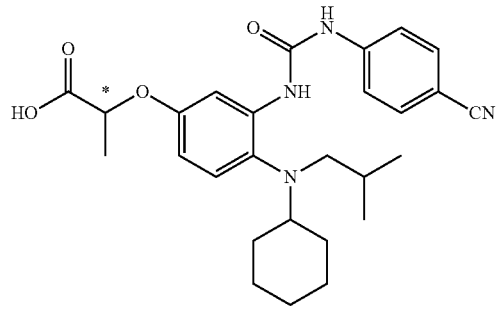 [SMILES: CC(C)CN(c1ccc(OC(C)C(=O)O)cc1NC(=O)Nc1ccc(C#N)cc1)C1CCCCC1]

Racemic Example 66 was obtained following the procedure for Racemic Example 58 using intermediate 58C and 4-aminobenzonitrile. LC-MS Anal. Calc'd for $C_{27}H_{34}N_4O_4$ 478.26, found [M+H] 479.26. $T_r$=1.721 min (Method B). $^1$H NMR (500 MHz, DMSO-$d_6$) δ: 10.07 (s, 1H), 8.37 (s, 1H), 7.67-7.74 (m, 2H), 7.61-7.65 (m, 2H), 7.03-7.13 (m, 2H), 6.43 (d, J=8.8 Hz, 1H), 4.66 (q, J=6.7 Hz, 1H), 1.83-1.94 (m, 2H), 1.58-1.70 (m, 2H), 1.46-1.52 (m, 1H), 1.45 (d, J=6.6 Hz, 3H), 1.25 (dt, J=13.1, 6.7 Hz, 1H), 0.85-1.19 (m, 8H), 0.77 (br. s., 6H)

Example 66 Enantiomer 1 and Enantiomer 2: Chiral separation of the racemic sample (Method E) gave Enantiomer 1—$T_r$=7.80 min (Method L) and Enantiomer 2—$T_r$=9.25 min (Method L) Absolute stereochemistry was not determined.

Enantiomer 1: LC-MS Anal. Calc'd for $C_{27}H_{34}N_4O_4$ 478.26, found [M+H]479.26. $T_r$=1.707 min (Method B). $^1$H NMR (500 MHz, DMSO-$d_6$) δ: 10.16 (br. s., 1H), 8.42 (br. s., 1H), 7.72-7.76 (m, 2H), 7.65-7.70 (m, 2H), 7.04-7.28 (m, 2H), 6.47 (d, J=6.1 Hz, 1H), 4.64-4.73 (m, J=6.7 Hz, 1H), 1.87-1.97 (m, 2H), 1.62-1.73 (m, 2H), 1.52 (d, J=0.9 Hz, 1H), 1.48 (d, J=6.6 Hz, 3H), 1.24-1.33 (m, J=6.6, 4.7 Hz, 1H), 0.84-1.22 (m, 8H), 0.80 (br. s., 6H)

Enantiomer 2: LC-MS Anal. Calc'd for $C_{27}H_{34}N_4O_4$ 478.26 found [M+H]479.26. $T_r$=1.707 min (Method B). $^1$H NMR (500 MHz, DMSO-$d_6$) δ: 10.14 (s, 1H), 8.42 (br. s., 1H), 7.72-7.76 (m, 2H), 7.71 (br. s., 1H), 7.65-7.69 (m, 2H), 7.12 (d, J=8.7 Hz, 1H), 6.46 (d, J=7.0 Hz, 1H), 4.69 (d, J=6.5 Hz, 1H), 1.91 (br. s., 2H), 1.67 (br. s., 2H), 1.51 (br. s., 1H), 1.48 (d, J=6.6 Hz, 3H), 1.23-1.31 (m, J=12.7, 6.4 Hz, 1H), 0.83-1.23 (m, 8H), 0.79 (br. s., 6H)

Example 67

(±)-ethyl 2-(3-(3-(4-chloro-2-fluorophenyl)ureido)-4-(cyclohexyl(isobutyl)amino)phenoxy)propanoate

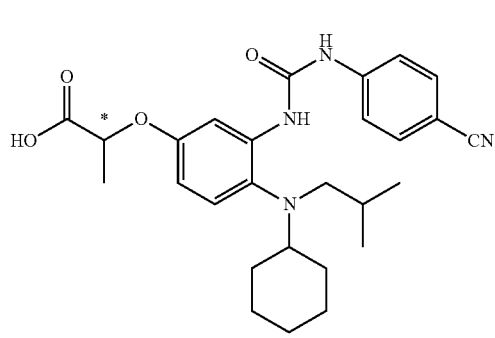 [SMILES: CC(C)CN(c1ccc(OC(C)C(=O)O)cc1NC(=O)Nc1ccc(C#N)cc1)C1CCCCC1]

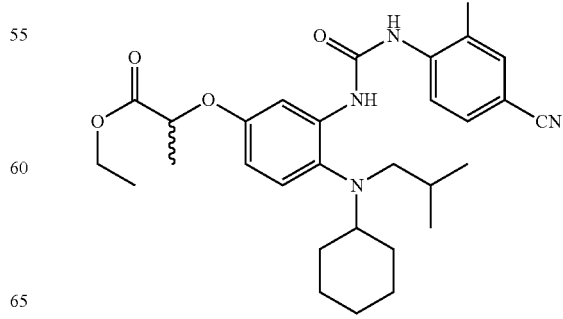

Enantiomer 1 ethyl 2-(3-(3-(4-chloro-2-fluorophenyl)ureido)-4-(cyclohexyl(isobutyl)amino)phenoxy)propanoate (Homochiral, Absolute Stereochemistry Unknown)

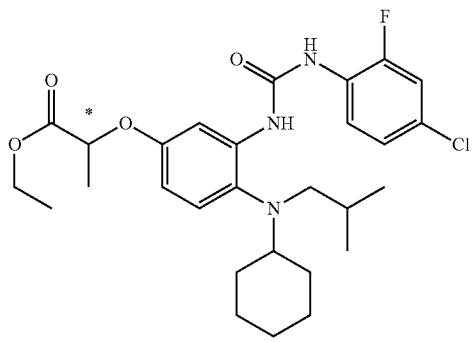 [SMILES: CCOC(=O)C(C)Oc1ccc(N(CC(C)C)C2CCCCC2)c(NC(=O)Nc2ccc(Cl)cc2F)c1]

Enantiomer 2 ethyl 2-(3-(3-(4-chloro-2-fluorophenyl)ureido)-4-(cyclohexyl(isobutyl)amino)phenoxy)propanoate (Homochiral, Absolute Stereochemistry Unknown)

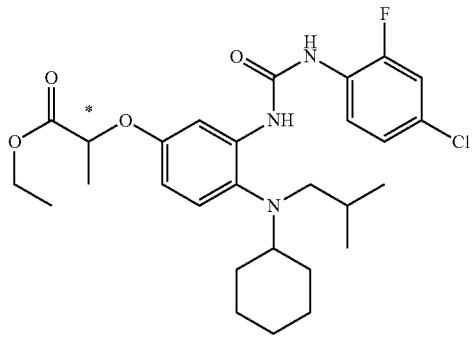 [SMILES: CCOC(=O)C(C)Oc1ccc(N(CC(C)C)C2CCCCC2)c(NC(=O)Nc2ccc(Cl)cc2F)c1]

A suspension of 58C (23 mg, 0.064 mmol) in THF (423 μl) was treated with 1-isocyanato-4-chloro-2-fluorobenzene (12 μl, 0.089 mmol). This reaction was concentrated in vacuo. The crude residue was dissolved in 2 mL DMF, filtered, and purified via preparatory HPLC to give racemic example 67 (10 mg, 0.054 mmol, 84%). LC-MS Anal. Calc'd for $C_{28}H_{37}ClFN_3O_4$ 533.25, found [M+H] 534.25. $T_r$=2.857 min (Method B). $^1$H NMR (500 MHz, DMSO-$d_6$) δ: 9.60 (s, 1H), 8.50 (s, 1H), 8.01 (t, J=8.8 Hz, 1H), 7.67 (d, J=2.6 Hz, 1H), 7.46 (d, J=11.0 Hz, 1H), 7.24 (d, J=8.3 Hz, 1H), 7.09 (d, J=8.7 Hz, 1H), 6.46 (dd, J=8.6, 2.7 Hz, 1H), 4.78 (q, J=6.7 Hz, 1H), 4.15 (q, J=7.1 Hz, 2H), 1.85-1.94 (m, 2H), 1.62-1.73 (m, 2H), 1.49-1.57 (m, 1H), 1.48 (d, J=6.6 Hz, 3H), 1.25-1.33 (m, 1H), 0.90-1.22 (m, 11H), 0.79 (br. s., 6H)

Example 67 Enantiomer 1 and Enantiomer 2: Chiral separation of the racemic sample (Method G) gave Enantiomer 1 $T_r$=5.05 min (Method O) and Enantiomer 2—$T_r$=6.10 min (Method O) Absolute stereochemistry was not determined.

Enantiomer 1: LC-MS Anal. Calc'd for $C_{28}H_{37}ClFN_3O_4$ 533.25, found [M+H]534.25. $T_r$=2.847 min (Method B). $^1$H NMR (500 MHz, DMSO-$d_6$) δ: 9.60 (s, 1H), 8.49 (s, 1H), 7.99 (t, J=8.8 Hz, 1H), 7.66 (d, J=2.6 Hz, 1H), 7.45 (d, J=10.9 Hz, 1H), 7.23 (d, J=9.0 Hz, 1H), 7.09 (d, J=8.8 Hz, 1H), 6.45 (dd, J=8.6, 2.7 Hz, 1H), 4.77 (q, J=6.5 Hz, 1H), 4.14 (q, J=7.0 Hz, 2H), 1.83-1.94 (m, 2H), 1.62-1.71 (m, 2H), 1.49-1.55 (m, 1H), 1.47 (d, J=6.6 Hz, 3H), 1.28 (dt, J=13.0, 6.5 Hz, 1H), 0.84-1.24 (m, 11H), 0.78 (br. s., 6H)

Enantiomer 2: LC-MS Anal. Calc'd for $C_{28}H_{37}ClFN_3O_4$ 533.25, found [M+H]534.25. $T_r$=2.841 min (Method B). $^1$H NMR (500 MHz, DMSO-$d_6$) δ: 9.60 (br. s., 1H), 8.49 (s, 1H), 7.99 (t, J=8.8 Hz, 1H), 7.65 (br. s., 1H), 7.45 (d, J=10.9 Hz, 1H), 7.23 (d, J=8.3 Hz, 1H), 7.09 (d, J=8.6 Hz, 1H), 6.45 (d, J=8.7 Hz, 1H), 4.77 (q, J=6.6 Hz, 1H), 4.14 (q, J=7.0 Hz, 2H), 1.82-1.93 (m, 2H), 1.61-1.70 (m, 2H), 1.49-1.54 (m, 1H), 1.47 (d, J=6.6 Hz, 3H), 1.28 (dt, J=12.9, 6.2 Hz, 1H), 0.89-1.23 (m, 11H), 0.78 (br. s., 6H)

Example 68

(±)-2-(4-(cyclohexyl(isobutyl)amino)-3-(3-(3-methylisoxazol-5-yl)ureido)phenoxy)propanoic acid

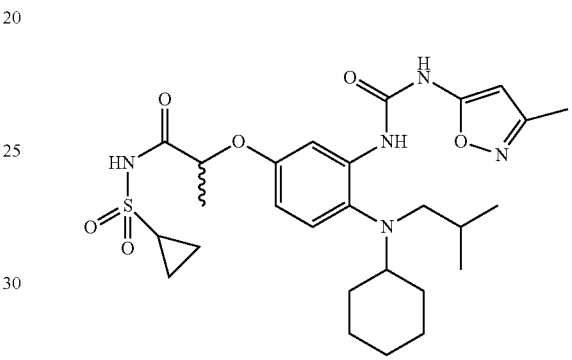

Racemic 68A: (±)-2-(4-(cyclohexyl(isobutyl)amino)-3-(3-(3-methylisoxazol-5-yl)ureido)phenoxy)propanoic acid Intermediate 58C (40 mg, 0.110 mmol) taken up in THF and phenyl (3-methylisoxazol-5-yl)carbamate (28.9 mg, 0.132 mmol) added along with triethylamine (23.07 μl, 0.166 mmol). Reaction heated to 60° C. After 1 hour, reaction cooled to room temperature. and stirred overnight. After 16 hours, water (1 mL), MeOH (0.3 mL) and lithium hydroxide (26.4 mg, 1.103 mmol) were added. After 3 hours, the reaction was concentrated in vacuo, acidified with 1N HCl, extracted with EtOAc, dried with sodium sulfate, filtered, and concentrated in vacuo. The crude residue was purified via silica gel column chromatography to give 68A (tan oil, 25 mg, 0.055 mmol, 49.4% yield).

Example 68

Intermediate 68A (25 mg, 0.055 mmol) was dissolved in THF (1090 μl) and N,N-carbonyldiimidazole (13.26 mg, 0.082 mmol) was added. The mixture was heated to reflux for 1 hour. After 1 hour, DBU (13.15 μl, 0.087 mmol) and cyclopropane sulfonamide (9.91 mg, 0.082 mmol) were added to the reaction at room temperature and reaction stirred at room temperature. After 2 hours, the reaction was concentrated in vacuo, taken up in DMF, filtered, and purified via preparative HPLC to give Racemic Example 68 (12.8 mg, 0.023 mmol, 41%). LC-MS Anal. Calc'd for $C_{27}H_{39}N_5O_6S$ 561.26, found [M+H] 562.26. $T_r$=1.781 min (Method B). $^1$H NMR (500 MHz, DMSO-$d_6$) δ: 8.50 (br. s., 1H), 7.69 (br. s., 1H), 7.13 (d, J=8.8 Hz, 1H), 6.46-6.52 (m, 1H), 5.94 (s, 1H), 4.60 (d, J=6.2 Hz, 1H), 2.81-2.88 (m, 1H), 2.17 (s, 3H), 1.84-1.95 (m, 2H), 1.68 (d, J=6.0 Hz, 2H), 1.51 (d, J=12.2 Hz, 1H), 1.43 (d, J=6.5 Hz, 3H), 1.25 (dd, J=13.0, 6.4 Hz, 1H), 0.83-1.22 (m, 12H), 0.79 (br. s., 6H)

Example 69

(±)-2-(4-(cyclohexyl(isobutyl)amino)-3-(3-(p-tolyl)ureido)phenoxy)-N-(cyclopropylsulfonyl)propanamide

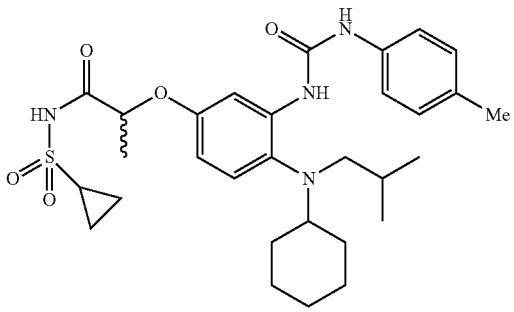 [SMILES: Cc1ccc(NC(=O)Nc2cc(OC(C)C(=O)NS(=O)(=O)C3CC3)ccc2N(CC(C)C)C2CCCCC2)cc1]

Racemic Example 69 was obtained following the procedure for Racemic Example 68 using Racemic Example 60 and cyclopropane sulfonamide. LC-MS Anal. Calc'd for $C_{30}H_{42}N_4O_5S$ 570.29, found [M+H] 571.29 $T_r$=2.000 min (Method B). $^1$H NMR (500 MHz, DMSO-$d_6$) δ: 9.45 (s, 1H), 8.18 (br. s., 1H), 7.76 (br. s., 1H), 7.35 (d, J=8.2 Hz, 2H), 7.09 (d, J=7.7 Hz, 3H), 6.43 (dd, J=8.6, 2.6 Hz, 1H), 4.69 (q, J=6.1 Hz, 1H), 2.90-2.96 (m, J=4.4 Hz, 1H), 2.24 (s, 3H), 1.82-1.95 (m, 2H), 1.67 (br. s., 2H), 1.51 (d, J=12.2 Hz, 1H), 1.46 (d, J=6.6 Hz, 3H), 1.28 (dt, J=13.0, 6.4 Hz, 1H), 0.89-1.20 (m, 12H), 0.80 (br. s., 6H)

Racemic Example 70

(±)-2-(3-(3-(4-chloro-2-fluorophenyl)ureido)-4-(cyclohexyl(isobutyl)amino)phenoxy)-N-(cyclopropylsulfonyl) propanamide

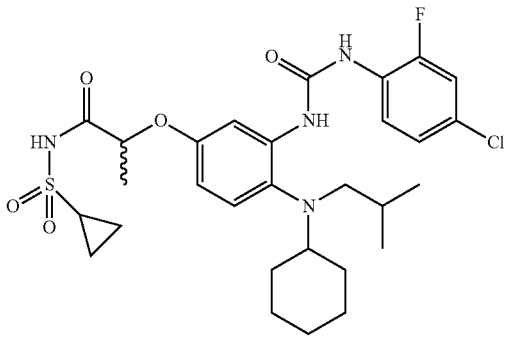 [SMILES: CC(C)CN(c1ccc(OC(C)C(=O)NS(=O)(=O)C2CC2)cc1NC(=O)Nc1ccc(Cl)cc1F)C1CCCCC1]

Racemic Example 70 was obtained following the procedure for Racemic Example 68 using Racemic Example 61 and cyclopropane sulfonamide. LC-MS Anal. Calc'd for $C_{29}H_{38}ClFN_4O_5S$ 608.22, found [M+H] 609.22 $T_r$=2.098 min (Method B). $^1$H NMR (500 MHz, DMSO-$d_6$) δ: 9.59 (s, 1H), 8.46 (s, 1H), 7.93-7.99 (m, 1H), 7.64 (d, J=2.5 Hz, 1H), 7.45 (dd, J=10.9, 2.0 Hz, 1H), 7.23 (d, J=8.5 Hz, 1H), 7.09 (d, J=8.8 Hz, 1H), 6.46 (dd, J=8.7, 2.7 Hz, 1H), 4.65 (d, J=6.6 Hz, 1H), 3.45-3.50 (m, 1H), 1.84-1.92 (m, 2H), 1.67 (br. s., 2H), 1.50 (d, J=12.1 Hz, 1H), 1.44 (d, J=6.6 Hz, 3H), 1.28 (dt, J=13.0, 6.4 Hz, 1H), 0.84-1.21 (m, 12H), 0.78 (br. s., 6H)

Racemic Examples 71-76

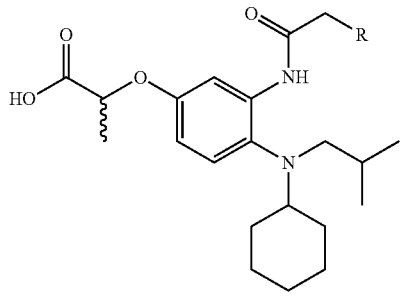

Examples 71-76 were prepared from racemic intermediate 58C following the procedure for Example 54 using the corresponding phenylacetic acids.

| Ex. No. | Name | R | Tr (min) Method B | [M + H]$^+$ |
|---|---|---|---|---|
| 71 | 2-(4-(cyclohexyl(isobutyl)amino)-3-(2-(2,4-difluorophenyl)acetamido)phenoxy)propanoic acid | 2,4-difluorophenyl | 1.938 | 489.25 |

| Ex. No. | Name | R | Tr (min) Method B | [M + H]+ |
|---|---|---|---|---|
| 72 | 2-(3-(2-(4-chloro-3-fluorophenyl) acetamido)-4-(cyclohexyl (isobutyl)amino)phenoxy)propanoic acid | 3-F, 4-Cl phenyl | 2.268 | 505.22 |
| 73 | 2-(3-(2-(4-chloro-2-fluorophenyl) acetamido-4-(cyclohexyl (isobutyl)amino)phenoxy) propanoic acid | 2-F, 4-Cl phenyl | 2.063 | 505.22 |
| 74 | 2-(4-(cyclohexyl(isobutyl)amino)-3-(2-(4-fluorophenyl)acetamido)phenoxy)propanoic acid | 4-F phenyl | 1.922 | 471.26 |
| 75 | 2-(4-(cyclohexyl(isobutyl)amino)-3-(2-(p-tolyl)acetamido) phenoxy)propanoic acid | p-tolyl | 2.035 | 467.28 |
| 76 | 2-(4-(cyclohexyl(isobutyl)amino)-3-(2-(2-fluoro-4-methylphenyl) acetamido)phenoxy)propanoic acid | 2-F, 4-Me phenyl | 2.030 | 485.27 |

Example 77

(±)-2-(3-(2-(4-chloro-2-fluorophenyl) acetamido)-4-(cyclohexyl(isobutyl)amino)phenoxy)-N-(cyclopropylsulfonyl) propanamide

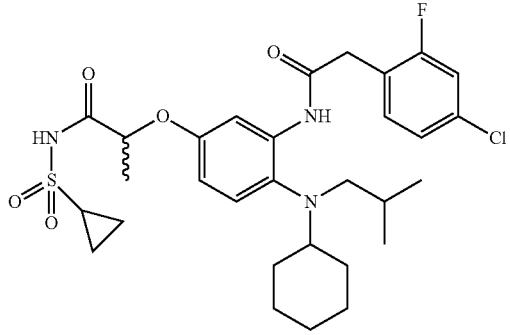 [SMILES: CC(C)CN(c1ccc(OC(C)C(=O)NS(=O)(=O)C2CC2)cc1NC(=O)Cc1ccc(Cl)cc1F)C1CCCCC1]

Racemic Example 77 was obtained following the procedure for Racemic Example 68 using Racemic Example 73 and cyclopropane sulfonamide. LC-MS Anal. Calc'd for $C_{30}H_{39}ClFN_3O_5S$ 607.23, found [M+H] 608.23 $T_r$=2.236 min (Method B). $^1$H NMR (500 MHz, DMSO-d$_6$) δ: 8.74 (br. s., 1H), 7.92 (br. s., 1H), 7.48 (d, J=5.4 Hz, 2H), 7.34 (d, J=7.2 Hz, 1H), 7.15 (d, J=8.5 Hz, 1H), 6.53 (d, J=6.1 Hz, 1H), 4.67 (br. s., 1H), 3.81 (br. s., 2H), 2.82-2.92 (m, 1H), 2.58-2.69 (m, 1H), 2.22-2.34 (m, 1H), 1.54-1.67 (m, 2H), 1.47-1.54 (m, 1H), 1.44 (d, J=5.8 Hz, 3H), 1.10-1.20 (m, J=6.4 Hz, 1H), 0.75-1.09 (m, 12H), 0.69 (br. s., 6H)

Example 78

(±)-2-(4-(cyclohexyl(isobutyl)amino)-3-(2-(p-tolyl) acetamido)phenoxy)-N-(cyclopropylsulfonyl)propanamide

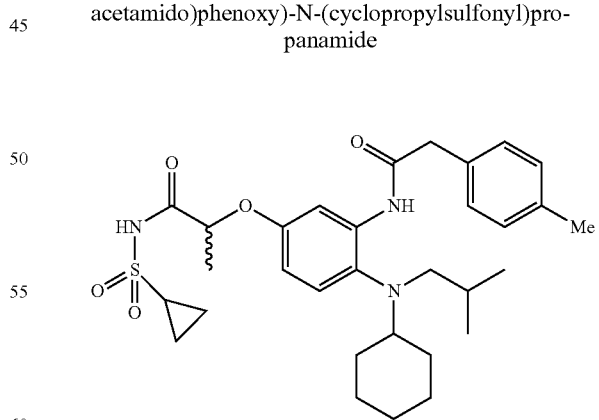

Racemic Example 78 was obtained following the procedure for Racemic Example 68 using Racemic Example 75 and cyclopropane sulfonamide. LC-MS Anal. Calc'd for $C_{31}H_{43}N_3O_5S$ 569.29, found [M+H] 570.29 $T_r$=2.229 min (Method B). $^1$H NMR (500 MHz, DMSO-d$_6$) δ: 8.66 (s, 1H), 7.94 (br. s., 1H), 7.19-7.24 (m, 2H), 7.15-7.19 (m, 2H), 7.08

(d, J=8.8 Hz, 1H), 6.49 (d, J=8.7 Hz, 1H), 4.56 (d, J=5.5 Hz, 1H), 3.68 (br. s., 2H), 2.82 (br. s., 1H), 2.28 (s, 3H), 2.17 (br. s., 2H), 1.55 (d, J=9.1 Hz, 2H), 1.46 (d, J=8.7 Hz, 1H), 1.41 (d, J=6.3 Hz, 3H), 1.06-1.17 (m, 1H), 0.71-1.04 (m, 12H), 0.67 (d, J=4.8 Hz, 6H)

Example 79

(±)-2-(3-(2-(4-chloro-3-fluorophenyl) acetamido)-4-(cyclohexyl(isobutyl)amino)phenoxy)-N-(cyclopropylsulfonyl) propanamide

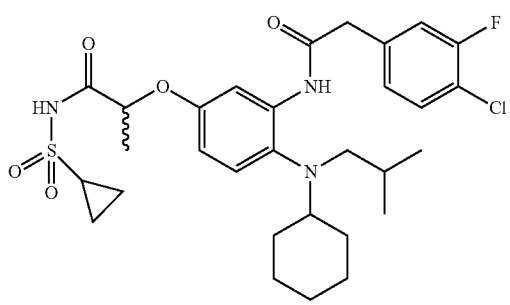 [SMILES: CC(C)CN(c1ccc(OC(C)C(=O)NS(=O)(=O)C2CC2)cc1NC(=O)Cc1ccc(Cl)c(F)c1)C1CCCCC1]

Racemic Example 79 was obtained following the procedure for Racemic Example 68 using Racemic Example 72 and cyclopropane sulfonamide. LC-MS Anal. Calc'd for $C_{30}H_{38}ClFN_3O_5S$ 607.23, found [M+H] 608.23, $T_r$=2.188 min (Method B). $^1$H NMR (500 MHz, DMSO-$d_6$) δ: 8.66 (s, 1H), 7.93 (br. s., 1H), 7.60 (t, J=8.1 Hz, 1H), 7.45 (d, J=10.0 Hz, 1H), 7.24 (d, J=7.9 Hz, 1H), 7.13 (d, J=8.8 Hz, 1H), 6.52 (dd, J=8.5, 2.4 Hz, 1H), 4.66 (br. s., 1H), 3.83 (s, 2H), 2.84-2.90 (m, 1H), 2.19-2.28 (m, 2H), 1.59 (d, J=11.0 Hz, 2H), 1.48 (d, J=10.4 Hz, 1H), 1.44 (d, J=6.5 Hz, 3H), 1.13 (dt, J=12.8, 6.2 Hz, 1H), 0.79-1.05 (m, 12H), 0.68 (d, J=6.0 Hz, 6H)

Example 80

Enantiomer 1 and Enantiomer 2

Enantiomer 1: 2-(3-(3-(4-chloro-2-fluorophenyl)ureido)-4-(cyclohexyl(isobutyl)amino)phenoxy)butanoic acid (Homochiral, Stereochemistry Unknown)

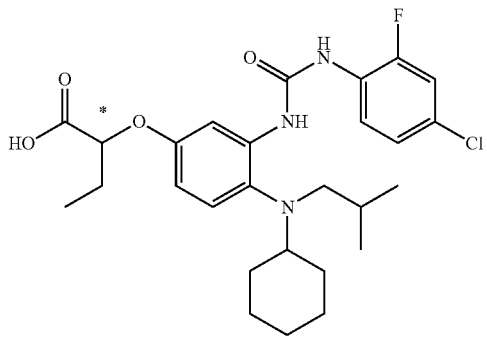 [SMILES: CCC(Oc1ccc(N(CC(C)C)C2CCCCC2)c(NC(=O)Nc2ccc(Cl)cc2F)c1)C(=O)O]

Enantiomer 2: 2-(3-(3-(4-chloro-2-fluorophenyl)ureido)-4-(cyclohexyl(isobutyl)amino)phenoxy)butanoic acid (Homochiral, Stereochemistry Unknown

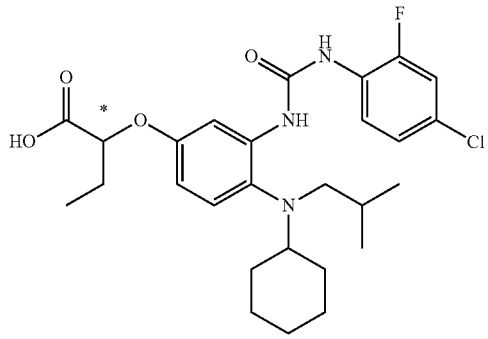 [SMILES: CCC(Oc1ccc(N(CC(C)C)C2CCCCC2)c(NC(=O)Nc2ccc(Cl)cc2F)c1)C(=O)O]

80A. Racemic ethyl 2-(4-fluoro-3-nitrophenoxy)butanoate 4-fluoro-3-nitrophenol (500 mg, 3.18 mmol) was dissolved in DMF (6365 μl) at room temperature. Cesium Carbonate (1244 mg, 3.82 mmol) was added followed by methyl 2-bromobutanoate (403 μl, 3.50 mmol). The mixture was stirred at 60° C. After 2 hours, the reaction was diluted with water and brine (1:1) and extracted with EtOAc. The organics were combined, dried with sodium sulfate, filtered, and concentrated in vacuo. The crude oil was dried on high vac to give intermediate 80A (tan oil, 787 mg, 3.06 mmol, 96% yield) as a tan oil. LC-MS Anal. Calc'd for $C_{11}H_{12}FNO_5$ 257.70, $T_r$=0.92 min (Method A) (Note: product does not ionize well). $^1$H NMR (400 MHz, chloroform-d) δ: 7.51 (dd, J=5.9, 2.9 Hz, 1H), 7.13-7.23 (m, 2H), 4.60 (dd, J=6.7, 5.4 Hz, 1H), 3.77 (s, 3H), 1.96-2.09 (m, 2H), 1.08 (t, J=7.4 Hz, 3H)

80B. Racemic ethyl 2-(4-(cyclohexyl(isobutyl)amino)-3-nitrophenoxy)butanoate

Intermediate 80A (0.78 g, 3.03 mmol) was dissolved in Ethanol (3.03 ml). Intermediate 1B (1.413 g, 9.10 mmol) was added and the reaction was heated to 100° C. in a sealed tube. After 48 hours, the reaction was diluted with EtOAc, washed with 1N HCl, dried with sodium sulfate, filtered, and concentrated in vacuo. The crude residue was purified via silica gel column chromatography to 80B (orange oil, 0.476 g, 1.171 mmol, 38.6% yield). LC-MS Anal. Calc'd for $C_{22}H_{34}N_2O_5$ 406.25, found [M+H] 407.5, $T_r$=1.27 min (Method A). $^1$H NMR (400 MHz, chloroform-d) δ: 7.16-7.19 (m, 1H), 7.12 (d, J=2.9 Hz, 1H), 6.99 (dd, J=9.0, 3.1 Hz, 1H), 4.49 (dd, J=6.7, 5.6 Hz, 1H), 4.24 (q, J=7.1 Hz, 2H), 2.78-2.83 (m, 1H), 2.77 (d, J=7.0 Hz, 2H), 1.94-2.04 (m, 2H), 1.82 (d, J=10.8 Hz, 2H), 1.74 (d, J=12.6 Hz, 2H), 1.55-1.62 (m, 1H), 1.46 (dt, J=13.4, 6.7 Hz, 1H), 1.10-1.38 (m, 8H), 1.05-1.10 (m, 3H), 0.81 (d, J=6.6 Hz, 6H)

80C. Racemic ethyl 2-(3-amino-4-(cyclohexyl(isobutyl)amino)phenoxy)butanoate

To a stirred solution of 80B (0.279, 0.686 mmol) in Ethanol (6.86 ml) was added 0.69 mL of water. The solution was then treated with zinc (0.269 g, 4.12 mmol) and ammonium chloride (0.220 g, 4.12 mmol). This mixture was stirred at room temperature. After 3 hours, the reaction was filtered, concentrated, diluted with EtOAc, washed with NaHCO$_3$, dried with sodium sulfate, filtered, and concentrated. The crude product was purified on via silica gel column chromatography to give 80C (clear oil, 153 mg, 0.407 mmol, 59%). LC-MS Anal. Calc'd for C$_{22}$H$_{36}$N$_2$O$_3$ 376.26, found [M+H] 377.2, T$_r$=0.88 min (Method A). $^1$H NMR (400 MHz, chloroform-d) δ: 6.91 (d, J=8.7 Hz, 1H), 6.30 (d, J=2.9 Hz, 1H), 6.19 (dd, J=8.6, 2.9 Hz, 1H), 4.46 (t, J=6.3 Hz, 1H), 4.22 (qd, J=7.1, 3.2 Hz, 2H), 4.09 (br. s., 2H), 1.93 (dd, J=7.3, 6.4 Hz, 2H), 1.77-1.89 (m, 2H), 1.73 (d, J=13.3 Hz, 2H), 1.57-1.63 (m, 1H), 1.37-1.49 (m, 1H), 1.25 (td, J=7.1, 6.5 Hz, 3H), 1.10-1.36 (m, 8H), 1.02-1.09 (m, 3H), 0.81 (d, J=5.9 Hz, 6H)

Racemic Example 80. (±)-2-(3-(3-(4-chloro-2-fluorophenyl)ureido)-4-(cyclohexyl(isobutyl)amino)phenoxy)butanoic acid A suspension of 80C (50 mg, 0.133 mmol) in THF (443 μl) was treated with 4-chloro-2-fluoro-1-isocyanatobenzene (23.55 μl, 0.186 mmol). After 1 hour, the reaction was diluted with more THF (443 μl) and Water (1 mL) and MeOH (0.5 mL) were added. Lithium hydroxide (31.8 mg, 1.328 mmol) was then added and the reaction stirred at room temperature. After 1 hour, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Racemic Example 80 (33 mg, 0.064 mmol, 48% yield). LC-MS Anal. Calc'd for C$_{27}$H$_{35}$ClFN$_3$O$_4$ 519.23, found [M+H]520.23 T$_r$=1.94 min (Method C).

Example 80 Enantiomer 1 and Enantiomer 2: Chiral separation of the racemic sample (Method E) gave Enantiomer 1—T$_r$=7.05 min (Method L) and Enantiomer 2 T$_r$=9.25 min (Method L) Absolute stereochemistry was not determined.

Enantiomer 1: LC-MS Anal. Calc'd for C$_{27}$H$_{35}$ClFN$_3$O$_4$ 519.23, found [M+H]520.23 T$_r$=1.91 min (Method C). $^1$H NMR (500 MHz, DMSO-d$_6$) δ: 9.59 (s, 1H), 8.48 (s, 1H), 7.99 (t, J=8.8 Hz, 1H), 7.66 (d, J=2.8 Hz, 1H), 7.46 (dd, J=11.0, 2.1 Hz, 1H), 7.24 (d, J=8.3 Hz, 1H), 7.09 (d, J=8.8 Hz, 1H), 6.45 (dd, J=8.7, 2.8 Hz, 1H), 4.49 (t, J=5.9 Hz, 1H), 1.77-1.94 (m, 4H), 1.64-1.71 (m, 2H), 1.51 (d, J=11.8 Hz, 1H), 1.29 (dt, J=13.1, 6.5 Hz, 1H), 1.05-1.18 (m, 7H), 0.99 (t, J=7.3 Hz, 3H), 0.90-1.03 (m, 1H), 0.80 (br. s., 6H)

Enantiomer 2: LC-MS Anal. Calc'd for C$_{27}$H$_{35}$ClFN$_3$O$_4$ 519.23, found [M+H]520.23 T$_r$=1.92 min (Method C). $^1$H NMR (500 MHz, DMSO-d$_6$) δ: 9.59 (s, 1H), 8.48 (s, 1H), 7.99 (t, J=8.8 Hz, 1H), 7.66 (d, J=2.7 Hz, 1H), 7.46 (dd, J=11.0, 2.1 Hz, 1H), 7.24 (d, J=8.4 Hz, 1H), 7.09 (d, J=8.8 Hz, 1H), 6.45 (dd, J=8.7, 2.7 Hz, 1H), 4.49 (t, J=5.9 Hz, 1H), 1.78-1.93 (m, 4H), 1.67 (d, J=4.2 Hz, 2H), 1.51 (d, J=11.9 Hz, 1H), 1.29 (dt, J=13.2, 6.6 Hz, 1H), 1.05-1.18 (m, 8H), 0.99 (t, J=7.4 Hz, 3H), 0.80 (br. s., 6H)

Example 81

Enantiomer 1 and Enantiomer 2

Enantiomer 1: 2-(4-(cyclohexyl(isobutyl)amino)-3-(3-(2-fluorophenyl)ureido)phenoxy)butanoic acid (Homochiral, Stereochemistry Unknown)

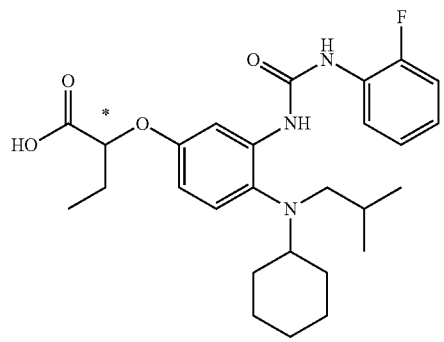 [SMILES: CCC(Oc1ccc(N(CC(C)C)C2CCCCC2)c(NC(=O)Nc2ccccc2F)c1)C(=O)O]

Enantiomer 2: 2-(4-(cyclohexyl(isobutyl)amino)-3-(3-(2-fluorophenyl)ureido)phenoxy)butanoic acid (Homochiral, Stereochemistry Unknown)

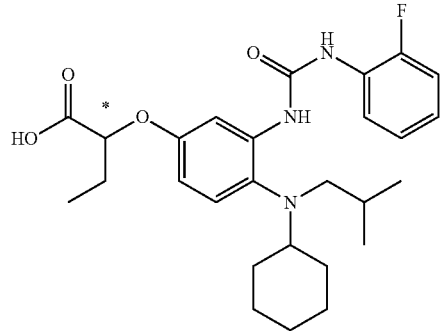 [SMILES: CCC(Oc1ccc(N(CC(C)C)C2CCCCC2)c(NC(=O)Nc2ccccc2F)c1)C(=O)O]

Racemic Example 81: (±)-2-(4-(cyclohexyl(isobutyl)amino)-3-(3-(2-fluorophenyl)ureido)phenoxy)butanoic acid Racemic Example 81 was obtained following the procedure for Racemic Example 58 using intermediate 80C and 2-fluoroaniline. LC-MS Anal. Calc'd for C$_{27}$H$_{36}$FN$_3$O$_4$ 485.27, found [M+H] 486.6. T$_r$=0.95 min (Method A).

Example 81 Enantiomer 1 and Enantiomer 2: Chiral separation of the racemic sample (Method D) gave Enantiomer 1 T$_r$=4.95 min (Method K) and Enantiomer 2-T$_r$=6.20 min (Method K) Absolute stereochemistry was not determined.

Enantiomer 1: LC-MS Anal. Calc'd for C$_{27}$H$_{36}$FN$_3$O$_4$ 485.27, found [M+H]486.27. T$_r$=1.80 min (Method C). $^1$H NMR (500 MHz, DMSO-d$_6$) δ: 9.45 (s, 1H), 8.41 (s, 1H), 7.89 (t, J=7.8 Hz, 1H), 7.64 (br. s., 1H), 7.19-7.26 (m, 1H), 7.12-7.17 (m, 1H), 7.06 (d, J=8.6 Hz, 2H), 6.43 (d, J=6.2 Hz, 1H), 4.44 (br. s., 1H), 1.76-1.91 (m, 4H), 1.61-1.70 (m, 1H), 1.50 (d, J=11.9 Hz, 1H), 1.23-1.32 (m, 1H), 1.01-1.18 (m, 8H), 0.98 (t, J=7.3 Hz, 4H), 0.78 (br. s., 6H)

Enantiomer 2: LC-MS Anal. Calc'd for C$_{27}$H$_{36}$FN$_3$O$_4$ 485.27, found [M+H]486.27. T$_r$=1.80 min (Method C). $^1$H NMR (500 MHz, DMSO-d$_6$) δ: 9.44 (s, 1H), 8.40 (br. s., 1H), 7.89 (t, J=8.3 Hz, 1H), 7.62 (br. s., 1H), 7.20-7.25 (m, 1H), 7.13 (d, J=7.8 Hz, 1H), 7.03-7.10 (m, 2H), 6.43 (d, J=6.8 Hz, 1H), 4.34-4.41 (m, 1H), 1.73-1.92 (m, 4H), 1.67 (br. s., 2H), 1.50 (d, J=11.8 Hz, 1H), 1.28 (dt, J=13.2, 6.7 Hz, 1H), 1.00-1.15 (m, 8H), 0.97 (t, J=7.2 Hz, 3H), 0.78 (br. s., 6H)

Example 82

Enantiomer 1 and Enantiomer 2

Enantiomer 1: 2-(4-(cyclohexyl(isobutyl)amino)-3-(3-(p-tolyl)ureido)phenoxy)butanoic acid (Homochiral, Stereochemistry Unknown)

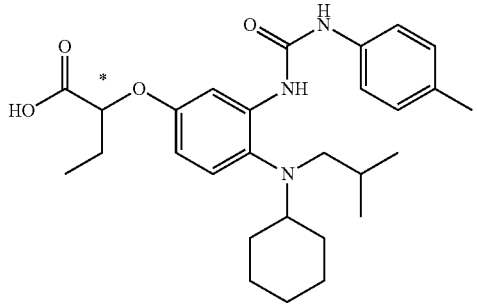 [SMILES: CCC(Oc1ccc(N(CC(C)C)C2CCCCC2)c(NC(=O)Nc2ccc(C)cc2)c1)C(=O)O]

Enantiomer 2: 2-(4-(cyclohexyl(isobutyl)amino)-3-(3-(p-tolyl)ureido)phenoxy)butanoic acid (Homochiral, Stereochemistry Unknown)

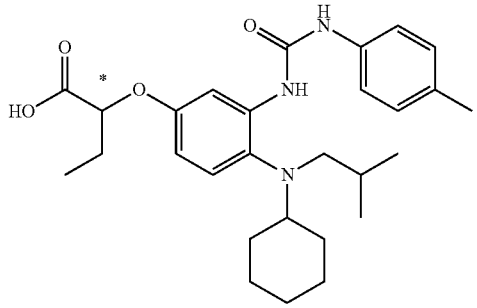 [SMILES: CCC(Oc1ccc(N(CC(C)C)C2CCCCC2)c(NC(=O)Nc2ccc(C)cc2)c1)C(=O)O]

Example 82: (±)-2-(4-(cyclohexyl(isobutyl)amino)-3-(3-(p-tolyl)ureido)phenoxy)butanoic acid Racemic Example 82 was obtained following the procedure for Racemic Example 80 using intermediate 80C and 1-isocyanato-4-methylbenzene. LC-MS Anal. Calc'd for $C_{27}H_{37}N_3O_4$ 481.29, found [M+H] 482.3 $T_r$=0.98 min (Method A).

Example 81 Enantiomer 1 and Enantiomer 2: Chiral separation of the racemic sample (Method D) gave Enantiomer 1-$T_r$=6.77 min (Method K) and Enantiomer 2 $T_r$=8.38 min (Method K) Absolute stereochemistry was not determined.

Enantiomer 1: LC-MS Anal. Calc'd for $C_{27}H_{37}N_3O_4$ 481.29, found [M+H]482.29. $T_r$=1.87 min (Method C). $^1$H NMR (500 MHz, DMSO-$d_6$) δ: 9.43 (s, 1H), 8.18 (br. s., 1H), 7.72 (br. s., 1H), 7.34 (d, J=8.2 Hz, 2H), 7.04-7.12 (m, 3H), 6.40 (d, J=8.7 Hz, 1H), 4.46 (t, J=5.5 Hz, 1H), 2.24 (s, 3H), 1.77-1.93 (m, 4H), 1.67 (br. s., 2H), 1.50 (d, J=12.1 Hz, 1H), 1.23-1.30 (m, 1H), 1.02-1.18 (m, 6H), 0.98 (t, J=7.3 Hz, 3H), 0.79 (br. s., 6H)

Enantiomer 2: LC-MS Anal. Calc'd for $C_{27}H_{37}N_3O_4$ 481.29, found [M+H]482.29. $T_r$=1.87 min (Method C). $^1$H NMR (DMSO-$d_6$) δ: 9.43 (s, 1H), 8.18 (br. s., 1H), 7.72 (br. s., 1H), 7.34 (d, J=8.2 Hz, 2H), 7.04-7.13 (m, 3H), 6.40 (d, J=6.4 Hz, 1H), 4.46 (br. s., 1H), 2.23 (s, 3H), 1.76-1.91 (m, 4H), 1.66 (d, J=4.2 Hz, 2H), 1.50 (d, J=11.9 Hz, 1H), 1.21-1.31 (m, 1H), 1.03-1.16 (m, 6H), 0.98 (t, J=7.3 Hz, 3H), 0.79 (br. s., 6H)

Example 83

(±)-ethyl 2-(4-fluoro-3-nitrophenoxy)-3-methylbutanoate

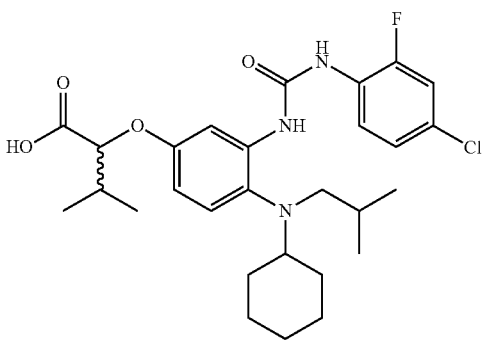 [SMILES: CC(C)CN(c1ccc(OC(C(=O)O)C(C)C)cc1NC(=O)Nc1ccc(Cl)cc1F)C1CCCCC1]

83A. Racemic ethyl 2-(4-fluoro-3-nitrophenoxy)-3-methylbutanoate 4-fluoro-3-nitrophenol (500 mg, 3.18 mmol) was dissolved in DMF (6.365 mL) at room temperature. Cesium Carbonate (1244 mg, 3.82 mmol) was added followed by ethyl 2-bromo-3-methylbutanoate (0.574 mL, 3.50 mmol). The mixture was stirred at 60° C. Reaction left at 60° C. overnight. Reaction was then diluted with water and a precipitate formed. The solid was filtered off and dried on high vacuum overnight to yield 83A (tan solid, 615 mg, 2.156 mmol, 67.7% yield). yield). LC-MS Anal. Calc'd for $C_{13}H_{16}FNO_5$ 285.10, $T_r$=1.04 min (Method A) (Note: product does not ionize well). $^1$H NMR (400 MHz, MeOH-$d_4$) δ: 7.60 (dd, J=6.0, 3.3 Hz, 1H), 7.53 (dd, J=10.9, 9.3 Hz, 1H), 7.38 (s, 1H), 4.84 (d, J=4.8 Hz, 1H), 4.16 (dd, J=7.1, 2.8 Hz, 2H), 2.20-2.30 (m, 1H), 1.15-1.20 (m, 3H), 1.01 (dd, J=6.8, 4.6 Hz, 6H)

83B. Racemic ethyl 2-(4-(cyclohexyl(isobutyl) amino)-3-nitrophenoxy)-3-methylbutanoate Intermediate 83A (0.614 g, 2.152 mmol) was dissolved in Ethanol (2.152 ml). Intermediate 1B (1.003 g, 6.46 mmol) was added and the reaction was heated to 100° C. in a sealed tube. After 48 hours, the reaction was diluted with EtOAc, washed with 1N HCl, dried with sodium sulfate, filtered, and concentrated in vacuo. Purification via silica gel column chromatography gave 83B (orange oil, 0.135 g, 0.321 mmol, 14.91% yield). LC-MS Anal. Calc'd for $C_{23}H_{36}N_2O_5$ 420.26, found [M+H] 421.5, $T_r$=1.30 min (Method A). $^1$H NMR (400 MHz, chloroform-d) δ: 7.18 (d, J=9.0 Hz, 1H), 7.12 (d, J=3.1 Hz, 1H), 6.99 (dd, J=9.0, 3.1 Hz, 1H), 4.31 (d, J=5.4 Hz, 1H), 4.24 (q, J=7.1 Hz, 2H), 2.78-2.85 (m, 1H), 2.76 (d, J=7.1 Hz, 2H), 2.24-2.33 (m, 1H), 1.81 (d, J=10.8 Hz, 2H), 1.74 (d, J=12.6 Hz, 2H), 1.58 (d, J=7.9 Hz, 1H), 1.45 (dt, J=13.3, 6.6 Hz, 1H), 1.10-1.38 (m, 7H), 1.07 (dd, J=6.8, 3.6 Hz, 6H), 0.82-0.87 (m, 1H), 0.81 (d, J=6.6 Hz, 6H)

83C. Racemic ethyl 2-(3-amino-4-(cyclohexyl (isobutyl)amino)phenoxy)-3-methylbutanoate To a stirred solution of Intermediate 83B (153 mg, 0.364 mmol) in Ethanol (3638 μl) was added 0.36 mL of water. The solution was then treated with zinc (143 mg, 2.183 mmol) and ammonium chloride (117 mg, 2.183 mmol). This mixture was stirred at room temperature. After 1 hour, the reaction was filtered, diluted with EtOAc, washed with NaHCO₃, dried with Sodium sulfate, filtered, and concentrated to give 83C (colorless oil, 110 mg, 280 mg, 77%). LC-MS Anal. Calc'd for $C_{23}H_{38}N_2O_3$ 390.27, found [M+H] 391.4, $T_r$=0.91 min (Method A).

Example 83

A suspension 83C (55 mg, 0.141 mmol) in THF (469 μl) was treated with 4-chloro-2-fluoro-1-isocyanatobenzene (24.98 μl, 0.197 mmol). After one hour, the reaction was diluted with more THF (469 μl) and Water (1 mL) and MeOH (0.5 mL) were added. Lithium hydroxide (33.7 mg, 1.408 mmol) was then added and the reaction stirred at room temperature for 2 hours. The reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Racemic Example 83 (4.1 mg, 0.008 mmol, 5.5%). LC-MS Anal. Calc'd for $C_{28}H_{37}ClFN_3O_4$ 533.25, found [M+H]534.25 $T_r$=2.07 min (Method C). ¹H NMR (500 MHz, DMSO-d₆) δ: 9.59 (s, 1H), 8.48 (s, 1H), 8.00 (t, J=8.8 Hz, 1H), 7.66 (d, J=2.4 Hz, 1H), 7.46 (dd, J=11.0, 2.1 Hz, 1H), 7.23 (d, J=8.8 Hz, 1H), 7.07 (d, J=8.8 Hz, 1H), 6.45 (dd, J=8.7, 2.7 Hz, 1H), 4.29 (d, J=4.6 Hz, 1H), 2.09-2.21 (m, J=12.1, 6.5 Hz, 1H), 1.84-1.94 (m, 2H), 1.62-1.72 (m, 2H), 1.51 (d, J=11.7 Hz, 1H), 1.25-1.35 (m, 1H), 1.10 (br. s., 5H), 1.00 (dd, J=6.5, 3.2 Hz, 9H), 0.80 (br. s., 6H)

Example 84

(±)-2-(4-(cyclohexyl(isobutyl)amino)-3-(3-(p-tolyl) ureido)phenoxy)-3-methylbutanoic acid

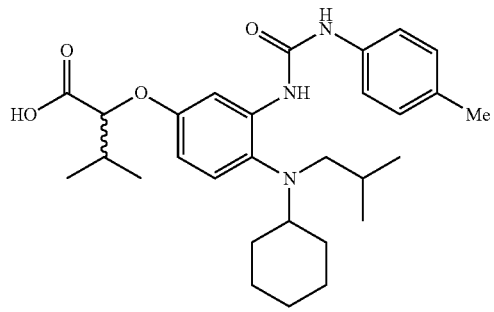 [SMILES: Cc1ccc(NC(=O)Nc2cc(OC(C(=O)O)C(C)C)ccc2N(CC(C)C)C2CCCCC2)cc1]

Racemic Example 84 was obtained following the procedure used to prepare Racemic Example 83 from intermediate 83C and 1-isocyanato-4-methylbenzene. LC-MS Anal. Calc'd for $C_{29}H_{41}N_3O_4$ 495.31, found [M+H] 496.31 $T_r$=1.99 min (Method C). ¹H NMR (500 MHz, DMSO-d₆) δ: 9.44 (s, 1H), 8.19 (br. s., 1H), 7.75 (br. s., 1H), 7.35 (d, J=8.2 Hz, 2H), 7.09 (d, J=8.0 Hz, 3H), 6.41 (d, J=6.7 Hz, 1H), 4.34 (d, J=4.9 Hz, 1H), 2.24 (s, 3H), 2.17 (dd, J=12.5, 6.4 Hz, 1H), 1.89 (d, J=4.4 Hz, 2H), 1.63-1.72 (m, 2H), 1.51 (d, J=11.2 Hz, 1H), 1.21-1.33 (m, 1H), 1.05-1.18 (m, 3H), 1.01 (dd, J=6.6, 3.7 Hz, 10H), 0.70-0.89 (m, 7H)

Example 85

Enantiomer 1 and Enantiomer 2

Enantiomer 1 2-(3-(3-(4-chloro-2-fluorophenyl) ureido)-4-(cyclohexyl(isobutyl)amino)phenoxy)pentanoic acid (Homochiral, Stereochemistry Unknown)

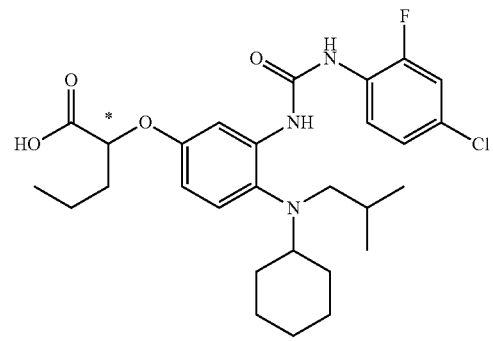 [SMILES: CCCC(Oc1ccc(N(CC(C)C)C2CCCCC2)c(NC(=O)Nc2ccc(Cl)cc2F)c1)C(=O)O]

Enantiomer 2 2-(3-(3-(4-chloro-2-fluorophenyl) ureido)-4-(cyclohexyl(isobutyl)amino)phenoxy)pentanoic acid (Homochiral, Stereochemistry Unknown)

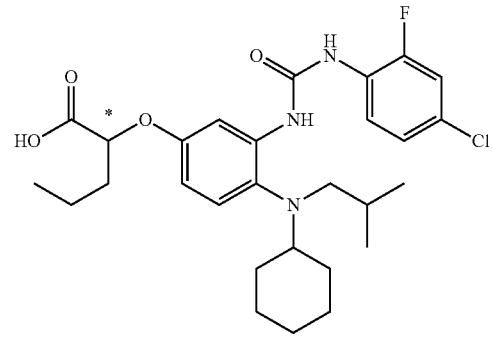 [SMILES: CCCC(Oc1ccc(N(CC(C)C)C2CCCCC2)c(NC(=O)Nc2ccc(Cl)cc2F)c1)C(=O)O]

85A. Racemic ethyl 2-(4-fluoro-3-nitrophenoxy)pentanoate 4-fluoro-3-nitrophenol (500 mg, 3.18 mmol) was dissolved in DMF (6.365 mL) at room temperature. Cesium Carbonate (1244 mg, 3.82 mmol) was added followed by ethyl 2-bromopentanoate (0.597 mL, 3.50 mmol). The mixture was stirred at 60° C. After 2 hours, the reaction was then diluted with water and brine (1:1) and extracted with EtOAc. The organics were combined, dried with sodium sulfate, filtered, and concentrated in vacuo. The resulting oil was dried to give 85A (tan oil, 863 mg, 3.03 mmol, 95% yield). LC-MS Anal. Calc'd for $C_{13}H_{16}FNO_5$ 285.10, $T_r$=0.95 min (Method A) (Note: product does not ionize well). $^1$H NMR (400 MHz, chloroform-d) δ: 7.50 (dd, J=5.8, 2.9 Hz, 1H), 7.12-7.23 (m, 2H), 4.58-4.63 (m, 1H), 4.23 (qd, J=7.1, 2.0 Hz, 2H), 1.87-2.03 (m, 2H), 1.47-1.60 (m, 2H), 1.27 (t, J=7.1 Hz, 3H), 0.99 (t, J=7.4 Hz, 3H)

85B. Racemic ethyl 2-(4-(cyclohexyl(isobutyl)amino)-3-nitrophenoxy)pentanoate

Intermediate 85A (0.863 g, 3.03 mmol) was dissolved in Ethanol (3.03 ml). Intermediate 1B (1.409 g, 9.08 mmol) was added and the reaction was heated to 100° C. in a sealed tube. After 48 hours, the reaction was diluted with EtOAc, washed with 1N HCl, dried with sodium sulfate, filtered, and concentrated in vacuo. Purification on silica gel column chromatography gave intermediate 85B (0.505 g, 1.201 mmol, 39.7% yield). LC-MS Anal. Calc'd for $C_{23}H_{36}N_2O_5$ 420.26, found [M+H] 421.5, $T_r$=1.30 min (Method A). $^1$H NMR (400 MHz, chloroform-d) δ: 7.15-7.18 (m, 1H), 7.11 (d, J=3.1 Hz, 1H), 6.98 (dd, J=8.9, 3.1 Hz, 1H), 4.54 (dd, J=7.7, 5.0 Hz, 1H), 4.20-4.27 (m, 2H), 2.72-2.84 (m, 3H), 1.87-1.99 (m, 2H), 1.81 (d, J=10.8 Hz, 2H), 1.74 (d, J=12.8 Hz, 2H), 1.56-1.62 (m, 2H), 1.41-1.54 (m, 3H), 1.11-1.36 (m, 6H), 0.94-1.09 (m, 4H), 0.81 (d, J=6.6 Hz, 6H)

85C. Racemic ethyl 2-(3-amino-4-cyclohexyl(isobutyl)amino)phenoxy)pentanoate

To a stirred solution of 85B (0.332 g, 0.789 mmol) in Ethanol (7.89 ml) was added 0.14 mL of water. The solution was then treated with zinc (0.310 g, 4.74 mmol) and ammonium chloride (0.253 g, 4.74 mmol). This mixture was stirred at room temperature. After 1 hour, the reaction was filtered, diluted with EtOAc, washed with NaHCO$_3$, dried with Sodium sulfate, filtered, and concentrated. Crude product was purified with silica gel column chromatography to give 85C (171 mg, 0.434 mmol, 56%). LC-MS Anal. Calc'd for $C_{23}H_{38}N_2O_3$ 390.28, found [M+H] 391.3, $T_r$=0.92 min (Method A).

Example 85: 2-(3-(3-(4-chloro-2-fluorophenyl)ureido)-4-(cyclohexyl(isobutyl)amino)phenoxy)pentanoic acid A suspension of 85C (42 mg, 0.108 mmol) in THF (358 μl) was treated with 4-chloro-2-fluoro-1-isocyanatobenzene (19.08 μl, 0.151 mmol). After one hour, the reaction was diluted with more THF (358 μl) and Water (1 mL) and MeOH (0.5 mL) were added. Lithium Hydroxide (25.8 mg, 1.075 mmol) was then added and the reaction stirred at room temperature for 2 hours. After 2 hours, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Racemic Example 85. LC-MS Anal. Calc'd for $C_{28}H_{37}ClFN_3O_4$ 533.25, found [M+H] 534.25 $T_r$=2.03 min (Method C).

Example 85 Enantiomer 1 and Enantiomer 2: Chiral separation of the racemic sample (Method I) gave Enantiomer 1-$T_r$=6.75 min (Method P) and Enantiomer 2-$T_r$=8.15 min (Method P) Absolute stereochemistry was not determined.

Enantiomer 1: LC-MS Anal. Calc'd for $C_{28}H_{37}ClFN_3O_4$ 533.25, found [M+H]534.25 $T_r$=2.00 min (Method C). $^1$H NMR (500 MHz, DMSO-d$_6$) δ: 9.58 (s, 1H), 8.46 (s, 1H), 7.96 (t, J=8.8 Hz, 1H), 7.62 (br. s., 1H), 7.44 (dd, J=11.0, 2.1 Hz, 1H), 7.23 (d, J=8.2 Hz, 1H), 7.07 (d, J=8.7 Hz, 1H), 6.44 (d, J=6.1 Hz, 1H), 4.48 (t, J=5.8 Hz, 1H), 1.83-1.92 (m, 2H), 1.78 (q, J=7.1 Hz, 2H), 1.61-1.71 (m, 2H), 1.36-1.52 (m, 3H), 1.28 (dt, J=13.1, 6.5 Hz, 1H), 0.94-1.17 (m, 8H), 0.91 (t, J=7.3 Hz, 3H), 0.71-0.87 (m, 6H)

Enantiomer 2: LC-MS Anal. Calc'd for $C_{28}H_{37}ClFN_3O_4$ 533.25, found [M+H]534.25 $T_r$=2.00 min (Method C). $^1$H NMR (500 MHz, DMSO-d$_6$) δ: 9.58 (s, 1H), 8.46 (s, 1H), 7.97 (t, J=8.8 Hz, 1H), 7.63 (d, J=2.4 Hz, 1H), 7.45 (d, J=10.9 Hz, 1H), 7.23 (d, J=9.2 Hz, 1H), 7.07 (d, J=8.8 Hz, 1H), 6.44 (dd, J=8.6, 2.5 Hz, 1H), 4.42-4.52 (m, 1H), 1.88 (br. s., 2H), 1.74-1.83 (m, 2H), 1.67 (br. s., 2H), 1.49 (br. s., 1H), 1.38-1.47 (m, 2H), 1.28 (br. s., 1H), 0.94-1.18 (m, 8H), 0.91 (t, J=7.3 Hz, 3H), 0.79 (br. s., 6H)

Example 86

Enantiomer 1 and Enantiomer 2

Enantiomer 1: 2-(4-(cyclohexyl(isobutyl)amino)-3-(3-(p-tolyl)ureido)phenoxy)pentanoic acid (Homochiral, Stereochemistry Unknown)

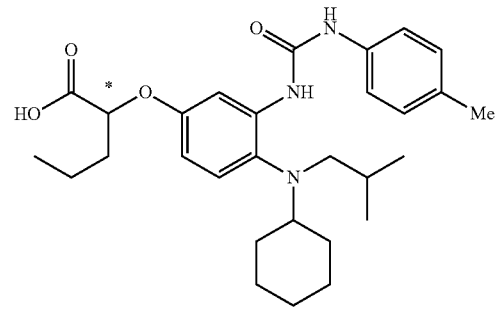 [SMILES: CCCC(Oc1ccc(N(CC(C)C)C2CCCCC2)c(NC(=O)Nc2ccc(C)cc2)c1)C(=O)O]

Enantiomer 2: 2-(4-(cyclohexyl(isobutyl)amino)-3-(3-(p-tolyl)ureido)phenoxy)pentanoic acid (Homochiral, Stereochemistry Unknown)

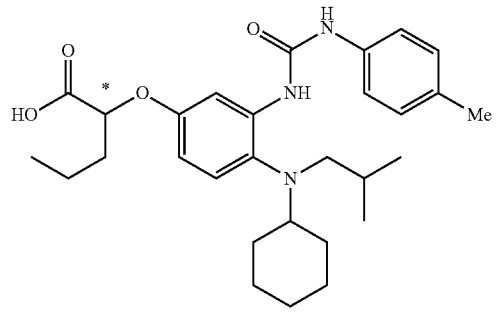 [SMILES: CCCC(Oc1ccc(N(CC(C)C)C2CCCCC2)c(NC(=O)Nc2ccc(C)cc2)c1)C(=O)O]

Racemic Example 86: (±)-2-(4-(cyclohexyl(isobutyl)amino)-3-(3-(p-tolyl)ureido)phenoxy)pentanoic acid Racemic Example 86 was obtained following the procedure for Racemic Example 85 using intermediate 85C and 1-isocyanato-4-methylbenzene. LC-MS Anal. Calc'd for $C_{29}H_{41}N_3O_4$ 495.31, found [M+H] 496.4 $T_r$=1.01 min (Method A).

Example 86 Enantiomer 1 and Enantiomer 2: Chiral separation of the racemic sample (Method D) gave Enantiomer 1-$T_r$=5.35 min (Method K) and Enantiomer 2-$T_r$=6.30 min (Method K) Absolute stereochemistry was not determined.

Enantiomer 1: LC-MS Anal. Calc'd for $C_{29}H_{41}N_3O_4$ 495.31, found [M+H] 496.31 $T_r$=1.93 min (Method C). $^1$H NMR (500 MHz, DMSO-$d_6$) δ: 9.43 (s, 1H), 8.18 (s, 1H), 7.71 (br. s., 1H), 7.34 (d, J=8.2 Hz, 2H), 7.02-7.11 (m, 3H), 6.36-6.43 (m, 1H), 4.50 (br. s., 1H), 2.24 (s, 3H), 1.82-1.93 (m, J=3.1 Hz, 2H), 1.75-1.82 (m, 2H), 1.63-1.72 (m, 2H), 1.36-1.54 (m, 4H), 1.27 (dt, J=13.1, 6.4 Hz, 1H), 0.94-1.17 (m, 7H), 0.91 (t, J=7.3 Hz, 3H), 0.79 (br. s., 6H)

Enantiomer 2: LC-MS Anal. Calc'd for $C_{29}H_{41}N_3O_4$ 495.31, found [M+H] 496.31 $T_r$=1.95 min (Method C). $^1$H NMR (500 MHz, DMSO-$d_6$) δ: 9.43 (s, 1H), 8.18 (s, 1H), 7.72 (d, J=2.4 Hz, 1H), 7.34 (d, J=8.2 Hz, 2H), 7.02-7.12 (m, 3H), 6.40 (dd, J=8.5, 2.6 Hz, 1H), 4.50 (s, 1H), 2.24 (s, 3H), 1.82-1.95 (m, 2H), 1.74-1.82 (m, 2H), 1.61-1.71 (m, 2H), 1.32-1.56 (m, 4H), 1.27 (dt, J=13.1, 6.7 Hz, 1H), 0.94-1.20 (m, 7H), 0.91 (t, J=7.3 Hz, 3H), 0.79 (br. s., 6H)

Example 87

Enantiomer 1 and Enantiomer 2

Enantiomer 1: 2-(4-(cyclohexyl(isobutyl)amino)-3-(3-(2-fluorophenyl)ureido)phenoxy)pentanoic acid (Homochiral, Stereochemistry Unknown)

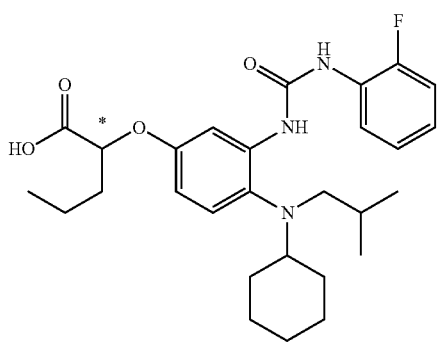 [SMILES: CCCC(Oc1ccc(N(CC(C)C)C2CCCCC2)c(NC(=O)Nc2ccccc2F)c1)C(=O)O]

Enantiomer 2: 2-(4-(cyclohexyl(isobutyl)amino)-3-(3-(2-fluorophenyl)ureido)phenoxy)pentanoic acid (Homochiral, Stereochemistry Unknown)

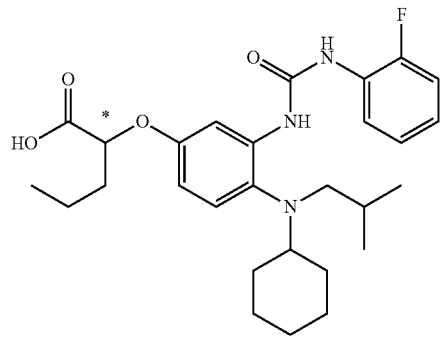

Racemic Example 87: (±)-2-(4-(cyclohexyl(isobutyl)amino)-3-(3-(2-fluorophenyl)ureido)phenoxy)pentanoic acid Racemic Example 87 was obtained following the procedure for Racemic Example 58 using intermediate 85C and 2-fluoroaniline. LC-MS Anal. Calc'd for $C_{28}H_{38}FN_3O_4$ 499.28, found [M+H] 500.6. $T_r$=0.98 min (Method A).

Example 87 Enantiomer 1 and Enantiomer 2: Chiral separation of the racemic sample (Method D) gave Enantiomer 1-$T_r$=4.90 min (Method K) and Enantiomer 2-$T_r$=6.25 min (Method K) Absolute stereochemistry was not determined.

Enantiomer 1: LC-MS Anal. Calc'd for $C_{28}H_{38}FN_3O_4$ 499.28, found [M+H]500.28 $T_r$=2.02 min (Method C). $^1$H NMR (500 MHz, DMSO-$d_6$) δ: 9.43 (s, 1H), 8.39 (br. s., 1H), 7.89 (t, J=7.8 Hz, 1H), 7.61 (br. s., 1H), 7.19-7.26 (m, 1H), 7.11-7.16 (m, 1H), 7.01-7.10 (m, 2H), 6.42 (d, J=6.9 Hz, 1H), 4.39 (br. s., 1H), 1.82-1.91 (m, 2H), 1.76 (q, J=6.8 Hz, 2H), 1.60-1.70 (m, 2H), 1.36-1.54 (m, 3H), 1.28 (dt, J=13.1, 6.4 Hz, 1H), 0.93-1.13 (m, 8H), 0.90 (t, J=7.3 Hz, 3H), 0.78 (br. s., 6H)

Enantiomer 2: LC-MS Anal. Calc'd for $C_{28}H_{38}FN_3O_4$ 499.28, found [M+H]500.28 $T_r$=1.89 min (Method C). $^1$H NMR (500 MHz, DMSO-$d_6$) δ: 9.45 (s, 1H), 8.41 (s, 1H), 7.89 (t, J=8.0 Hz, 1H), 7.64 (br. s., 1H), 7.20-7.26 (m, 1H), 7.11-7.17 (m, 1H), 7.03-7.09 (m, J=8.5 Hz, 2H), 6.43 (d, J=6.3 Hz, 1H), 4.50 (br. s., 1H), 1.82-1.92 (m, 2H), 1.74-1.82 (m, 2H), 1.62-1.71 (m, 2H), 1.38-1.54 (m, 3H), 1.28 (dt, J=13.1, 6.4 Hz, 1H), 0.94-1.17 (m, 8H), 0.91 (t, J=7.3 Hz, 3H), 0.78 (br. s., 6H)

Example 88

Enantiomer 1 and Enantiomer 2

Enantiomer 1: 2-(4-(cyclohexyl(isobutyl)amino)-3-(3-(pyrimidin-5-yl)ureido)phenoxy)pentanoic acid (Homochiral, Stereochemistry Unknown)

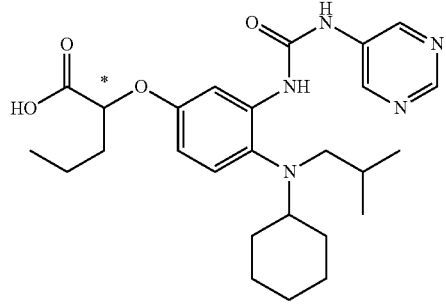 [SMILES: CCCC(Oc1ccc(N(CC(C)C)C2CCCCC2)c(NC(=O)Nc2cncnc2)c1)C(=O)O]

Enantiomer 2: 2-(4-(cyclohexyl(isobutyl)amino)-3-(3-(pyrimidin-5-yl)ureido)phenoxy)pentanoic acid (Homochiral, Stereochemistry Unknown)

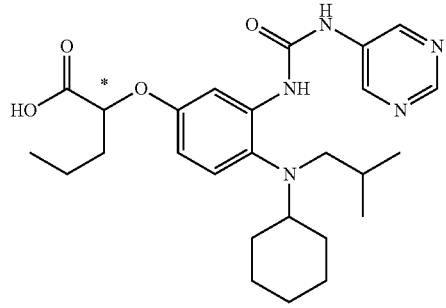 [SMILES: CCCC(Oc1ccc(N(CC(C)C)C2CCCCC2)c(NC(=O)Nc2cncnc2)c1)C(=O)O]

Racemic Example 88: (±)-2-(4-(cyclohexyl(isobutyl)amino)-3-(3-(pyrimidin-5-yl)ureido)phenoxy)pentanoic acid Racemic Example 88 was obtained following the procedure for Racemic Example 58 using intermediate 85C and 5-aminopyrimidine. LC-MS Anal. Calc'd for $C_{26}H_{37}N_5O_4$ 483.28, found [M+H] 484.6. $T_r$=0.91 min (Method A).

Example 87 Enantiomer 1 and Enantiomer 2: Chiral separation of the racemic sample (Method J) gave Enantiomer 1-$T_r$=5.90 min (Method Q) and Enantiomer 2-$T_r$=7.35 min (Method Q) Absolute stereochemistry was not determined.

Enantiomer 1: LC-MS Anal. Calc'd for $C_{26}H_{37}N_5O_4$ 483.28, found [M+H]484.28 $T_r$=1.52 min (Method C). $^1$H NMR (DMSO-$d_6$) δ: 10.05 (s, 1H), 8.92 (s, 2H), 8.81 (s, 1H), 8.44 (s, 1H), 7.72 (br. s., 1H), 7.11 (d, J=8.7 Hz, 1H), 6.45 (d, J=6.4 Hz, 1H), 4.50 (br. s., 1H), 1.86-1.97 (m, 2H), 1.79 (q, J=6.8 Hz, 2H), 1.63-1.73 (m, 2H), 1.37-1.55 (m, 4H), 1.28 (dt, J=13.1, 6.6 Hz, 1H), 1.13 (d, J=7.2 Hz, 7H), 0.91 (t, J=7.3 Hz, 3H), 0.68-0.86 (m, 6H)

Enantiomer 2: LC-MS Anal. Calc'd for $C_{26}H_{37}N_5O_4$ 483.28, found [M+H]484.28 $T_r$=1.52 min (Method C). $^1$H NMR (500 MHz, DMSO-$d_6$) δ: 10.04 (s, 1H), 8.91 (s, 2H), 8.81 (s, 1H), 8.45 (s, 1H), 7.73 (d, J=2.4 Hz, 1H), 7.12 (d, J=8.8 Hz, 1H), 6.46 (d, J=6.1 Hz, 1H), 4.52 (t, J=5.9 Hz, 1H), 1.92 (d, J=1.2 Hz, 2H), 1.75-1.84 (m, 2H), 1.63-1.72 (m, 2H), 1.33-1.55 (m, 3H), 1.28 (dt, J=13.2, 6.5 Hz, 1H), 1.13 (d, J=7.3 Hz, 8H), 0.92 (t, J=7.3 Hz, 3H), 0.80 (br. s., 6H)

Example 89

Enantiomer 1 and Enantiomer 2

Enantiomer 1: 2-(3-(3-(4-chloro-2-fluorophenyl)ureido)-4-(cyclohexyl(isobutyl)amino)phenoxy)-3-methoxypropanoic acid (Homochiral, Stereochemistry Unknown)

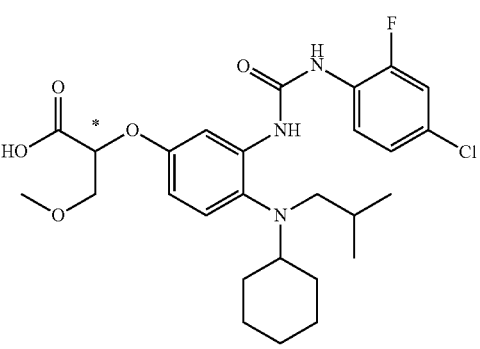 [SMILES: COCC(Oc1ccc(N(CC(C)C)C2CCCCC2)c(NC(=O)Nc2ccc(Cl)cc2F)c1)C(=O)O]

Enantiomer 2: 2-(3-(3-(4-chloro-2-fluorophenyl)ureido)-4-(cyclohexyl(isobutyl)amino)phenoxy)-3-methoxypropanoic acid (Homochiral, Stereochemistry Unknown)

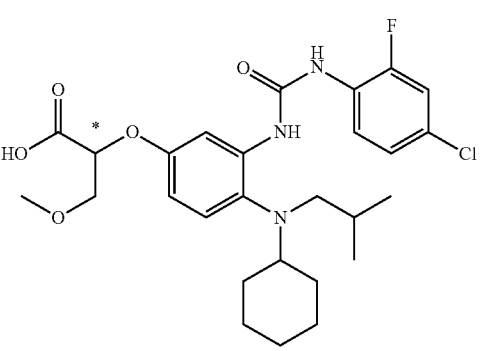 [SMILES: COCC(Oc1ccc(N(CC(C)C)C2CCCCC2)c(NC(=O)Nc2ccc(Cl)cc2F)c1)C(=O)O]

89A. Racemic methyl 2-(4-fluoro-3-nitrophenoxy)-3-methoxypropanoate 4-fluoro-3-nitrophenol (500 mg, 3.18 mmol) was dissolved in DMF (6.365 mL) at room temperature. Cesium Carbonate (1244 mg, 3.82 mmol) was added followed by methyl 2-bromo-3-methoxypropanoate (0.471 mL, 3.50 mmol). The mixture was stirred at 60° C. After 2 hours, the reaction was then diluted with water and brine (1:1) and extracted with EtOAc. The organics were combined, dried with sodium sulfate, filtered, and concentrated in vacuo. The resulting oil was dried on high vacuum 1 hour to give 89A (tan oil, 843 mg, 3.09 mmol, 97% yield). LC-MS Anal. Calc'd for $C_{11}H_{12}FNO_6$ 273.06, $T_r$=0.92 min (Method A) (Note: product does not ionize well). $^1$H NMR (400 MHz, chloroform-d) δ: 7.56 (dd, J=6.5, 2.2 Hz, 1H), 7.19-7.24 (m, 2H), 4.83 (dd, J=5.3, 3.6 Hz, 1H), 3.88-3.91 (m, 2H), 3.80 (s, 3H), 3.45 (s, 3H)

89B. Racemic ethyl 2-(4-(cyclohexyl(isobutyl) amino)-3-nitrophenoxy)-3-methoxypropanoate Intermediate 89A (0.843 g, 2.93 mmol) was dissolved in Ethanol (2.93 ml). Intermediate 1B (1.367 g, 8.80 mmol) was added and the reaction was heated to 100° C. in a sealed tube. After 48 hours, the reaction was diluted with EtOAc, washed with 1N HCl, dried with sodium sulfate, filtered, concentrated in vacuo, and purified via silica gel column chromatography to give 89B (orange oil, 192 mg, 0.454 mmol, 15.48% yield). LC-MS Anal. Calc'd for $C_{22}H_{34}N_2O_6$ 422.24, found [M+H] 423.6, $T_r$=1.21 min (Method A). $^1$H NMR (400 MHz, chloroform-d) δ: 7.21 (d, J=4.8 Hz, 1H), 7.20 (d, J=1.1 Hz, 1H), 7.07 (dd, J=9.1, 3.0 Hz, 1H), 4.77 (dd, J=5.4, 3.7 Hz, 1H), 4.24-4.36 (m, 2H), 3.87-3.91 (m, 2H), 3.48 (s, 3H), 2.76-2.85 (m, J=7.1 Hz, 3H), 1.84 (d, J=10.8 Hz, 2H), 1.77 (d, J=12.3 Hz, 2H), 1.61 (d, J=12.2 Hz, 1H), 1.44-1.54 (m, 1H), 1.13-1.42 (m, 7H), 1.01-1.12 (m, J=3.3, 3.3 Hz, 1H), 0.84 (d, J=6.6 Hz, 6H)

89C. Racemic ethyl 2-(3-amino-4-(cyclohexyl (isobutyl)amino)phenoxy)-3-methoxypropanoate To a stirred solution of Intermediate 89B (192 mg, 0.454 mmol) in Ethanol (4.54 mL) was added 0.45 mL of water. The solution was then treated with zinc (178 mg, 2.73 mmol) and ammonium chloride (146 mg, 2.73 mmol). This mixture was stirred at room temperature. After 1 hour, the reaction was filtered, diluted with EtOAc, washed with $NaHCO_3$, dried with Sodium sulfate, filtered, and concentrated to give 89C (clear oil, 170 mg, 0.431 mmol, 95%) LC-MS Anal. Calc'd for $C_{22}H_{36}N_2O_4$ 392.27, found [M+H]393.3, $T_r$=0.86 min (Method A).

Example 89

A suspension of ethyl Intermediate 89C (80 mg, 0.204 mmol) in THF (679 μl) was treated with 4-chloro-2-fluoro-1-isocyanatobenzene (36.2 μl, 0.285 mmol). After 1 hour, the reaction was diluted with more THF (679 μl) and Water (1 mL) and MeOH (0.5 mL) were added. Lithium hydroxide (48.8 mg, 2.038 mmol) was then added and the reaction stirred at room temperature. After 2 hours, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Racemic Example 89. LC-MS Anal. Calc'd for $C_{27}H_{35}ClFN_3O_5$ 535.22, found [M+H] 536.6 $T_r$=0.97 min (Method A).

Example 89 Enantiomer 1 and Enantiomer 2: Chiral separation of the racemic sample (Method D) gave Enantiomer 1—$T_r$=8.00 min (Method K) and Enantiomer 2-$T_r$=11.05 min (Method K) Absolute stereochemistry was not determined.

Enantiomer 1: LC-MS Anal. Calc'd for $C_{27}H_{35}ClFN_3O_5$ 535.22, found [M+H]536.22 $T_r$=1.83 min (Method C). $^1$H NMR (500 MHz, DMSO-$d_6$) δ: 9.57 (s, 1H), 8.44 (s, 1H), 7.96 (t, J=8.8 Hz, 1H), 7.58 (br. s., 1H), 7.44 (d, J=10.8 Hz, 1H), 7.23 (d, J=8.3 Hz, 1H), 7.04 (d, J=8.8 Hz, 1H), 6.43 (d, J=6.6 Hz, 1H), 4.55 (br. s., 1H), 3.48-3.56 (m, 2H), 3.28 (s, 3H), 1.82-1.92 (m, 2H), 1.61-1.69 (m, 2H), 1.50 (d, J=12.2 Hz, 1H), 1.23-1.32 (m, 1H), 0.88-1.16 (m, 8H), 0.78 (br. s., 6H)

Enantiomer 2: LC-MS Anal. Calc'd for $C_{27}H_{35}ClFN_3O_5$ 535.22, found [M+H]536.22 $T_r$=1.83 min (Method C). $^1$H NMR (500 MHz, DMSO-$d_6$) δ: 9.59 (s, 1H), 8.47 (s, 1H), 7.96 (t, J=8.8 Hz, 1H), 7.63 (br. s., 1H), 7.44 (d, J=10.9 Hz, 1H), 7.23 (d, J=8.3 Hz, 1H), 7.08 (d, J=8.8 Hz, 1H), 6.46 (d, J=6.2 Hz, 1H), 4.73 (br. s., 1H), 3.42-3.55 (m, 2H), 3.31 (s, 3H), 1.83-1.92 (m, 2H), 1.62-1.70 (m, 2H), 1.50 (d, J=11.6 Hz, 1H), 1.23-1.31 (m, J=6.5 Hz, 1H), 0.85-1.20 (m, 8H), 0.79 (br. s., 6H)

Example 90

Enantiomer 1 and Enantiomer 2

Enantiomer 1 2-(4-(cyclohexyl(isobutyl)amino)-3-(3-(p-tolyl)ureido)phenoxy)-3-methoxypropanoic acid (Homochiral, Stereochemistry Unknown)

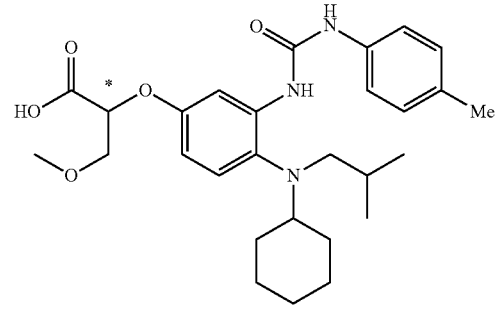 [SMILES: COCC(Oc1ccc(N(CC(C)C)C2CCCCC2)c(NC(=O)Nc2ccc(C)cc2)c1)C(=O)O]

Enantiomer 2: 2-(4-(cyclohexyl(isobutyl)amino)-3-(3-(p-tolyl)ureido)phenoxy)-3-methoxypropanoic acid (Homochiral, Stereochemistry Unknown)

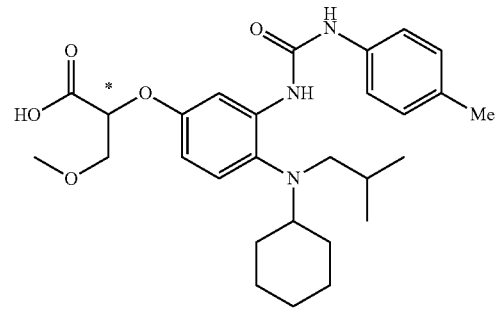 [SMILES: COCC(Oc1ccc(N(CC(C)C)C2CCCCC2)c(NC(=O)Nc2ccc(C)cc2)c1)C(=O)O]

Example 90: (±)-2-(4-(cyclohexyl(isobutyl)amino)-3-(3-(p-tolyl) ureido)phenoxy)-3-methoxypropanoic acid Racemic Example 90 was obtained following the procedure for Racemic Example 89 using intermediate 89C and 1-isocyanato-4-methylbenzene. LC-MS Anal. Calc'd for $C_{28}H_{39}N_3O_5$ 497.29, found [M+H] 498.6 $T_r$=0.95 min (Method A).

Example 90 Enantiomer 1 and Enantiomer 2: Chiral separation of the racemic sample (Method J) gave Enantiomer 1 $T_r$=9.45 min (Method Q) and Enantiomer 2-$T_r$=11.05 min (Method Q) Absolute stereochemistry was not determined.

Enantiomer 1: LC-MS Anal. Calc'd for $C_{28}H_{39}N_3O_5$ 497.29, found [M+H]498.29 $T_r$=1.76 min (Method C). $^1$H NMR (500 MHz, DMSO-$d_6$) δ: 9.43 (s, 1H), 8.18 (s, 1H), 7.71 (d, J=2.4 Hz, 1H), 7.34 (d, J=8.2 Hz, 2H), 7.01-7.12 (m, 3H), 6.41 (d, J=8.6 Hz, 1H), 4.70 (br. s., 1H), 3.66-3.79 (m, 2H), 3.31 (s, 3H), 2.23 (s, 3H), 1.81-1.92 (m, 2H), 1.63-1.69 (m, 2H), 1.50 (d, J=11.9 Hz, 1H), 1.27 (dt, J=13.1, 6.6 Hz, 1H), 0.89-1.18 (m, 8H), 0.79 (br. s., 6H)

Enantiomer 2: LC-MS Anal. Calc'd for $C_{28}H_{39}N_3O_5$ 497.29, found [M+H] 498.29 $T_r$=1.77 min (Method C). $^1$H NMR (500 MHz, DMSO-$d_6$) δ: 9.43 (s, 1H), 8.18 (s, 1H), 7.71 (br. s., 1H), 7.34 (d, J=8.2 Hz, 2H), 7.03-7.10 (m, 3H), 6.41 (d, J=6.3 Hz, 1H), 4.69 (br. s., 1H), 3.66-3.79 (m, 2H), 3.31 (s, 3H), 2.23 (s, 3H), 1.82-1.92 (m, 2H), 1.60-1.70 (m, 2H), 1.50 (d, J=11.9 Hz, 1H), 1.27 (dt, J=13.0, 6.4 Hz, 1H), 0.88-1.20 (m, 8H), 0.78 (br. s., 6H)

Example 91

2-(3-(3-(4-chloro-2-fluorophenyl)ureido)-4-(cyclohexyl(isobutyl)amino)phenoxy)-2-methylpropanoic acid

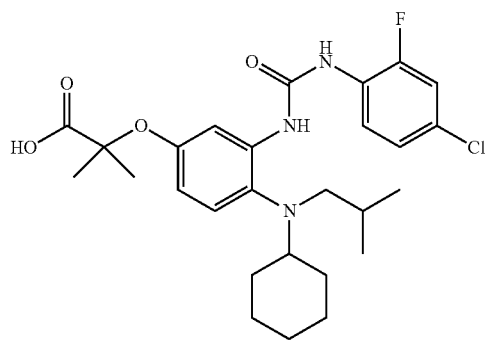 [SMILES: CC(C)CN(c1ccc(OC(C)(C)C(=O)O)cc1NC(=O)Nc1ccc(Cl)cc1F)C1CCCCC1]

91A. ethyl 2-(4-fluoro-3-nitrophenoxy)-2-methylpropanoate 4-fluoro-3-nitrophenol (500 mg, 3.18 mmol) was dissolved in DMF (6365 µl) at room temperature. Cesium Carbonate (1244 mg, 3.82 mmol) was added followed by ethyl 2-bromo-2-methylpropanoate (514 µl, 3.50 mmol). The mixture was stirred at 80° C. over night. The reaction was diluted with ½ saturated NaCl solution (aq), extracted with EtOAc, dried with $Na_2SO_4$, filtered and concentrated in vacuo to give 91A (tan oil, 597 mg, 2.201 mmol, 69% yield). $^1$H NMR (400 MHz, chloroform-d) δ: 7.53-7.57 (m, 1H), 7.09-7.20 (m, 2H), 4.26 (q, J=7.1 Hz, 2H), 1.61 (s, 6H), 1.28 (t, J=7.1 Hz, 3H)

91B. ethyl 2-(4-(cyclohexyl(isobutyl)amino)-3-nitrophenoxy)-2-methylpropanoate

Intermediate 91A (0.597 g, 2.201 mmol) was dissolved in Ethanol (2.201 ml). Intermediate 1B (1.025 g, 6.60 mmol) was added and the reaction was heated to 100° C. in a sealed tube. After 48 hours, the reaction was diluted with EtOAc, washed with 1N HCl, dried with sodium sulfate, filtered, and concentrated in vacuo. The crude residue was purified via silica gel column chromatography to give 91B (114 mg, 0.280 mmol, 12.74% yield). LC-MS Anal. Calc'd for $C_{22}H_{34}N_2O_5$ 406.25, found [M+H] 408.5 $T_r$=1.27 min (Method A). $^1$H NMR (400 MHz, chloroform-d) δ: 7.16 (d, J=3.1 Hz, 1H), 7.12 (d, J=8.9 Hz, 1H), 6.95 (dd, J=9.0, 2.9 Hz, 1H), 4.25 (q, J=7.1 Hz, 2H), 2.74-2.84 (m, J=7.1 Hz, 3H), 1.82 (d, J=12.8 Hz, 2H), 1.74 (d, J=9.7 Hz, 2H), 1.60-1.65 (m, 2H), 1.59 (s, 6H), 1.48 (dt, J=13.6, 6.8 Hz, 1H), 1.29-1.37 (m, 2H), 1.27 (t, J=7.1 Hz, 3H), 0.96-1.24 (m, 2H), 0.79-0.84 (m, 6H)

91C. ethyl 2-(3-amino-4-(cyclohexyl(isobutyl)amino)phenoxy)-2-methylpropanoate

To a stirred solution of Intermediate 91B (114 mg, 0.280 mmol) in Ethanol (2.8 ml) was added 0.28 mL of water. The solution was then treated with zinc (110 mg, 1.683 mmol) and ammonium chloride (90 mg, 1.683 mmol). This mixture was stirred at room temperature. After 1 hour, the reaction was filtered, diluted with EtOAc, washed with $NaHCO_3$, dried with Sodium sulfate, filtered, and concentrated to give 91C (86 mg, 0.227 mmol, 81%). LC-MS Anal. Calc'd for $C_{22}H_{36}N_2O_3$ 376.27, found [M+H] 377.6 $T_r$=0.87 min (Method A).

Example 91

Intermediate 91C (43 mg, 0.114 mmol) in THF (381 µl) was treated with 4-chloro-2-fluoro-1-isocyanatobenzene (20.26 µl, 0.160 mmol). After 30 minutes, the reaction was diluted with more THF (381 µl) and Water (0.8 mL) and MeOH (0.4 mL) were added. Lithium hydroxide (27.3 mg, 1.142 mmol) was then added and the reaction stirred at room temperature. After 1 hour, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Example 91 (20.3 mg, 0.039 mmol, 34%). LC-MS Anal. Calc'd for $C_{27}H_{35}ClFN_3O_4$ 519.23, found [M+H]520.23 $T_r$=1.91 min (Method C). $^1$H NMR (500 MHz, DMSO-$d_6$) δ: 9.56 (s, 1H), 8.39 (s, 1H), 7.98 (t, J=8.8 Hz, 1H), 7.58 (d, J=2.4 Hz, 1H), 7.45 (d, J=10.9 Hz, 1H), 7.23 (d, J=8.8 Hz, 1H), 7.05 (d, J=8.8 Hz, 1H), 6.40-6.46 (m, 1H), 1.89 (d, J=11.5 Hz, 2H), 1.68 (br. s., 2H), 1.49-1.53 (m, 1H), 1.47 (s, 6H), 1.29 (dt, J=12.6, 6.1 Hz, 1H), 0.88-1.20 (m, 8H), 0.79 (d, J=4.0 Hz, 6H)

Example 92

2-(4-(cyclohexyl(isobutyl)amino)-3-(3-(p-tolyl)ureido) phenoxy)-2-methylpropanoic acid

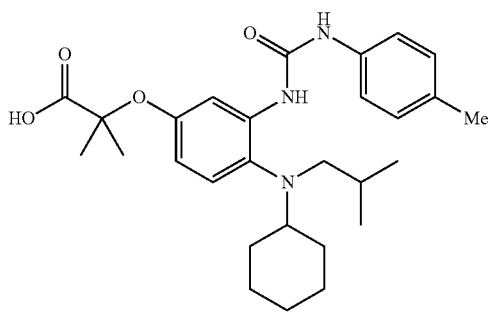 [SMILES: Cc1ccc(NC(=O)Nc2cc(OC(C)(C)C(=O)O)ccc2N(CC(C)C)C2CCCCC2)cc1]

Example 92 2-(4-(cyclohexyl(isobutyl)amino)-3-(3-(p-tolyl)ureido)phenoxy)-2-methylpropanoic acid Example 92 was obtained following the procedure for Example 91 from Intermediate 91C and 1-isocyanato-4-methylbenzene.

LC-MS Anal. Calc'd for $C_{28}H_{39}N_3O_4$ 481.29, found [M+H] 482.29. $T_r$=1.88 min (Method C). $^1$H NMR (500 MHz, DMSO-$d_6$) δ: 9.41 (s, 1H), 8.11 (br. s., 1H), 7.69 (br. s., 1H), 7.34 (d, J=8.1 Hz, 2H), 7.04-7.11 (m, 3H), 6.38 (d, J=8.1 Hz, 1H), 2.24 (s, 3H), 1.83-1.92 (m, 2H), 1.67 (d, J=6.5 Hz, 2H), 1.50-1.55 (m, 1H), 1.49 (s, 6H), 1.21-1.34 (m, 1H), 0.83-1.18 (m, 8H), 0.79 (br. s., 6H)

Example 93

1-(3-(3-(4-chloro-2-fluorophenyl)ureido)-4-(cyclohexyl(isobutyl)amino)phenoxy)cyclopropanecarboxylic acid

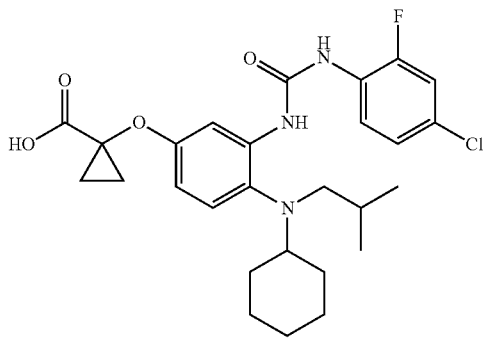 [SMILES: CC(C)CN(c1ccc(OC2(C(=O)O)CC2)cc1NC(=O)Nc1ccc(Cl)cc1F)C1CCCCC1]

93A. methyl 4-bromo-2-(4-fluoro-3-nitrophenoxy)butanoate 4-fluoro-3-nitrophenol (500 mg, 3.18 mmol) was dissolved in DMF (6365 μl) at room temperature. Cesium Carbonate (1244 mg, 3.82 mmol) was added followed by methyl 2,4-dibromobutanoate (910 mg, 3.50 mmol). The mixture was stirred at room temperature for 2 hours and then heated to 50 C for an additional hour. The reaction was diluted with ½ saturated NaCl solution (aq), extracted with EtOAc, dried with $Na_2SO_4$, filtered and concentrated to give 93A (tan oil, 0.99 g, 2.95 mmol, 93%) $^1$H NMR (400 MHz, chloroform-d) δ: 8.01 (s, 1H), 7.56-7.60 (m, 1H), 7.20-7.24 (m, 1H), 4.91 (dd, J=8.4, 4.4 Hz, 1H), 3.79 (s, 3H), 3.60 (dd, J=7.5, 5.3 Hz, 2H), 2.42-2.58 (m, 2H)

93B. methyl 1-(4-fluoro-3-nitrophenoxy)cyclopropanecarboxylate

Intermediate 93A (1.09 g, 3.24 mmol) was dissolved in THF (16.21 ml) and cooled to −15° C. (Salt/Ice bath). Potassium tert-butoxide (0.400 g, 3.57 mmol) was added. The mixture was allowed to warm and stirred at room temp. After 4 hours, the reaction was poured into EtOAc/1N HCl. Organic extracts were combined, dried with sodium sulfate, filtered, and concentrated in vacuo. The crude residue was purified via silica gel column chromatography to give methyl 93B (440 mg, 1.724 mmol, 53.2% yield). $^1$H NMR (400 MHz, chloroform-d) δ: 7.54-7.58 (m, 1H), 7.17-7.21 (m, 2H), 3.72-3.76 (m, 3H), 1.66-1.71 (m, 2H), 1.32-1.37 (m, 2H)

93C. methyl 1-(4-(cyclohexyl(isobutyl)amino)-3-nitrophenoxy)cyclopropane carboxylate Intermediate 93B (440 mg, 1.724 mmol) was dissolved in Ethanol (1.72 ml). Intermediate 1B (803 mg, 5.17 mmol) was added and the reaction was heated to 100° C. in a sealed tube. After 48 hours, the reaction was diluted with EtOAc, washed with 1N HCl, dried with sodium sulfate, filtered, and concentrated in vacuo. Purification via silica gel column chromatography gave 93C (orange oil, 219 mg, 0.541 mmol, 31.4% yield). LC-MS Anal. Calc'd for $C_{22}H_{32}N_2O_5$ 404.23, found [M+H] 405.6 $T_r$=1.25 min (Method A). $^1$H NMR (400 MHz, chloroform-d) δ: 7.15-7.20 (m, 2H), 6.99 (dd, J=9.0, 3.1 Hz, 1H), 3.76 (s, 3H), 2.74-2.84 (m, 3H), 1.82 (d, J=10.5 Hz, 2H), 1.74 (d, J=12.8 Hz, 2H), 1.55-1.65 (m, 3H), 1.44-1.51 (m, 3H), 1.11-1.43 (m, 9H), 0.82 (d, J=6.6 Hz, 4H)

93D. methyl 1-(3-amino-4-(cyclohexyl(isobutyl)amino)phenoxy)cyclopropane carboxylate To a stirred solution of Intermediate 93C (100 mg, 0.247 mmol) in Ethanol (2.47 ml) was added 0.25 mL of water. The solution was then treated with zinc (97 mg, 1.483 mmol) and ammonium chloride (79 mg, 1.483 mmol). This mixture was stirred at room temperature. After 1 hour, the reaction was filtered, concentrated, diluted with EtOAc, washed with $NaHCO_3$, dried with Sodium sulfate, filtered, and concentrated to give Intermediate 93D (colorless oil, 41 mg, 0.109 mmol, 44%). LC-MS Anal. Calc'd for $C_{21}H_{30}N_2O_5$ 360.24, found [M+H] 361.5 $T_r$=0.81 min (Method A).

Example 93. 1-(3-(3-(4-chloro-2-fluorophenyl)ureido)-4-(cyclohexyl(isobutyl)amino)phenoxy)cyclopropanecarboxylic acid A suspension of 93D (20 mg, 0.053 mmol) in THF (178 μl) was treated with 4-chloro-2-fluoro-1-isocyanatobenzene (9.47 μl, 0.075 mmol). After 30 minutes, the reaction was diluted with more THF (178 μl) and Water (0.8 mL) and MeOH (0.4 mL) were added. Lithium Hydroxide (12.79 mg, 0.534 mmol) was then added and the reaction stirred at room temperature. After 1 hour, the reaction heated to 50° C. for 1 hour. Then, the reaction was concentrated in vacuo to remove MeOH and THF, treated with 1N HCl until a precipitate forms and pH is acidic, then extracted with EtOAc three times. Organic extracts were combined, dried with sodium sulfate, filtered and concentrated in vacuo. The crude residue was dissolved in 2 mL DMF, filtered, and purified via preparative HPLC to give Example 93 (9.2 mg, 0.017 mmol, 33%). LC-MS Anal. Calc'd for $C_{27}H_{33}ClFN_3O_4$ 517.21, found [M+H] 518.21 $T_r$=1.90 min (Method C). $^1$H NMR (500 MHz, DMSO-$d_6$) δ: 9.57 (s, 1H), 8.45 (s, 1H), 7.95 (t, J=8.8 Hz, 1H), 7.68 (d, J=2.6 Hz, 1H), 7.45 (dd, J=10.9, 2.1 Hz, 1H), 7.23 (d, J=8.8 Hz, 1H), 7.07 (d, J=8.8 Hz, 1H), 6.49 (dd, J=8.6, 2.7 Hz, 1H), 1.84-1.92 (m, 2H), 1.62-1.70 (m, 2H), 1.50 (d, J=11.5 Hz, 1H), 1.39-1.46 (m, 2H), 1.29 (dt, J=13.4, 6.7 Hz, 1H), 0.87-1.22 (m, 10H), 0.80 (br. s., 6H)

Example 94

1-(4-(cyclohexyl(isobutyl)amino)-3-(3-(p-tolyl)ureido)phenoxy)cyclopropanecarboxylic acid

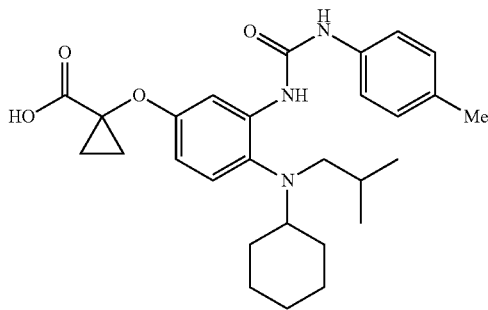 [SMILES: Cc1ccc(NC(=O)Nc2cc(OC3(C(=O)O)CC3)ccc2N(CC(C)C)C2CCCCC2)cc1]

Example 94 1-(4-(cyclohexyl(isobutyl)amino)-3-(3-(p-tolyl)ureido)phenoxy)cyclopropanecarboxylic acid Example 94 was obtained following the procedure for Example 93 from Intermediate 93D and 1-isocyanato-4-methylbenzene.

LC-MS Anal. Calc'd for $C_{28}H_{37}N_3O_4$ 479.28, found [M+H] 480.28. $T_r$=1.88 min (Method C). $^1$H NMR (500 MHz, DMSO-$d_6$) δ: 9.41 (s, 1H), 8.16 (s, 1H), 7.77 (d, J=2.4 Hz, 1H), 7.33 (d, J=8.2 Hz, 2H), 7.02-7.12 (m, 3H), 6.45 (dd, J=8.6, 2.7 Hz, 1H), 2.23 (s, 3H), 1.81-1.92 (m, 2H), 1.67 (d, J=7.2 Hz, 2H), 1.51 (d, J=11.9 Hz, 1H), 1.39-1.47 (m, 2H), 1.23-1.34 (m, 1H), 0.89-1.23 (m, 10H), 0.79 (br. s., 6H)

Example 95

1-(5-((1H-tetrazol-5-yl)methoxy)-2-(diisobutylamino)-4-fluorophenyl)-3-(p-tolyl)urea

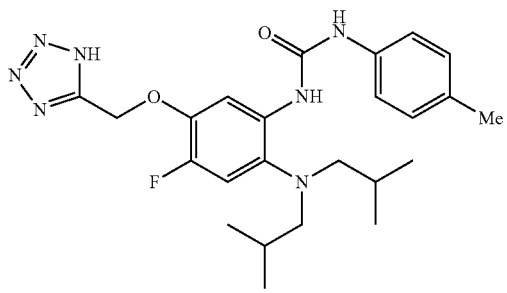 [SMILES: Cc1ccc(NC(=O)Nc2cc(OCc3nnn[nH]3)c(F)cc2N(CC(C)C)CC(C)C)cc1]

Example 95A 4-(cyclohexyl(isobutyl)amino)-2-fluoro-5-nitrophenol

A sealed tube containing 2,4-difluoro-5-nitrophenol (0.100 g, 0.571 mmol) in diisobutylamine (0.998 ml, 5.71 mmol) was heated to 100° C. 1 h. Reaction temperature increased to 130° C. for 5 h. The mixture was diluted with water and EtOAc. The layers were separated and the aqueous phase extracted three times with EtOAc. The organics were combined, washed with water and brine, then dried over anhydrous sodium sulfate. Filtration and concentration afforded a dark brown oil. Crude material was purified via flash chromatography to give Intermediate 95A (0.095 g, 0.327 mmol, 57%). LC-MS Anal. Calc'd for $C_{14}H_{21}FN_2O_3$ 284.16, found [M+H] 285.2 $T_r$=1.10 min (Method A).

Example 95B 4-((1H-tetrazol-5-yl)methoxy)-N-cyclohexyl-5-fluoro-N-isobutyl-2-nitroaniline To a suspension containing Intermediate 95A (0.025 g, 0.088 mmol) and potassium carbonate (0.061 g, 0.440 mmol) in Acetonitrile (0.5 ml) at RT was added 2-bromoacetonitrile (7.36 μl, 0.106 mmol). The vessel was sealed and heated to 60° C. 2 h. The vessel was cooled to RT and diluted with water and EtOAc. The layers were separated and the aqueous phase extracted twice with 10 mL EtOAc. The organics were combined, washed with water and brine, then dried over anhydrous sodium sulfate. Filtration and concentration afforded a brown oil. The crude material was transferred to a microwave vial, dissolved in Dioxane (1.000 ml), treated with dibutyloxostannane (6.57 mg, 0.026 mmol) and TMS-N3 (0.015 ml, 0.110 mmol), then heated to 120° C. for 20 min in a CEM Discover microwave at 300W power. The reaction was concentrated in vacuo, and purified via flash chromatography to give Intermediate 95B (9 mg, 0.025 mmol, 28%). LC-MS Anal. Calc'd for $C_{16}H_{23}FN_6O_3$ 366.18, found [M+H] 367.1 $T_r$=1.05 min (Method A).

Example 95: 1-(5-((1H-tetrazol-5-yl)methoxy)-2-(diisobutylamino)-4-fluorophenyl)-3-(p-tolyl)urea Intermediate 95B was dissolved in Ethanol (195 μl) at RT and ammonium chloride (26.3 mg, 0.491 mmol) was added followed by Water (19.50 μl). After stirring 5 min, zinc (32.1 mg, 0.491 mmol) was added and the mixture stirred 5 min. The suspension was diluted with 10 mL DCM and filtered through Celite. The filtrate was placed in a sep funnel and water was added and washed with EtOAc 3 times. The organics were combined, dried over sodium sulfate, filtered, and concentrated to afford the desired aniline. The residue was then dissolved in THF (195 μl) and treated with p-tolylisocyanate (3.09 μl, 0.025 mmol) at room temperature for 6 hours. The crude reaction mixture was concentrated, taken up in DMF, filtered, and purified directly via preparative HPLC to give Example 95 (2.2 mg, 0.005 mmol, 18%). LC-MS Anal. Calc'd for $C_{24}H_{32}FN_7O_2$ 469.26, found [M+H] 270.26 $T_r$=1.81 min (Method C). $^1$H NMR (500 MHz, DMSO-$d_6$) δ: 9.40 (s, 1H), 7.98-7.89 (m, 1H), 7.85 (s, 1H), 7.36 (d, J=8.4 Hz, 2H), 7.20 (d, J=12.4 Hz, 1H), 7.10 (d, J=7.9 Hz, 2H), 5.39 (s, 2H), 2.62 (d, J=6.9 Hz, 4H), 2.25 (s, 3H), 1.61 (dt, J=13.3, 6.5 Hz, 2H), 0.85 (d, J=6.4 Hz, 12H).

Example 96

1-(5-((1H-tetrazol-5-yl)methoxy)-2-(cyclohexyl(isobutyl)amino)phenyl)-3-(4-chloro-2-fluorophenyl)urea

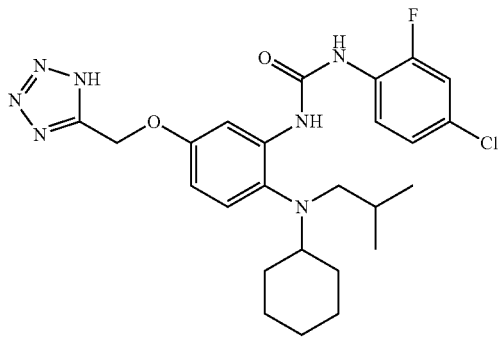 [SMILES: CC(C)CN(c1ccc(OCc2nnn[nH]2)cc1NC(=O)Nc1ccc(Cl)cc1F)C1CCCCC1]

96A. 2-(4-fluoro-3-nitrophenoxy)acetonitrile 4-fluoro-3-nitrophenol (933 mg, 5.94 mmol) was dissolved in DMF (11.900 ml) and cesium carbonate (2709 mg, 8.31 mmol) was added at room temperature. Then, 2-bromoacetonitrile (0.496 ml, 7.13 mmol) was added and the reaction stirred at 50° C. After 30 minutes, the reaction was diluted with water and extracted with EtOAc three times. The organics were combined and washed with half-saturated aq. NaCl solution, dried with sodium sulfate, filtered, and concentrated in vacuo to give 96A (deep, red oil, 1.12 g, 5.42 mmol, 91% yield). $^1$H NMR (400 MHz, chloroform-d) δ: 7.67 (dd, J=6.1, 2.8 Hz, 1H), 7.27-7.36 (m, 2H), 4.84 (s, 2H).

96B. 2-(4-(cyclohexyl(isobutyl)amino)-3-nitrophenoxy)acetonitrile

Intermediate 96A (1.12 g, 5.71 mmol) and Intermediate 1B (2.217 g, 14.28 mmol) were combined (neat) and heated to 100° C. After 3 hours the crude reaction mixture was directly purified via column chromatography on silica to give 96B (bright, orange, thick oil, 551 mg, 1.663 mmol, 29.1% yield). $^1$H NMR (chloroform-d) δ: 7.29 (d, J=3.1 Hz, 1H), 7.23 (d, J=9.0 Hz, 1H), 7.10 (dd, J=9.0, 3.1 Hz, 1H), 4.76 (s, 2H), 2.78-2.88 (m, 3H), 1.82 (dd, J=12.6, 1.7 Hz, 2H), 1.75 (d, J=13.0 Hz, 2H), 1.59 (d, J=12.6 Hz, 1H), 1.50 (dt, J=13.5, 6.8 Hz, 1H), 1.35 (qd, J=12.2, 2.9 Hz, 2H), 1.12-1.23 (m, 2H), 1.06 (tt, J=12.7, 3.4 Hz, 1H), 0.84 (d, J=6.6 Hz, 6H)

96C. 2-(3-amino-4-(cyclohexyl(isobutyl)amino)phenoxy)acetonitrile

To a stirred solution of Intermediate 96B (0.500 g, 1.509 mmol) in Ethanol (7.54 ml) was added 0.75 mL of water. The cloudy solution was warmed slightly until it became clear then treated with zinc (0.592 g, 9.05 mmol) and ammonium chloride (0.484 g, 9.05 mmol). This mixture was stirred at room temperature. After 1 hour, the reaction was diluted with EtOAc, dried with Sodium Sulfate, filtered over celite, and concentrated in vacuo. The crude residue was purified with flash chromatography to give Intermediate 96C (light tan, thick oil, 377 mg, 83% yield). LC-MS Anal. Calc'd for $C_{18}H_{27}N_3O$ 301.22, found [M+H] 302.2 $T_r$=0.78 min (Method A).

96D. 1-(4-chloro-2-fluorophenyl)-3-(5-(cyanomethoxy)-2-(cyclohexyl(isobutyl)amino)phenyl)urea A suspension of Intermediate 96C in THF (0.387 ml) was treated with 4-chloro-2-fluoro-1-isocyanatobenzene (0.021 ml, 0.163 mmol). After 30 minutes, the reaction was concentrated in vacuo and purified directly flash chromatography to give Intermediate 96D (clear glass, 43 mg, 70.5% yield). LC-MS Anal. Calc'd for $C_{25}H_{30}ClFN_4O_2$ 472.20, found [M+H] 473.7 $T_r$=1.08 min (Method A).

Example 96. 1-(5-((1H-tetrazol-5-yl)methoxy)-2-(cyclohexyl(isobutyl)amino)phenyl)-3-(4-chloro-2-fluorophenyl)urea Intermediate 96D (0.020 g, 0.042 mmol) was dissolved in DMF (0.423 ml). ammonium chloride (6.79 mg, 0.127 mmol) and sodium azide (8.25 mg, 0.127 mmol) were added. The reaction was sealed, vacated and flushed with nitrogen several times and heated to 100° C. After 3 hours, the reaction was diluted with 1 N HCl and extracted with EtOAc three times. The organic extracts were combined, dried with sodium sulfate, filtered, and concentrated in vacuo. The crude residue was taken up in 2 mL DMF, filtered, and purified via preparative HPLC to give Example 96 (5.1 mg, 0.099 mmol, 23% yield). LC-MS Anal. Calc'd for $C_{25}H_{31}ClFN_7O_2$ 515.22, found [M+H] 516.22 $T_r$=1.95 min (Method B). $^1$H NMR (500 MHz, DMSO-d$_6$) δ: 9.60 (s, 1H), 8.50 (s, 1H), 8.01 (t, J=8.8 Hz, 1H), 7.75 (d, J=2.8 Hz, 1H), 7.45 (dd, J=11.0, 2.1 Hz, 1H), 7.23 (d, J=8.8 Hz, 1H), 7.12 (d, J=8.8 Hz, 1H), 6.69 (dd, J=8.7, 2.8 Hz, 1H), 5.23 (s, 2H), 2.98-3.03 (m, 1H), 1.85-1.95 (m, 3H), 1.60-1.73 (m, 4H), 1.51 (d, J=11.7 Hz, 1H), 1.30 (dt, J=13.2, 6.6 Hz, 1H), 0.90-1.19 (m, 5H), 0.80 (br. s., 6H)

Example 97

1-(5-((1H-tetrazol-5-yl)methoxy)-2-(cyclohexyl(isobutyl)amino)phenyl)-3-(2-fluorophenyl)urea

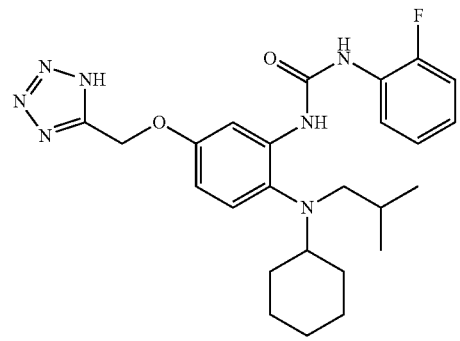 [SMILES: CC(C)CN(c1ccc(OCc2nnn[nH]2)cc1NC(=O)Nc1ccccc1F)C1CCCCC1]

Example 97: 1-(5-((1H-tetrazol-5-yl)methoxy)-2-(cyclohexyl(isobutyl)amino)phenyl)-3-(2-fluorophenyl)urea Example 97 was obtained following the procedure for Example 96D using Intermediate 96C and 2-fluoro-1-isocyanatobenzene followed by tetrazole formation with sodium azide following the procedure for Example 96. LC-MS Anal. Calc'd for $C_{25}H_{32}FN_7O_2$ 481.26, found [M+H] 482.26 $T_r$=1.84 min (Method B).

Example 98

2-(3-(3-(4-Chloro-2-fluorophenyl)ureido)-4-((4,4-difluorocyclohexyl)(isobutyl)amino)-phenoxy)acetic acid

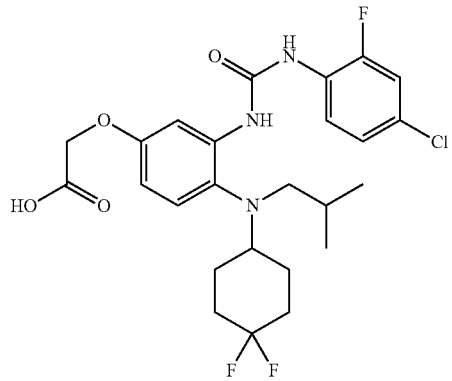 [SMILES: CC(C)CN(c1ccc(OCC(=O)O)cc1NC(=O)Nc1ccc(Cl)cc1F)C1CCC(F)(F)CC1]

Example 98. 2-(3-(3-(4-Chloro-2-fluorophenyl)ureido)-4-((4,4-difluorocyclohexyl)(isobutyl)amino) phenoxy)acetic acid The title compound (52.5 mg, 63%) was prepared following a procedure analogous to that for the synthesis of Example 101 A, except that 4,4-difluoro-N-isobutylcyclohexanamine (Example 518 from 11606-WO-PCT) was used instead of N-isobutylcyclohexanamine and 4-bromo-1-fluoro-2-nitrobenzene was used instead of 5-bromo-2-fluoro-3-nitropyridine in Example 101. MS(ES): m/z=528 [M+H]$^+$, HPLC $T_r$: 1.71 min (Method C).

Example 99

2-(3-(3-(4-Bromo-2-fluorophenyl)ureido)-4-((4,4-difluorocyclohexyl)(isobutyl)amino)-phenoxy)acetic acid

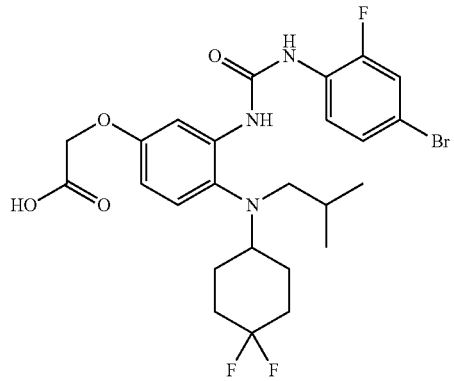 [SMILES: CC(C)CN(c1ccc(OCC(=O)O)cc1NC(=O)Nc1ccc(Br)cc1F)C1CCC(F)(F)CC1]

Example 99. 2-(3-(3-(4-Bromo-2-fluorophenyl) ureido)-4-((4,4-difluorocyclohexyl)(isobutyl)amino) phenoxy)acetic acid The title compound (37.7 mg, 83%) was prepared following a procedure analogous to that for the synthesis of Example 98, except that 4-bromo-2-fluoro-1-isocyanatobenzene was used instead of 4-chloro-2-fluoro-1-isocyanatobenzene in Example 101. MS(ES): m/z=572 [M+H]$^+$, HPLC $T_r$: 1.75 min (Method C).

Example 100

2-(4-((4,4-Difluorocyclohexyl)(isobutyl)amino)-3-(3-(4-ethoxyphenyl)ureido)phenoxy)acetic acid

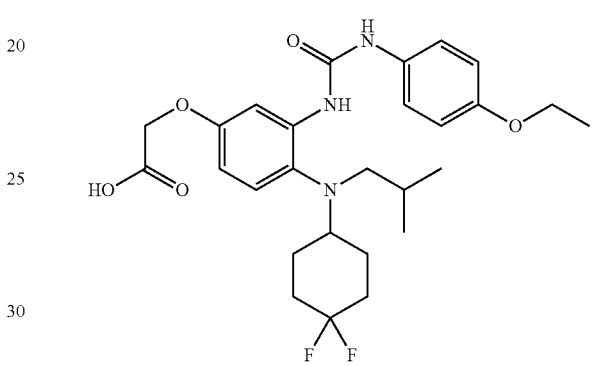

Example 100. 2-(4-((4,4-Difluorocyclohexyl)(isobutyl)amino)-3-(3-(4-ethoxyphenyl)ureido)phenoxy) acetic acid The title compound (26.7 mg, 67%) was prepared following a procedure analogous to that for the synthesis of Example 98, except that 1-ethoxy-4-isocyanatobenzene was used instead of 4-chloro-2-fluoro-1-isocyanatobenzene in Example 101. MS(ES): m/z=520 [M+H]$^+$, HPLC $T_r$: 1.66 min (Method C).

Example 101 ethyl 2-((5-(3-(4-chloro-2-fluorophenyl)ureido)-6-(cyclohexyl(isobutyl)amino)pyridin-3-yl)oxy)acetate

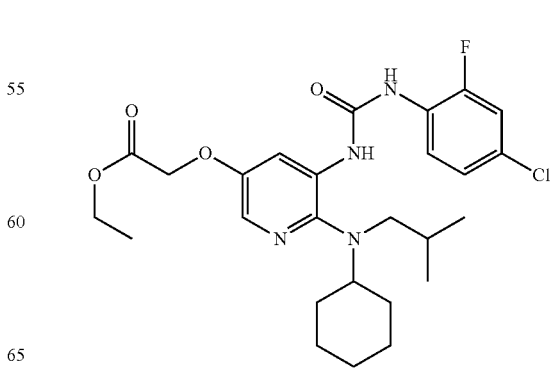

101A. 5-bromo-N-cyclohexyl-N-isobutyl-3-nitropyridin-2-amine

A solution of 5-bromo-2-fluoro-3-nitropyridine (1.105 g, 5 mmol) and DIEA (1.223 mL, 7.00 mmol) in NMP (2 mL) was treated with Intermediate 1B (1.553 g, 10.00 mmol) and heated to 100° C. After 1 h, the reaction was treated with an additional 0.6 mL of Intermediate 1B and heated to 100° C. for an additional 30 min. The reaction was then cooled to ambient temperature and dissolved in EtOAc. This solution was washed sequentially with 10% aq. HOAc and sat. aq. sodium bicarbonate then dried and stripped to afford a dark oil. Chromatography on silica gel (0-10% EtOAc-hexanes) afforded Intermediate 101A (1.62 g, 91% yield) as a dark oil. MS (ES): m/z=356 [M+H]$^+$, T$_r$=1.33 min (Method A).

101B. N-cyclohexyl-5-(5,5-dimethyl-1,3,2-dioxaborinan-2-yl)-N-isobutyl-3-nitropyridin-2-amine A solution of Intermediate 101A (0.713 g, 2 mmol) and 5,5,5',5'-tetramethyl-2,2'-bi(1,3,2-dioxaborinane) (0.587 g, 2.60 mmol) in DMSO (3.33 ml) was degassed by purging with nitrogen briefly. It was then treated with potassium acetate (0.589 g, 6.00 mmol) and 1,1'-bis(diphenylphosphino)ferrocene-palladium(II)dichloride dichloromethane complex (0.049 g, 0.060 mmol), placed under nitrogen, and heated to 80° C. ON. The reaction was cooled and purified by flash chromatography (gradient elution with 5-20% EtOAc-hexanes). Concentration of the appropriate fractions afforded Intermediate 101 B (0.75 g, 96% yield) as a viscous red oil. MS (ES): m/z=322 [M+H]$^+$ for parent boronic acid. T$_r$=1.07 min (Method A).

101C. 6-(cyclohexyl(isobutyl)amino)-5-nitropyridin-3-ol

A solution of Intermediate 101B (0.066 g, 0.170 mmol) in THF (0.5 mL) was treated with sodium 1,2,3-dioxaboriran-3-olate, 4H$_2$O (0.029 g, 0.186 mmol) in Water (0.5 mL). This mixture was stirred 1.5 h at RT then diluted with EtOAc. This solution was washed with half-saturated ammonium chloride then dil. aq. sodium bicarbonate. The org. phase was dried and stripped to afford Intermediate 101C (0.048 g, 92% yield) as a red glass. MS (ES): m/z=294 [M+H]$^+$. T$_r$=1.11 min (Method A).

101D. ethyl 2-((6-(cyclohexyl(isobutyl)amino)-5-nitropyridin-3-yl)oxy)acetate A solution of Intermediate 101C (0.045 g, 0.153 mmol) in DMF (0.256 ml) was treated with cesium carbonate (0.070 g, 0.215 mmol) followed by ethyl 2-bromoacetate (0.038 g, 0.230 mmol). This mixture was stirred 30 min. at 60° C., after which time TLC indicated complete conversion to a spot at higher Rf (~0.3 in 10% ether-hexanes). The reaction was applied directly to a silica gel column and eluted with 5-25% ether-hexanes. Concentration of the appropriate fractions afforded Intermediate 101D (0.051 g, 83% yield) as an orange oil. MS (ES): m/z=380 [M+H]$^+$. T$_r$=1.21 min (Method A).

Example 101. ethyl 2-((5-(3-(4-chloro-2-fluorophenyl)ureido)-6-(cyclohexyl(isobutyl)amino)pyridin-3-yl)oxy)acetate A solution of Intermediate 101D (0.047 g, 0.124 mmol) in Ethanol (3 mL)-THF (1 mL) was treated simultaneously with zinc (0.081 g, 1.239 mmol) and a solution of ammonium chloride (0.066 g, 1.239 mmol) in 1 mL of water. This mixture was stirred 1 h at RT then diluted with dichloromethane and treated with 2 g of MgSO$_4$. This mixture was stirred briefly then filtered. The filtrate was concentrated and dissolved in 1 mL of THF. This solution was treated with 4-chloro-2-fluoro-1-isocyanatobenzene (0.025 g, 0.149 mmol), and the reaction was stirred 1 h at RT. The reaction was applied directly to a silica gel column and eluted with a gradient of EtOAc-hexanes. Concentration of the appropriate fractions afforded ethyl 2-((5-(3-(4-chloro-2-fluorophenyl)ureido)-6-(cyclohexyl(isobutyl)amino)pyridin-3-yl)oxy)acetate (0.06 g, 92% yield) as a colorless foam. MS (ES): m/z=521 [M+H]$^+$. T$_r$=1.12 min (Method A).

Example 102

2-((5-(3-(4-chloro-2-fluorophenyl)ureido)-6-(cyclohexyl(isobutyl)amino)pyridin-3-yl)oxy)acetic acid

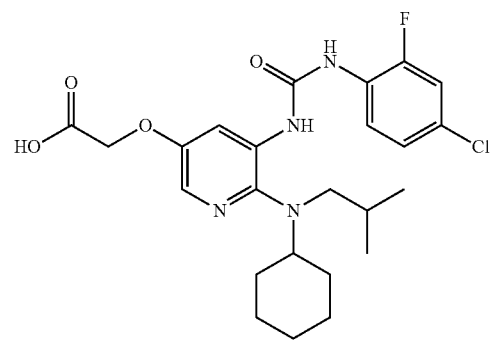 [SMILES: CC(C)CN(c1ncc(OCC(=O)O)cc1NC(=O)Nc1ccc(Cl)cc1F)C1CCCCC1]

Example 102. 2-((5-(3-(4-chloro-2-fluorophenyl)ureido)-6-(cyclohexyl(isobutyl)amino)pyridin-3-yl)oxy)acetic acid To a solution of ethyl 2-((5-(3-(4-chloro-2-fluorophenyl)ureido)-6-(cyclohexyl(isobutyl)amino)pyridin-3-yl)oxy)acetate (0.05 g, 0.096 mmol) in THF (1 mL) was added a solution of lithium hydroxide (0.011 g, 0.480 mmol) in water (1 mL). Methanol, ~0.4 mL was added to give a single phase, and the reaction was stirred 2 h at 50° C. The reaction was poured into 5% aq. HOAc, and the resulting mixture was ext. with EtOAc. The org. ext. was dried, stripped, and lyophilized from benzene to example 102 (0.043 g, 86% yield) as an off-white powder. MS (ES): m/z=493 [M+H]$^+$. T$_r$=0.99 min (Method A).

Example 103

2-((5-(3-(4-chloro-2-fluorophenyl)ureido)-6-(cyclohexyl(isobutyl)amino)pyridin-3-yl)oxy)-N-(cyclopropylsulfonyl)acetamide

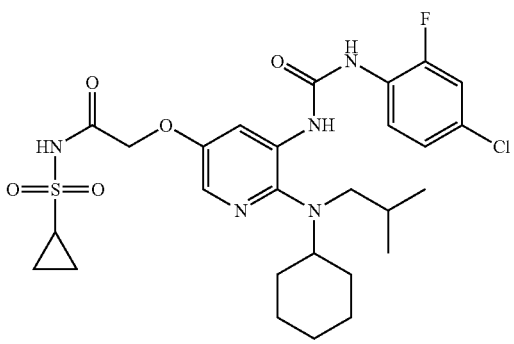 [SMILES: CC(C)CN(c1ncc(OCC(=O)NS(=O)(=O)C2CC2)cc1NC(=O)Nc1ccc(Cl)cc1F)C1CCCCC1]

Example 103. 2-((5-(3-(4-chloro-2-fluorophenyl)ureido)-6-(cyclohexyl(isobutyl)amino)pyridin-3-yl)oxy)-N-(cyclopropylsulfonyl)acetamide 2-((5-(3-(4-chloro-2-fluorophenyl)ureido)-6-(cyclohexyl(isobutyl)amino)pyridin-3-yl)oxy)acetic acid (15 mg, 0.030 mmol) was dissolved in THF (150 µl) and CDI (8.9 mg, 0.055 mmol) was added. The mixture was heated to reflux for 40 min. The reaction was transferred into a stirred solution of cyclopropanesulfonamide (5.53 mg, 0.046 mmol) in ~0.15 mL of THF. This solution was then treated with DBU (8.7 µl, 0.058 mmol), and the reaction was stirred at RT. After 3 h at RT, the reaction was diluted with DMF and purified by prep. HPLC. Concentration of the appropriate fractions afforded example 103 as the TFA salt (0.0095 g, 45% yield). MS (ES): m/z=596 [M+H]$^+$. T$_r$=1.81 min (Method C).

Example 104

2-(3-(3-(4-chloro-2-fluorophenyl)ureido)-4-(cyclohexyl(isobutyl)amino)-5-fluorophenoxy)acetic acid

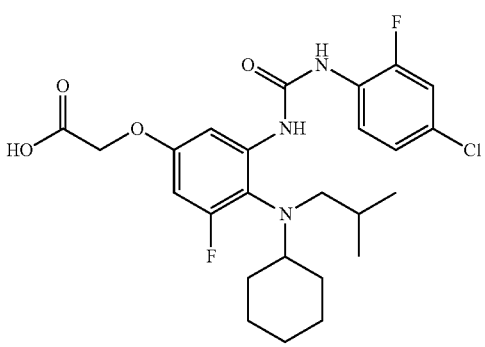 [SMILES: CC(C)CN(c1c(F)cc(OCC(=O)O)cc1NC(=O)Nc1ccc(Cl)cc1F)C1CCCCC1]

104A. 4-bromo-N-cyclohexyl-2-fluoro-N-isobutyl-6-nitroaniline

A solution of 5-bromo-1,2-difluoro-3-nitrobenzene (0.76 g, 3.19 mmol) and N-isobutylcyclohexanamine (1.488 g, 9.58 mmol) was placed under nitrogen and heated at 130° C. for 1 h then for 3 h at 135° C. The reaction was cooled to RT, diluted with ether and washed with 5% aq. HOAc. The org. phase was dried, stripped, and chromatographed on silica gel (gradient elution with 0.5% to 2% EtOAc-hexanes. Concentration of the appropriate fractions afforded 4-bromo-N-cyclohexyl-2-fluoro-N-isobutyl-6-nitroaniline (0.89 g, 70.9% yield) as an orange oil. MS (ES): m/z=373 [M+H]$^+$, T$_r$=1.36 min (Method A).

104B. N-cyclohexyl-4-(5,5-dimethyl-1,3,2-dioxaborinan-2-yl)-2-fluoro-N-isobutyl-6-nitroaniline Reaction of 4-bromo-N-cyclohexyl-2-fluoro-N-isobutyl-6-nitroaniline under the conditions described for the synthesis of 101B afforded N-cyclohexyl-4-(5,5-dimethyl-1,3,2-dioxaborinan-2-yl)-2-fluoro-N-isobutyl-6-nitroaniline (0.27 g, 89% yield) as a red oil. MS (ES): m/z=339 [M+H]$^+$ for parent boronic acid. T$_r$=1.17 min (Method A).

104C. 4-(cyclohexyl(isobutyl)amino)-3-fluoro-5-nitrophenol

Reaction of N-cyclohexyl-4-(5,5-dimethyl-1,3,2-dioxaborinan-2-yl)-2-fluoro-N-isobutyl-6-nitroaniline under the conditions described for the synthesis of 101C afforded 4-(cyclohexyl(isobutyl)amino)-3-fluoro-5-nitrophenol (0.17 g, 81% yield) as a dark oil. MS (ES): m/z=311 [M+H]$^+$. T$_r$=1.19 min (Method A).

104D. ethyl 2-(4-(cyclohexyl(isobutyl)amino)-3-fluoro-5-nitrophenoxy)acetate Reaction of 4-(cyclohexyl(isobutyl)amino)-3-fluoro-5-nitrophenol under the conditions described for the synthesis of example 101D afforded ethyl 2-(4-(cyclohexyl(isobutyl)amino)-3-fluoro-5-nitrophenoxy)acetate (0.097 g, 72% yield) as an orange oil. MS (ES): m/z=397 [M+H]$^+$. T$_r$=1.26 min (Method A).

104E. ethyl 2-(3-(3-(4-chloro-2-fluorophenyl)ureido)-4-(cyclohexyl(isobutyl)amino)-5-fluorophenoxy)acetate Reaction of ethyl 2-(4-(cyclohexyl(isobutyl)amino)-3-fluoro-5-nitrophenoxy)acetate under the conditions described for the synthesis of Example 101 afforded ethyl 2-(3-(3-(4-chloro-2-fluorophenyl)ureido)-4-(cyclohexyl(isobutyl)amino)-5-fluorophenoxy)acetate (0.052 g, 81% yield) as a colorless foam. MS (ES): m/z=538 [M+H]$^+$. T$_r$=1.25 min (Method A).

104. 2-(3-(3-(4-chloro-2-fluorophenyl)ureido)-4-(cyclohexyl(isobutyl)amino)-5-fluorophenoxy)acetic acid Reaction of ethyl 2-(3-(3-(4-chloro-2-fluorophenyl)ureido)-4-(cyclohexyl(isobutyl)amino)-5-fluorophenoxy)acetate under the conditions described for the synthesis of Example 102 afforded example 104 (0.03 g, 85% yield) an off-white powder. MS (ES): m/z=510 [M+H]$^+$. T$_r$=1.14 min (Method A).

Example 105

2-(3-(3-(4-chloro-2-fluorophenyl)ureido)-4-(cyclohexyl(isobutyl)amino)-5-fluorophenoxy)-N-(cyclopropylsulfonyl)acetamide

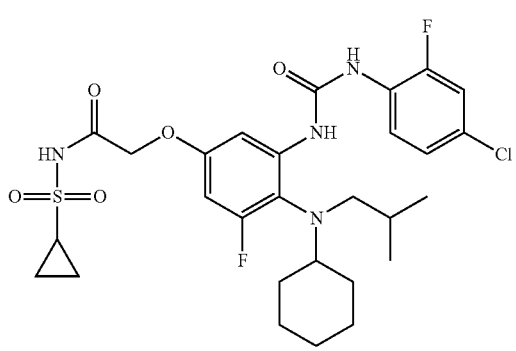 [SMILES: CC(C)CN(c1c(F)cc(OCC(=O)NS(=O)(=O)C2CC2)cc1NC(=O)Nc1ccc(Cl)cc1F)C1CCCCC1]

105. 2-(3-(3-(4-chloro-2-fluorophenyl)ureido)-4-(cyclohexyl(isobutyl)amino)-5-fluorophenoxy)-N-(cyclopropylsulfonyl)acetamide Reaction of 2-(3-(3-(4-chloro-2-fluorophenyl)ureido)-4-(cyclohexyl(isobutyl)amino)-5-fluorophenoxy)acetic acid under the conditions described for the synthesis of Example 103 afforded example 105 (0.014 g, 74% yield). MS (ES): m/z=613 [M+H]$^+$. T$_r$=2.01 min (Method C).

Example 106

2-(4-(cyclohexyl(isobutyl)amino)-3-(3-(2,5-difluorophenyl)ureido)-5-fluorophenoxy)acetic acid

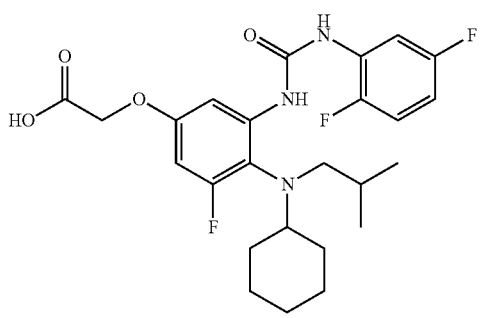 [SMILES: CC(C)CN(c1c(F)cc(OCC(=O)O)cc1NC(=O)Nc1cc(F)ccc1F)C1CCCCC1]

106. 2-(4-(cyclohexyl(isobutyl)amino)-3-(3-(2,5-difluorophenyl)ureido)-5-fluorophenoxy)acetic acid A solution of ethyl 2-(4-(cyclohexyl(isobutyl)amino)-3-fluoro-5-nitrophenoxy)acetate (104D) (0.045 g, 0.114 mmol) in Ethanol-THF was treated simultaneously with zinc (0.074 g, 1.135 mmol) and a solution of ammonium chloride (0.061 g, 1.135 mmol) in 0.3 mL of water. This mixture was rapidly stirred for 1 h then diluted with dichloromethane and treated with MgSO$_4$. This mixture was filtered, and the filtrate was stripped to afford an oil. The crude product was dissolved in 1 mL of THF, charged into a 1 dram vial, and treated with 1,4-difluoro-2-isocyanatobenzene (0.024 g, 0.153 mmol). The resulting solution was stirred 1 h at RT then warmed to 60° C. and treated with lithium hydroxide (0.028 g, 1.173 mmol) in 0.8 mL of water. Methanol, ~1 mL was added to give a single phase. The reaction was stirred at 60° C. for 2 h, and most of the solvent was removed under a stream of nitrogen. The residue was treated with 0.1 mL of glacial HOAc and purified by prep HPLC to afford example 106 (0.032 g, 55% yield). MS (ES): m/z=494 [M+H]$^+$. T$_r$=1.77 min (Method C).

Example 107

2-(3-(3-(4-chloro-2-fluorophenyl)ureido)-4-(cyclohexyl(isobutyl)amino)-2-fluorophenoxy)acetic acid

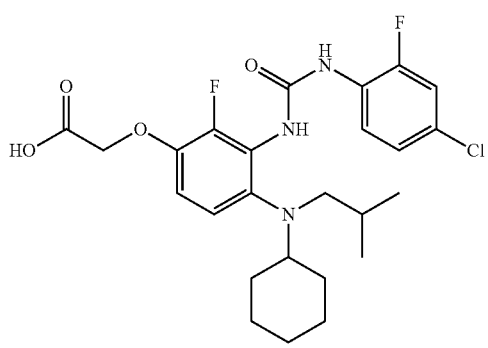 [SMILES: CC(C)CN(c1ccc(OCC(=O)O)c(F)c1NC(=O)Nc1ccc(Cl)cc1F)C1CCCCC1]

107A. 4-bromo-N-cyclohexyl-3-fluoro-N-isobutyl-2-nitroaniline

A solution of 1-bromo-2,4-difluoro-3-nitrobenzene (0.476 g, 2 mmol) in N-isobutylcyclohexanamine (1.242 g, 8.00 mmol) was heated to 140° C. After 4 h, the reaction was cooled and worked up extractively. The crude product was purified by flash chromatography. (EtOAc-hexanes). Concentration of the appropriate fractions afforded 4-bromo-N-cyclohexyl-3-fluoro-N-isobutyl-2-nitroaniline (0.56 g, 74% yield) as an orange oil which crystallized upon standing. MS (ES): m/z=373 [M+H]$^+$, T$_r$=1.33 min (Method A).

107B. 4-bromo-N1-cyclohexyl-3-fluoro-N1-isobutylbenzene-1,2-diamine

A flask containing 4-bromo-N-cyclohexyl-3-fluoro-N-isobutyl-2-nitroaniline (0.4 g, 1.072 mmol) in Ethanol (9 mL)-THF (3 mL) was immersed in a small water bath and treated simultaneously with zinc (0.701 g, 10.72 mmol) and a solution of ammonium chloride (0.573 g, 10.72 mmol) in 1 mL of water. This mixture was stirred rapidly for 1 h then diluted with dichloromethane and treated with 4 g of MgSO$_4$. The resulting mixture was stirred briefly then filtered. The filtrate was stripped to afford 4-bromo-N1-cyclohexyl-3-fluoro-N1-isobutylbenzene-1,2-diamine as a straw-colored oil. MS (ES): m/z=343 [M+H]$^+$. T$_r$=1.25 min (Method A).

107C. 1-(3-bromo-6-(cyclohexyl(isobutyl)amino)-2-fluorophenyl)-3-(4-chloro-2-fluorophenyl)urea A solution of 4-bromo-N1-cyclohexyl-3-fluoro-N1-isobutylbenzene-1,2-diamine (0.17 g, 0.495 mmol) in THF (1 mL) was treated with 4-chloro-2-fluoro-1-isocyanatobenzene (0.093 g, 0.545 mmol). This solution was stirred two days at RT then purified by flash chromatography (EtOAc-hexanes).

Concentration of the appropriate fractions afforded 1-(3-bromo-6-(cyclohexyl(isobutyl)amino)-2-fluorophenyl)-3-(4-chloro-2-fluorophenyl)urea (0.22 g, 86% yield) as a white powder. MS (ES): m/z=514 [M+H]$^+$. T$_r$=1.21 min (Method A).

107D. 1-(4-chloro-2-fluorophenyl)-3-(6-(cyclohexyl(isobutyl)amino)-3-(5,5-dimethyl-1,3,2-dioxaborinan-2-yl)-2-fluorophenyl)urea Reaction of 1-(3-bromo-6-(cyclohexyl(isobutyl)amino)-2-fluorophenyl)-3-(4-chloro-2-fluorophenyl)urea under the conditions described for the synthesis of 101B afforded 1-(4-chloro-2-fluorophenyl)-3-(6-(cyclohexyl(isobutyl)amino)-3-(5,5-dimethyl-1,3,2-dioxaborinan-2-yl)-2-fluorophenyl)urea (0.075 g, 47% yield) as a pale yellow oil. MS (ES): m/z=480 [M+H]$^+$ for parent boronic acid. T$_r$=0.99 min (Method A).

107E. 1-(4-chloro-2-fluorophenyl)-3-(6-(cyclohexyl(isobutyl)amino)-2-fluoro-3-hydroxyphenyl)urea Reaction of 1-(4-chloro-2-fluorophenyl)-3-(6-(cyclohexyl(isobutyl)amino)-3-(5,5-dimethyl-1,3,2-dioxaborinan-2-yl)-2-fluorophenyl)urea under the conditions described for the synthesis of 101C afforded 1-(4-chloro-2-fluorophenyl)-3-(6-(cyclohexyl(isobutyl)amino)-2-fluoro-3-hydroxyphenyl)urea (0.040 g, 65% yield) as a colorless foam. MS (ES): m/z=452 [M+H]$^+$. T$_r$=0.91 min (Method A).

107F. 2-(3-(3-(4-chloro-2-fluorophenyl)ureido)-4-(cyclohexyl(isobutyl)amino)-5-fluorophenoxy)acetic acid A solution of 1-(4-chloro-2-fluorophenyl)-3-(6-(cyclohexyl(isobutyl)amino)-2-fluoro-3-hydroxyphenyl)urea (0.038 g, 0.084 mmol) in DMF (0.4 mL) was treated with cesium carbonate (0.030 g, 0.092 mmol). The stirred mixture was then treated with ethyl 2-bromoacetate (9.32 μl, 0.084 mmol) and warmed to 60° C. The reaction was stirred for 30 min. then cooled to RT and quenched with 5% aq. HOAc. This mixture was ext. twice with chloroform, and the comb. org. ext. dried and stripped to afford ethyl 2-(3-(3-(4-chloro-2-fluorophenyl)ureido)-4-(cyclohexyl(isobutyl)amino)-2-fluorophenoxy)acetate (0.042 g, 91% yield) as a colorless oil which solidified upon evacuation under house vac. MS (ES): m/z=538 [M+H]$^+$. T$_r$=1.02 min (Method A).

Example 107. 2-(3-(3-(4-chloro-2-fluorophenyl)ureido)-4-(cyclohexyl(isobutyl)amino)-2-fluorophenoxy)acetic acid A solution of ethyl 2-(3-(3-(4-chloro-2-fluorophenyl)ureido)-4-(cyclohexyl(isobutyl)amino)-2-fluorophenoxy)acetate (0.038 g, 0.071 mmol) in THF (1.5 mL) was treated with lithium hydroxide (0.017 g, 0.706 mmol) in Water (1.5 mL). Methanol, ~1 mL, was added to give a single phase, and the reaction was stirred at 60° C. for 1 h. Organic solvents removed under a stream of nitrogen, and the resulting white paste was suspended in 3 mL of water. Upon warming, most of the solids dissolved to give a cloudy suspension. This was treated with 0.3 mL of glacial HOAc, and the resulting solid was filtered, rinsed with water, and air-dried to afford example 107 (0.031 g, 85% yield) as a white solid. MS (ES): m/z=510 [M+H]$^+$. T$_r$=0.92 min (Method A).

Example 108

2-(3-(3-(4-chloro-2-fluorophenyl)ureido)-5-cyano-4-(cyclohexyl(isobutyl)amino)phenoxy)acetic acid

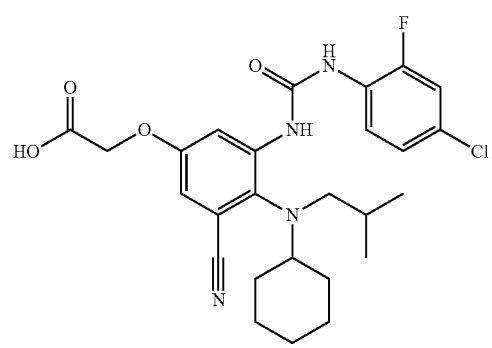 [SMILES: CC(C)CN(c1c(C#N)cc(OCC(=O)O)cc1NC(=O)Nc1ccc(Cl)cc1F)C1CCCCC1]

108A. 5-bromo-2-(cyclohexyl(isobutyl)amino)-3-nitrobenzoic acid

Reaction of 5-bromo-2-fluoro-3-nitrobenzoic acid under the conditions described for the synthesis of 104A afforded 5-bromo-2-(cyclohexyl(isobutyl)amino)-3-nitrobenzoic acid (0.37 g, 93% yield) as an orange oil. MS (ES): m/z=399 [M+H]$^+$, T$_r$=1.13 min (Method A).

108B. 5-bromo-2-(cyclohexyl(isobutyl)amino)-3-nitrobenzamide

A solution of 5-bromo-2-(cyclohexyl(isobutyl)amino)-3-nitrobenzoic acid (0.36 g, 0.902 mmol) in DMF (3 mL) was treated with triethylamine (0.503 mL, 3.61 mmol) followed by BOP (0.877 g, 1.984 mmol). This solution was stirred for 5 min. at RT then treated dropwise with a suspension of ammonium chloride (0.145 g, 2.70 mmol) in conc. ammonium hydroxide (0.281 mL, 7.21 mmol). The reaction was stirred 15 min. at RT, after which time LCMS indicates complete conversion to the desired amide. The reaction was dil. with EtOAc and washed with dil. aq. sodium bicarbonate then dil. aq. HCl. The org. phase was dried and stripped to afford a red oil. This was chromatographed on silica gel (EtOAc-hexanes). Concentration of the appropriate fractions afforded 5-bromo-2-(cyclohexyl(isobutyl)amino)-3-nitrobenzamide (0.28 g, 76% yield) as an orange foam. MS (ES): m/z=398 [M+H]$^+$. T$_r$=1.11 min (Method A).

108C. 5-bromo-2-(cyclohexyl(isobutyl)amino)-3-nitrobenzonitrile

A solution of 5-bromo-2-(cyclohexyl(isobutyl)amino)-3-nitrobenzamide (0.275 g, 0.690 mmol) in dichloromethane (6.90 ml) was treated with triethylamine (0.385 ml, 2.76 mmol) followed by trifluoroacetic anhydride (0.293 ml, 2.071 mmol). The reaction was stirred 25 min. then quenched with 5% aq. HOAc. The resulting mixture was ext. with EtOAc, and the org. ext was washed with aq. sodium bicarbonate then dried and stripped to afford an orange oil. The crude product was chromatographed on silica gel (2-10% EtOAc-hexanes). Concentration of that appropriate fractions afforded 5-bromo-2-(cyclohexyl(isobutyl)amino)-3-nitrobenzonitrile (0.236 g, 88% yield) as a yellow oil which crystallized upon standing. MS (ES): m/z=380 [M+H]$^+$. T$_r$=1.26 min (Method A).

108D. 1-(5-bromo-3-cyano-2-(cyclohexyl(isobutyl)amino)phenyl)-3-(4-chloro-2-fluorophenyl)urea Reaction of 5-bromo-2-(cyclohexyl(isobutyl)amino)-3-nitrobenzonitrile under the conditions described for the synthesis of Example 101 followed by prep. HPLC afforded 1-(5-bromo-3-cyano-2-(cyclohexyl(isobutyl)amino)phenyl)-3-(4-chloro-2-fluorophenyl)urea (0.17 g, 69% yield) as a white powder. MS (ES): m/z=521 [M+H]$^+$, T$_r$=1.31 min (Method A).

108E. 1-(4-chloro-2-fluorophenyl)-3-(3-cyano-2-(cyclohexyl(isobutyl)amino)-5-(5,5-dimethyl-1,3,2-dioxaborinan-2-yl)phenyl)urea Reaction of 1-(5-bromo-3-cyano-2-(cyclohexyl(isobutyl)amino)phenyl)-3-(4-chloro-2-fluorophenyl)urea under the conditions described for the synthesis of 101B afforded 1-(4-chloro-2-fluorophenyl)-3-(3-cyano-2-(cyclohexyl(isobutyl)amino)-5-(5,5-dimethyl-1,3,2-dioxaborinan-2-yl)phenyl)urea (0.09 g, 60% yield) as a colorless glass. MS (ES): m/z=487 [M+H]$^+$ for parent boronic acid. T$_r$=1.09 min (Method A).

108F. 1-(4-chloro-2-fluorophenyl)-3-(3-cyano-2-(cyclohexyl(isobutyl)amino)-5-hydroxyphenyl)urea Reaction of 1-(4-chloro-2-fluorophenyl)-3-(3-cyano-2-(cyclohexyl(isobutyl)amino)-5-(5,5-dimethyl-1,3,2-dioxaborinan-2-yl)phenyl)urea under the conditions described for the synthesis of 101C afforded 1-(4-chloro-2-fluorophenyl)-3-(3-cyano-2-(cyclohexyl(isobutyl)amino)-5-hydroxyphenyl)urea (0.05 g, 86% yield) as a pale amber oil. MS (ES): m/z=459 [M+H]$^+$. T$_r$=1.13 min (Method A).

108G. ethyl 2-(3-(3-(4-chloro-2-fluorophenyl)ureido)-5-cyano-4-(cyclohexyl(isobutyl)amino)phenoxy)acetate Reaction of 1-(4-chloro-2-fluorophenyl)-3-(3-cyano-2-(cyclohexyl(isobutyl)amino)-5-hydroxyphenyl)urea under the conditions described for the synthesis of 101D afforded ethyl 2-(3-(3-(4-chloro-2-fluorophenyl)ureido)-5-cyano-4-(cyclohexyl(isobutyl)amino)phenoxy)acetate (0.0064 g, 11% yield) as a white powder. MS (ES): m/z=545 [M+H]$^+$. T$_r$=1.20 min (Method A).

Example 108. 2-(3-(3-(4-chloro-2-fluorophenyl)ureido)-5-cyano-4-(cyclohexyl(isobutyl)amino)phenoxy)acetic acid Reaction of ethyl 2-(3-(3-(4-chloro-2-fluorophenyl)ureido)-5-cyano-4-(cyclohexyl(isobutyl)amino)phenoxy)acetate under the conditions described for the synthesis of Example 102 afforded Example 108 (0.0058 g, 95% yield) as an off-white powder. MS (ES): m/z=517 [M+H]$^+$. T$_r$=1.10 min (Method A).

Example 109

2-(4-(cyclohexyl(isobutyl)amino)-3-(3-(p-tolyl)ureido)phenoxy)acetic acid

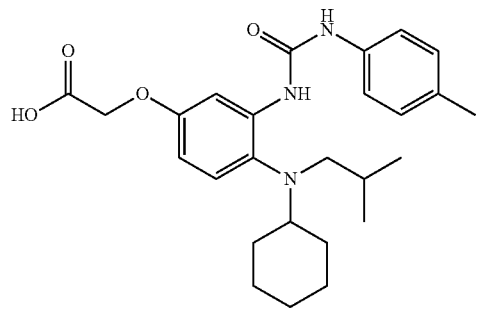 [SMILES: Cc1ccc(NC(=O)Nc2cc(OCC(=O)O)ccc2N(CC(C)C)C2CCCCC2)cc1]

109A. ethyl 2-(4-(cyclohexyl(isobutyl)amino)-3-(3-(p-tolyl)ureido)phenoxy)acetate Reaction of ethyl 2-(3-amino-4-(cyclohexyl(isobutyl)amino)phenoxy)acetate (1E) and 4-methylphenylisocyanate under the conditions described for the synthesis of 107C afforded ethyl 2-(4-(cyclohexyl(isobutyl)amino)-3-(3-(p-tolyl)ureido)phenoxy)acetate (0.018 g, 65% yield) as a colorless solid. MS (ES): m/z=482 [M+H]$^+$, T$_r$=1.03 min (Method A).

Example 109

Reaction of ethyl 2-(4-(cyclohexyl(isobutyl)amino)-3-(3-(p-tolyl)ureido)phenoxy)acetate under the conditions described for the synthesis of Example 102 afforded 2-(4-(cyclohexyl(isobutyl)amino)-3-(3-(p-tolyl)ureido)phenoxy)acetic acid (0.0085 g, 56% yield) as a colorless solid. MS (ES): m/z=454 [M+H]$^+$, T$_r$=1.81 min (Method C).

Example 110

2-(3-(2-(4-chloro-2-fluorophenyl)acetamido)-4-(cyclohexyl(isobutyl)amino)phenoxy)acetic acid

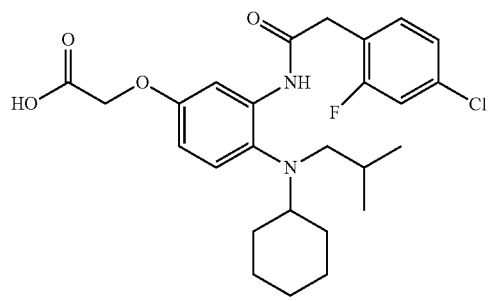 [SMILES: CC(C)CN(c1ccc(OCC(=O)O)cc1NC(=O)Cc1ccc(Cl)cc1F)C1CCCCC1]

110A. ethyl 2-(3-(2-(4-chloro-2-fluorophenyl)acetamido)-4-(cyclohexyl(isobutyl)amino)phenoxy)acetate A solution of ethyl 2-(3-amino-4-(cyclohexyl(isobutyl)amino)phenoxy)acetate (1E) (0.02 g, 0.057 mmol) and triethylamine (0.016 mL, 0.12 mmol) in DMF (0.4 mL) was treated with 2-(4-chloro-2-fluorophenyl)acetic acid (0.013 g, 0.069 mmol) then Bop (0.03 g, 0.069 mmol), and the resulting solution was stirred 1 h at RT. The reaction was purified by prep. HPLC. The appropriate fraction was concentrated under reduced pressure to afford ethyl 2-(3-(2-(4-chloro-2-fluorophenyl)acetamido)-4-(cyclohexyl(isobutyl)amino)phenoxy)acetate (0.019 g, 64% yield) as a glass. MS (ES): m/z=519 [M+H]$^+$, T$_r$=1.18 min (Method A).

Example 110. 2-(3-(2-(4-chloro-2-fluorophenyl) acetamido)-4 (cyclohexyl (isobutyl)amino)phenoxy) acetic acid Reaction of ethyl 2-(3-(2-(4-chloro-2-fluorophenyl)acetamido)-4-(cyclohexyl(isobutyl)amino)phenoxy)acetate under the conditions described for the synthesis of Example 102 afforded 2-(3-(2-(4-chloro-2-fluorophenyl)acetamido)-4-(cyclohexyl(isobutyl)amino)phenoxy)acetic acid (0.01 g, 58% yield) as a pale yellow solid. MS (ES): m/z=491 [M+H]$^+$, T$_r$=1.08 min (Method A).

Example 111

2-(3-(3-(4-chloro-2-fluorophenyl)ureido)-4-(cyclohexyl(isobutyl)amino)phenoxy)-N-(5-methylthiazol-2-yl)acetamide

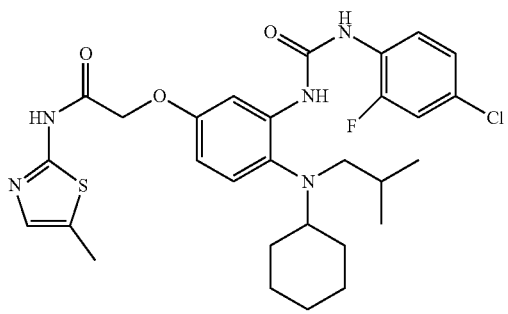 [SMILES: Cc1cnc(NC(=O)COc2ccc(N(CC(C)C)C3CCCCC3)c(NC(=O)Nc3ccc(Cl)cc3F)c2)s1]

Example 111. 2-(3-(3-(4-chloro-2-fluorophenyl) ureido)-4-(cyclohexyl(isobutyl)amino)phenoxy)-N-(5-methylthiazol-2-yl)acetamide A solution of 2-(3-(3-(4-chloro-2-fluorophenyl)ureido)-4-(cyclohexyl(isobutyl)amino)phenoxy)acetic acid (Example 1) (0.02 g, 0.041 mmol) in DMF (0.3 mL) was treated with 5-methylthiazol-2-amine (9.28 mg, 0.081 mmol) followed by triethylamine (0.014 mL, 0.102 mmol) then BOP (0.023 g, 0.053 mmol). The reaction was stirred at 45° C. for 1 h then purified by prep. HPLC. Concentration of the appropriate fractions afforded 2-(3-(3-(4-chloro-2-fluorophenyl) ureido)-4-(cyclohexyl(isobutyl)amino)phenoxy)-N-(5-methylthiazol-2-yl)acetamide.TFA (0.023 g, 80% yield). MS (ES): m/z=588 [M+H]$^+$, T$_r$=2.61 min (Method C).

Example 112

2-(4-(diisobutylamino)-3-(3-(p-tolyl)ureido)phenoxy)acetic acid

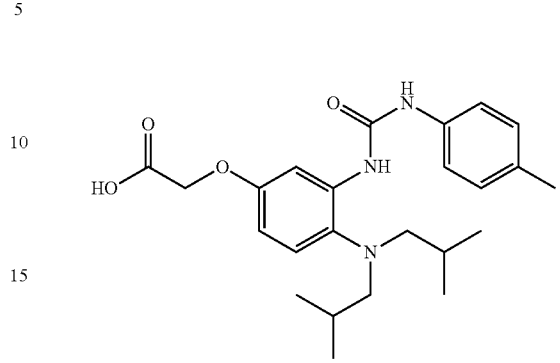

112A. ethyl 2-(4-(diisobutylamino)-3-nitrophenoxy)acetate

A solution of ethyl 2-(4-fluoro-3-nitrophenoxy)acetate (0.05 g, 0.206 mmol) in diisobutylamine (0.133 g, 1.028 mmol) was heated to 95° C. for 24 h. The reaction was cooled and purified by flash (gradient elution with EtOAc-hexanes). Concentration of the appropriate fractions afforded ethyl 2-(4-(diisobutylamino)-3-nitrophenoxy)acetate (0.055 g, 75% yield) as an orange oil. MS (ES): m/z=353 [M+H]$^+$, T$_r$=1.16 min (Method A).

112B. 2-(4-(diisobutylamino)-3-nitrophenoxy)acetic acid

A solution of ethyl 2-(4-(diisobutylamino)-3-nitrophenoxy)acetate (0.048 g, 0.136 mmol) in THF (2 mL) was treated with lithium hydroxide (0.033 g, 1.362 mmol) in Water (2 mL). This mixture was warmed to −40° C. and treated with MeOH (~0.5 mL) to give a single phase. The solution was stirred 40 min. at 40° C., after which time LCMS indicates the reaction is complete. Most of the THF was removed under a stream of nitrogen, and the residue was transferred by pipette into 10 mL of 10% aq. HOAc. Product oiled out, so the mixture was ext. with EtOAc. The org. phase was dried and stripped to afford 2-(4-(diisobutylamino)-3-nitrophenoxy)acetic acid (0.04 g, 90% yield) as a red oil. MS (ES): m/z=325 [M+H]$^+$. T$_r$=1.04 min (Method A).

112C. 2-(3-amino-4-(diisobutylamino)phenoxy)acetic acid

Reaction of 2-(4-(diisobutylamino)-3-nitrophenoxy)acetic acid under the conditions described for the synthesis of 107B afforded 2-(3-amino-4-(diisobutylamino)phenoxy) acetic acid (0.03 g, 94% yield) as a tan glass. MS (ES): m/z=295 [M+H]$^+$. T$_r$=0.71 min (Method A).

Example 112 2-(4-(diisobutylamino)-3-(3-(p-tolyl) ureido)phenoxy)acetic acid

A solution of 2-(3-amino-4-(diisobutylamino)phenoxy) acetic acid (0.015 g, 0.051 mmol) in THF (0.170 ml) was treated with 1-isocyanato-4-methylbenzene (0.014 g, 0.102 mmol). The reaction was stirred 1 h at RT then diluted with DMF and purified by prep. HPLC to afford 2-(4-(diisobutylamino)-3-(3-(p-tolyl)ureido)phenoxy)acetic acid (0.0048 g, 22% yield). MS (ES): m/z=428 [M+H]⁺. $T_r$=1.26 min (Method A).

Example 113

2-(5-(3-(4-chloro-2-fluorophenyl)ureido)-2-fluoro-4-((2-methylallyl)(4,4,4-trifluorobutyl)amino)phenoxy)acetic acid

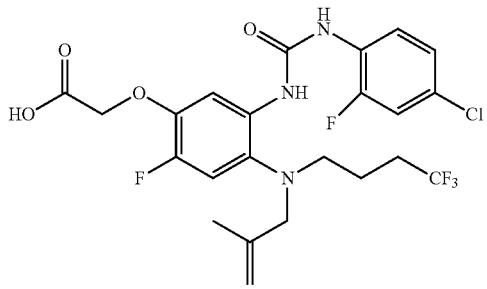 [SMILES: C=C(C)CN(CCCC(F)(F)F)c1cc(F)c(OCC(=O)O)cc1NC(=O)Nc1ccc(Cl)cc1F]

113A. ethyl 2-(2-fluoro-4-((2-methylallyl)(4,4,4-trifluorobutyl)amino)-5-nitrophenoxy)acetate A solution of ethyl 2-(2,4-difluoro-5-nitrophenoxy)acetate (0.261 g, 1 mmol) (prepared from 2,4-difluoro-5-nitrophenol using the procedure described for 1C) and 4,4,4-trifluoro-N-(2-methylallyl)butan-1-amine (0.906 g, 5.00 mmol) was heated to 100° C. The reaction was purified by flash chromatography (EtOAc-hexanes). Concentration of the appropriate fractions afforded ethyl 2-(2-fluoro-4-((2-methylallyl)(4,4,4-trifluorobutyl)amino)-5-nitrophenoxy)acetate (0.17 g, 38% yield) as an orange oil. MS (ES): m/z=423 [M+H]⁺, $T_r$=1.10 min (Method A).

113B. ethyl 2-(5-amino-2-fluoro-4-((2-methylallyl)(4,4,4-trifluorobutyl)amino)phenoxy)acetate Reaction of ethyl 2-(2-fluoro-4-((2-methylallyl)(4,4,4-trifluorobutyl)amino)-5-nitrophenoxy)acetate under the conditions described for the synthesis of 107B followed by chromatography on silica gel (EtOAc-hexane), afforded ethyl 2-(5-amino-2-fluoro-4-((2-methylallyl)(4,4,4-trifluorobutyl)amino)phenoxy)acetate (014 g, 89% yield) as a pale amber glass. MS (ES): m/z=393 [M+H]⁺. $T_r$=0.99 min (Method A).

Example 113 2-(5-(3-(4-chlorophenyl)ureido)-2-fluoro-4-((2-methylallyl)(4,4,4-trifluorobutyl)amino)phenoxy)acetic acid A solution of ethyl 2-(5-amino-2-fluoro-4-((2-methylallyl)(4,4,4-trifluorobutyl)amino)phenoxy)acetate (0.04 g, 0.102 mmol) in THF (0.3 mL) was treated with 4-chloro-2-fluoro-1-isocyanatobenzene (0.021 g, 0.122 mmol). The solution was stirred for 2 h at RT, after which time 0.5 mL of THF and 0.5 mL of MeOH were added. This solution was then treated with lithium hydroxide (0.037 g, 1.529 mmol) in 0.5 mL of water, and the saponification reaction was stirred for 2 h at 60° C. Volatile solvents were removed under a stream of nitrogen, and the residue was dissolved in DMF and purified by prep. HPLC. Concentration of the appropriate fraction afforded 2-(5-(3-(4-chloro-2-fluorophenyl)ureido)-2-fluoro-4-((2-methylallyl)(4,4,4-trifluorobutyl)amino)phenoxy)acetic acid (0.018 g, 33% yield). MS (ES): m/z=536 [M+H]⁺. $T_r$=1.04 min (Method A).

Example 114

2-(4-(cyclohexyl(isobutyl)amino)-2-fluoro-5-(3-(3-methylisoxazol-5-yl)ureido)phenoxy)acetic acid

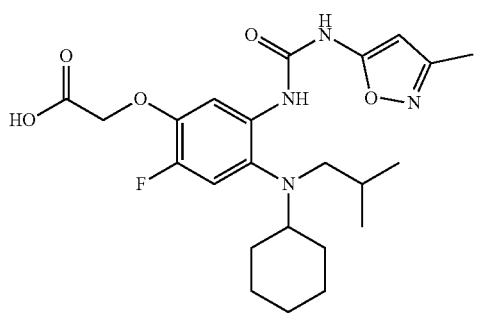 [SMILES: Cc1cc(NC(=O)Nc2cc(OCC(=O)O)c(F)cc2N(CC(C)C)C2CCCCC2)on1]

Example 114. 2-(4-(cyclohexyl(isobutyl)amino)-2-fluoro-5-(3-(3-methylisoxazol-5-yl)ureido)phenoxy) acetic acid A solution of ethyl 2-(5-amino-4-(cyclohexyl(isobutyl)amino)-2-fluorophenoxy)acetate (115B) (0.06 g, 0.164 mmol) in THF (1 mL) was treated with triethylamine (0.03 mL) followed by phenyl (3-methylisoxazol-5-yl)carbamate (0.039 g, 0.180 mmol). The reaction was stirred 1 h at 60° C. then treated with lithium hydroxide (0.653 g, 1.637 mmol), 6 wt % in water. Methanol, 0.5 mL was added to give a single phase, and the reaction was stirred for 1 h. at RT. Most of the solvent was then removed under a stream of nitrogen, and the residue was quenched with 0.2 mL of glacial HOAc, dissolved in ~2 mL of DMF, and purified by prep. HPLC. Concentration of the appropriate fractions afforded Example 114(0.042 g, 55% yield). MS (ES): m/z=463 [M+H]⁺, $T_r$=1.53 min (Method C).

Example 115

2-(5-(3-(4-chloro-2-fluorophenyl)ureido)-4-(cyclohexyl(isobutyl)amino)-2-fluorophenoxy)acetic acid

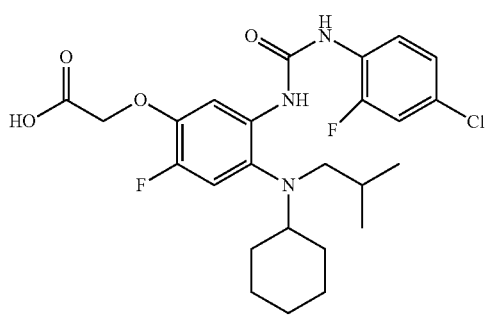 [SMILES: CC(C)CN(c1cc(F)c(OCC(=O)O)cc1NC(=O)Nc1ccc(Cl)cc1F)C1CCCCC1]

115A. ethyl 2-(4-(cyclohexyl(isobutyl)amino)-2-fluoro-5-nitrophenoxy)acetate A solution of ethyl 2-(2,4-difluoro-5-nitrophenoxy)acetate (0.261 g, 1 mmol) and N-isobutylcyclohexanamine (0.908 ml, 5.00 mmol) was heated to for 5 h at 110° C. The reaction was then cooled and flushed through a plug of silica gel (EtOAc-hexanes gradient). Concentration of the appropriate fractions afforded ethyl 2-(4-(cyclohexyl(isobutyl)amino)-2-fluoro-5-nitrophenoxy)acetate (0.23 g, 58% yield) as an orange oil. MS (ES): m/z=397 [M+H]$^+$, T$_r$=1.23 min (Method A). The $^1$H NMR spectrum of this material suggests that it is a mixture of two regioisomers.

115B. ethyl 2-(5-amino-4-(cyclohexyl(isobutyl)amino)-2-fluorophenoxy)acetate Reaction of ethyl 2-(4-(cyclohexyl(isobutyl)amino)-2-fluoro-5-nitrophenoxy)acetate under the conditions described for the synthesis of 107B afforded a mixture of primary anilines. Chromatography on silica gel (EtOAc-hexane) afforded the less polar isomer ethyl 2-(5-amino-4-(cyclohexyl(isobutyl)amino)-2-fluorophenoxy)acetate (0.08 g, 36% yield) as a pale purple oil. MS (ES): m/z=367 [M+H]$^+$. T$_r$=0.93 min (Method A).

Example 115. 2-(5-(3-(4-chloro-2-fluorophenyl)ureido)-4-(cyclohexyl(isobutyl)amino)-2-fluorophenoxy)acetic acid, TFA Reaction of ethyl 2-(5-amino-4-(cyclohexyl(isobutyl)amino)-2-fluorophenoxy)acetate under the conditions described for the synthesis of Example 113 afforded Example 115, TFA (0.026 g) as a white powder. MS (ES): m/z=510 [M+H]$^+$. T$_r$=1.07 min (Method A).

Example 116

2-(3-(3-(4-chloro-2-fluorophenyl)ureido)-4-(cyclohexyl(2-methoxyethyl)amino)phenoxy)acetic acid

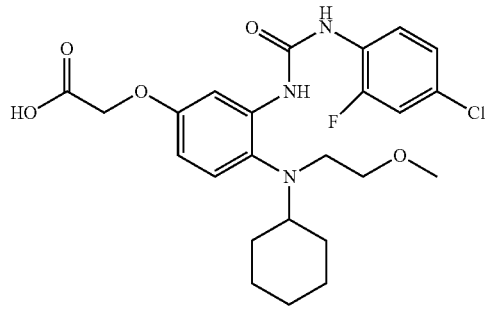 [SMILES: COCCN(c1ccc(OCC(=O)O)cc1NC(=O)Nc1ccc(Cl)cc1F)C1CCCCC1]

116A. 2-(4-(cyclohexyl(2-methoxyethyl)amino)-3-nitrophenoxy)acetic acid

A solution of ethyl 2-(4-fluoro-3-nitrophenoxy)acetate (0.170 g, 0.7 mmol) and N-(2-methoxyethyl)cyclohexanamine (0.330 g, 2.100 mmol) was heated to 125° C. for 24 h. The reaction appears to be quite slow, so the temperature was raised to 140° C. for 9 h. The temperature was then lowered to 135° C. and stirring was continued ON. The reaction was purified by prep. HPLC. Concentration of the appropriate fractions afforded 2-(4-(cyclohexyl(2-methoxyethyl)amino)-3-nitrophenoxy)acetic acid (0.17 g, 62% yield) as a dark oil. MS (ES): m/z=353 [M+H]$^+$, T$_r$=0.88 min (Method A).

116B. 2-(3-amino-4-(cyclohexyl(2-methoxyethyl)amino)phenoxy)acetic acid

Reaction of 2-(4-(cyclohexyl(2-methoxyethyl)amino)-3-nitrophenoxy)acetic acid under the conditions described for the synthesis of 107B afforded 2-(3-amino-4-(cyclohexyl(2-methoxyethyl)amino)phenoxy)acetic acid as an amber foam. MS (ES): m/z=323 [M+H]$^+$. T$_r$=0.59 min (Method A).

Example 116. 2-(3-(3-(4-chloro-2-fluorophenyl)ureido)-4-(cyclohexyl(2-methoxyethyl)amino)phenoxy)acetic acid Reaction of 2-(3-amino-4-(cyclohexyl(2-methoxyethyl)amino)phenoxy)acetic acid and 2-fluoro-4-chlorophenylisocyanate under the conditions described for the synthesis of Example 112 afforded Example 116 (0.013 g, 21% yield). MS (ES): m/z=494 [M+H]$^+$. T$_r$=1.56 min (Method C).

Example 117

2-(4-(cyclohexyl(2-methoxyethyl)amino)-3-(3-(2,4-difluorophenyl)ureido)phenoxy)acetic acid

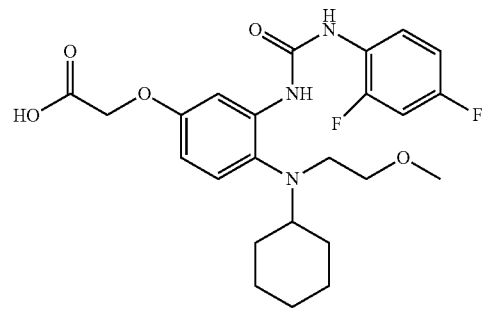 [SMILES: COCCN(c1ccc(OCC(=O)O)cc1NC(=O)Nc1ccc(F)cc1F)C1CCCCC1]

Example 117. 2-(4-(cyclohexyl(2-methoxyethyl)amino)-3-(3-(2,4-difluorophenyl)ureido)phenoxy)acetic acid Reaction of 2-(3-amino-4-(cyclohexyl(2-methoxyethyl)amino)phenoxy)acetic acid (116B) and 2,4-difluorophenylisocyanate under the conditions described for the synthesis of Example 112 afforded Example 117 (0.011 g, 25% yield). MS (ES): m/z=478 [M+H]$^+$. T$_r$=0.86 min (Method A).

Example 118

2-(3-(3-(4-chloro-2-fluorophenyl)ureido)-4-(cyclohexyl(cyclopropylmethyl)amino)phenoxy)acetic acid

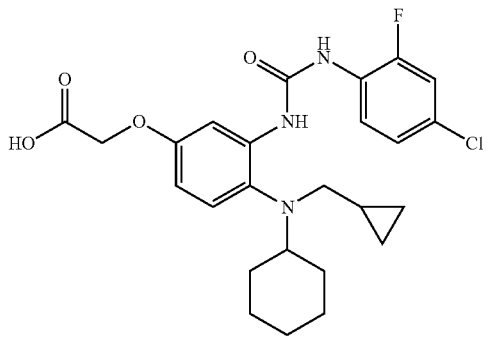 [SMILES: O=C(O)COc1ccc(N(CC2CC2)C2CCCCC2)c(NC(=O)Nc2ccc(Cl)cc2F)c1]

118A. 4-bromo-N-cyclohexyl-N-(cyclopropylmethyl)-2-nitroaniline

Reaction of 4-bromo-1-fluoro-2-nitrobenzene and N-(cyclopropylmethyl)cyclohexanamine under the conditions described for the synthesis of 101A afforded 4-bromo-N-cyclohexyl-N-(cyclopropylmethyl)-2-nitroaniline (2.4 g, 99% yield) as an orange oil. MS (ES): m/z=353 [M+H]$^+$. T$_r$=1.26 min (Method A).

118B. N-cyclohexyl-N-(cyclopropylmethyl)-4-(5,5-dimethyl-1,3,2-dioxaborinan-2-yl)-2-nitroaniline Reaction of 4-bromo-N-cyclohexyl-N-(cyclopropylmethyl)-2-nitroaniline under the conditions described for the synthesis of 101B afforded N-cyclohexyl-N-(cyclopropylmethyl)-4-(5,5-dimethyl-1,3,2-dioxaborinan-2-yl)-2-nitroaniline (0.94 g, 86% yield) as a red oil. MS (ES): m/z=319 [M+H]$^+$ for parent boronic acid. T$_r$=0.96 min (Method A).

118C. 4-(cyclohexyl(cyclopropylmethyl)amino)-3-nitrophenol

Reaction of N-cyclohexyl-N-(cyclopropylmethyl)-4-(5,5-dimethyl-1,3,2-dioxaborinan-2-yl)-2-nitroaniline under the conditions described for the synthesis of 101C afforded 4-(cyclohexyl(cyclopropylmethyl)amino)-3-nitrophenol (0.69 g, quantitative yield) as a dark oil. MS (ES): m/z=291 [M+H]$^+$. T$_r$=0.80 min (Method A).

118D. ethyl 2-(4-(cyclohexyl(cyclopropylmethyl)amino)-3-nitrophenoxy)acetate Reaction of 4-(cyclohexyl(isobutyl)amino)-3-fluoro-5-nitrophenol under the conditions described for the synthesis of 101D afforded ethyl 2-(4-(cyclohexyl(cyclopropylmethyl)amino)-3-nitrophenoxy)acetate (0.78 g, 99% yield) as an orange oil. MS (ES): m/z=377 [M+H]$^+$. T$_r$=1.04 min (Method A).

118E. ethyl 2-(3-amino-4-(cyclohexyl(cyclopropylmethyl)amino)phenoxy)acetate Reduction of ethyl 2-(4-(cyclohexyl(cyclopropylmethyl)amino)-3-nitrophenoxy)acetate under the conditions described for the synthesis of Example 107B afforded ethyl 2-(3-amino-4-(cyclohexyl(cyclopropylmethyl)amino)phenoxy)acetate (0.37 g, quantitative yield) as a colorless oil. MS (ES): m/z=347 [M+H]$^+$. T$_r$=0.73 min (Method A).

Example 118. 2-(3-(3-(4-chloro-2-fluorophenyl)ureido)-4-(cyclohexyl(cyclopropylmethyl)amino)phenoxy)acetic acid Reaction of ethyl 2-(3-amino-4-(cyclohexyl(cyclopropylmethyl)amino)phenoxy)acetate under the conditions described for the synthesis of Example 113 afforded 2-(3-(3-(4-chloro-2-fluorophenyl)ureido)-4-(cyclohexyl(cyclopropylmethyl)amino)phenoxy)acetic acid (0.04 g, 31% yield) an off-white powder. MS (ES): m/z=490 [M+H]$^+$. T$_r$=1.77 min (Method C).

Example 119

2-(2-chloro-5-(3-(4-chloro-2-fluorophenyl)ureido)-4-(cyclohexyl(isobutyl)amino)phenoxy)acetic acid

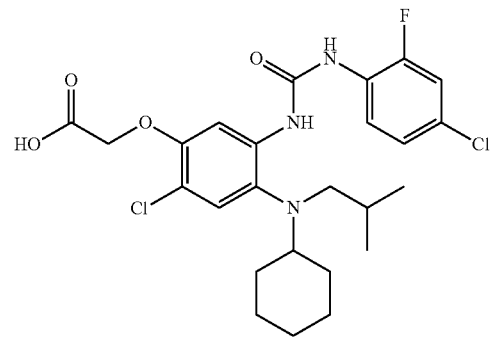 [SMILES: CC(C)CN(c1cc(Cl)c(OCC(=O)O)cc1NC(=O)Nc1ccc(Cl)cc1F)C1CCCCC1]

119A. ethyl 2-(2-chloro-4-fluoro-5-nitrophenoxy)acetate

Reaction of 2-chloro-4-fluoro-5-nitrophenol under the conditions described for the synthesis of 1C afforded ethyl 2-(2-chloro-4-fluoro-5-nitrophenoxy)acetate (0.26 g, 85% yield) as a pale yellow oil. $^1$H NMR (400 MHz, DMSO-d$_6$) δ 7.98 (d, J=10.8 Hz, 1H), 7.88 (d, J=6.6 Hz, 1H), 5.09 (s, 2H), 4.20 (q, J=7.1 Hz, 2H), 1.23 (t, J=7.1 Hz, 3H).

119B. ethyl 2-(2-chloro-4-(cyclohexyl(isobutyl)amino)-5-nitrophenoxy)acetate Reaction of ethyl 2-(2-chloro-4-fluoro-5-nitrophenoxy)acetate under the conditions described for the synthesis of 104A afforded ethyl 2-(2-chloro-4-(cyclohexyl(isobutyl)amino)-5-nitrophenoxy)acetate (0.14 g, 38% yield) as an pale yellow oil which solidified upon standing. MS (ES): m/z=413 [M+H]$^+$. T$_r$=1.26 min (Method A).

119C. ethyl 2-(5-amino-2-chloro-4-(cyclohexyl(isobutyl)amino)phenoxy)acetate Reduction of ethyl 2-(2-chloro-4-(cyclohexyl(isobutyl)amino)-5-nitrophenoxy)acetate under the conditions described for the synthesis of 107B afforded ethyl 2-(5-amino-2-chloro-4-(cyclohexyl(isobutyl)amino)phenoxy)acetate (0.12 g, quantitative yield) as a pale amber glass. MS (ES): m/z=383. T$_r$=1.01 min (Method A).

Example 119. 2-(2-chloro-5-(3-(4-chloro-2-fluorophenyl)ureido)-4-(cyclohexyl(isobutyl)amino)phenoxy)acetic acid Reaction of ethyl 2-(3-amino-4-(cyclohexyl(cyclopropylmethyl)amino)phenoxy)acetate under the conditions described for the synthesis of Example 113 afforded 2-(2-chloro-5-(3-(4-chloro-2-fluorophenyl)ureido)-4-(cyclohexyl(isobutyl)amino)phenoxy)acetic acid (0.017 g, 62% yield). MS (ES): m/z=526 [M+H]$^+$. T$_r$=1.96 min (Method C).

Examples 120-121

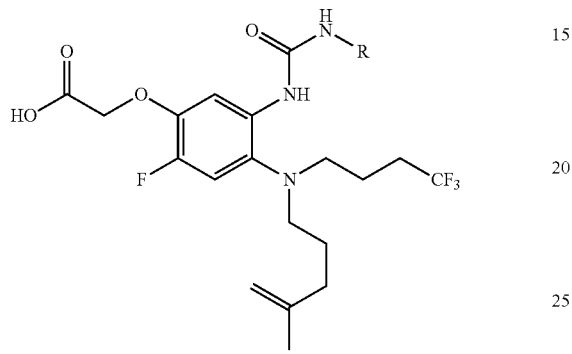

Examples 120-121 were prepared from intermediate 113B using the procedures outlined above and the appropriate electrophiles.

| Ex. No. | Name | R | Tr (min) Method C | [M + H]+ |
|---|---|---|---|---|
| 120 | 2-(2-fluoro-4-((2-methylallyl(4,4,4-trifluorobutyl)amino)-5-(3-(p-tolyl)ureido)phenoxy)acetic acid | (p-tolyl) | 1.65 | 498 |
| 121 | 2-(2-fluoro-4-((2-methylallyl)(4,4,4-trifluorobutyl)amino)-5-(3-(3-methylisoxazol-5-yl)ureido)phenoxy)acetic acid | (3-methylisoxazol-5-yl) | 1.42 | 489 |

Examples 122-129

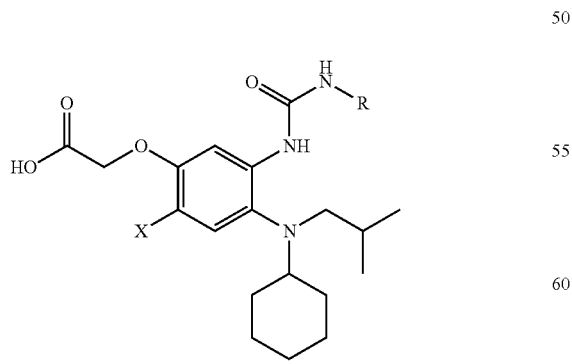

Examples 122-129 were prepared from intermediates 119C (X=Cl) and 115B (X=F) using the procedures outlined above and the appropriate electrophiles.

| Ex. No. | Name | R | X | Tr (min) Method C | [M + H]+ |
|---|---|---|---|---|---|
| 122 | 2-(2-chloro-4-(cyclohexyl(isobutyl)amino)-5-(3-(p-tolyl)ureido)phenoxy)acetic acid | 4-methylphenyl | Cl | 1.94 | 488 |
| 123 | 2-(5-(3-(2-chlorophenyl)ureido)-4-(cyclohexyl(isobutyl)amino)-2-fluorophenoxy)acetic acid | 2-chlorophenyl | F | 1.83 | 492 |
| 124 | 2-(4-(cyclohexyl(isobutyl)amino)-5-(3-(2,4-difluorophenyl)ureido)-2-fluorophenoxy)acetic acid | 2,4-difluorophenyl | F | 1.77 | 494 |
| 125 | 2-(5-(3-(4-bromo-2-fluorophenyl)ureido)-4-(cyclohexyl(isobutyl)amino)-2-fluorophenoxy)acetic acid | 4-bromo-2-fluorophenyl | F | 1.91 | 554 |
| 126 | 2-(4-(cyclohexyl(isobutyl)amino)-5-(3-(2,5-difluorophenyl)ureido)-2-fluorophenoxy)acetic acid | 2,5-difluorophenyl | F | 1.78 | 494 |
| 127 | 2-(4-(cyclohexyl(isobutyl)amino)-2-fluoro-5-(3-(4-(trifluoromethoxy)phenyl)ureido)phenoxy)acetic acid | 4-(trifluoromethoxy)phenyl | F | 1.97 | 542 |
| 128 | 2-(5-(3-(6-cyanopyridin-3-yl)ureido)-4-(cyclohexyl(isobutyl)amino)-2-fluorophenoxy)acetic acid | 6-cyanopyridin-3-yl | F | 1.64 | 484 |
| 129 | 2-(4-(cyclohexyl(isobutyl)amino)-2-fluoro-5-(3-(2-fluorophenyl)ureido)phenoxy acetic acid | 2-fluorophenyl | F | 1.81 | 476 |

Examples 130-132

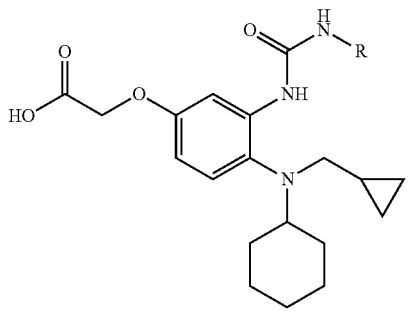

Examples 130-132 were prepared from intermediate 118E using the procedures outlined above and the appropriate electrophiles.

| Ex. No. | Name | R | Tr (min) Method C | [M + H]⁺ |
|---|---|---|---|---|
| 130 | 2-(4-cyclohexyl(cyclopropylmethyl)amino)-3-(3-(2,5-difluorophenyl)ureido)phenoxy)acetic acid | 2,5-difluorophenyl | 1.67 | 474 |
| 131 | 2-(4-(cyclohexyl(cyclopropylmethyl)amino)-3-(3-(p-tolyl)ureido)phenoxy)acetic acid | p-tolyl | 1.73 | 452 |
| 132 | 2-(4-(cyclohexyl(isobutyl)amino)-5-(3-(2,4-difluorophenyl)ureido)-2-fluorophenoxy)acetic acid | 2,4-difluorophenyl | 1.66 | 474 |

Example 133

2-(5-(2-(4-chloro-2-fluorophenyl)acetamido)-4-(cyclohexyl(isobutyl)amino)-2-fluorophenoxy)acetic acid

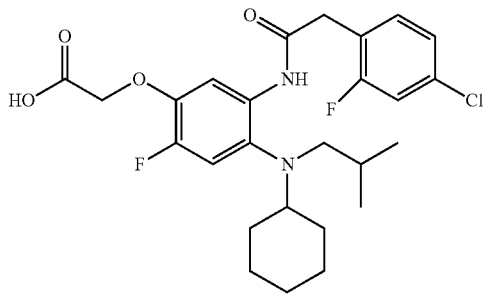 [SMILES: CC(C)CN(c1cc(F)c(OCC(=O)O)cc1NC(=O)Cc1ccc(Cl)cc1F)C1CCCCC1]

Example 133. 2-(5-(2-(4-chloro-2-fluorophenyl)acetamido)-4-(cyclohexyl(isobutyl)amino)-2-fluorophenoxy)acetic acid A solution of ethyl 2-(5-amino-4-(cyclohexyl(isobutyl)amino)-2-fluorophenoxy)acetate (115B) (0.015 g, 0.041 mmol) in DMF (0.4 mL) was treated with 2-(4-chloro-2-fluorophenyl)acetic acid (9.26 mg, 0.049 mmol) followed by triethylamine (0.011 mL, 0.082 mmol) then BOP (0.022 g, 0.049 mmol). The reaction was stirred ON at ambient temperature then diluted with 0.5 mL of THF. MeOH, 0.5 mL was added, and this solution was treated with lithium hydroxide (0.020 g, 0.819 mmol) in 0.5 mL of water. The reaction was stirred at 60° C. for 1 h then most of the organic solvents were removed under a stream of nitrogen. The reaction was then diluted with 1 mL of DMF, treated with 0.2 mL of glacial HOAc, and purified by prep. HPLC. 2-(5-(2-(4-chloro-2-fluorophenyl)acetamido)-4-(cyclohexyl(isobutyl)amino)-2-fluorophenoxy)acetic acid (0.012 g, 57%) as a white powder. MS (ES): m/z=509 [M+H]⁺. T$_r$=1.83 min (Method C).

Example 134

2-(4-(cyclohexyl(isobutyl)amino)-5-(3-(2,4-difluorophenyl)ureido)-2-fluorophenoxy)-N-(cyclopropylsulfonyl)acetamide

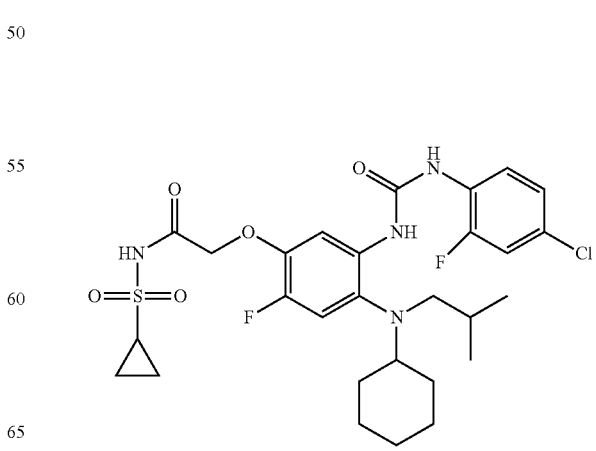

Example 134 2-(4-(cyclohexyl(isobutyl)amino)-5-(3-(2,4-difluorophenyl)ureido)-2-fluorophenoxy)-N-(cyclopropylsulfonyl)acetamide Reaction of 2-(5-(3-(4-chloro-2-fluorophenyl)ureido)-4-(cyclohexyl(isobutyl)amino)-2-fluorophenoxy)acetic acid (Example 115) under the conditions described for the synthesis of Example 103 afforded 2-(4-(cyclohexyl(isobutyl)amino)-5-(3-(2,4-difluorophenyl)ureido)-2-fluorophenoxy)-N-(cyclopropylsulfonyl)acetamide (0.011 g, 60% yield) as a white powder. MS (ES): m/z=597 [M+H]$^+$. T$_r$=1.95 min (Method C).

Example 135

2-(3-(3-(4-chloro-2-fluorophenyl)ureido)-4-(cyclohexyl(isobutyl)amino)phenoxy)-N-(2,2,2-trifluoroethyl)acetamide

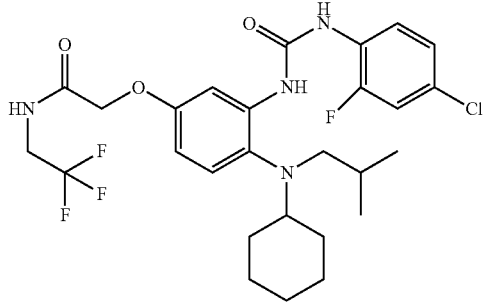 [SMILES: CC(C)CN(c1ccc(OCC(=O)NCC(F)(F)F)cc1NC(=O)Nc1ccc(Cl)cc1F)C1CCCCC1]

Example 135. 2-(3-(3-(4-chloro-2-fluorophenyl)ureido)-4-(cyclohexyl(isobutyl)amino)phenoxy)-N-(2,2,2-trifluoroethyl)acetamide Reaction of 2-(3-(3-(4-chloro-2-fluorophenyl)ureido)-4-(cyclohexyl(isobutyl)amino)phenoxy)acetic acid (Example 1) at ambient temperature under the conditions otherwise described for the synthesis of Example 111 afforded 2-(3-(3-(4-chloro-2-fluorophenyl)ureido)-4-(cyclohexyl(isobutyl)amino)phenoxy)-N-(2,2,2-trifluoroethyl)acetamide (0.014 g, 81% yield) as a white powder. MS (ES): m/z=573 [M+H]$^+$. T$_r$=2.04 min (Method C).

Example 136

(+/−) 2-(5-(3-(4-chloro-2-fluorophenyl)ureido)-4-(cyclohexyl(isobutyl)amino)-2-fluorophenoxy)propanoic acid.TFA

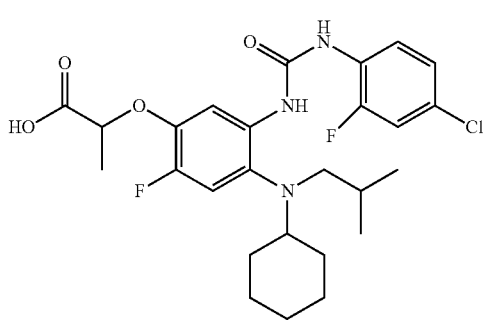 [SMILES: CC(C)CN(c1cc(F)c(OC(C)C(=O)O)cc1NC(=O)Nc1ccc(Cl)cc1F)C1CCCCC1]

136A. (+/−) ethyl 2-(2,4-difluoro-5-nitrophenoxy)propanoate

A solution of 2,4-difluoro-5-nitrophenol (1.86 g, 10.62 mmol) in DMF (10 mL) was treated with cesium carbonate (4.15 g, 12.75 mmol) followed by ethyl 2-bromopropanoate (1.517 mL, 11.69 mmol). This mixture was stirred 1 h at 60° C. then poured into water. The resulting precipitate was filtered, rinsed with water, air-dried briefly then dried under vacuum for 2 h to afford (+/−) ethyl 2-(2,4-difluoro-5-nitrophenoxy)propanoate (2.0 g, 68% yield) as a yellow solid. $^1$H NMR (400 MHz, DMSO-d$_6$) δ 7.93 (dd, J=8.2, 7.6 Hz, 1H), 7.83 (at, J=11.1 Hz, 1H), 5.29 (q, J=6.7 Hz, 1H), 4.17 (q, J=7.1 Hz, 2H), 1.56 (d, J=6.9 Hz, 3H), 1.19 (t, J=7.1 Hz, 3H).

136B. (+/−) ethyl 2-(4-(cyclohexyl(isobutyl)amino)-2-fluoro-5-nitrophenoxy)propanoate Reaction of (+/−) ethyl 2-(2,4-difluoro-5-nitrophenoxy)propanoate under the conditions described for the synthesis of 101A afforded (+/−) ethyl 2-(4-(cyclohexyl(isobutyl)amino)-2-fluoro-5-nitrophenoxy)propanoate (0.5 g, 34% yield) as an orange oil. MS (ES): m/z=411 [M+H]$^+$, T$_r$=1.25 min (Method A).

136C. (+/−) ethyl 2-(5-amino-4-(cyclohexyl(isobutyl)amino)-2-fluorophenoxy)propanoate Reaction of (+/−) ethyl 2-(4-(cyclohexyl(isobutyl)amino)-2-fluoro-5-nitrophenoxy)propanoate under the conditions described for the synthesis of 107B afforded (+/−) ethyl 2-(5-amino-4-(cyclohexyl(isobutyl)amino)-2-fluorophenoxy)propanoate (0.14 g, 37% yield) as a pale purple oil. MS (ES): m/z=381 [M+H]$^+$. T$_r$=0.98 min (Method A).

Example 136. (+/−) 2-(5-(3-(4-chloro-2-fluorophenyl)ureido)-4-(cyclohexyl(isobutyl)amino)-2-fluorophenoxy)propanoic acid.TFA Reaction of (+/−) ethyl 2-(5-amino-4-(cyclohexyl(isobutyl)amino)-2-fluorophenoxy)propanoate under the conditions described for the synthesis of Example 113 afforded (+/−) 2-(5-(3-(4-chloro-2-fluorophenyl)ureido)-4-(cyclohexyl(isobutyl)amino)-2-fluorophenoxy)propanoic acid.TFA (0.071 g, 85%) as a white powder. MS (ES): m/z=524 [M+H]$^+$. T$_r$=1.96 min (Method C). Enantiomer 1 and Enantiomer 2

Enantiomer 1: Example 136 2-(5-(3-(4-chloro-2-fluorophenyl)ureido)-4-(cyclohexyl(isobutyl)amino)-2-fluorophenoxy)propanoic acid.TFA (Homochiral, Stereochemistry Unknown)

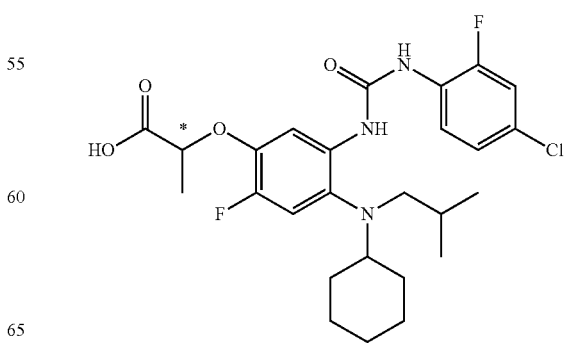

Enantiomer 2: Example 136 2-(5-(3-(4-chloro-2-fluorophenyl)ureido)-4-(cyclohexyl(isobutyl)amino)-2-fluorophenoxy)propanoic acid.TFA (Homochiral, Stereochemistry Unknown)

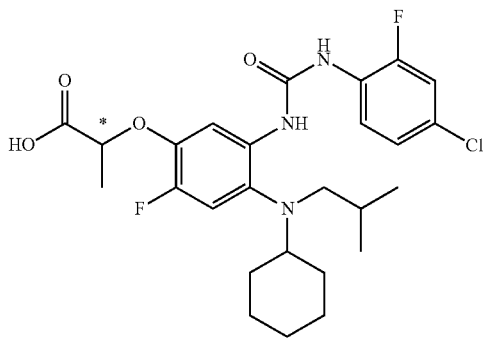 [SMILES: CC(C)CN(c1cc(F)c(OC(C)C(=O)O)cc1NC(=O)Nc1ccc(Cl)cc1F)C1CCCCC1]

Example 136 Enantiomer 1 and Enantiomer 2: Chiral separation of the racemic sample (Method R) gave Enantiomer 1 T$_r$=16.25 min (Method S) and Enantiomer 2 T$_r$=17.62 min (Method S) Absolute stereochemistry was not determined. Some decomposition of the samples occurred during processing of the fractions from chiral separation, so these samples were further purified by prep. HPLC.

Enantiomer 1: MS (ES): m/z=524 [M+H]$^+$. T$_r$=1.12 min (Method A).

Enantiomer 2: MS (ES): m/z=524 [M+H]$^+$. T$_r$=1.12 min (Method A).

Example 137

2-(3-(3-(4-chloro-2-fluorophenyl)ureido)-4-((2-methylallyl)(tetrahydro-2H-pyran-4-yl)amino)phenoxy)acetic acid

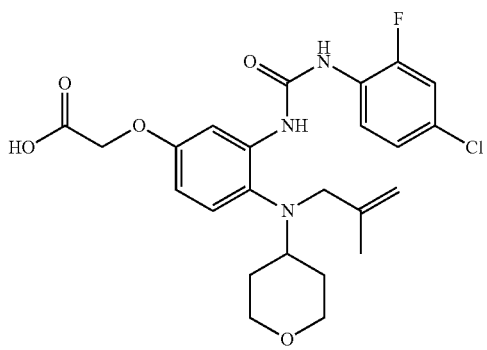 [SMILES: C=C(C)CN(c1ccc(OCC(=O)O)cc1NC(=O)Nc1ccc(Cl)cc1F)C1CCOCC1]

137A. ethyl 2-(3-nitro-4-((tetrahydro-2H-pyran-4-yl)amino)phenoxy)acetate

To ethyl 2-(4-fluoro-3-nitrophenoxy)acetate (300 mg, 1.234 mmol) was added tetrahydro-2H-pyran-4-amine (137 mg, 1.357 mmol) and dioxane (1 mL) and heated at 115° C. for 16 h. The reaction was cooled to RT. Solvent was removed. The residue was purified with ISCO 80 g column, 60 mL/min. 0-50% EtOAc/Hexane. The desired product was eluted with 50% EtOAc/Hexane. Combined fractions containing the product and concentrated to give Intermediate 137A (115 mg, 0.351 mmol, 28.5% yield)$^1$H NMR (400 MHz, DMSO-d$_6$) δ 7.85 (d, J=7.7 Hz, 1H), 7.52 (d, J=2.9 Hz, 1H), 7.33 (dd, J=9.4, 3.0 Hz, 1H), 7.21 (d, J=9.5 Hz, 1H), 4.79 (s, 2H), 4.18 (q, J=7.2 Hz, 2H), 3.87 (dt, J=11.8, 3.6 Hz, 3H), 3.49 (td, J=11.4, 2.1 Hz, 2H), 1.95 (d, J=12.0 Hz, 2H), 1.62-1.46 (m, 2H), 1.28-1.17 (m, 3H) MS: Anal. Calc'd for C$_{15}$H$_{20}$N$_2$O$_6$ 324.13, found [M+H]. 325.5.

137B: ethyl 2-(4-((2-methylallyl)(tetrahydro-2H-pyran-4-yl)amino)-3-nitrophenoxy)acetate To a solution of Intermediate 137B (57 mg, 0.176 mmol) in DMF (1 mL) at Rt was added cesium carbonate (115 mg, 0.351 mmol), followed by 3-bromo-2-methylprop-1-ene (356 mg, 2.64 mmol). The reaction was stirred at 115° C. for 16 h. trace amount of desired product formed. Most starting material remaining. Hunig's Base (0.153 mL, 0.879 mmol) was added. the mixture was heated at 115° C. for 16 h. The mixture cooled to RT. Then it was filtered through celite and the filtrate was diluted with MeOH and purified with prep HPLC (Phen Luna 5 u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm to afford Intermediate 137B (30 mg, 0.060 mmol, 34.3% yield)$^1$H NMR (400 MHz, DMSO-d$_6$) δ 7.44 (d, J=9.0 Hz, 1H), 7.35-7.29 (m, 1H), 7.14 (dd, J=9.0, 3.1 Hz, 1H), 4.86-4.80 (m, 2H), 4.76 (s, 1H), 4.69 (s, 1H), 4.17 (q, J=7.1 Hz, 2H), 3.86 (d, J=11.0 Hz, 2H), 3.25-3.14 (m, 2H), 3.07-2.95 (m, 1H), 1.63-1.50 (m, 7H), 1.26-1.14 (m, 3H) MS: Anal. Calc'd for C$_{19}$H$_{26}$N$_2$O$_6$ 378.18, found [M+H] 379.5.

137C: ethyl 2-(3-amino-4-((2-methylallyl)(tetrahydro-2H-pyran-4-yl)amino)phenoxy)acetate To a solution of Intermediate 301B (23 mg, 0.047 mmol) in EtOH (0.5 mL) and Water (0.1 mL) was added ammonium chloride (7.50 mg, 0.140 mmol), followed by zinc (30.6 mg, 0.467 mmol). The reaction was stirred at room temperature for 2 h. The reaction mixture was diluted with EtOAc and water, filtered through celite. The filtrate was transferred into a separatory funnel. Organic was separated and washed with brine, dried over MgSO$_4$, filtered and concentrated to give Intermediate 137C (12 mg, 0.031 mmol, 66.3% yield) MS: Anal. Calc'd for C$_{19}$H$_{28}$N$_2$O$_4$ 348.205, found [M+H] 349.5.

Example 137: 2-(3-(3-(4-chloro-2-fluorophenyl)ureido)-4-((2-methylallyl)(tetrahydro-2H-pyran-4-yl)amino)phenoxy)acetic acid To a solution of ethyl Intermediate 137C (12 mg, 0.034 mmol) in THF (0.5 mL) at RT was added 4-chloro-2-fluoro-1-isocyanatobenzene (17.72 mg, 0.103 mmol). The reaction was stirred at RT for 2 h. MeOH (0.2 mL) was added, followed by 1N NaOH (0.5 mL). The mixture was stirred at Rt for 1.5 h. pH was adjusted to 5 with concentrated HCl. The mixture was filtered through 0.45 um membrane. The filtrate was purified via preparative LC/MS with the following conditions: Column: Waters XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-100% B over 20 minutes, then a 5-minute hold at 100% B; Flow: 20 mL/min. Fractions containing the desired product were combined and dried via centrifugal evaporation to give Example 137 (10.1 mg, 0.021 mmol, 60% yield) was obtained. ¹H NMR (500 MHz, DMSO-d₆) δ 9.64 (s, 1H), 8.64 (s, 1H), 8.04 (t, J=8.8 Hz, 1H), 7.75-7.55 (m, 1H), 7.46 (d, J=10.9 Hz, 1H), 7.24 (d, J=7.6 Hz, 1H), 7.13 (d, J=8.8 Hz, 1H), 6.49 (dd, J=8.7, 2.6 Hz, 1H), 4.70 (br. s., 1H), 4.65 (br. s., 1H), 4.58 (s, 2H), 3.84 (d, J=8.3 Hz, 2H), 3.21 (t, J=11.7 Hz, 2H), 2.89 (t, J=11.4 Hz, 1H), 2.55 (s, 2H), 1.77 (d, J=11.4 Hz, 2H), 1.65 (s, 3H), 1.44 (d, J=8.2 Hz, 2H) MS: Anal. Calc'd for C₂₄H₂₇ClFN₃O₅ 491.162, found [M+H] 492.10 T$_r$=1.399 min. (Method B).

Example 138

2-(3-(3-(4-chloro-2-fluorophenyl)ureido)-4-((2-methylallyl)(tetrahydro-2H-pyran-4-yl)amino)phenoxy)propanoic acid

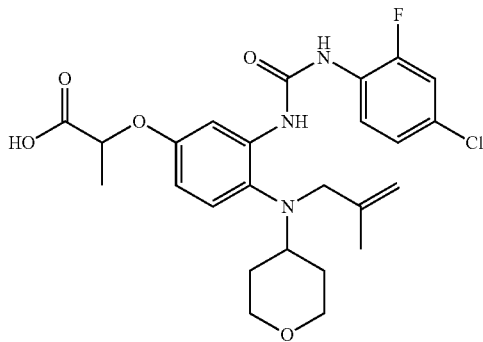 [SMILES: C=C(C)CN(c1ccc(OC(C)C(=O)O)cc1NC(=O)Nc1ccc(Cl)cc1F)C1CCOCC1]

Example 302 was obtained following the procedures in Example 301 using ethyl 2-(4-fluoro-3-nitrophenoxy)propanoate. ¹H NMR (500 MHz, DMSO-d₆) δ 9.64 (s, 1H), 8.63 (s, 1H), 8.07 (t, J=8.8 Hz, 1H), 7.72 (d, J=2.7 Hz, 1H), 7.50-7.37 (m, 1H), 7.25 (d, J=8.6 Hz, 1H), 7.12 (d, J=8.8 Hz, 1H), 6.44 (dd, J=8.7, 2.7 Hz, 1H), 4.75-4.60 (m, 3H), 3.85 (d, J=8.4 Hz, 2H), 3.55 (s, 1H), 3.21 (t, J=11.7 Hz, 2H), 2.94-2.74 (m, 1H), 1.78 (br. s., 2H), 1.69-1.59 (m, 2H), 1.52-1.41 (m, 6H) MS: Anal. Calc'd for C₂₅H₂₉ClFN₃O₅ 505.178, found [M+H] 506.6 T$_r$=1.44 min. (Method B).

Example 139

Enantiomer 1: 2-(3-(3-(4-chloro-2-fluorophenyl)ureido)-4-((2-methylallyl)(tetrahydro-2H-pyran-4-yl)amino)phenoxy)propanoic acid (Homochiral, Absolute Stereochemistry Unknown)

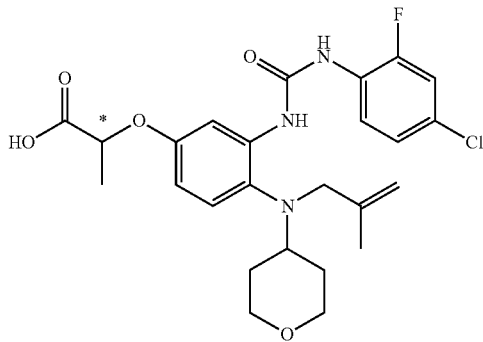 [SMILES: C=C(C)CN(c1ccc(OC(C)C(=O)O)cc1NC(=O)Nc1ccc(Cl)cc1F)C1CCOCC1]

Enantiomer 2

2-(3-(3-(4-chloro-2-fluorophenyl)ureido)-4-((2-methylallyl)(tetrahydro-2H-pyran-4-yl)amino)phenoxy)propanoic acid (Homochiral, Absolute Stereochemistry Unknown)

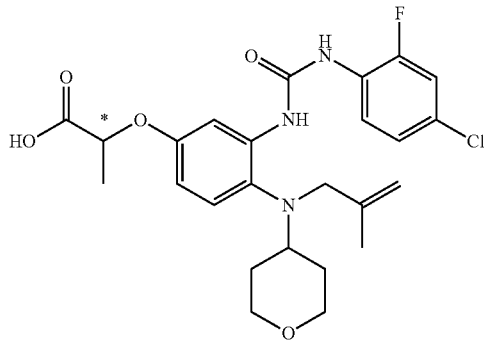 [SMILES: C=C(C)CN(c1ccc(OC(C)C(=O)O)cc1NC(=O)Nc1ccc(Cl)cc1F)C1CCOCC1]

Example 139 Enantiomer 1 was the first eluent peak (T$_r$=5.15 min) prepared from Example 302 by using the following conditions: UV visualization at 220 nm; Column: Chiral IC 25×3 cm ID, 5 μm; Flow rate: 85 mL/min, Mobile Phase: 75/25, CO₂/MeOH. ¹H NMR (500 MHz, DMSO-d₆) δ 9.64 (s, 1H), 8.63 (s, 1H), 8.07 (t, J=8.8 Hz, 1H), 7.72 (d, J=2.7 Hz, 1H), 7.50-7.37 (m, 1H), 7.25 (d, J=8.6 Hz, 1H), 7.12 (d, J=8.8 Hz, 1H), 6.44 (dd, J=8.7, 2.7 Hz, 1H), 4.75-4.60 (m, 3H), 3.85 (d, J=8.4 Hz, 2H), 3.55 (s, 1H), 3.21 (t, J=11.7 Hz, 2H), 2.94-2.74 (m, 1H), 1.78 (br. s., 2H), 1.69-1.59 (m, 2H), 1.52-1.41 (m, 6H) MS: Anal. Calc'd for C₂₅H₂₉ClFN₃O₅ 505.178, found [M+H] 506.6 T$_r$=1.44 min. (Method B).

Example 139 Enantiomer 2 was the second eluent peak (T$_r$=7.8 min) prepared from Example 138 by using the following conditions: UV visualization at 220 nm; Column: Chiral IC 25×3 cm ID, 5 μm; Flow rate: 85 mL/min, Mobile Phase: 75/25, CO₂/MeOH. ¹H NMR (500 MHz, DMSO-d₆) δ 9.64 (s, 1H), 8.63 (s, 1H), 8.07 (t, J=8.8 Hz, 1H), 7.72 (d, J=2.7 Hz, 1H), 7.50-7.37 (m, 1H), 7.25 (d, J=8.6 Hz, 1H), 7.12 (d, J=8.8 Hz, 1H), 6.44 (dd, J=8.7, 2.7 Hz, 1H), 4.75-4.60 (m, 3H), 3.85 (d, J=8.4 Hz, 2H), 3.55 (s, 1H), 3.21 (t, J=11.7 Hz, 2H), 2.94-2.74 (m, 1H), 1.78 (br. s., 2H), 1.69-1.59 (m, 2H), 1.52-1.41 (m, 6H) MS: Anal. Calc'd for C₂₅H₂₉ClFN₃O₅ 505.178, found [M+H] 506.6 T$_r$=1.44 min. (Method B).

Example 140

(+/−)-2-(4-((2-methylallyl)(tetrahydro-2H-pyran-4-yl)amino)-3-(3-(p-tolyl)ureido)phenoxy)propanoic acid

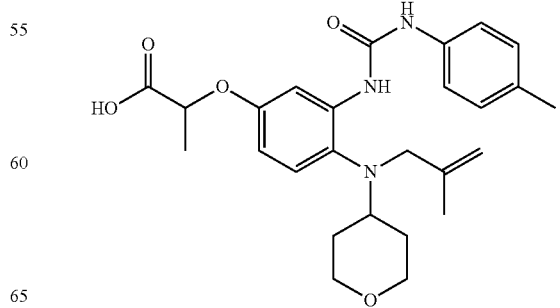

Example 140 was obtained following the procedures in Example 138 using the corresponding isocyanate. $^1$H NMR (500 MHz, DMSO-d$_6$) δ 8.27 (s, 1H), 7.77 (d, J=2.6 Hz, 1H), 7.35 (d, J=8.2 Hz, 2H), 7.10 (d, J=8.2 Hz, 3H), 6.40 (dd, J=8.6, 2.7 Hz, 1H), 4.76-4.60 (m, 3H), 3.84 (d, J=9.3 Hz, 2H), 3.28-3.13 (m, 2H), 2.87-2.80 (m, 1H), 2.25 (s, 3H), 1.75 (br. s., 2H), 1.68-1.56 (m, 3H), 1.53-1.32 (m, 6H) MS: Anal. Calc'd for C$_{26}$H$_{33}$N$_3$O$_5$ 467.242, found [M+H] 468.7 T$_r$=1.36 min. (Method B).

Example 141

2-(3-(3-(4-chloro-2-fluorophenyl)ureido)-4-((2-methylallyl)(oxetan-3-yl)amino)phenoxy)acetic acid

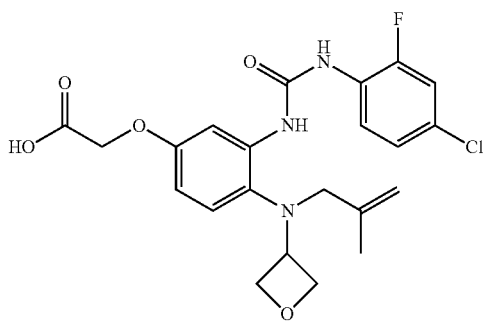 [SMILES: C=C(C)CN(c1ccc(OCC(=O)O)cc1NC(=O)Nc1ccc(Cl)cc1F)C1COC1]

Example 141 was obtained following the procedures in Example 137 using oxetan-3-amine. $^1$H NMR (500 MHz, DMSO-d$_6$) δ 9.59 (s, 1H), 8.78 (s, 1H), 8.16 (t, J=8.8 Hz, 1H), 7.65 (br. s., 1H), 7.47 (d, J=11.0 Hz, 1H), 7.24 (d, J=9.0 Hz, 1H), 7.04 (d, J=8.8 Hz, 1H), 6.42 (d, J=6.4 Hz, 1H), 4.73 (br. s., 2H), 4.47 (d, J=5.8 Hz, 2H), 4.44-4.31 (m, 3H), 4.20 (s, 2H), 1.91 (s, 4H), 1.72 (s, 3H) MS: Anal. Calc'd for C$_{22}$H$_{23}$ClFN$_3$O$_5$ 463.131, found [M+H] 464.4 T$_r$=1.28 min. (Method B).

Example 142

2-(3-(3-(4-chloro-2-fluorophenyl)ureido)-4-((2-methylallyl)(1-(2-methylallyl)piperidin-4-yl)amino)phenoxy)acetic acid

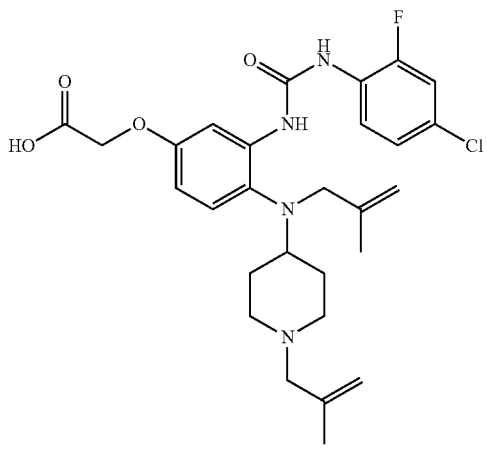 [SMILES: C=C(C)CN1CCC(N(CC(=C)C)c2ccc(OCC(=O)O)cc2NC(=O)Nc2ccc(Cl)cc2F)CC1]

Example 142 was obtained following the procedures in Example 137 using tert-butyl 4-aminopiperidine-1-carboxylate. $^1$H NMR (500 MHz, DMSO-d$_6$) δ 9.65 (s, 1H), 8.62 (s, 1H), 8.04 (t, J=8.8 Hz, 1H), 7.68 (br. s., 1H), 7.45 (d, J=11.1 Hz, 1H), 7.24 (d, J=8.6 Hz, 1H), 7.10 (d, J=8.8 Hz, 1H), 6.46 (d, J=8.8 Hz, 1H), 4.83 (s, 2H), 4.70 (br. s., 1H), 4.65 (br. s., 1H), 4.51 (s, 2H), 2.82 (br. s., 4H), 2.75-2.61 (m, 1H), 1.86 (d, J=11.9 Hz, 4H), 1.68-1.59 (m, 6H), 1.45 (d, J=11.8 Hz, 2H) MS: Anal. Calc'd for C$_{28}$H$_{34}$ClFN$_4$O$_4$ 544.225, found [M+H] 545.2 T$_r$=1.37 min. (Method B).

Example 143

Enantiomer 1 and Enantiomer 2

Enantiomer 1: (2-(3-(3-(4-chloro-2-fluorophenyl)ureido)-4-(isobutyl(tetrahydro-2H-pyran-4-yl)amino)phenoxy)butanoic acid (Homochiral, Absolute Stereochemistry Unknown)

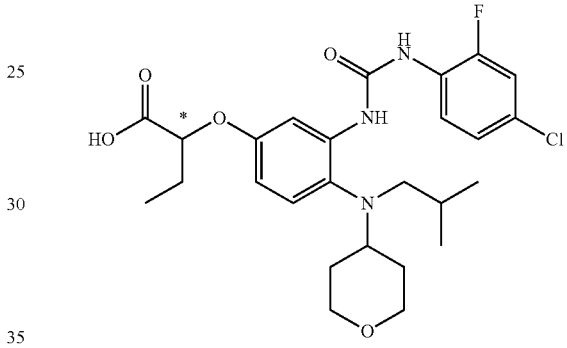

143A: N-(tetrahydro-2H-pyran-4-yl)isobutyramide

To a suspension of tetrahydro-2H-pyran-4-amine (10 g, 99 mmol) in THF (100 mL) at 0° C. was added triethylamine (16.54 mL, 119 mmol). To this mixture was added isobutyryl chloride (10.36 mL, 99 mmol) dropwise. It became slurry. The reaction was stirred at RT for 16 h. Filtered to remove the solid. Rinsed the solid with THF. The solid contained most Et$_3$N HCl salt. The filtrate contained the desired product with small amount of Et$_3$N HCl salt by LC-MS. The filtrate was concentrated to dryness and then it was dissolved in minimum amount of CH$_2$Cl$_2$ and purified with ISCO. 220 g column, 150 mL/min. 0-100% EtOAc/CH$_2$Cl$_2$ in 35 min. The desired product was eluted with 35% EtOAc/CH$_2$Cl$_2$. Combined fractions containing desired product. After concentration, Intermediate 143A (9.0 g, 52 mol, 52%) was obtained. $^1$H NMR (400 MHz, chloroform-d) δ 5.33 (br. s., 1H), 4.06-3.90 (m, 3H), 3.50 (td, J=11.7, 2.2 Hz, 2H), 2.33 (dt, J=13.8, 6.9 Hz, 1H), 1.97-1.85 (m, 2H), 1.52-1.38 (m, 2H), 1.22-1.12 (m, 6H) Anal. Calc'd for C$_9$H$_{17}$NO$_2$ 171.126, found [M+H] 172.1.

143B: N-isobutyltetrahydro-2H-pyran-4-amine

To a solution of Intermediate 143A (9 g, 52.6 mmol) in THF (100 mL) cooled to 0° C. was added BH$_3$-Me$_2$S in Et$_2$O (21.02 mL, 105 mmol) slowly. The reaction was stirred at RT for 3 days. Then it was cooled to 0° C. in an ice bath. Methanol was slowly added dropwise until evolution of gas ceased. The material was concentrated to remove the solvent. The crude material was taken up in MeOH (150 mL) and stirred at RT for 2 days and heated at 80° C. for 5 h to break up the borane complex. The reaction was allowed to cool to rt. The solvent was evaporated to give Intermediate 143B (8.0 g, 40.7 mmol, 77%) $^1$H NMR (400 MHz, chloroform-d) δ 4.05-3.94 (m, 2H), 3.42 (td, J=11.7, 2.2 Hz, 2H), 2.71-2.59 (m, 1H), 2.46 (d, J=6.8 Hz, 2H), 1.90-1.79 (m, 2H), 1.78-1.63 (m, 1H), 1.49-1.29 (m, 2H), 0.98-0.89 (m, 6H) MS: Anal. Calc'd for $C_9H_{19}NO$ 157.141, found [M+H] 158.1.

Example 143 Enantiomer 1. 2-(3-(3-(4-chloro-2-fluorophenyl)ureido)-4-(isobutyl(tetrahydro-2H-pyran-4-yl)amino)phenoxy)butanoic acid Example 143 enantiomer 1 was obtained following the procedures in Example 80 using N-isobutyltetrahydro-2H-pyran-4-amine 308B. 1$^{st}$ eluent peak (T$_r$=5.9 min.) by using the following conditions: UV visualization at 220 nm; Column: Chiral IC 25×3 cm ID, 5 μm; Flow rate: 85 mL/min, Mobile Phase: 80/20, CO$_2$/MeOH. $^1$H NMR (500 MHz, DMSO-d$_6$) δ 9.64 (s, 1H), 8.62 (s, 1H), 8.03 (t, J=8.8 Hz, 1H), 7.74 (d, J=2.6 Hz, 1H), 7.47 (d, J=11.0 Hz, 1H), 7.25 (d, J=8.2 Hz, 1H), 7.15 (d, J=8.8 Hz, 1H), 6.49 (dd, J=8.6, 2.7 Hz, 1H), 4.52 (t, J=5.8 Hz, 1H), 3.84 (d, J=8.5 Hz, 2H), 3.21 (br. s., 1H), 2.83 (br. s., 1H), 2.74 (br. s., 1H), 1.95-1.74 (m, 3H), 1.42 (d, J=8.4 Hz, 2H), 1.34-1.26 (m, 1H), 1.24 (br. s., 1H), 1.17 (t, J=7.2 Hz, 1H), 1.00 (t, J=7.3 Hz, 3H), 0.81 (br. s., 6H) MS: Anal. Calc'd for $C_{26}H_{33}ClFN_3O_5$ 521.209, found [M+H] 522.1 T$_r$=1.622 min (Method B).

Enantiomer 2

2-(3-(3-(4-chloro-2-fluorophenyl)ureido)-4-(isobutyl (tetrahydro-2H-pyran-4-yl)amino)phenoxy)butanoic acid (Homochiral, Absolute Stereochemistry Unknown)

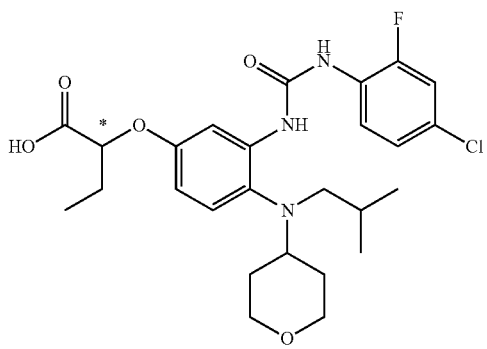 [SMILES: CCC(Oc1ccc(N(CC(C)C)C2CCOCC2)c(NC(=O)Nc2ccc(Cl)cc2F)c1)C(=O)O]

Example 143, enantiomer 2 was obtained 2$^{nd}$ eluent peak (T$_r$=7.7 min.) by using the following conditions: UV visualization at 220 nm; Column: Chiral IC 25×3 cm ID, 5 μm; Flow rate: 85 mL/min, Mobile Phase: 80/20, CO$_2$/MeOH. $^1$H NMR (500 MHz, DMSO-d$_6$) δ 9.64 (s, 1H), 8.62 (s, 1H), 8.03 (t, J=8.8 Hz, 1H), 7.74 (d, J=2.6 Hz, 1H), 7.47 (d, J=11.0 Hz, 1H), 7.25 (d, J=8.2 Hz, 1H), 7.15 (d, J=8.8 Hz, 1H), 6.49 (dd, J=8.6, 2.7 Hz, 1H), 4.52 (t, J=5.8 Hz, 1H), 3.84 (d, J=8.5 Hz, 2H), 3.21 (br. s., 1H), 2.83 (br. s., 1H), 2.74 (br. s., 1H), 1.95-1.74 (m, 3H), 1.42 (d, J=8.4 Hz, 2H), 1.34-1.26 (m, 1H), 1.24 (br. s., 1H), 1.17 (t, J=7.2 Hz, 1H), 1.00 (t, J=7.3 Hz, 3H), 0.81 (br. s., 6H) MS: Anal. Calc'd for $C_{26}H_{33}ClFN_3O_5$ 521.209, found [M+H] 522.1 T$_r$=1.622 min (Method B).

Example 144

2-(3-(3-(4-chloro-2-fluorophenyl)ureido)-4-(isobutyl (tetrahydrofuran-3-yl)amino)phenoxy)acetic acid

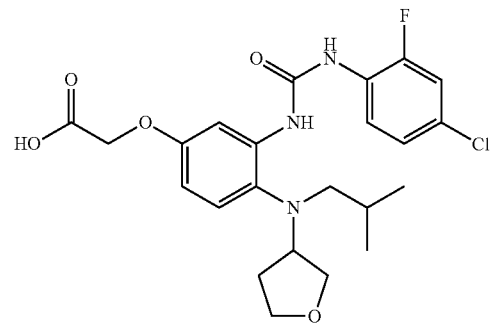 [SMILES: CC(C)CN(c1ccc(OCC(=O)O)cc1NC(=O)Nc1ccc(Cl)cc1F)C1CCOC1]

144A: N-isobutyltetrahydrofuran-3-amine

To a solution of dihydrofuran-3(2H)-one (0.6 g, 6.97 mmol) in MeOH (10 mL) at RT was added 2-methylpropan-1-amine (0.831 mL, 8.36 mmol). The reaction was heated at 40° C. for 2 h. Then it was cooled to RT and sodium borohydride (0.396 g, 10.45 mmol) was added slowly. The reaction was stirred at rt for 16 h. The crude reaction mixture was diluted with EtOAc and water. Organic was separated and washed with brine, dried over MgSO$_4$, filtered and concentrated to give a crude material. Then it was dissolved in CH$_2$Cl$_2$ and purified flash chromatograph to give Intermediate 144A (150 mg, 1.037 mmol, 14.88% yield). $^1$H NMR (400 MHz, chloroform-d) δ 3.94 (td, J=8.1, 6.6 Hz, 1H), 3.87-3.73 (m, 2H), 3.58 (dd, J=8.8, 4.2 Hz, 1H), 3.38 (ddt, J=7.2, 5.7, 4.3 Hz, 1H), 2.45-2.36 (m, 2H), 2.17-2.04 (m, 1H), 1.80-1.65 (m, 2H), 1.40 (br. s., 1H), 1.01-0.87 (m, 6H) MS: Anal. Calc'd for $C_8H_{17}NO$ 143.227, found [M+H] 144.2.

Example 144. 2-(3-(3-(4-chloro-2-fluorophenyl) ureido)-4-(isobutyl(tetrahydrofuran-3-yl)amino)phenoxy)acetic acid Example 144 was obtained following the procedures in Example 1 using 144A rather than Intermediate 1B. MS: Anal. Calc'd for $C_{23}H_{27}ClFN_3O_5$ 479.162, found [M+H] 480.0 T$_r$=1.45 min. (method B).

Example 145

2-(3-(3-(4-chloro-2-fluorophenyl)ureido)-4-(isobutyl(tetrahydrofuran-3-yl)amino)phenoxy)propanoic acid

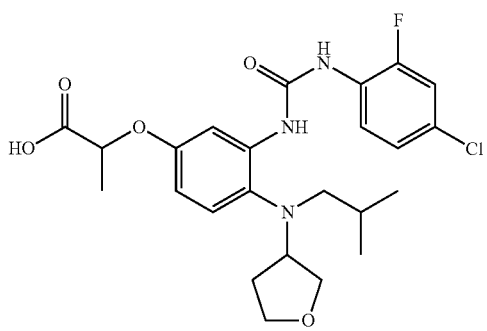

Example 145. 2-(3-(3-(4-chloro-2-fluorophenyl)ureido)-4-(isobutyl(tetrahydrofuran-3-yl)amino)phenoxy)propanoic acid Example 145 was obtained following the procedures in Example 58 using 144A rather than Intermediate 1B. $^1$H NMR (500 MHz, DMSO-d$_6$) δ 9.62 (br. s., 1H), 8.64 (br. s., 1H), 8.06 (t, J=8.8 Hz, 1H), 7.70 (br. s., 1H), 7.48 (d, J=11.1 Hz, 1H), 7.24 (t, J=7.8 Hz, 2H), 6.48 (d, J=6.6 Hz, 1H), 4.61 (br. s., 1H), 3.80 (br. s., 1H), 3.61 (br. s., 1H), 1.92 (s, 2H), 1.45 (d, J=6.4 Hz, 3H), 1.26 (d, J=7.1 Hz, 1H), 0.81 (br. s., 6H) MS: Anal. Calc'd for C$_{24}$H$_{29}$ClFN$_3$O$_5$ 479.162, found [M+H] 494.1 T$_r$=1.47 min. (method B).

Example 146

Enantiomer 1 and Enantiomer 2

Enantiomer 1: 2-(3-(3-(4-chloro-2-fluorophenyl)ureido)-4-(isobutyl(tetrahydrofuran-3-yl)amino)phenoxy)propanoic acid (Homochiral, Absolute Stereochemistry Unknown)

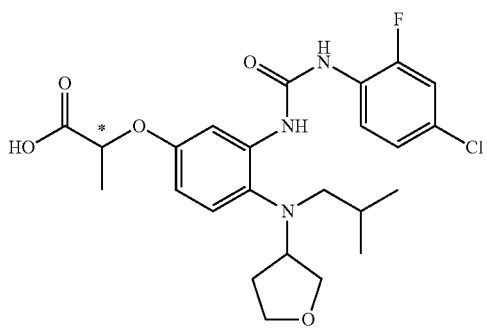 [SMILES: CC(C)CN(c1ccc(OC(C)C(=O)O)cc1NC(=O)Nc1ccc(Cl)cc1F)C1CCOC1]

Example 146 enantiomer 1 was obtained the 1st eluent peak (tr=10.2 min) from Example 309 by using the following conditions: UV visualization at 220 nm; Column: Chiral IC 25×3 cm ID, 5 µm; Flow rate: 85 mL/min, Mobile Phase: 85/15, CO$_2$/MeOH. $^1$H NMR (500 MHz, DMSO-d$_6$) δ 9.62 (br. s., 1H), 8.64 (br. s., 1H), 8.06 (t, J=8.8 Hz, 1H), 7.70 (br. s., 1H), 7.48 (d, J=11.1 Hz, 1H), 7.24 (t, J=7.8 Hz, 2H), 6.48 (d, J=6.6 Hz, 1H), 4.61 (br. s., 1H), 3.80 (br. s., 1H), 3.61 (br. s., 1H), 1.92 (s, 2H), 1.45 (d, J=6.4 Hz, 3H), 1.26 (d, J=7.1 Hz, 1H), 0.81 (br. s., 6H) MS: Anal. Calc'd for C$_{24}$H$_{29}$ClFN$_3$O$_5$ 479.162, found [M+H] 494.1 T$_r$=1.47 min. (method B).

Enantiomer 2: 2-(3-(3-(4-chloro-2-fluorophenyl)ureido)-4-(isobutyl(tetrahydrofuran-3-yl)amino)phenoxy)propanoic acid (Homochiral, Absolute Stereochemistry Unknown)

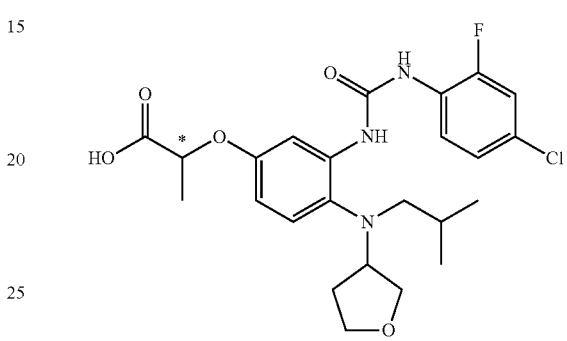

Example 146 enantiomer 2 was obtained the 2nd eluent peak (T$_r$=13.8 min.) from Example 309 by using the following conditions: UV visualization at 220 nm; Column: Chiral IC 25×3 cm ID, 5 µm; Flow rate: 85 mL/min, Mobile Phase: 85/15, CO$_2$/MeOH. $^1$H NMR (500 MHz, DMSO-d$_6$) δ 9.62 (br. s., 1H), 8.64 (br. s., 1H), 8.06 (t, J=8.8 Hz, 1H), 7.70 (br. s., 1H), 7.48 (d, J=11.1 Hz, 1H), 7.24 (t, J=7.8 Hz, 2H), 6.48 (d, J=6.6 Hz, 1H), 4.61 (br. s., 1H), 3.80 (br. s., 1H), 3.61 (br. s., 1H), 1.92 (s, 2H), 1.45 (d, J=6.4 Hz, 3H), 1.26 (d, J=7.1 Hz, 1H), 0.81 (br. s., 6H) MS: Anal. Calc'd for C$_{24}$H$_{29}$ClFN$_3$O$_5$ 479.162, found [M+H] 494.1 T$_r$=1.47 min. (method B).

Example 147

2-(3-(3-(4-chloro-2-fluorophenyl)ureido)-4-(isobutyl(oxetan-3-yl)amino)phenoxy)acetic acid

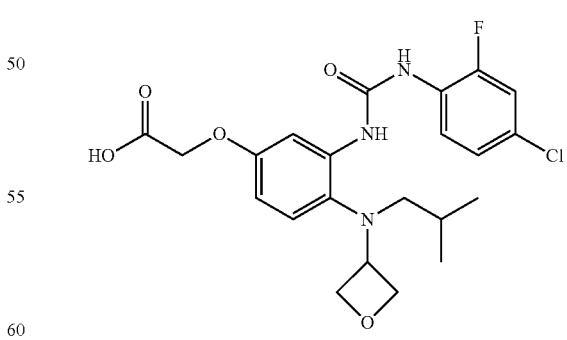

147A: N-isobutyloxetan-3-amine

A solution of oxetan-3-one (0.5 g, 6.94 mmol) and 2-methylpropan-1-amine (0.507 g, 6.94 mmol) in MeOH (20 mL) was heated at 40° C. for 1 h, then allowed to cool to rt. Sodium borohydride (0.394 g, 10.41 mmol) was added. An exotherm was observed. The reaction was allowed to stir at rt overnight. LC-MS shows desired product. The solvent was evaporated and the crude material taken up in EtOAc and H$_2$O. Layers were separated. The aqueous phase was extracted with EtOAc two times. The combined organic phases were dried over Na$_2$SO$_4$, filtered, and concentrated to afford crude material. This material was purified with flash chromatography to give Intermediate 147A (80 mg, 0.607 mmol, 8.75% yield) was obtained as slight yellow liquid. $^1$H NMR (400 MHz, chloroform-d) δ 4.84 (t, J=6.9 Hz, 2H), 4.46 (t, J=6.5 Hz, 2H), 4.01-3.89 (m, 1H), 2.38 (d, J=6.7 Hz, 2H), 1.78-1.64 (m, 1H), 1.50 (br. s., 1H), 1.01-0.89 (m, 6H) MS: Anal. Calc'd for C$_7$H$_{15}$NO 129.115, found [M+H] 130.2.

Example 147. 2-(3-(3-(4-chloro-2-fluorophenyl)ureido)-4-(isobutyl(oxetan-3-yl)amino)phenoxy)acetic acid Example 147 was obtained following the procedures in Example 1 using Intermediate 147A rather than Intermediate 1B. $^1$H NMR (500 MHz, DMSO-d$_6$) δ 9.64 (s, 1H), 8.84 (s, 1H), 8.11 (t, J=8.9 Hz, 1H), 7.77 (d, J=2.8 Hz, 1H), 7.54-7.39 (m, 1H), 7.25 (d, J=9.3 Hz, 2H), 7.19 (d, J=8.8 Hz, 1H), 6.53 (dd, J=8.7, 2.8 Hz, 1H), 4.61 (s, 2H), 4.48 (br. s., 2H), 4.43 (br. s., 3H), 4.34-4.23 (m, 1H), 3.0 (m 2H), 1.42-1.28 (m, 1H), 1.17 (t, J=7.3 Hz, 1H), 0.83 (d, J=6.2 Hz, 6H) MS: Anal. Calc'd for C$_{22}$H$_{25}$ClFN$_3$O$_5$ 465.147, found [M+H] 466.4 T$_r$=1.37 min. (method B).

Example 148

2-(3-(3-(4-chloro-2-fluorophenyl)ureido)-4-((tetrahydro-2H-pyran-4-yl)(3,3,3-trifluoropropyl)amino)phenoxy)propanoic acid

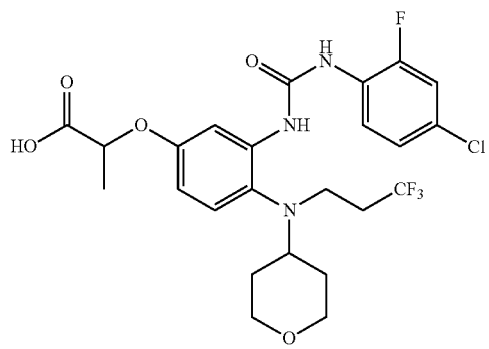 [SMILES: CC(Oc1ccc(N(CCC(F)(F)F)C2CCOCC2)c(NC(=O)Nc2ccc(Cl)cc2F)c1)C(=O)O]

148A: 3,3,3-trifluoro-N-(tetrahydro-2H-pyran-4-yl)propanamide

To a solution of 3,3,3-trifluoropropanoic acid (0.5 g, 3.90 mmol) in THF (20 mL) at Rt was added tetrahydro-2H-pyran-4-amine (0.395 g, 3.90 mmol), followed by EDC (0.749 g, 3.90 mmol), 1-Hydroxybenzotriazole (0.528 g, 3.90 mmol) and Hunig's Base (1.023 mL, 5.86 mmol). The reaction was stirred at room temperature for 16 h. Diluted with EtOAc and 1N HCl. Organic was separated and washed with 1N NaOH, H$_2$O, brine, dried over MgSO$_4$, filtered and concentrated to give Intermediate 148A (0.7 g, 3.28 mmol, 84% yield) as white solid. $^1$H NMR (400 MHz, chloroform-d) δ 5.59 (br. s., 1H), 4.13-4.02 (m, 1H), 4.01-3.90 (m, 2H), 3.50 (td, J=11.7, 2.3 Hz, 2H), 3.08 (q, J=10.6 Hz, 2H), 2.00-1.86 (m, 2H), 1.56-1.38 (m, 2H) MS: Anal. Calc'd for C$_8$H$_{12}$NO$_2$ 211.082, found [M+H] 212.1.

148B: N-(3,3,3-trifluoropropyl)tetrahydro-2H-pyran-4-amine

To a solution of Intermediate 148A (0.6 g, 2.84 mmol) in THF (10 mL) cooled to 0° C. was added BH$_3$-Me$_2$S in Et$_2$O (5.68 mL, 28.4 mmol) slowly. The reaction was stirred at RT for 3 days. The mixture was cooled to 0° C. in an ice bath. Methanol (15 ml) was slowly added dropwise until evolution of gas ceased. The solvent was evaporated from the reaction mixture. The crude material was taken up in MeOH (10 mL) and heated at 80° C. overnight to break up the borane complex. After 24 h, the reaction was allowed to cool to rt. The solvent was evaporated. The crude material was dissolved in a minimal amount of CH$_2$Cl$_2$ and chromatographed. Purification of the crude material by silica gel chromatography gave Intermediate 148B (380 mg, 1.888 mmol, 66.5% yield) was obtained. $^1$H NMR (400 MHz, chloroform-d) δ 4.00 (dt, J=11.4, 3.4 Hz, 2H), 3.42 (td, J=11.7, 2.2 Hz, 2H), 2.97-2.87 (m, 2H), 2.70 (tt, J=10.5, 4.1 Hz, 1H), 2.32 (qt, J=10.9, 7.3 Hz, 2H), 1.90-1.79 (m, 2H), 1.49-1.33 (m, 2H), 1.29-1.03 (m, 1H) MS: Anal. Calc'd for C$_8$H$_{14}$F$_3$NO 197.103, found [M+H] 198.2.

Example 148. 2-(3-(3-(4-chloro-2-fluorophenyl)ureido)-4-((tetrahydro-2H-pyran-4-yl)(3,3,3-trifluoropropyl)amino)phenoxy)propanoic acid Example 148 was obtained following the procedures in Example 58 using 148B rather than Intermediate 1B. $^1$H NMR (500 MHz, DMSO-d$_6$) δ 9.55 (s, 1H), 8.83 (s, 1H), 8.12 (t, J=8.8 Hz, 1H), 7.89-7.77 (m, 1H), 7.47 (d, J=11.2 Hz, 1H), 7.24 (d, J=8.1 Hz, 2H), 6.51 (d, J=6.3 Hz, 1H), 4.80-4.60 (m, 1H), 3.83 (d, J=10.1 Hz, 2H), 3.27-3.13 (m, 3H), 3.03 (br. s., 1H), 2.20 (br. s., 2H), 1.72 (br. s., 2H), 1.50 (d, J=6.6 Hz, 3H), 1.35 (d, J=10.2 Hz, 2H) MS: Anal. Calc'd for C$_{24}$H$_{26}$ClF$_4$N$_3$O$_5$ 547.150, found [M+H] 548.1 T$_r$=1.47 min. (method B).

Example 149

2-(3-(3-(4-chloro-2-fluorophenyl)ureido)-4-((0-4-hydroxycyclohexyl)(isobutyl)amino)phenoxy)acetic acid

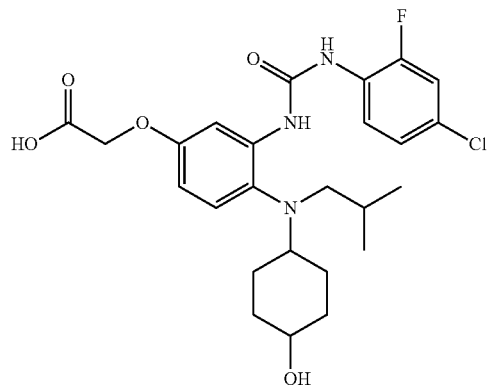 [SMILES: CC(C)CN(c1ccc(OCC(=O)O)cc1NC(=O)Nc1ccc(Cl)cc1F)C1CCC(O)CC1]

149A: 4-(isobutylamino)cyclohexanol

To a solution of 4-hydroxycyclohexanone (0.5 g, 4.38 mmol) in $CH_2Cl_2$ (100 mL) at Rt was added 2-methylpropan-1-amine (3.29 g, 45 mmol), acetic acid (0.251 mL, 4.38 mmol), sodium triacetoxyborohydride (1.393 g, 6.57 mmol). The mixture was stirred at rt for 16 h. The reaction was diluted with water. Organic was separated and then it was washed with saturated $NaHCO_3$, brine, dried over $MgSO_4$, filtered and concentrated. Intermediate 149A (85 mg, 0.496 mmol, 11% yield) was obtained as mixture of diastereomers. MS: Anal. Calc'd for $C_{10}H_{21}NO$ 171.162, found [M+H] 172.2.

Example 149. 2-(3-(3-(4-chloro-2-fluorophenyl)ureido)-4-((( )-4-hydroxycyclohexyl)(isobutyl)amino)phenoxy)acetic acid Example 313 was obtained following the procedures in Example 1 using 149A rather than Intermediate 1B. $^1$H NMR (500 MHz, DMSO-$d_6$) δ 9.63 (br. s., 1H), 8.51 (br. s., 1H), 8.03 (t, J=8.7 Hz, 1H), 7.64 (br. s., 1H), 7.46 (d, J=10.5 Hz, 1H), 7.23 (d, J=8.2 Hz, 1H), 7.08 (d, J=8.4 Hz, 1H), 6.46 (d, J=7.6 Hz, 1H), 4.30 (br. s., 2H), 3.72 (br. s., 1H), 2.90 (s, 1H), 2.74 (s, 1H), 1.91 (s, 2H), 1.68-1.48 (m, 6H), 1.30 (d, J=13.4 Hz, 3H), 0.81 (br. s., 6H) MS: Anal. Calc'd for $C_{25}H_{31}ClFN_3O_5$ 507.194, found [M+H] 508.1 $T_r$=1.36 min. (method B).

Example 150

2-(3-(3-(4-chloro-2-fluorophenyl)ureido)-4-(( )-4 hydroxycyclohexyl)(isobutyl)amino)phenoxy)acetic acid

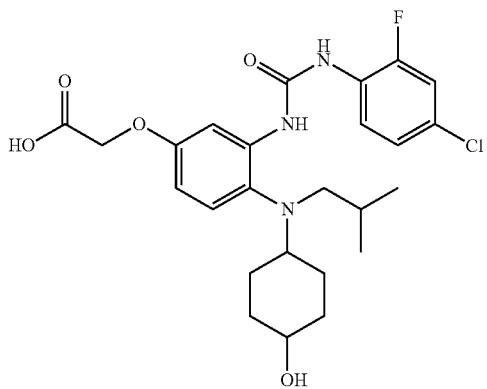 [SMILES: CC(C)CN(c1ccc(OCC(=O)O)cc1NC(=O)Nc1ccc(Cl)cc1F)C1CCC(O)CC1]

Example 150. 2-(3-(3-(4-chloro-2-fluorophenyl)ureido)-4-((( )-4 hydroxycyclohexyl)(isobutyl)amino)phenoxy)acetic acid Example 150 was obtained following the procedures in Example 1 using Intermediate 149A rather than Intermediate 1B. $^1$H NMR (500 MHz, DMSO-$d_6$) δ 9.57 (s, 1H), 8.46 (s, 1H), 8.02 (t, J=8.9 Hz, 1H), 7.57 (br. s., 1H), 7.45 (d, J=10.9 Hz, 1H), 7.23 (d, J=8.8 Hz, 1H), 7.03 (d, J=8.8 Hz, 1H), 6.43 (d, J=7.9 Hz, 1H), 4.09 (br. s., 2H), 3.25 (br. s., 1H), 2.89 (s, 1H), 1.85 (br. s., 2H), 1.82-1.60 (m, 4H), 1.28 (d, J=5.9 Hz, 1H), 1.23 (br. s., 1H), 1.18 (br. s., 1H), 1.13-0.95 (m, 3H), 0.79 (br. s., 6H) MS: Anal. Calc'd for $C_{25}H_{31}ClFN_3O_5$ 507.194, found [M+H] 508.1 $T_r$=1.32 min. (method B).

Example 151

2-(3-(3-(4-chloro-2-fluorophenyl)ureido)-4-(isobutyl(tetrahydro-2H-pyran-4-yl)amino)phenoxy)acetic acid

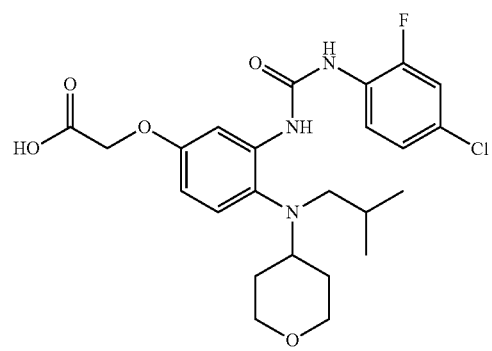 [SMILES: CC(C)CN(c1ccc(OCC(=O)O)cc1NC(=O)Nc1ccc(Cl)cc1F)C1CCOCC1]

Example 151. 2-(3-(3-(4-chloro-2-fluorophenyl)ureido)-4-(isobutyl(tetrahydro-2H-pyran-4-yl)amino)phenoxy)acetic acid Example 151 was obtained following the procedures in Example 1 using Intermediate 143B rather than Intermediate 1B. $^1$H NMR (500 MHz, DMSO-$d_6$) δ 9.64 (s, 1H), 8.63 (s, 1H), 8.01 (t, J=8.8 Hz, 1H), 7.77-7.63 (m, 1H), 7.45 (d, J=10.9 Hz, 1H), 7.24 (d, J=8.8 Hz, 1H), 7.15 (d, J=8.8 Hz, 1H), 6.59-6.47 (m, 1H), 4.54 (s, 2H), 3.83 (d, J=9.2 Hz, 2H), 3.65 (br. s., 1H), 3.57 (br. s., 1H), 3.19 (d, J=16.4 Hz, 2H), 2.83 (br. s., 1H), 2.73 (br. s., 1H), 1.91 (s, 3H), 1.50-1.34 (m, 2H), 1.34-1.12 (m, 1H), 0.80 (br. s., 6H) MS: Anal. Calc'd for $C_{24}H_{29}ClFN_3O_5$ 493.178, found [M+H] 494.0 $T_r$=1.48 min. (Method B).

Example 152

2-(3-(3-(4-chloro-2-fluorophenyl)ureido)-4-(isobutyl(0-4-methoxycyclohexyl)amino)phenoxy)acetic acid

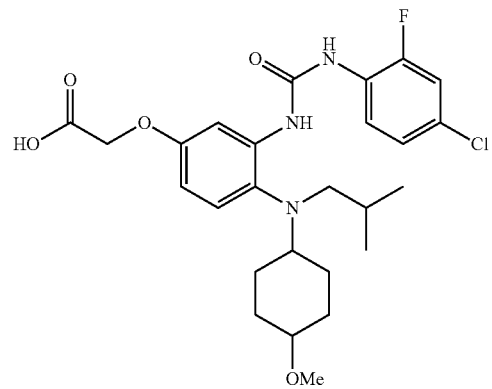 [SMILES: COC1CCC(N(CC(C)C)c2ccc(OCC(=O)O)cc2NC(=O)Nc2ccc(Cl)cc2F)CC1]

152A: 4-(isobutylamino)cyclohexanol

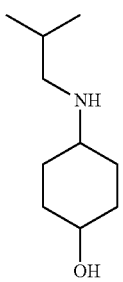

A solution of 4-hydroxycyclohexanone (3.5 g, 30.7 mmol) and 2-methylpropan-1-amine (3.35 ml, 33.7 mmol) in MeOH (61.3 ml) was heated at 40° C. for 1 hour, then allowed to cool to room temperature. Sodium borohydride (1.740 g, 46.0 mmol) was added slowly. The reaction was allowed to stir at room temperature overnight. The solvent was evaporated and the crude material was taken up in EtOAc and H$_2$O. Layers were separated. The aqueous phase was extracted with EtOAc (2×). The combined organic phases were dried over Na$_2$SO$_4$, filtered, and concentrated to afford 152A (4.0 g, 23.35 mmol, 76% yield) as a colorless oil. $^1$H NMR (400 MHz, chloroform-d) δ 5.30 (s, 1H), 3.87 (br. s., 1H), 3.61 (br. s., 1H), 2.50 (d, J=3.8 Hz, 1H), 2.41 (dd, J=6.7, 2.0 Hz, 2H), 2.07-1.87 (m, 2H), 1.80-1.66 (m, 2H), 1.67-1.50 (m, 3H), 1.39-1.22 (m, 1H), 1.22-1.05 (m, 1H), 0.96-0.85 (m, 6H).

Preparation 152B.
N-isobutyl-4-methoxycyclohexanamine

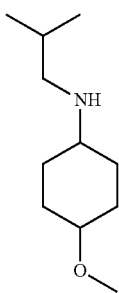

To a solution of 152A (0.5 g, 2.92 mmol) in DCM (5.84 ml) was added TEA (0.814 ml, 5.84 mmol) and di-tert-butyl dicarbonate (0.765 g, 3.50 mmol). The mixture was stirred at rt overnight. The mixture was diluted with DCM, washed with water, brine, dried over Na$_2$SO$_4$ and concentrated to yield a yellow oil, which was dissolved in THF (1474 μl), then Ag$_2$O (768 mg, 3.3 mmol) and iodomethane (210 μl, 3.3 mmol) were added. The mixture was heated at 50° C. overnight. The mixture was filtered. The filtrate was concentrated, then treated with 4M HCl (737 μl, 2.95 mmol) in dioxane. After 2 h, the mixture was concentrated and the resultant residue dissolved in EtOAc, washed with sodium bicarbonate solution, water, brine, dried over Na$_2$SO$_4$ and concentrated to yield 152B (300 mg, 1.62 mmol, 73.2% yield) as a light yellow oil. $^1$H NMR (400 MHz, chloroform-d) δ 3.89-3.67 (m, 1H), 3.42-3.26 (m, 3H), 3.19-3.01 (m, 1H), 2.54-2.38 (m, 2H), 2.10-1.84 (m, 3H), 1.77-1.62 (m, 2H), 1.58-1.39 (m, 2H), 1.28-1.14 (m, 2H), 0.98-0.84 (m, 6H).

Example 152. 2-(3-(3-(4-chloro-2-fluorophenyl) ureido)-4-(isobutyl-4-methoxycyclohexyl)amino) phenoxy)acetic acid Example 152 was obtained following the procedures in Example 1 using Intermediate 152B rather than Intermediate 1B. $^1$H NMR (500 MHz, DMSO-d$_6$) δ 9.61 (s, 1H), 8.54 (s, 1H), 8.01 (t, J=8.7 Hz, 1H), 7.68 (br. s., 1H), 7.47 (d, J=10.9 Hz, 1H), 7.24 (d, J=8.8 Hz, 1H), 7.11 (d, J=8.8 Hz, 1H), 6.49 (d, J=6.5 Hz, 1H), 4.50 (s, 2H), 3.54 (br. s., 1H), 3.17 (s, 3H), 2.96 (br. s., 1H), 2.59 (br. s., 1H), 1.96 (d, J=10.3 Hz, 3H), 1.91 (s, 4H), 1.37-1.21 (m, 2H), 1.16 (br. s., 2H), 1.09-0.93 (m, 2H), 0.80 (br. s., 6H) MS: Anal. Calc'd for C$_{26}$H$_{33}$ClFN$_3$O$_5$ 521.209 found [M+H] 522.0 T$_r$=1.77 min. (Method B).

Example 152

2-(3-(3-(4-chloro-2-fluorophenyl)ureido)-4-(isobutyl (0-4-methoxycyclohexyl)amino)phenoxy)acetic acid

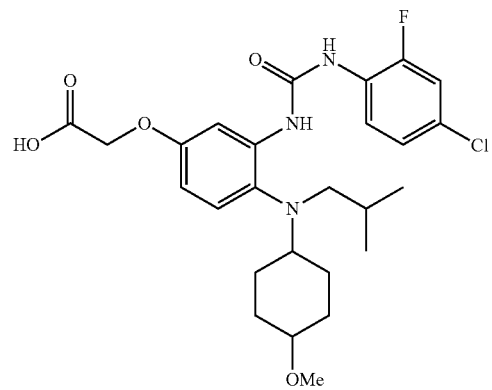 [SMILES: COC1CCC(N(CC(C)C)c2ccc(OCC(=O)O)cc2NC(=O)Nc2ccc(Cl)cc2F)CC1]

152A: 4-(isobutylamino)cyclohexanol

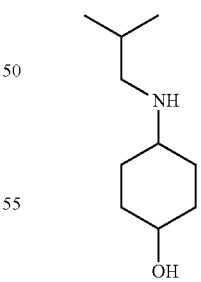

A solution of 4-hydroxycyclohexanone (3.5 g, 30.7 mmol) and 2-methylpropan-1-amine (3.35 ml, 33.7 mmol) in MeOH (61.3 ml) was heated at 40° C. for 1 hour, then allowed to cool to room temperature. Sodium borohydride (1.740 g, 46.0 mmol) was added slowly. The reaction was allowed to stir at room temperature overnight. The solvent was evaporated and the crude material was taken up in EtOAc and H$_2$O. Layers were separated. The aqueous phase

145 was extracted with EtOAc (2×). The combined organic phases were dried over Na$_2$SO$_4$, filtered, and concentrated to afford 152A (4.0 g, 23.35 mmol, 76% yield) as a colorless oil. $^1$H NMR (400 MHz, chloroform-d) δ 5.30 (s, 1H), 3.87 (br. s., 1H), 3.61 (br. s., 1H), 2.50 (d, J=3.8 Hz, 1H), 2.41 (dd, J=6.7, 2.0 Hz, 2H), 2.07-1.87 (m, 2H), 1.80-1.66 (m, 2H), 1.67-1.50 (m, 3H), 1.39-1.22 (m, 1H), 1.22-1.05 (m, 1H), 0.96-0.85 (m, 6H).

Preparation 152B.
N-isobutyl-4-methoxycyclohexanamine

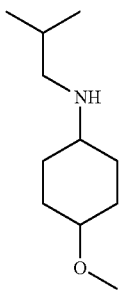

To a solution of 152A (0.5 g, 2.92 mmol) in DCM (5.84 ml) was added TEA (0.814 ml, 5.84 mmol) and di-tert-butyl dicarbonate (0.765 g, 3.50 mmol). The mixture was stirred at rt overnight. The mixture was diluted with DCM, washed with water, brine, dried over Na$_2$SO$_4$ and concentrated to yield a yellow oil, which was dissolved in THF (1474 µl), then Ag$_2$O (768 mg, 3.3 mmol) and iodomethane (210 µl, 3.3 mmol) were added. The mixture was heated at 50° C. overnight. The mixture was filtered. The filtrate was concentrated, then treated with 4M HCl (737 µl, 2.95 mmol) in dioxane. After 2 h, the mixture was concentrated and the resultant residue dissolved in EtOAc, washed with sodium bicarbonate solution, water, brine, dried over Na$_2$SO$_4$ and concentrated to yield 152B (300 mg, 1.62 mmol, 73.2% yield) as a light yellow oil. $^1$H NMR (400 MHz, chloroform-d) δ 3.89-3.67 (m, 1H), 3.42-3.26 (m, 3H), 3.19-3.01 (m, 1H), 2.54-2.38 (m, 2H), 2.10-1.84 (m, 3H), 1.77-1.62 (m, 2H), 1.58-1.39 (m, 2H), 1.28-1.14 (m, 2H), 0.98-0.84 (m, 6H).

Example 152. 2-(3-(3-(4-chloro-2-fluorophenyl)
ureido)-4-(isobutyl-4-methoxycyclohexyl)amino)
phenoxy)acetic acid Example 152 was obtained following the procedures in Example 1 using Intermediate 152B rather than Intermediate 1B. $^1$H NMR (500 MHz, DMSO-d$_6$) δ 9.61 (s, 1H), 8.54 (s, 1H), 8.01 (t, J=8.7 Hz, 1H), 7.68 (br. s., 1H), 7.47 (d, J=10.9 Hz, 1H), 7.24 (d, J=8.8 Hz, 1H), 7.11 (d, J=8.8 Hz, 1H), 6.49 (d, J=6.5 Hz, 1H), 4.50 (s, 2H), 3.54 (br. s., 1H), 3.17 (s, 3H), 2.96 (br. s., 1H), 2.59 (br. s., 1H), 1.96 (d, J=10.3 Hz, 3H), 1.91 (s, 4H), 1.37-1.21 (m, 2H), 1.16 (br. s., 2H), 1.09-0.93 (m, 2H), 0.80 (br. s., 6H) MS: Anal. Calc'd for C$_{26}$H$_{33}$ClFN$_3$O$_5$ 521.209 found [M+H] 522.0 T$_r$=1.77 min. (Method B).

146

Experiment 153

2-(3-(3-(4-chloro-2-fluorophenyl)ureido)-4-(cyclo-hexyl(isobutyl)amino)phenoxy)acetamide

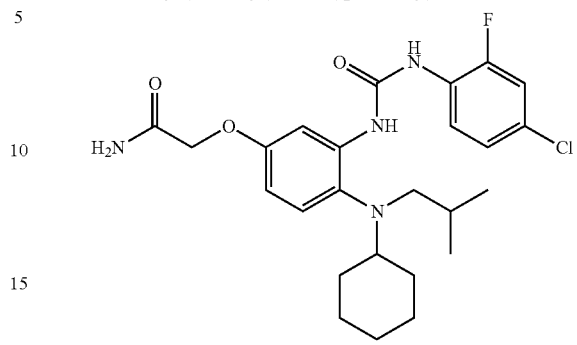

Example 153. 2-(3-(3-(4-chloro-2-fluorophenyl)
ureido)-4-(cyclohexyl(isobutyl)amino)phenoxy)acet-
amide To a solution of Example 1 (15 mg, 0.030 mmol) in DMF (0.5 mL) at room temperature was added 1-(3-dimethylaminopropyl)-3-ethylcarbodiimide hydrochloride (11.69 mg, 0.061 mmol), 4-hydroxybenzotriazole (8.24 mg, 0.061 mmol), ammonium chloride (4.89 mg, 0.091 mmol) and Hunig's Base (0.016 mL, 0.091 mmol). The reaction was stirred at room temperature for 16 h. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 50-100% B over 5 minutes, then a 20-minute hold at 100% B; Flow: 20 mL/min. Fractions containing the desired product were combined and dried via centrifugal evaporation. Example 153 (10.7 mg, 0.022 mmol, 71% yield) was obtained. $^1$H NMR (500 MHz, DMSO-d$_6$) δ 9.62 (s, 1H), 8.52 (s, 1H), 8.01 (t, J=8.8 Hz, 1H), 7.73 (br. s., 1H), 7.53 (br. s., 1H), 7.47 (d, J=10.9 Hz, 1H), 7.37 (br. s., 1H), 7.24 (d, J=8.7 Hz, 1H), 7.12 (d, J=8.7 Hz, 1H), 6.55 (dd, J=8.7, 2.5 Hz, 1H), 4.36 (s, 2H), 1.91 (br. s., 2H), 1.69 (br. s., 2H), 1.52 (d, J=12.1 Hz, 1H), 1.31 (dt, J=13.1, 6.5 Hz, 1H), 1.11 (br. s., 4H), 0.99 (br. s., 1H), 0.81 (br. s., 6H) MS: Anal. Calc'd for C$_{25}$H$_{32}$ClFN$_4$O$_3$ 490.215 found [M+H] 490.9 T$_r$=2.34 min. (Method B).

Example 154 2-(3-(3-(4-chloro-2-fluorophenyl)
ureido)-4-(cyclohexyl(isobutyl)amino)phenoxy)-N-
(oxazol-2-yl)acetamide

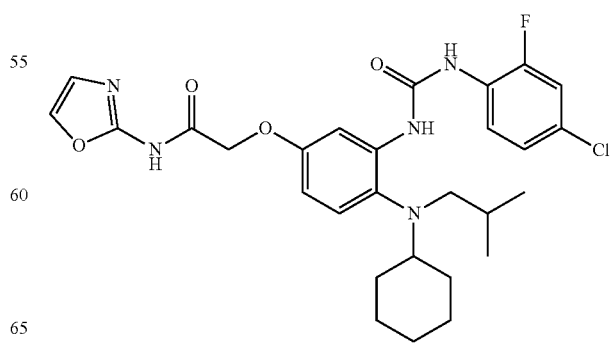

Example 154. 2-(3-(3-(4-chloro-2-fluorophenyl)ureido)-4-(cyclohexyl(isobutyl)amino)phenoxy)-N-(oxazol-2-yl)acetamide Example 154 was obtained following the procedures in Example 153 using oxazol-2-amine. $^1$H NMR (500 MHz, DMSO-$d_6$) δ 9.63 (s, 1H), 8.53 (s, 1H), 8.07-7.98 (m, 1H), 7.88 (s, 1H), 7.75 (br. s., 1H), 7.47 (d, J=10.9 Hz, 1H), 7.25 (d, J=8.8 Hz, 1H), 7.18-6.98 (m, 2H), 6.61-6.48 (m, 1H), 4.73 (br. s., 2H), 2.01-1.81 (m, 3H), 1.68 (br. s., 2H), 1.52 (d, J=11.9 Hz, 1H), 1.38-1.25 (m, 1H), 1.12 (br. s., 5H), 0.99 (br. s., 1H), 0.81 (br. s., 6H) MS: Anal. Calc'd for $C_{28}H_{33}ClFN_5O_4$ 557.221 found [M+H] 558.4 $T_r$=2.4 min. (Method B).

Example 155

2-(3-(3-(4-chloro-2-fluorophenyl)ureido)-4-(cyclohexyl(isobutyl)amino)phenoxy)-N-(thiazol-2-yl)acetamide

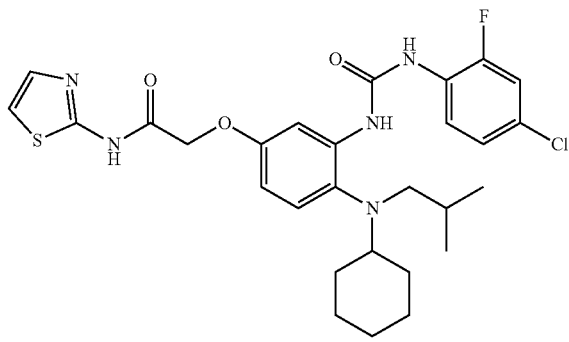 [SMILES: CC(C)CN(c1ccc(OCC(=O)Nc2nccs2)cc1NC(=O)Nc1ccc(Cl)cc1F)C1CCCCC1]

Example 155. 2-(3-(3-(4-chloro-2-fluorophenyl)ureido)-4-(cyclohexyl(isobutyl)amino)phenoxy)-N-(thiazol-2-yl)acetamide Example 155 was obtained following the procedures in Example 153 using thiazol-2-amine. $^1$H NMR (500 MHz, DMSO-$d_6$) δ 9.62 (s, 1H), 8.52 (s, 1H), 8.07-7.85 (m, 1H), 7.75 (d, J=2.4 Hz, 1H), 7.56-7.38 (m, 2H), 7.28-7.19 (m, 2H), 7.13 (d, J=8.8 Hz, 1H), 6.56 (dd, J=8.8, 2.7 Hz, 1H), 4.79 (s, 2H), 1.89 (d, J=15.5 Hz, 3H), 1.68 (br. s., 2H), 1.52 (d, J=11.5 Hz, 1H), 1.31 (dt, J=13.2, 6.6 Hz, 1H), 1.11 (br. s., 4H), 0.99 (br. s., 1H), 0.81 (br. s., 6H) MS: Anal. Calc'd for $C_{28}H_{33}ClFN_5O_3S$ 573.198 found [M+H]573.9 $T_r$=2.63 min. (Method B).

Example 156

1-(4-chloro-2-fluorophenyl)-3-(2-(cyclohexyl(isobutyl)amino)-5-(oxazol-2-ylmethoxy)phenyl)urea

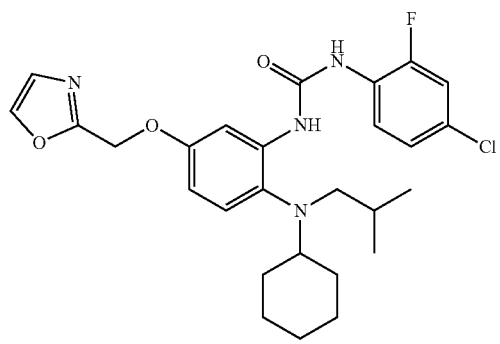 [SMILES: CC(C)CN(c1ccc(OCc2ncco2)cc1NC(=O)Nc1ccc(Cl)cc1F)C1CCCCC1]

156A: N-cyclohexyl-N-isobutyl-2-nitro-4-(oxazol-2-ylmethoxy)aniline

To a solution of 4-(cyclohexyl(isobutyl)amino)-3-nitrophenol (50 mg, 0.171 mmol) in THF (0.5 mL) at RT was added oxazol-2-ylmethanol (16.95 mg, 0.171 mmol) and triphenylphosphine (58.3 mg, 0.222 mmol). Then diisopropyl azodicarboxylate (45.0 mg, 0.222 mmol) in 0.1 mL of THF was added dropwise. The color of the reaction turned to brown. The reaction was stirred at RT for 16 h. The color of the reaction turned to lighter. The solvent was removed and the crude was purified with flash chromatography to give 156A (44 mg, 0.117 mmol, 68.2% yield)$^1$H NMR (400 MHz, chloroform-d) δ 7.73 (d, J=0.9 Hz, 1H), 7.32 (d, J=2.9 Hz, 1H), 7.27-7.18 (m, 2H), 7.17-7.02 (m, 1H), 5.16 (s, 2H), 2.90-2.66 (m, 3H), 1.91-1.71 (m, 4H), 1.66-1.58 (m, 1H), 1.49 (dt, J=13.4, 6.6 Hz, 1H), 1.42-1.13 (m, 4H), 1.13-0.98 (m, 1H), 0.84 (d, J=6.6 Hz, 6H) MS: Anal. Calc'd for $C_{20}H_{27}N_3O_4$ 373.200 found [M+H] 374.0.

Example 156. 1-(4-chloro-2-fluorophenyl)-3-(2-(cyclohexyl(isobutyl)amino)-5-(oxazol-2-ylmethoxy)phenyl)urea Example 156 was obtained following the procedures in Example 301B and 301 from 320A. $^1$H NMR (500 MHz, DMSO-$d_6$) δ 9.63 (s, 1H), 8.51 (s, 1H), 8.18 (s, 1H), 8.01 (t, J=8.8 Hz, 1H), 7.75 (d, J=2.5 Hz, 1H), 7.47 (d, J=10.9 Hz, 1H), 7.33-7.21 (m, 2H), 7.14 (d, J=8.8 Hz, 1H), 6.67 (dd, J=8.7, 2.6 Hz, 1H), 5.15 (s, 2H), 1.92 (br. s., 2H), 1.69 (br. s., 2H), 1.52 (d, J=11.8 Hz, 1H), 1.31 (dt, J=13.1, 6.5 Hz, 1H), 1.12 (br. s., 4H), 0.99 (br. s., 1H), 0.81 (br. s., 6H) MS: Anal. Calc'd for $C_{27}H_{32}ClFN_4O_3$ 514.215 found [M+H] 515.5 $T_r$=2.66 min. (Method B).

Example 157

1-(4-chloro-2-fluorophenyl)-3-(2-(cyclohexyl(isobutyl)amino)-5-(1-(oxazol-2-yl)ethoxy)phenyl)urea

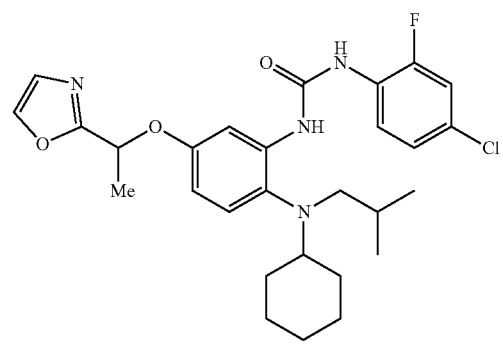 [SMILES: CC(C)CN(c1ccc(OC(C)c2ncco2)cc1NC(=O)Nc1ccc(Cl)cc1F)C1CCCCC1]

157A: 1-(oxazol-2-yl)ethanol

To a solution of 1-(Oxazol-2-yl)ethanone (0.5 g, 4.50 mmol) in MeOH (10 mL) at room temperature was added sodium borohydride (0.255 g, 6.75 mmol). The reaction was stirred at room temperature for 3 h. Then it was rotavap to remove the solvent. The residue was diluted with EtOAc and saturated $NH_4Cl_1$. Organic was separated and washed with brine, dried over $MgSO_4$, filtered and concentrated to give 1-(oxazol-2-yl)ethanol (0.22 g, 1.945 mmol, 43.2% yield).

$^1$H NMR (400 MHz, DMSO-d$_6$) δ 8.03 (d, J=0.9 Hz, 1H), 7.14 (d, J=0.9 Hz, 1H), 5.64 (d, J=5.6 Hz, 1H), 4.77 (qd, J=6.6, 5.6 Hz, 1H), 1.42 (d, J=6.6 Hz, 3H)

Example 157: 1-(4-chloro-2-fluorophenyl)-3-(2-(cyclohexyl(isobutyl)amino)-5-(1-(oxazol-2-yl)ethoxy)phenyl)urea Example 157 was obtained following the procedures in Example 159 using 1-(oxazol-2-yl)ethanol $^1$H NMR (500 MHz, DMSO-d$_6$) δ 9.61 (s, 1H), 8.47 (s, 1H), 8.12 (s, 1H), 8.05-7.90 (m, 1H), 7.72 (d, J=2.4 Hz, 1H), 7.47 (d, J=10.9 Hz, 1H), 7.30-7.20 (m, 2H), 7.10 (d, J=8.8 Hz, 1H), 6.62 (dd, J=8.7, 2.6 Hz, 1H), 5.52 (q, J=6.4 Hz, 1H), 1.91 (d, J=8.5 Hz, 2H), 1.74-1.59 (m, 5H), 1.51 (d, J=11.8 Hz, 1H), 1.29 (dt, J=13.0, 6.5 Hz, 1H), 1.11 (br. s., 4H), 0.99 (br. s., 1H), 0.80 (br. s., 6H) MS: Anal. Calc'd for C$_{28}$H$_{34}$ClFN$_4$O$_3$ 528.230 found [M+H] 529.5 T$_r$=2.69 min. (Method B).

Example 158

2-(4-(benzyl(propyl)amino)-3-(3-(4-chloro-2-fluorophenyl)ureido)phenoxy)acetic acid

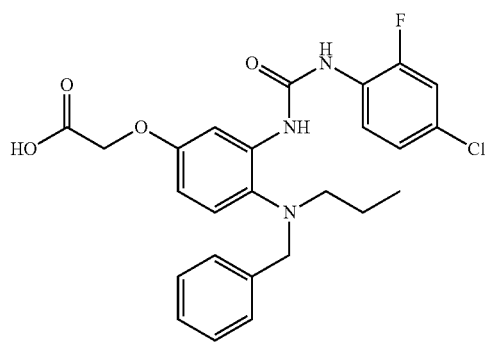 [SMILES: CCCN(Cc1ccccc1)c1ccc(OCC(=O)O)cc1NC(=O)Nc1ccc(Cl)cc1F]

158A: 4-(benzyl(propyl)amino)-3-nitrophenol

To 4-fluoro-3-nitrophenol (500 mg, 3.18 mmol) in a 2 dram vial was added N-benzylpropan-1-amine (570 mg, 3.82 mmol). The mixture was stirred at 120° C. for 3 h. Cooled to RT. The mixture was purified with flash chromatography to Intermediate 158A (700 mg, 1.222 mmol, 38.4% yield) as an orange liquid. $^1$H NMR (400 MHz, DMSO-d$_6$) δ 7.39-7.12 (m, 13H), 7.03 (d, J=2.8 Hz, 1H), 6.96 (dd, J=8.8, 2.9 Hz, 1H), 4.09-3.91 (m, 2H), 2.81-2.73 (m, 2H), 2.44 (t, J=7.1 Hz, 2H), 1.48-1.34 (m, 2H), 1.34-1.22 (m, 2H), 0.86 (t, J=7.4 Hz, 3H), 0.71 (t, J=7.3 Hz, 3H) MS: Anal. Calc'd for C$_{16}$H$_{18}$N$_2$O$_3$ 286.132 found [M+H] 287.2.

158B: ethyl 2-(4-(benzyl(propyl)amino)-3-nitrophenoxy)acetate

To a solution of Intermediate 158A (0.7 g, 2.445 mmol) in DMF (15 mL) at RT was added cesium carbonate (0.956 g, 2.93 mmol), followed by ethyl 2-bromoacetate (0.449 g, 2.69 mmol). The reaction was heated at 60° C. for 3 h. Cooled to RT and diluted with EtOAc and water. Organic was separated and washed with water three times, brine, dried over MgSO$_4$ and concentrated to give a crude material. This crude material was purified with flash chromatography to give Intermediate 158B (480 mg, 1.224 mmol, 50.1% yield) as an orange solid. $^1$H NMR (400 MHz, DMSO-d$_6$) δ 7.42 (d, J=9.0 Hz, 1H), 7.35 (d, J=3.1 Hz, 1H), 7.32-7.19 (m, 5H), 7.15 (dd, J=8.9, 3.1 Hz, 1H), 4.83 (s, 2H), 4.17 (q, J=7.1 Hz, 2H), 4.10 (s, 2H), 2.87-2.76 (m, 2H), 1.38-1.26 (m, 2H), 1.23-1.15 (m, 3H), 0.73 (t, J=7.3 Hz, 3H) MS: Anal. Calc'd for C$_{20}$H$_{24}$N$_2$O$_5$ 372.169 found [M+H] 373.2.

158C: ethyl 2-(3-amino-4-(benzyl(propyl)amino)phenoxy)acetate

To a solution of Intermediate 158B (480 mg, 1.289 mmol) in Ethanol (10 mL), THF (1 mL) and Water (2.00 mL) was added ammonium chloride (207 mg, 3.87 mmol) followed by Zinc (838 mg, 12.89 mmol). The mixture was stirred at room temperature for 2 h and then diluted with EtOAc and water. The mixture was filtered through celite. The filtrate was transferred into a separatory funnel. The organic was separated and washed with brine, dried over MgSO$_4$, filtered and concentrated to give Intermediate 158C (420 mg, 1.104 mmol, 86% yield). $^1$H NMR (400 MHz, DMSO-d$_6$) δ 7.40-7.23 (m, 5H), 7.23-7.13 (m, 1H), 6.87 (d, J=8.7 Hz, 1H), 6.22 (d, J=2.8 Hz, 1H), 6.04 (dd, J=8.7, 2.9 Hz, 1H), 4.95 (s, 2H), 4.59 (s, 2H), 4.23-4.07 (m, 3H), 3.92 (s, 2H), 2.77-2.63 (m, 2H), 1.41-1.28 (m, 2H), 1.21 (t, J=7.2 Hz, 3H), 0.76 (t, J=7.3 Hz, 3H) MS: Anal. Calc'd for C$_{20}$H$_{26}$N$_2$O$_3$ 342.194 found [M+H] 343.2.

Example 158: 2-(4-(benzyl(propyl)amino)-3-(3-(4-chloro-2-fluorophenyl)ureido)phenoxy)acetic acid To a solution of Intermediate 158C (20 mg, 0.058 mmol) in THF (0.5 mL) at RT was added 4-chloro-2-fluoro-1-isocyanatobenzene (20.04 mg, 0.117 mmol). The reaction was stirred at RT for 16 h. Then MeOH (0.2 mL) and 1N NaOH (0.5 mL) were added. The reaction was stirred at room temperature for 3 h. pH was adjusted to 5 with conc. HCl. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-80% B over 20 minutes, then a 5-minute hold at 100% B; Flow: 20 mL/min. Fractions containing the desired product were combined and dried via centrifugal evaporation. Example 158 (25.6 mg, 0.05 mmol, 86% yield) was obtained. $^1$H NMR (500 MHz, DMSO-d$_6$) δ 9.66 (s, 1H), 8.89 (s, 1H), 8.12 (t, J=8.9 Hz, 1H), 7.68 (d, J=2.9 Hz, 1H), 7.48 (dd, J=11.1, 2.2 Hz, 1H), 7.33-7.12 (m, 11H), 7.10-6.97 (m, 3H), 6.43 (dd, J=8.7, 2.9 Hz, 1H), 4.55 (s, 2H), 4.05 (s, 2H), 2.87-2.76 (m, 2H), 1.43-1.25 (m, 2H), 0.79 (t, J=7.4 Hz, 3H) MS: Anal. Calc'd for C$_{25}$H$_{25}$ClFN$_3$O$_4$ 485.152 found [M+H] 486.2 T$_r$=2.69 min. (Method B) These compounds were obtained following the procedures in Example 325 using the corresponding isocyanate.

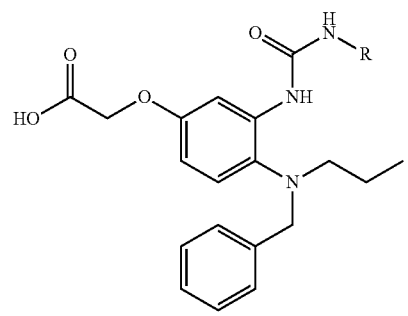

| Example # | Name | R | Tr (min) (*) | [M + H]+ |
|---|---|---|---|---|
| 159 | 2-(4-(benzyl(propyl)amino)-3-(3-(p-tolyl)ureido)phenoxy)acetic acid | | 1.60 | 448.3 |
| 160 | 2-(4-(benzyl(propyl)amino)-3-(3-(4-(trifluoromethoxy)phenyl)ureido)phenoxy)acetic acid | | 1.83 | 518.3 |
| 161 | 2-(4-(benzyl(propyl)amino)-3-(3-(4-ethoxyphenyl)ureido)phenoxy)acetic acid | | 1.64 | 478.3 |
| 162 | 2-(4-(benzyl(propyl)amino)-3-(3-(4-(trifluoromethyl)phenyl)ureido)phenoxy)acetic acid | | 1.85 | 502.1 |

(*)—Method B

Example 163

2-(3-(3-(4-chloro-2-fluorophenyl)ureido)-4-((4-chlorobenzyl)(isobutyl)amino)phenoxy)acetic acid

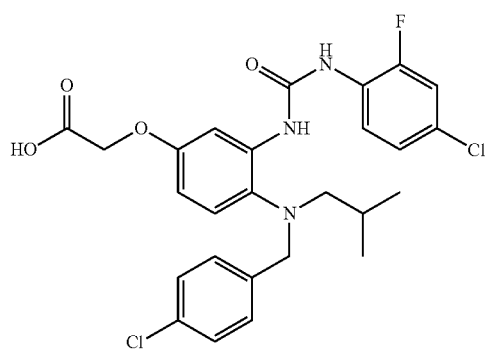 [SMILES: CC(C)CN(Cc1ccc(Cl)cc1)c1ccc(OCC(=O)O)cc1NC(=O)Nc1ccc(Cl)cc1F]

Example 164

2-(3-(3-(4-chloro-2-fluorophenyl)ureido)-4-((4-chlorobenzyl)(propyl)amino)phenoxy)acetic acid

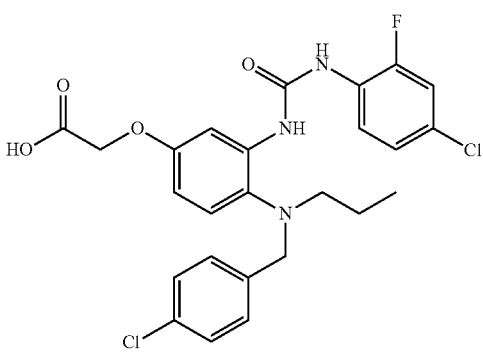 [SMILES: CCCN(Cc1ccc(Cl)cc1)c1ccc(OCC(=O)O)cc1NC(=O)Nc1ccc(Cl)cc1F]

Example 163: 2-(3-(3-(4-chloro-2-fluorophenyl)ureido)-4-((4-chlorobenzyl)(isobutyl)amino)phenoxy)acetic acid Example 163 was obtained following the procedures in Example 158 using N-(4-chlorobenzyl)-2-methylpropan-1-amine and 4-chloro-2-fluoro-1-isocyanatobenzene. MS: Anal. Calc'd for $C_{26}H_{26}C_{12}FN_3O_4$ 533.128 found [M+H] 534.2 HPLC: $T_r$=1.84 min (Method B).

Example 164: 2-(3-(3-(4-chloro-2-fluorophenyl)ureido)-4-((4-chlorobenzyl)(propyl)amino)phenoxy)acetic acid Example 164 was obtained following the procedures in Example 158 using N-(4-chlorobenzyl)propan-1-amine and 4-chloro-2-fluoro-1-isocyanatobenzene. MS: Anal. Calc'd for $C_{25}H_{24}C_{12}FN_3O_4$ 519.113 found [M+H] 520.5 HPLC: $T_r$=1.75 min (Method B).

Example 165

2-(4-(benzyl(propyl)amino)-3-(2-(4-chloro-2-fluorophenyl)acetamido)phenoxy)acetic acid

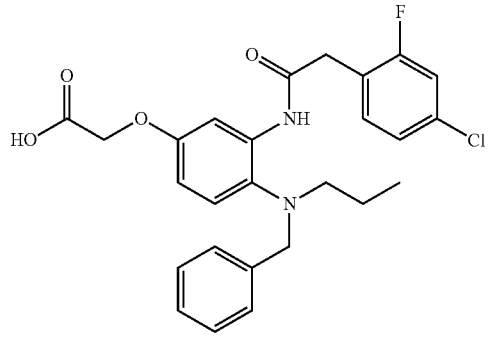 [SMILES: CCCN(Cc1ccccc1)c1ccc(OCC(=O)O)cc1NC(=O)Cc1ccc(Cl)cc1F]

Example 165: 2-(4-(benzyl(propyl)amino)-3-(2-(4-chloro-2-fluorophenyl)acetamido) phenoxy)acetic acid To a solution of ethyl 2-(3-amino-4-(benzyl(propyl)amino)phenoxy)acetate (20 mg, 0.058 mmol) in THF (1 mL) at RT was added 2-(4-chloro-2-fluorophenyl)acetic acid (33.0 mg, 0.175 mmol), EDC (33.6 mg, 0.175 mmol), 1-hydroxybenzotriazole (23.68 mg, 0.175 mmol), followed by Hunig's Base (0.051 mL, 0.292 mmol). The reaction was stirred at Rt for 16 h. MeOH (0.2 mL) and 1N NaOH (1 mL) were added. The reaction was stirred at room temperature for 3 h. pH was adjusted to 5 with concentrated HCl. The mixture was filtered through 0.45 uM membrane. The filtrate was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-80% B over 20 minutes, then a 5-minute hold at 100% B; Flow: 20 mL/min. Fractions containing the desired product were combined and dried via centrifugal evaporation. Example 165 (21.3 mg, 0.043 mmol, 73% yield) was obtained. $^1$H NMR (500 MHz, DMSO-d$_6$) δ 8.91 (s, 1H), 7.70 (br. s., 1H), 7.52-7.41 (m, 2H), 7.31 (d, J=8.2 Hz, 1H), 7.27-7.15 (m, 5H), 7.10 (d, J=7.2 Hz, 2H), 6.53 (dd, J=8.7, 2.7 Hz, 1H), 4.42 (s, 2H), 3.77 (s, 1H), 2.70-2.60 (m, 2H), 1.29-1.08 (m, 2H), 0.71 (t, J=7.3 Hz, 3H) MS: Anal. Calc'd for C$_{26}$H$_{26}$ClFN$_2$O$_4$ 484.157 found [M+H] 485.2 HPLC: T$_r$=1.72 min (Method B).

Example 166

2-(4-(benzyl(propyl)amino)-3-(2-(p-tolyl)acetamido)phenoxy)acetic acid

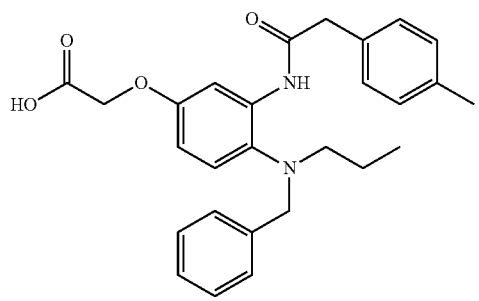 [SMILES: CCCN(Cc1ccccc1)c1ccc(OCC(=O)O)cc1NC(=O)Cc1ccc(C)cc1]

Example 166 was obtained following the procedures in Example 165 using 2-(p-tolyl)acetic acid. $^1$H NMR (500 MHz, DMSO-d$_6$) δ 8.80 (s, 1H), 7.79 (d, J=2.7 Hz, 1H), 7.32-7.11 (m, 9H), 7.03 (d, J=6.7 Hz, 2H), 6.52 (dd, J=8.8, 2.9 Hz, 1H), 4.53 (s, 2H), 3.68 (s, 2H), 2.60-2.54 (m, 4H), 2.29 (s, 3H), 1.20-0.99 (m, 2H), 0.67 (t, J=7.3 Hz, 3H) MS: Anal. Calc'd for C$_{27}$H$_{30}$N$_2$O$_4$ 446.211 found [M+H] 447.3 HPLC: T$_r$=1.71 min (Method B).

Example 167

2-(3-(2-(4-chloro-2-fluorophenyl)acetamido)-4-((4-chlorobenzyl)(isobutyl)amino)phenoxy)acetic acid

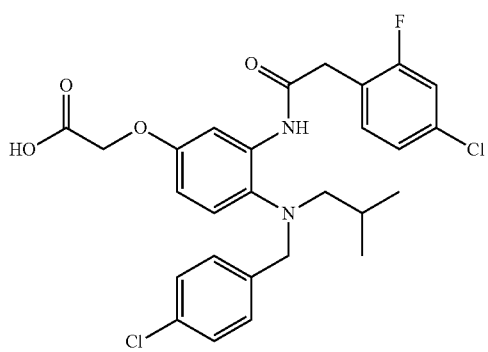 [SMILES: CC(C)CN(Cc1ccc(Cl)cc1)c1ccc(OCC(=O)O)cc1NC(=O)Cc1ccc(Cl)cc1F]

This compound was obtained following the procedures in Example 165 using ethyl 2-(3-amino-4-((4-chlorobenzyl)(isobutyl)amino)phenoxy)acetate. $^1$H NMR (500 MHz, DMSO-d$_6$) δ 8.83 (s, 1H), 7.69 (br. s., 1H), 7.52-7.40 (m, 2H), 7.37-7.24 (m, 3H), 7.12 (d, J=7.7 Hz, 3H), 6.55 (dd, J=8.7, 2.7 Hz, 1H), 4.46 (s, 2H), 3.76 (s, 1H), 2.61-2.53 (m, 3H), 1.51 (dt, J=13.4, 6.6 Hz, 1H), 0.76 (d, J=6.6 Hz, 6H) MS: Anal. Calc'd for C$_{27}$H$_{27}$C$_{12}$FN$_2$O$_4$ 532.133 found [M+H] 533.1 HPLC: T$_r$=1.91 min (Method B).

Evaluation of Biological Activity

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 uL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% CO$_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader. Compound $IC_{50}$ values were calculated using the counts of 500 nM of a reference standard treatment as one hundred percent inhibition, and counts of no compound but DMSO treatment as zero percent inhibition.

Compounds with an $IC_{50}$ greater than or equal to 100 nM are shown with (*), compounds with an $IC_{50}$ less than 100 nM are shown with () and those with an $IC_{50}$ less than 5 nM are shown with (*).

Results of the IDO assays are shown in the table below.
HEK Human IDO-1

| Example # | HEK Human IDO-1 $IC_{50}$ (nM) |
|---|---|
| 1 | *** |
| 2 | * |
| 3 | * |
| 4 | ** |
| 5 | * |
| 6 | * |
| 7 | * |
| 8 | * |
| 9 | * |
| 10 | * |
| 11 | * |
| 12 | * |
| 13 | * |
| 14 | * |
| 15 | * |
| 16 | * |
| 17 | ** |
| 18 | *** |
| 19 | * |
| 20 | *** |
| 21 | |
| 22 | ** |
| 23 | *** |
| 24 | * |
| 25 | *** |
| 26 | * |
| 27 | * |
| 28 | * |
| 29 | ** |
| 30 | * |
| 31 | ** |
| 32 | * |
| 33 | ** |
| 34 | * |
| 35 | * |
| 36 | ** |
| 37 | * |
| 38 | * |
| 39 | * |
| 40 | * |
| 41 | * |
| 42 | *** |
| 43 | *** |
| 44 | * |
| 45 | * |
| 46 | *** |
| 47 | *** |
| 48 | *** |
| 49 | *** |
| 50 | * |
| 51 | *** |
| 52 | ** |
| 53 | ** |
| 54 | * |
| 55 | ** |
| 56 | * |
| 57 | * |
| 58-1 | * |
| 58-2 | ** |
| 59-1 | ** |
| 59-1 | *** |
| 60-1 | *** |
| 60-2 | |
| 61-1 | *** |
| 61-2 | *** |
| 62 | * |
| 63 | * |
| racemic 64 | *** |
| 64-1 | ** |
| 64-2 | *** |
| racemic 65 | *** |
| 65-1 | ** |
| 65-2 | *** |
| racemic 66 | * |
| 66-1 | ** |
| 66-2 | *** |
| racemic 67 | *** |
| 67-1 | ** |
| 67-2 | *** |
| 68 | * |
| 69 | *** |
| 70 | *** |
| 71 | ** |
| 72 | ** |
| 73 | ** |
| 74 | * |
| 75 | ** |
| 76 | ** |
| 77 | ** |
| 78 | ** |
| 79 | * |
| 80-1 | *** |
| 80-2 | *** |
| 81-1 | *** |
| 81-2 | *** |
| 82-1 | *** |
| 82-2 | ** |
| 83 | *** |
| 84 | ** |
| 85-1 | *** |
| 85-2 | *** |
| 86-1 | ** |
| 86-2 | *** |
| 87-1 | *** |
| 87-2 | *** |
| 88-1 | * |
| 88-2 | ** |
| 89-1 | *** |
| 89-2 | ** |
| 90-1 | * |
| 90-2 | ** |
| 91 | *** |
| 92 | *** |
| 93 | *** |
| 94 | *** |
| 95 | ** |
| 96 | *** |
| 97 | *** |
| 98 | *** |
| 99 | *** |
| 100 | * |
| 101 | |
| 102 | *** |
| 103 | *** |
| 104 | *** |
| 105 | *** |
| 106 | *** |
| 107 | * |
| 108 | ** |
| 109 | ** |
| 110 | ** |
| 111 | * |
| 112 | * |
| 113 | *** |
| 114 | * |
| 115 | *** |
| 116 | ** |

-continued

| Example # | HEK Human IDO-1 IC$_{50}$ (nM) |
|---|---|
| 117 | * |
| 118 | ** |
| 119 | ** |
| 120 | ** |
| 121 | ** |
| 122 | * |
| 123 | * |
| 124 | ** |
| 125 | *** |
| 126 | *** |
| 127 | ** |
| 128 | * |
| 129 | ** |
| 130 | ** |
| 131 | * |
| 132 | ** |
| 133 | ** |
| 134 | *** |
| 135 | * |
| racemic 136 | *** |
| 136-1 | *** |
| 136-2 | *** |
| 137 | ** |
| 138 | ** |
| 139-1 | ** |
| 139-2 | *** |
| 140 | * |
| 141 | * |
| 142 | ** |
| 143-1 | ** |
| 143-2 | *** |
| 144 | * |
| 145 | ** |
| 146-1 | * |
| 146-2 | ** |
| 147 | * |
| 148 | * |
| 149 | * |
| 150 | * |
| 151 | * |
| 152 | * |
| 153 | * |
| 154 | *** |
| 155 | * |
| 156 | ** |
| 157 | ** |
| 158 | ** |
| 159 | * |
| 160 | * |
| 161 | * |
| 162 | * |
| 163 | ** |
| 164 | ** |
| 165 | * |
| 166 | * |
| 167 | * |

What is claimed is:

1. A compound of Formula (I)

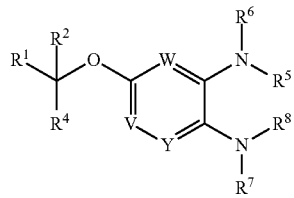

(I)

wherein:
W is $CR^x$,
V is $CR^x$,
Y is $CR^x$;
Z is —O—;
$R^x$ is hydrogen;
$R^1$ is hydrogen, optionally substituted $C_1$-$C_6$ alkyl or $C_1$-$C_4$ alkoxy;
$R^2$ is hydrogen or methyl, or
$R^1$ and $R^2$ are taken together with the carbon to which they are attached to form a 3-6 membered cycloakyl ring;
$R^4$ is —$COZR^3$; wherein when Z is —O—, $R^3$ is H or $C_1$-$C_4$ alkyl;
$R^5$ is hydrogen;
$R^6$ is —$COR^{10}$ or $CONR^5R^9$;
$R^7$ and $R^8$ are independently optionally substituted $C_1$-$C_6$ alkyl, optionally substituted aryl, optionally substituted $C_1$-$C_6$ alkoxy, optionally substituted $C_3$-$C_8$ cycloalkyl, optionally substituted $C_2$-$C_{10}$ alkynyl, optionally substituted 5- to 7-membered monocyclic heterocyclyl, optionally substituted 8- to 10-membered bicyclic heterocyclyl, optionally substituted aryl $C_1$-$C_6$ alkyl, or optionally substituted $C_2$-$C_6$ alkenyl; $R^9$ is optionally substituted $C_1$-$C_6$ alkyl, optionally substituted $C_3$-$C_8$ cycloalkyl, optionally substituted aryl, optionally substituted heteroaryl or optionally substituted heterocyclyl; wherein the optional substituents are 1-4 $R^y$;
$R^y$ is hydrogen, halogen, CN, $CF_3$, $C_1$-$C_6$ alkyl, $C_1$-$C_6$ alkoxy or aryloxy;
$R^{10}$ is optionally substituted aryl; wherein the optional substituents are 1-4 $R^z$;
$R^z$ is hydrogen, halogen, CN, $CF_3$, $C_1$-$C_6$ alkyl, $C_1$-$C_6$ alkoxy or aryloxy;
$R^{11}$ is optionally substituted $C_1$-$C_6$ alkyl, optionally substituted $C_3$-$C_8$ cycloalkyl, trifluoromethyl, phenyl or optionally substituted heterocyclyl;
$R^{12}$ is hydrogen or optionally substituted $C_1$-$C_6$ alkyl;
$R^{13}$ is hydrogen or optionally substituted $C_1$-$C_6$ alkyl;
and/or a stereoisomer, a tautomer or a pharmaceutically acceptable salt thereof.

2. The compound according to claim 1 wherein $R^1$ and $R^2$ are independently H, $C_1$ to $C_4$ alkyl, $C_1$ to $C_4$ alkoxy, or join together to form cyclopropyl or cyclobutyl.

3. The compound according to claim 1 wherein Z is O and $R^3$ is H.

4. The compound according to claim 1 wherein $R^4$ is —$CO_2R^3$.

5. The compound according to claim 1 wherein $R^5$ is H and $R^6$ is —$COR^{10}$ or —$CONR^9R^{10}$; $R^9$ is H, and $R^{10}$ is phenyl, pyridyl, isoxazolyl, thiadiazolyl, indolinyl, or benzyl, wherein $R^{10}$ may optionally be substituted with from 1 to 3 substituents selected from the group consisting of halo, amino, phenoxy, benzoxy, isoxalyl, $C_1$ to $C_4$ alkoxy, $C_1$ to $C_4$ alkyl, halo-$C_1$ to $C_4$ alkyl, and CN.

6. The compound according to claim 1 wherein $R^7$ is $C_3$ to $C_7$ cycloalkyl optionally substituted with halo, —OH or $C_1$ to $C_4$ alkoxy; $C_1$ to $C_4$ alkyl optionally substituted with halo, —OH or phenyl, wherein said phenyl is optionally substituted with $C_1$ to $C_4$ haloalkyl, $C_1$ to $C_4$ alkoxy, halo or $C_1$ to $C_4$ alkyl; $C_1$ to $C_4$ alkenyl; $C_1$ to $C_4$ alkoxy; or benzyl optionally substituted with $C_1$ to $C_4$ alkyl, halo, $C_1$ to $C_4$ alkoxy, or haloalkyl.

7. The compound according to claim 1 wherein R is a $C_3$ to $C_7$ heterocycloalkyl containing from 1 to 4 heteroatoms selected from O, N or S.

8. The compound according to claim 7 wherein R is furanyl, oxetanyl, piperidinyl optionally substituted with $C_1$ to $C_4$ alkenyl.

9. The compound according to claim 7 wherein $R^7$ is cyclohexyl optionally substituted with halo, —OH or $C_1$ to $C_4$ alkoxy or $C_1$ to $C_4$ alkenyl.

10. The compound according to claim 1 wherein $R^8$ is $C_1$ to $C_4$ alkyl or alkenyl wherein said alkyl is optionally substituted with halo, $C_1$ to $C_4$ alkoxy, $C_3$ to $C_6$ or cycloalkyl.

11. The compound according to claim 1 wherein W, V, and Y are —$CR^X$ wherein $R^X$ is H.

12. A compound having the following Formula I, or a pharmaceutically acceptable salt thereof:

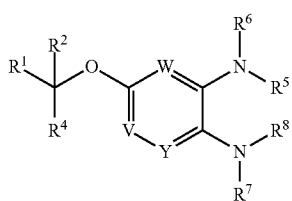

Formula I wherein
$R^1$ H, $C_1$ to $C_4$ alkyl, or $C_3$ to $C_6$ cycloalkyl;
$R^2$ is H, $C_1$ to $C_4$ alkyl, or $C_1$ to $C_2$ alkoxy;
$R^3$ is H, $C_1$ to $C_4$ alkyl;
$R^4$ is —$COZR^3$;
$R^5$ is H;
$R^6$ is —$COR^{10}$ or —CO $R^9R^{10}$;
$R^7$ is $C_1$ to $C_4$ alkyl; $C_1$ to $C_4$ alkenyl; cyclohexl; morpholinyl; oxetanyl; pipendinyl; furanyl; or benzyl; any of which may be optionally substituted with halo, —OH, alkyenyl, $C_1$ to $C_4$ alkyl, methoxy, ethoxy, haloalkyl;
$R^8$ is $C_1$ to $C_4$ alkyl, $C_1$ to $C_4$ alkoxy-$C_1$ to $C_4$ alkyl; —$C_1$ to $C_4$ alkyl-$C_3$ to $C_6$ cycloalkyl;
$R^9$ is H;
$R^{10}$ is phenyl, optionally substituted with halo, amino, $C_1$ to $C_4$ alkyl, haloalkyl, alkoxy, haloalkoxy, CN, isoxazolyl, benzoxy, phenoxy;
Z is O and $R^3$ is H or $C_1$ to $C_4$ alkyl.

13. A compound selected from the group consisting of:
2-(3-(3-(4-chloro-2-fluorophenyl)ureido)-4-(cyclohexyl (isobutyl)amino)phenoxy)acetic acid;
2-(4-(cyclohexyl(isobutyl)amino)-3-(3-(pyrimidin-5-yl) ureido)phenoxy)acetic acid;
2-(4-(cyclohexyl(isobutyl)amino)-3-(3-(pyridin-3-yl) ureido) phenoxy) acetic acid;
2-(4-(cyclohexyl(isobutyl)amino)-3-(3-(3-methylisoxazol-5-yl)ureido)phenoxy)acetic acid;
2-(4-(cyclohexyl(isobutyl)amino)-3-(3-(pyridin-4-yl) ureido) phenoxy) acetic acid;
2-(3-(3-(1,3,4-thiadiazol-2-yl)ureido)-4-(cyclohexyl (isobutyl) amino)phenoxy)acetic acid; 2-(4-(cyclohexyl(isobutyl)amino)-3-(3-(5-methylisoxazol-3-yl) ureido)phenoxy)acetic acid;
2-(4-(cyclohexyl(isobutyl)amino)-3-(3-(5-(trifluoromethyl)-1,3,4-thiadiazol-2-yl)ureido)phenoxy) acetic acid;
2-(4-(cyclohexyl(isobutyl)amino)-3-(3-(4-(dimethylamino) phenyl)ureido)phenoxy)acetic acid;
2-(4-(cyclohexyl(isobutyl)amino)-3-(3-(isoxazol-3-yl) ureido) phenoxy) acetic acid;
2-(4-(cyclohexyl(isobutyl)amino)-3-(3-(5-methyl-1,3,4-thiadiazol-2-yl)ureido)phenoxy)acetic acid;

2-(4-(cyclohexyl(isobutyl)amino)-3-(3-(thiazol-2-yl) ureido) phenoxy)acetic acid;
2-(4-(cyclohexyl(isobutyl)amino)-3-(3-(4-phenoxyphenyl)ureido) phenoxy)acetic acid; 2-(4-(cyclohexyl (isobutyl)amino)-3-(3-(4-(oxazol-5-yl)phenyl) ureido) phenoxy)acetic acid;
2-(3-(3-(4-(benzyloxy)phenyl)ureido)-4-(cyclohexyl (isobutyl)amino)phenoxy)acetic acid; 2-(4-(cyclohexyl (isobutyl)amino)-3-(indoline-1-carboxamido)phenoxy) acetic acid;
2-(4-(cyclohexyl(isobutyl)amino)-3-(3-(4-fluorophenyl) ureido) phenoxy)acetic acid; 2-(4-(cyclohexyl(isobutyl)amino)-3-(3-(2-fluorophenyl)ureido) phenoxy)acetic acid; 2-(4-(cyclohexyl(isobutyl)amino)-3-(3-(2,6-difluorophenyl)ureido) phenoxy)acetic acid; 2-(4-(cyclohexyl(isobutyl)amino)-3-(3-(2,5-difluorophenyl) ureido) phenoxy)acetic acid; 2-(4-(cyclohexyl (isobutyl)amino)-3-(3-(2,4-difluorophenyl)ureido) phenoxy)acetic acid; 2-(3-(3-(5-chloro-2-fluorophenyl) ureido)-4-(cyclohexyl(isobutyl)amino)phenoxy)acetic acid;
2-(4-(cyclohexyl(isobutyl)amino)-3-(3-(2-fluoro-4-methylphenyl)ureido)phenoxy)acetic acid;
2-(3-(3-(3-chloro-2,4-difluorophenyl)ureido)-4-(cyclohexyl(isobutyl)amino)phenoxy)acetic acid;
2-(4-(cyclohexyl(isobutyl)amino)-3-(3-(2-fluoro-4-methoxyphenyl) ureido)phenoxy)acetic acid;
2-(3-(3-(3-chloro-2-fluorophenyl)ureido)-4-(cyclo-hexyl (isobutyl)amino)phenoxy)acetic acid;
2-(4-(cyclohexyl(isobutyl)amino)-3-(3-(2-fluoro-3-(trifluoromethyl)phenyl)ureido)phenoxy)acetic acid;
2-(4-(cyclohexyl(isobutyl)amino)-3-(3-(3-fluoro-2-methylphenyl) ureido)phenoxy)acetic acid;
2-(4-(cyclohexyl(isobutyl)amino)-3-(3-(2,5-difluoro-4-methoxy-phenyl)ureido)phenoxy)acetic acid;
2-(4-(cyclohexyl(isobutyl)amino)-3-(3-(5-fluoro-2-methylphenyl)ureido)phenoxy)acetic acid;
2-(4-(cyclohexyl(isobutyl)amino)-3-(3-(3,4-difluorophenyl) ureido)phenoxy)acetic acid; 2-(4-(cyclohexyl (isobutyl)amino)-3-(3-(3,5-difluorophenyl) ureido) phenoxy)acetic acid; 2-(4-(cyclohexyl(isobutyl) amino)-3-(3-(3-fluoro-4-methylphenyl) ureido) phenoxy)acetic acid; 2-(4-(cyclohexyl(isobutyl) amino)-3-(3-(3-fluoro-4-methoxyphenyl)ureido) phenoxy)acetic acid;
2-(4-(cyclohexyl(isobutyl)amino)-3-(3-(3-fluoro-4-(trifluoromethyl)phenyl)ureido)phenoxy)acetic acid;
2-(3-(3-(4-chloro-3-fluorophenyl)ureido)-4-(cyclohexyl (isobutyl)amino)phenoxy)acetic acid;
2-(3-(3-(3-chloro-5-fluorophenyl)ureido)-4-(cyclo-hexyl (isobutyl)amino)phenoxy)acetic acid;
2-(4-(cyclohexyl(isobutyl)amino)-3-(3-(4-fluoro-2-methylphenyl)ureido)phenoxy)acetic acid;
2-(4-(cyclohexyl(isobutyl)amino)-3-(3-(4-fluoro-2-methylphenyl)ureido)phenoxy)acetic acid;
2-(3-(3-(4-cyanophenyl)ureido)-4-(cyclohexyl(isobutyl) amino)phenoxy)acetic acid;
2-(4-(cyclohexyl(isobutyl)amino)-3-(3-methyl-3-(p-tolyl)ureido)phenoxy)acetic acid;
2-(4-(cyclohexyl(isobutyl)amino)-3-(3-(4-fluorophenyl)-3-methyl-ureido)phenoxy)acetic acid;
ethyl 2-(3-(3-(4-chloro-2-fluorophenyl)ureido)-4-(cyclohexyl(isobutyl)amino)phenoxy)acetate;
2-(3-(3-(4-cyano-2-fluorophenyl)ureido)-4-(cyclohexyl (isobutyl)amino)phenoxy)acetic acid;
2-(3-(benzo[d]oxazol-2-ylamino)-4-(cyclohexyl(isobutyl)amino)phenoxy)acetic acid;

ethyl 2-(4-(cyclohexyl(isobutyl)amino)-3-(2,2,2-trifluoroacetamido)phenoxy)acetate;
2-(3-(3-(4-chloro-2-fluorophenyl)ureido)-4-(cyclohexyl (isobutyl) amino)phenoxy)-N-(cyclopropyl-sulfonyl) acetamide;
2-(3-(3-(4-chloro-2-fluorophenyl)ureido)-4-(cyclohexyl (isobutyl)amino)phenoxy)-N—(N,N-dimethyl-sulfamoyl)acetamide;
N-(tert-butylsulfonyl)-2-(3-(3-(4-chloro-2-fluorophenyl) ureido)-4-(cyclohexyl(isobutyl)amino)phenoxy)acetamide;
2-(3-(3-(4-chloro-2-fluorophenyl)ureido)-4-(cyclohexyl (isobutyl) amino)phenoxy)-N-(thiophen-2-ylsulfonyl) acetamide;
2-(4-(cyclohexyl(isobutyl)amino)-3-(3-(5-methyl-isoxazol-3-yl)ureido)phenoxy)-N-(cyclopropylsulfonyl)acetamide;
2-(4-(cyclohexyl(isobutyl)amino)-N—(N,N-dimethyl-sulfamoyl)acetamide;
2-(4-(cyclohexyl(isobutyl)amino)-3-(3-(p-tolyl)ureido) phenoxy)-N—(N,N-dimethyl-sulfamoyl)acetamide;
2-(4-(cyclohexyl(isobutyl)amino)-3-(3-(p-tolyl)ureido) phenoxy)-N-(cyclopropyl-sulfonyl)acetamide;
2-(3-(2-(4-chloro-3-fluorophenyl)acetamido)-4-(cyclohexyl(isobutyl) amino)phenoxy)acetic acid;
2-(4-(cyclohexyl(isobutyl)amino)-3-(2-(2-fluoro-4-methylphenyl)acetamido)phenoxy) acetic acid;
2-(4-(cyclohexyl(isobutyl)amino)-3-(2-(2,4-difluorophenyl) acetamido)phenoxy)acetic acid;
2-(4-(cyclohexyl(isobutyl)amino)-3-(2-(4-fluorophenyl) acetamido) phenoxy)acetic acid;
2-(4-(cyclohexyl(isobutyl)amino)-3-(3-(pyrimidin-5-yl) ureido)phenoxy)propanoic acid;
2-(4-(cyclohexyl(isobutyl)amino)-3-(3-(2-fluoro-phenyl) ureido)phenoxy)propanoic acid;
2-(4-(cyclohexyl(isobutyl)amino)-3-(3-(p-tolyl)ureido) phenoxy)propanoic acid;
2-(3-(3-(4-chloro-2-fluorophenyl)ureido)-4-(cyclo-hexyl (isobutyl)amino)phenoxy)propanoic acid;
(±)-2-(3-(benzo[d]oxazol-2-ylamino)-4-(cyclohexyl (isobutyl)amino)phenoxy)propanoic acid;
(±)-2-(4-(cyclohexyl(isobutyl)amino)-3-((5-methoxypyrimidin-2-yl)amino)phenoxy)propanoic acid;
(±)-2-(4-(cyclohexyl(isobutyl)amino)-3-(3-(2-fluoro-4-methoxyphenyl)ureido)phenoxy)propanoic acid;
(±)-2-(4-(cyclohexyl(isobutyl)amino)-3-(3-(2-fluoro-4-methylphenyl)ureido)phenoxy)propanoic acid;
(±)-2-(3-(3-(4-cyanophenyl)ureido)-4-(cyclohexyl(isobutyl)amino)phenoxy)propanoic acid;
(±)-ethyl 2-(3-(3-(4-chloro-2-fluorophenyl)ureido)-4-(cyclohexyl(isobutyl)amino)phenoxy)propanoate;
(±)-2-(4-(cyclohexyl(isobutyl)amino)-3-(3-(3-methylisoxazol-5-yl)ureido)phenoxy)propanoic acid;
(±)-2-(4-(cyclohexyl(isobutyl)amino)-3-(3-(p-tolyl) ureido)phenoxy)-N-(cyclopropylsulfonyl)propanamide;
(±)-2-(3-(3-(4-chloro-2-fluorophenyl)ureido)-4-(cyclohexyl(isobutyl)amino)phenoxy)-N-(cyclopropylsulfonyl)propanamide;
2-(4-(cyclohexyl(isobutyl)amino)-3-(2-(2,4-difluorophenyl)acetamido)phenoxy)propanoic acid;
2-(3-(2-(4-chloro-3-fluorophenyl) acetamido)-4-(cyclohexyl(isobutyl)amino)phenoxy) propanoic acid;
2-(3-(2-(4-chloro-2-fluorophenyl) acetamido)-4-(cyclohexyl(isobutyl)amino)phenoxy) propanoic acid;

2-(4-(cyclohexyl(isobutyl)amino)-3-(2-(4-fluorophenyl) acet-amido)phenoxy)propanoic acid;
2-(4-(cyclohexyl(isobutyl)amino)-3-(2-(p-tolyl)acet-amido) phenoxy)propanoic acid;
2-(4-(cyclohexyl(isobutyl)amino)-3-(2-(2-fluoro-4-methylphenyl)acetamido)phenoxy) propanoic acid;
(±)-2-(3-(2-(4-chloro-2-fluorophenyl) acetamido)-4-(cyclohexyl(isobutyl)amino)phenoxy)-N-(cyclopropylsulfonyl) propanamide;
(±)-2-(4-(cyclohexyl(isobutyl)amino)-3-(2-(p-tolyl)acetamido)phenoxy)-N-(cyclopropyl-sulfonyl)propanamide;
(±)-2-(3-(2-(4-chloro-3-fluorophenyl) acetamido)-4-(cyclohexyl(isobutyl)amino)phenoxy)-N-(cyclopropylsulfonyl) propanamide;
2-(3-(3-(4-chloro-2-fluorophenyl)ureido)-4-(cyclohexyl (isobutyl)amino)phenoxy)butanoic acid;
2-(4-(cyclohexyl(isobutyl)amino)-3-(3-(2-fluorophenyl) ureido)phenoxy)butanoic acid;
2-(4-(cyclohexyl(isobutyl)amino)-3-(3-(p-tolyl)ureido) phenoxy)butanoic acid;
(±)-2-(4-(cyclohexyl(isobutyl)amino)-3-(3-(p-tolyl) ureido)phenoxy)butanoic acid;
(±)-ethyl 2-(4-fluoro-3-nitrophenoxy)-3-methylbutanoate;
(±)-2-(4-(cyclohexyl(isobutyl)amino)-3-(3-(p-tolyl) ureido)phenoxy)-3-methylbutanoic acid;
2-(3-(3-(4-chloro-2-fluorophenyl)ureido)-4-(cyclohexyl (isobutyl)amino)phenoxy)pentanoic acid;
2-(4-(cyclohexyl(isobutyl)amino)-3-(3-(p-tolyl)ureido) phenoxy)pentanoic acid;
2-(4-(cyclohexyl(isobutyl)amino)-3-(3-(2-fluorophenyl) ureido)phenoxy)pentanoic acid;
2-(4-(cyclohexyl(isobutyl)amino)-3-(3-(pyrimidin-5-yl) ureido)phenoxy)pentanoic acid;
2-(3-(3-(4-chloro-2-fluorophenyl)ureido)-4-(cyclohexyl (isobutyl)amino)phenoxy)-3-methoxypropanoic acid;
2-(4-(cyclohexyl(isobutyl)amino)-3-(3-(p-tolyl)ureido) phenoxy)-3-methoxypropanoic acid;
2-(3-(3-(4-chloro-2-fluorophenyl)ureido)-4-(cyclohexyl (isobutyl)amino)phenoxy)-2-methylpropanoic acid;
2-(4-(cyclohexyl(isobutyl)amino)-3-(3-(p-tolyl)ureido) phenoxy)-2-methylpropanoic acid;
1-(3-(3-(4-chloro-2-fluorophenyl)ureido)-4-(cyclohexyl (isobutyl)amino)phenoxy)cyclopropanecarboxylic acid;
1-(4-(cyclohexyl(isobutyl)amino)-3-(3-(p-tolyl)ureido) phenoxy)cyclopropanecarboxylic acid;
1-(5-((1H-tetrazol-5-yl)methoxy)-2-(diisobutylamino)-4-fluorophenyl)-3-(p-tolyl)urea;
1-(5-((1H-tetrazol-5-yl)methoxy)-2-(cyclohexyl(isobutyl)amino)phenyl)-3-(4-chloro-2-fluorophenyl)urea;
1-(5-((1H-tetrazol-5-yl)methoxy)-2-(cyclohexyl(isobutyl)amino)phenyl)-3-(2-fluorophenyl)urea;
2-(3-(3-(4-Chloro-2-fluorophenyl)ureido)-4-(4,4-difluorocyclohexyl)(isobutyl)amino)-phenoxy)acetic acid;
2-(3-(3-(4-Bromo-2-fluorophenyl)ureido)-4-(4,4-difluorocyclohexyl)(isobutyl)amino)-phenoxy)acetic acid;
2-(4((4,4-Difluorocyclohexyl)(isobutyl)amino)-3-(3-(4-ethoxyphenyl)ureido)phenoxy)acetic acid;
ethyl 2-((5-(3-(4-chloro-2-fluorophenyl)ureido)-6-(cyclohexyl(isobutyl)amino)pyridin-3-yl)oxy)acetate;
2-((5-(3-(4-chloro-2-fluorophenyl)ureido)-6-(cyclohexyl (isobutyl)amino)pyridin-3-yl)oxy)acetic acid;
2-((5-(3-(4-chloro-2-fluorophenyl)ureido)-6-(cyclohexyl (isobutyl)amino)pyridin-3-yl)oxy)-N-(cyclopropylsulfonyl)acetamide;

2-(3-(3-(4-chloro-2-fluorophenyl)ureido)-4-(cyclohexyl (isobutyl)amino)-5-fluorophenoxy)acetic acid;
2-(3-(3-(4-chloro-2-fluorophenyl)ureido)-4-(cyclohexyl (isobutyl)amino)-5-fluorophenoxy)-N-(cyclopropyl-sulfonyl)acetamide;
2-(4-(cyclohexyl(isobutyl)amino)-3-(3-(2,5-difluorophe-nyl)ureido)-5-fluorophenoxy)acetic acid;
2-(3-(3-(4-chloro-2-fluorophenyl)ureido)-4-(cyclohexyl (isobutyl)amino)-2-fluorophenoxy)acetic acid;
2-(3-(3-(4-chloro-2-fluorophenyl)ureido)-5-cyano-4-(cy-clohexyl(isobutyl)amino)phenoxy)acetic acid;
2-(4-(cyclohexyl(isobutyl)amino)-3-(3-(p-tolyl)ureido) phenoxy)acetic acid;
2-(3-(2-(4-chloro-2-fluorophenyl)acetamido)-4-(cyclo-hexyl(isobutyl)amino)phenoxy)acetic acid;
2-(3-(3-(4-chloro-2-fluorophenyl)ureido)-4-(cyclohexyl (isobutyl)amino)phenoxy)-methylthiazol-2-yl)acet-amide;
2-(4-(diisobutylamino)-3-(3-(p-tolyl)ureido)phenoxy) acetic acid;
2-(5-(3-(4-chloro-2-fluorophenyl)ureido)-2-fluoro-4-((2-methylallyl)(4,4,4-rifluorobutyl)amino)phenoxy)acetic acid;
2-(4-(cyclohexyl(isobutyl)amino)-2-fluoro-5-(3-(3-meth-ylisoxazol-5-yl)ureido)phenoxy)acetic acid;
2-(5-(3-(4-chloro-2-fluorophenyl)ureido)-4-(cyclohexyl (isobutyl)amino)-2-fluorophenoxy)acetic acid;
2-(3-(3-(4-chloro-2-fluorophenyl)ureido)-4-(cyclohexyl (2-methoxyethyl)amino)phenoxy)acetic acid;
2-(4-(cyclohexyl(2-methoxyethyl)amino)-3-(3-(2,4-dif-luorophenyl)ureido)phenox5 acid;
2-(3-(3-(4-chloro-2-fluorophenyl)ureido)-4-(cyclohexyl (cyclopropylmethyl)amino)phenoxy)acetic acid;
2-(2-chloro-5-(3-(4-chloro-2-fluorophenyl)ureido)-4-(cy-clohexyl(isobutyl)amino)phenoxy)acetic acid;
2-(2-fluoro-4-((2-methylallyl)(4,4,4-trifluorobutyl) amino)-5-(3-(p-tolyl)ureido)phenoxy)acetic acid;
2-(2-fluoro-4-((2-methylallyl)(4,4,4-trifluorobutyl) amino)-5-(3-(3-methylisoxazol-5-yl)ureido)phenoxy) acetic acid;
2-(2-chloro-4-(cyclohexyl(isobutyl)amino)-5-(3-(p-tolyl) ureido)phenoxy)acetic acid;
2-(5-(3-(2-chlorophenyl)ureido)-4-(cyclohexyl(isobutyl) amino)-2-fluorophenoxy)acetic acid;
2-(4-(cyclohexyl(isobutyl)amino)-5-(3-(2,4-difluorophe-nyl)ureido)-2-fluorophenoxy)acetic acid;
2-(5-(3-(4-bromo-2-fluorophenyl)ureido)-4-(cyclohexyl (isobutyl)amino)-2-fluorophenoxy)acetic acid;
2-(4-(cyclohexyl(isobutyl)amino)-5-(3-(2,5-difluorophe-nyl)ureido)-2-fluorophenoxy)acetic acid;
2-(4-(cyclohexyl(isobutyl)amino)-2-fluoro-5-(3-(4-(trif-luoromethoxy)phenyl)ureido)phenoxy)acetic acid;
2-(5-(3-(6-cyanopyridin-3-yl)ureido)-4-(cyclohexyl (isobutyl)amino)-2-fluorophenoxy)acetic acid;
2-(4-(cyclohexyl(isobutyl)amino)-2-fluoro-5-(3-(2-fluo-rophenyl)ureido)phenoxy)acetic acid;
2-(4-(cyclohexyl(cyclopropylmethyl)amino)-3-(3-(2,5-difluorophenyl)ureido)phenoxy)acetic acid;
2-(4-(cyclohexyl(cyclopropylmethyl)amino)-3-(3-(p-tolyl)ureido)phenoxy)acetic acid;
2-(4-(cyclohexyl(isobutyl)amino)-5-(3-(2,4-difluorophe-nyl)ureido)-2-fluorophenoxy)acetic acid;
2-(5-(2-(4-chloro-2-fluorophenyl)acetamido)-4-(cyclo-hexyl(isobutyl)amino)-2-fluorophenoxy)acetic acid;
2-(4-(cyclohexyl(isobutyl)amino)-5-(3-(2,4-difluorophe-nyl)ureido)-2-fluorophenoxy)-N-(cyclopropylsulfonyl) acetamide;

2-(3-(3-(4-chloro-2-fluorophenyl)ureido)-4-(cyclohexyl (isobutyl)amino)phenoxy)-N-(2,2,2-trifluoroethyl)ac-etamide;
(+/−) 2-(5-(3-(4-chloro-2-fluorophenyl)ureido)-4-(cyclo-hexyl(isobutyl)amino)-2-fluorophenoxy)propanoic acid TFA;
2-(3-(3-(4-chloro-2-fluorophenyl)ureido)-4-((2-methylal-lyl)(tetrahydro-2H-pyran-4-yl)amino)phenoxy)acetic acid;
2-(3-(3-(4-chloro-2-fluorophenyl)ureido)-4-((2-methylal-lyl)(tetrahydro-2H-pyran-4-yl)amino)phenoxy)pro-panoic acid;
2-(3-(3-(4-chloro-2-fluorophenyl)ureido)-4-((2-methylal-lyl)(tetrahydro-2H-pyran-4-yl)amino)phenoxy)pro-panoic acid;
(+/−)-2-(4-((2-methylallyl)(tetrahydro-2H-pyran-4-yl) amino)-3-(3-(p-tolyl)ureido)phenoxy)propanoic acid;
2-(3-(3-(4-chloro-2-fluorophenyl)ureido)-4-((2-methylal-lyl)(oxetan-3-yl)amino)phenoxy)acetic acid;
2-(3-(3-(4-chloro-2-fluorophenyl)ureido)-4-((2-methylal-lyl)(1-(2-methylallyl)piperidin-4-yl)amino)phenoxy) acetic acid;
(2-(3-(3-(4-chloro-2-fluorophenyl)ureido)-4-(isobutyl (tetrahydro-2H-pyran-4-yl)amino)phenoxy)butanoic acid;
2-(3-(3-(4-chloro-2-fluorophenyl)ureido)-4-(isobutyl(tet-rahydrofuran-3-yl)amino)phenoxy)acetic acid;
2-(3-(3-(4-chloro-2-fluorophenyl)ureido)-4-(isobutyl(tet-rahydrofuran-3-yl)amino)phenoxy)propanoic acid;
2-(3-(3-(4-chloro-2-fluorophenyl)ureido)-4-(isobutyl(tet-rahydrofuran-3-yl)amino)phenoxy)propanoic acid;
2-(3-(3-(4-chloro-2-fluorophenyl)ureido)-4-(isobutyl(ox-etan-3-yl)amino)phenoxy)acetic acid;
2-(3-(3-(4-chloro-2-fluorophenyl)ureido)-4-((tetrahydro-2H-pyran-4-yl)(3,3,3-trifluoropropyl)amino)phenoxy) propanoic acid;
2-(3-(3-(4-chloro-2-fluorophenyl)ureido)-4-(((    )-4-hy-droxycyclohexyl)(isobutyl)amino)phenoxy)acetic acid;
2-(3-(3-(4-chloro-2-fluorophenyl)ureido)-4-(((    )-4 hydroxycyclohexyl)(isobutyl)amino)phenoxy)acetic acid;
2-(3-(3-(4-chloro-2-fluorophenyl)ureido)-4-(isobutyl(tet-rahydro-2H-pyran-4-yl)amino)phenoxy)acetic acid;
2-(3-(3-(4-chloro-2-fluorophenyl)ureido)-4-(isobutyl((    )-4-methoxycyclohexyl)amino)phenoxy)acetic acid;
2-(3-(3-(4-chloro-2-fluorophenyl)ureido)-4-(cyclohexyl (isobutyl)amino)phenoxy)-N-(oxazol-2-yl)acetamide;
2-(3-(3-(4-chloro-2-fluorophenyl)ureido)-4-(cyclohexyl (isobutyl)amino)phenoxy)-N-(thiazol-2-yl)acetamide;
1-(4-chloro-2-fluorophenyl)-3-(2-(cyclohexyl(isobutyl) amino)-5-(oxazol-2-ylmethoxy)phenyl)urea;
1-(4-chloro-2-fluorophenyl)-3-(2-(cyclohexyl(isobutyl) amino)-5-(1-(oxazol-2-yl)ethoxy)phenyl)urea;
2-(4-(benzyl(propyl)amino)-3-(3-(4-chloro-2-fluorophe-nyl)ureido)phenoxy)acetic acid;
2-(4-(benzyl(propyl)amino)-3-(3-(p-tolyl)ureido)phe-noxy)acetic acid;
2-(4-(benzyl(propyl)amino)-3-(3-(4-(trifluoromethoxy) phenyl)ureido)phenoxy)acetic acid;
2-(4-(benzyl(propyl)amino)-3-(3-(4-ethoxyphenyl) ureido)phenoxy)acetic acid;
2-(4-(benzyl(propyl)amino)-3-(3-(4-(trifluoromethyl) phenyl)ureido)phenoxy)acetic acid;
2-(3-(3-(4-chloro-2-fluorophenyl)ureido)-4-((4-chlo-robenzyl)(isobutyl)amino)phenoxy)acetic acid;

2-(3-(3-(4-chloro-2-fluorophenyl)ureido)-4-((4-chlorobenzyl)(propyl)amino)phenoxy)acetic acid;

2-(4-(benzyl(propyl)amino)-3-(2-(4-chloro-2-fluorophenyl)acetamido)phenoxy)acetic acid;

2-(4-(benzyl(propyl)amino)-3-(2-(p-tolyl)acetamido)phenoxy)acetic acid; and 2-(3-(2-(4-chloro-2-fluorophenyl)acetamido)-4-((4-chlorobenzyl)(isobutyl)amino)phenoxy)acetic acid.

14. A method for lessening, reducing, modulating or ameliorating a cancer that is susceptible to IDO inhibition in a patient in need thereof comprising administering to said patient a therapeutically acceptable amount of a compound according to claim 1.

15. The method of claim 14 wherein said cancer is selected from the group consisting of bladder, pancreatic, prostate, lung, leukemia, breast, colorectal, melanoma, head and neck, ovarian, lymphoma and cervical.

16. The method of claim 15 further comprising administering an additional anti-cancer agent.

17. The method of claim 16 wherein said anti-cancer agent is selected from the group consisting of a chemotherapeutic agent or an immune-checkpoint inhibitor.

\* \* \* \* \*

UNITED STATES PATENT AND TRADEMARK OFFICE
CERTIFICATE OF CORRECTION

PATENT NO. : 10,689,331 B2  
APPLICATION NO. : 15/737798  
DATED : June 23, 2020  
INVENTOR(S) : Balog et al.

Page 1 of 1

It is certified that error appears in the above-identified patent and that said Letters Patent is hereby corrected as shown below:

In the Claims

Column 158, Line 10 (Claim 1), delete "cycloakyl" and insert -- cycloalkyl -- therefor Column 158, Line 17 (Claim 1), delete "$C_3$-$C_8$cycloalkyl," and insert -- $C_3$-$C_8$ cycloalkyl, -- therefor Column 158, Line 52 (Claim 5), delete "isoxalyl" and insert -- isoxazolyl -- therefor Column 159, Line 31 (Claim 12), delete "cyclohexl;" and insert -- cyclohexyl; -- therefor Column 159, Line 32 (Claim 12), delete "pipendinyl;" and insert -- piperidinyl; -- therefor Column 161, Line 4 (Claim 13), delete "(cyclopropyl-sulfonyl)" and insert -- cylopropylsulfonyl -- therefor Column 162, Line 2 (Claim 13), delete "acet-amido)" and insert -- acetamido) -- therefor Column 162, Line 11 (Claim 13), delete "(cyclopropyl-sulfonyl)" and insert -- cylopropylsulfonyl -- therefor Signed and Sealed this  
Twentieth Day of October, 2020

Andrei Iancu  
*Director of the United States Patent and Trademark Office*